US010240128B2

(12) United States Patent
Thirion et al.

(10) Patent No.: US 10,240,128 B2
(45) Date of Patent: Mar. 26, 2019

(54) MEANS AND METHODS TO INCREASE ADENOVIRUS PRODUCTION

(71) Applicant: SIRION BIOTECH GMBH, Planegg/Martinsried (DE)

(72) Inventors: Christian Thirion, München (DE); Zsolt Ruzsics, Diessen am Ammersee (DE)

(73) Assignee: SIRION Biotech GmbH, Planegg/Martinsried (DE)

( * ) Notice: Subject to any disclaimer, the term of this patent is extended or adjusted under 35 U.S.C. 154(b) by 0 days.

(21) Appl. No.: 14/412,665

(22) PCT Filed: Jul. 4, 2013

(86) PCT No.: PCT/EP2013/064165
§ 371 (c)(1),
(2) Date: Jan. 3, 2015

(87) PCT Pub. No.: WO2014/006146
PCT Pub. Date: Jan. 9, 2014

(65) Prior Publication Data
US 2015/0126410 A1 May 7, 2015

(30) Foreign Application Priority Data
Jul. 4, 2012 (EP) .................................... 12175028

(51) Int. Cl.
*C12N 7/00* (2006.01)

(52) U.S. Cl.
CPC ...... *C12N 7/00* (2013.01); *C12N 2710/10043* (2013.01); *C12N 2710/10052* (2013.01)

(58) Field of Classification Search
None
See application file for complete search history.

(56) References Cited

U.S. PATENT DOCUMENTS 7,115,391 B1 * 10/2006 Chen ..................... C12N 15/86 435/69.1
2005/0112765 A1 * 5/2005 Li ......................... C12N 15/86 424/93.2

(Continued)

OTHER PUBLICATIONS

Babiss et al., "Promoter of the Adenovirus Polypeptide IX Gene: Similarity to E1B and Inactivation by Substitution of the Simian Virus 40 TATA Element," Journal of Virology, vol. 65, No. 2: 598-605 (1991).*

(Continued)

*Primary Examiner* — Michelle S Horning
(74) *Attorney, Agent, or Firm* — Perdue IP Law, APC

(57) ABSTRACT

The invention relates to a method for increasing the yield of replication-incompetent adenoviruses having at least a partial deletion in the E1-region, wherein the adenoviruses are generated in a production cell by: (a) expressing an adenoviral pIX polypeptide from a nucleic acid sequence encoding adenoviral pIX polypeptide under the control of at least a minimal endogenous pIX promoter and a heterologous promoter; and (b) expressing the elements necessary for the production and assembly of the adenoviruses, thereby increasing the yield of adenoviruses generated in the production cell in comparison to the yield in the absence of nucleic acid sequence encoding the adenoviral pIX polypeptide. Further, the invention relates to a method for constructing an adenovirus library, a production cell, and the use of an adenoviral pIX polypeptide for increasing the yield of replication-incompetent adenoviruses having at least a partial deletion in the E1-region.

12 Claims, 4 Drawing Sheets

Figure 1A:
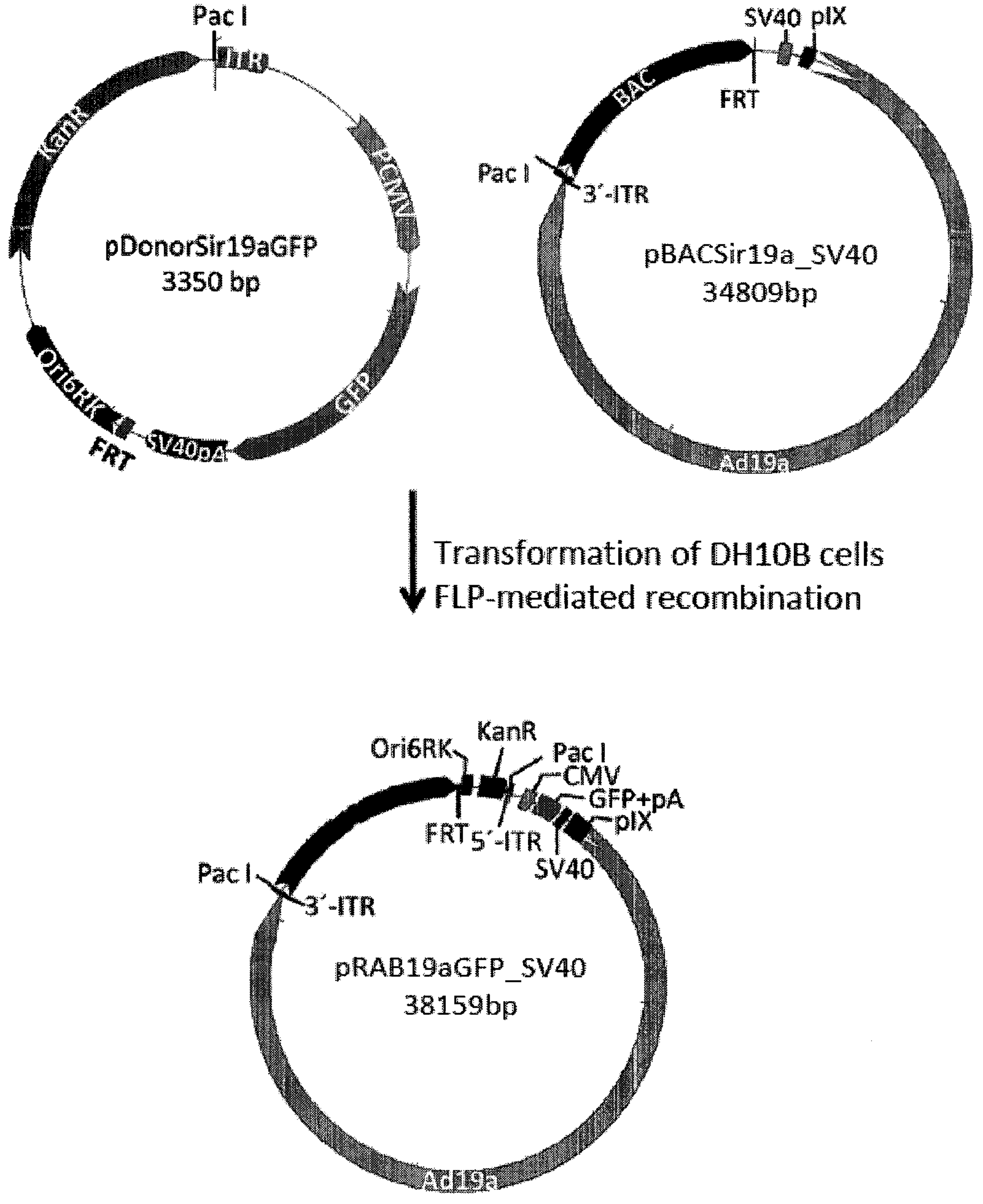
Figure 1B:
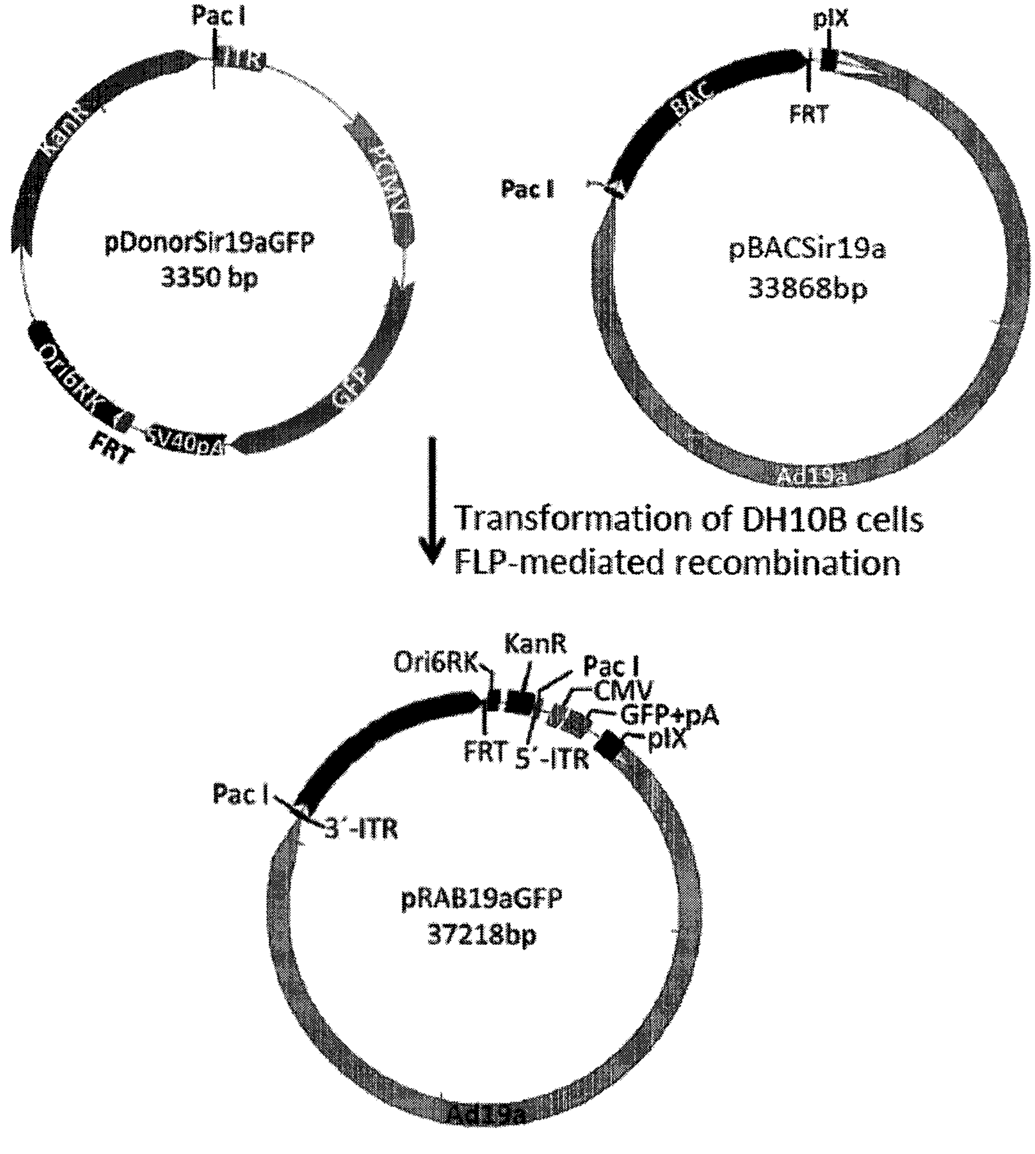
Figure 1C:
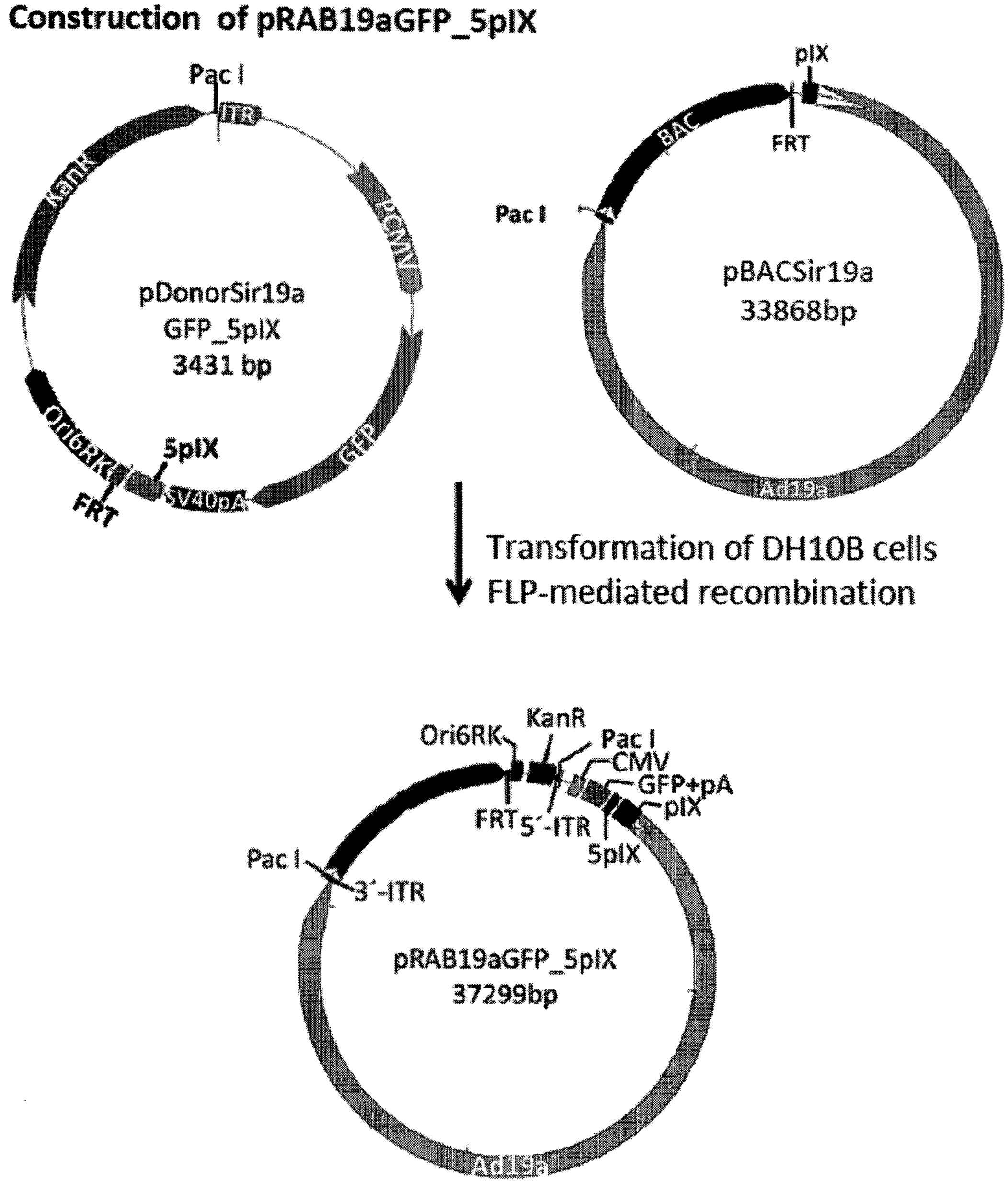
Figure 1D:
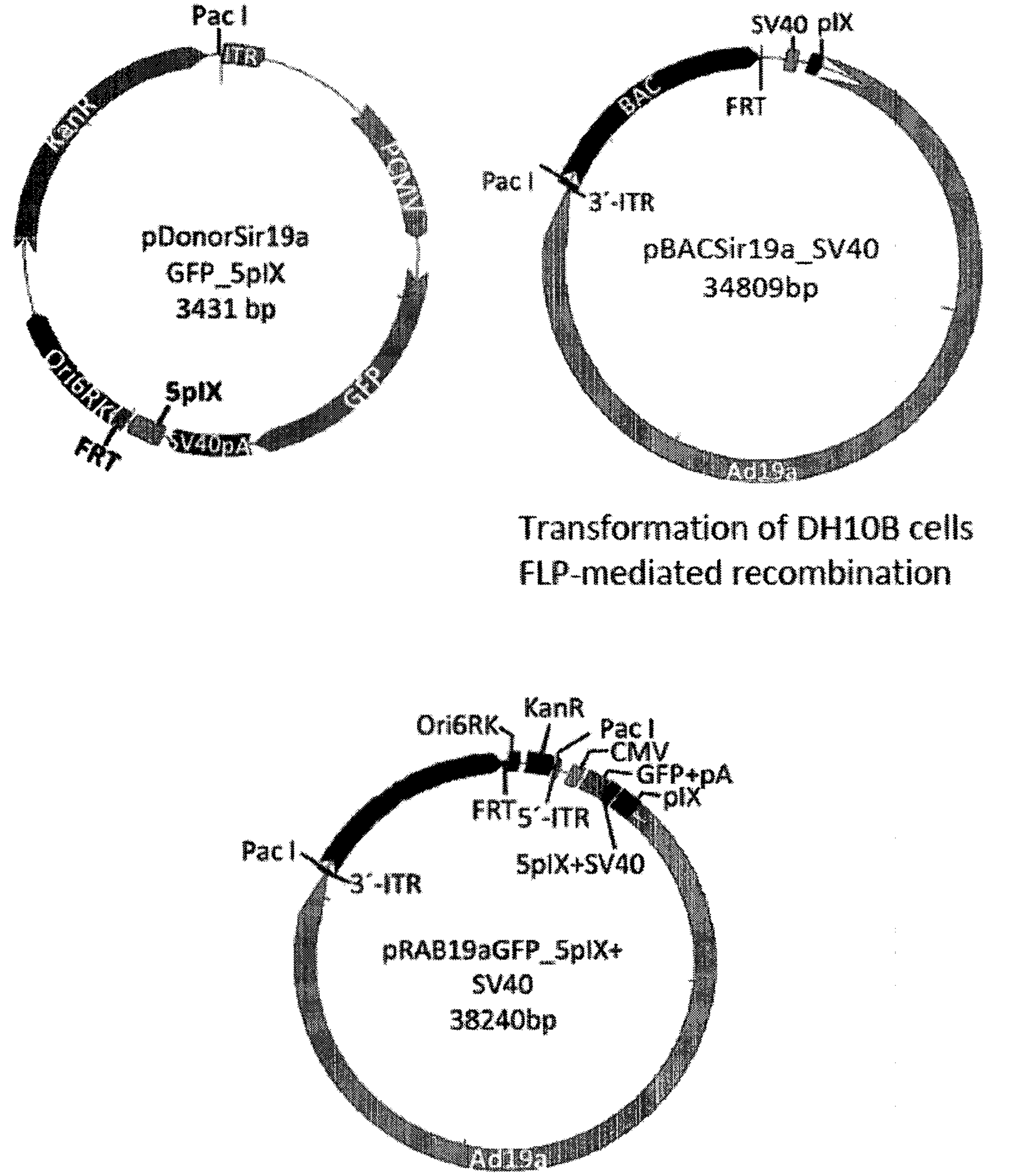

Specification includes a Sequence Listing.

(56) References Cited

U.S. PATENT DOCUMENTS

| | | | | |
|---|---|---|---|---|
| 2008/0206837 | A1* | 8/2008 | Vogels | C12N 15/86 435/235.1 |
| 2009/0022759 | A1* | 1/2009 | Burgert | C12N 7/00 424/199.1 |
| 2009/0253184 | A1* | 10/2009 | Clarke | C12N 7/00 435/91.4 |

OTHER PUBLICATIONS

V. Krougliak et al: "Development of Cell Lines Capable of Complementing E1, E4, and Protein IX Defective Adenovirus Type 5 Mutants", Human Gene Therapy, Mary Ann Liebert, New York ,NY, US, vol. 6, No. 12, Dec. 1, 1995 (Dec. 1, 1995), pp. 1575-1586.
A. Lemckert et al: "Generation of a novel replication-incompetent adenoviral vector derived from human adenovirus type 49: manufacture on PER.C6 cells, tropism and immunogenicity", Journal of General Virology, Society for General Microbiology, Spencers Wood, GB, vol. 87, No. Part 10, Oct. 1, 2006 (Oct. 1, 2006), pp. 2891-2899.
Z. Ruzsics et al: "Transposon-Assisted Cloning and Traceless Mutagenesis of Adenoviruses: Development of a Novel Vector Based on Species D", Journal of Virology, vol. 80, No. 16, Jul. 26, 2006 (Jul. 26, 2006) , pp. 8100-8113.
C. Thirion et al: "Adenovirus vectors based on human adenovirus type 19a have high potential for human muscle-directed gene therapy", Human Gene Therapy, Mary Ann Liebert, New York ,NY, US, vol. 17, No. 2, Feb. 1, 2006 (Feb. 1, 2006), pp. 193-205.
S.M. Elahi et al.: "Adenovirus-based libraries: efficient generation of recombinant adenoviruses by positive selection with the adenovirus protease", Gene Ther., vol. 9, 2002, pp. 1238-1246.
M. Havenga et al.: "Novel replication-incompetent adenoviral B-groupvectors: high vector stability and yield in PER.C6cells", J.Gen.Virol., vol. 87, 2006, pp. 2135-2143, XP002496482, cited in the application.
I. Kovesdi ; S.J. Hedley: "Adenoviral Producer Cells", Viruses, vol. 2, 2010, pp. 1681-1703.
K. L. Sargent et al: "Activation of Adenoviral Gene Expression by Protein IX is Not Required for Efficient Virus Replication", Journal of Virology, vol. 78, No. 10, Apr. 27, 2004 (Apr. 27, 2004), pp. 5032-5037.
International Search Report for PCT/EP2013/064165.
Vellinga J et al. "A system for efficient generation of adenovirus protein IX-producing helper cell lines" The Journal of Gene Medicine (Nov. 16, 2005) vol. 8, No. 2, p. 147-154 DOI: 10.1002/JGM.844.

* cited by examiner

Construction of pRAB19aGFP_SV40

Construction of pRAB19aGFP

Construction of pRAB19aGFP_5pIX

Construction of pRAB19aGFP_5pIX

MEANS AND METHODS TO INCREASE ADENOVIRUS PRODUCTION

RELATED APPLICATIONS

This application is a national stage application under 35 U.S.C. § 371 of PCT/EP2013/064165 filed Jul. 4, 2013, which claims benefit of priority to European Application No. 12175028.5 filed Jul. 4, 2012, and the contents of both applications are hereby incorporated by reference into the specification in their entireties.

SUBMISSION OF SEQUENCE LISTING

The sequence listing associated with this application is filed in electronic format via EFS-Web and is hereby incorporated by reference into the specification in its entirety. The name of the text file containing the Sequence Listing is Sequence_Listing_1111_104. The size of the text file is 290 KB and the text file was created on Dec. 22, 2014.

The invention relates in a first embodiment to a method for increasing the yield of replication-incompetent adenoviruses having at least a partial deletion in the E1-region, wherein said adenoviruses are generated in a production cell, the method comprising the steps of: (a) expressing in said production cell an adenoviral pIX polypeptide from a nucleic acid sequence encoding said adenoviral pIX polypeptide under the control of (i) at least a minimal endogenous pIX promoter and a heterologous promoter; or (ii) a heterologous promoter; and (b) expressing in said production cell the elements necessary for the production and assembly of said adenoviruses from corresponding coding sequences, thereby increasing the yield of said adenoviruses generated in said production cell in comparison to the yield of replication-incompetent adenoviruses having at least a partial deletion in the E1-region generated in said production cell in the absence of said nucleic acid sequence encoding said adenoviral pIX polypeptide. In another embodiment, the invention relates to a method for constructing an adenovirus library, a production cell as well as the use of an adenoviral pIX polypeptide for increasing the yield of replication-incompetent adenoviruses having at least a partial deletion in the E1-region.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The development of recombinant viruses for gene expression since the '80s led to their wide application as gene expression vectors in vitro as well as in vivo. Cloning and expression of numerous genes, including non-coding nucleic acids such as small interfering RNAs using viral or non-viral expression libraries, is recognized as a powerful tool in functional genomics and already led to the discovery and validation of new drug target genes.

In particular adenoviral vectors are often employed as viral vectors. The construction of adenoviral vectors can be effected by various means. The first protocols provided in the literature involved co-transfection of permissive cells, usually gene complementing cell lines such as 293 or 911 cells, with a shuttle plasmid containing the left end of the viral genome, where the E1 region typically was replaced with a nucleic acid to be expressed or a transcription unit, and isolated viral DNA cut near the left end of the genome by an appropriate restriction enzyme. Homologous recombination occurs in vivo between overlapping sequences of the shuttle plasmid and the adenoviral DNA yielding a recombined virus genome that can replicate. One variation of this system comprises the use of two plasmids each providing a part of the adenovirus genome individually unable to replicate which are co-transfected into the complementing production cell line to produce replicable viral DNA through homologous recombination. The disadvantage of wild type virus contamination, also referred to as wt-Virus contamination, has been overcome by this variation. The use of this method to generate large numbers of recombinant adenovirus vectors is limited by the low recombination efficiency and transfection efficiency of large vector DNAs in producer cells such as 293, however. In general, adenovirus vector construction through homologous recombination between two DNA entities in eukaryotic cells supporting replication of E1-deleted adenoviruses is time consuming, and requires screening and purification of individual virus clones by plaque purification.

As an improvement over classical cloning and methods involving homologous recombination for adenovirus vector construction, a system was developed for construction of adenovirus vectors by site-specific recombination mediated by Cre from bacteriophage P1 (Hardy et al., J. Virol. 71:1842-1849, 1997). This method provides a means to generate E1-substituted adenoviruses with insertion of foreign DNA in this region upon recombination between a shuttle plasmid containing the gene transduction unit and one IoxP site, and a helper adenovirus vector deleted for its packaging signal through intramolecular recombination between two IoxP sites in Cre-expressing cells. An application of this method for construction of recombinant adenoviruses through Cre-lox mediated site-specific recombination between two plasmids in 293Cre cells was disclosed in U.S. Pat. No. 6,379,943, herein incorporated by reference. In a different approach Farmer and Quinn (US patent application US2003/0054555) describe a method for the generation of human type 5 recombinant adenoviral vectors using Cre-lox mediated site-specific recombination between a donor vector and an acceptor vector encoding a gene-deleted adenovirus genome. Site-specific recombinases as involved in the recombination processes of the viral DNA fragments, are proteins that have both endonuclease and ligase properties and exist in multiple organisms. These recombinases recognize specific sequences of bases in DNA and mediate the exchange of the DNA segments flanking those segments. Thus, the resulting recombination product either consists of an insertion of the first nucleic acid into the second nucleic acid. In such case the plasmids are circular plasmids containing one recombinase recognition sequence on each nucleic acid. Alternatively, there is an excision of the nucleic acid fragment in between two recombinase recognition sequences on the same nucleic acid, or an exchange of parts of nucleic acids between two nucleic acids having each of the exchanged nucleic acids in between two recognition sites present on each of the nucleic acids. Two nucleic acid molecules having each one site-specific recombinase binding site able to react with each other will form a mixture of reaction products when contacted in the presence of a recombinase binding to these sites. Numerous recombination systems from various organisms have been described. (Landy A., Curr Opin Genet Dev. 3:699-707, 1993; Hoess R H., et al. Proc. Natl. Acad. Sci. USA 79:3398-3402, 1982; Abremski et al., J Biol Chem 261:391-396, 1986; Esposito D, Scocca J J, Nucl Acids Res 25:3605-3614, 1997). The best-studied members of the integrase family of recombinases are the Integrase/att system from bacteriophage lamda, (Landy A., Current Opinions in Genetics and Devel. 3:699-707, 1993) and the Cre/IoxP system from bacteriophage P1. A system was developed for construction of adenovirus vectors by site-specific recombination mediated by Cre from bacteriophage P1 (Hardy et al., J. Virol. 71:1842-1849, 1997). This method provides a means to generate E1-substituted adenoviruses with insertion of foreign DNA in this region upon recombination between a shuttle plasmid containing the gene transduction unit and one IoxP site, and a helper adenovirus vector deleted for its packaging signal through intramolecular recombination between two IoxP sites in Cre-expressing cells. An application of this method for construction of recombinant adenoviruses through Cre-lox mediated site-specific recombination between two plasmids in 293 Cre cells was disclosed in U.S. Pat. No. 6,379,943.

A critical issue remains the inefficient reconstitution of adenovirus vectors following transfection of a recombinant genome coding for an adenovirus in 293 production cells. It is known in the art that infectivity of adenovirus DNA is augmented up to 100-fold if DNA-TP complexes are used instead of plasmid-derived DNA. The viral DNA is purified such that the terminal protein (TP), which is covalently attached to the 5' end of each strand of the duplex adenovirus, is left intact. Co-transfection of DNA-TP complexes harboring a IoxP site together with a second plasmid yielding replication competent adenoviral DNA upon site-specific recombination in the presence of Cre recombinase can increase the number of viral plaques generated per μg viral DNA transfected significantly (Sharp P A et al., Virology 75:442-456, 1976; Chinnadurai G et al., J. Virol. 26:195-199, 1978). The construction of recombinant adenovirus genomes through homologous recombination of two fragments in 293 cells using DNA-TPC (DNA-terminal protein complexes) was further used in combination with a positive selection with library efficiency (Elahi S M et al., Gene Ther. 9:1238-1246, 2002); technical details are provided in U.S. Pat. Appl. No. 2006210965. Here, co-transfection of a plasmid harboring an ITR and the adenovirus protease expression cassette along with viral DNA-TPC deleted for the adenovirus protease gene yielded higher amounts of recombinant viral vectors.

The use of DNA-TP complexes involves the risk of contamination with parental infectious adenovirus DNA from which the DNA-TP complexes are derived by restriction digestion. Moreover, a library of adenovirus vector genomes constructed by site-specific or homologous recombination in 293 cells can be subject to a significant degree of bias due to DNA rearrangements and selection of virus mutants which have variable growth properties (e.g in the case of cDNA expression libraries where the expression of the cDNA confers a growth advantage or disadvantage), and thus are over- or underrepresented in the library population. Propagation of such a library is critical, and moreover requires intensive cell culture work such as plaque purification, and exclusion of replication competent adenoviruses. The construction of an unbiased and pure library of adenovirus vector genomes containing an expression cassette is desired.

Based on an analysis of the molecular evolution of adenoviruses the family of adenoviruses can be divided into 5 genera. Based on genome organization these genera, the genus Mastadenovirus can be more closely defined. In this respect, the early 1 genome region encompasses the EIA and E1B-19K and E1B-55K gene products followed by the protein IX gene. Among the Mastadenoviruses human serotypes show this genome organization as well. Currently the human adenovirus serotypes are further divided into 5 species (A-F) with currently 57 members identified. The 6 human adenovirus species form a relatively uniform cluster albeit the showing differences regarding replication, cell and tissue tropism, receptor usage and pathogenicity. Primate, non-human adenoviruses show similar genome organization to human adenoviruses and thus similar behavior is expected (BenköM and Harrach B, pp 3-36 in Adenoviruses: Model and vector in Virus-host interactions. Dörfler W., Böhm P. editors, Springer Verlag 2003). A range of methods exists for generating subgroup C Ad5 vectors containing expression cassettes. Recombinant Ads based on other human serotypes (e.g., Ad4, Ad7, Ad11 or Ad35) or animal Adenoviruses 0 generated by traditional homologous recombination in cells or in *E. coli* or by classical cloning techniques.

Instability of human adenovirus genomes in *E. coli*, particularly of the subgroup D adenoviruses, when cloned in high copy plasmids is frequently observed. Examples apply to large viral genomes cloned in plasmid vectors (Bzymek M and Lovett S T, Proc Natl Acad Sci USA. 98:8319-8325, 2001) and adenovirus vector genomes from other subgroups (Ruzsics Z. et al., J. Virol. 80:8100-8113, 2006). The human subgroup D adenovirus 19a vector was cloned by means of classical cloning strategies in cosmids and transposon-assisted mutagenesis of an Ad19a BAC clone. Although genomes can be maintained stably and manipulated in BACs, the selection procedure involves multiple steps and no method is available yet for simple and fast and reliable construction of adenovirus vector genomes using BACs. Fast, generally applicable, and efficient methods for cloning and precise manipulation of non-human type 5 serotype adenovirus genomes for detailed studies of the various functional activities and exploration of their potential as vectors are not yet available.

Several production cell lines exist for high titer production of human adenovirus type 5 vectors. Cell lines with no overlapping sequences are used for GMP-conform production of Ad5 vectors without contamination with replication competent adenoviruses (RCA). Production of adenovirus vectors deleted for the E1 gene region is efficient in cell lines which complement for the gene defect. The classical cell line in use for production of first generation adenoviruses deleted for the E1 region is HEK293. Other cell lines with similar properties include 911, pTG6559, Per.C6, GH329, N52.E6, HeLa-E1, UR, and VLI-293. All the cell lines complement the human adenovirus type 5E1A and E1B gene products. Differences among the cell lines exist regarding the complementation of protein pIX. The integrated part of the human adenovirus type 5 sequence in Per.C6 and UR and N52.E6 lacks the reading frame coding for protein pIX (Kovesdi I and Hedley S J. Viruses 2010; 2:1681-1703).

For the production of serotype B adenovirus vectors, the Per.C6 cell has been successfully used, however the hAd35 had to retain the E1B gene (Seshidhar R et al. Virology 2003; 311:384-393). Production of subgroup B adenoviruses was efficient in cell lines based on 293 cells and 911 cells expressing the E1B-55K gene, overcoming the inability of human adenovirus type 5 E1B to complement for human non-type 5 adenovirus E1B55K gene function. The observation that E1-deleted hAd35 vectors replicate in Per.C6 cells when the hAd35 E4-ORF6 gene was exchanged for the hAd5 E4-ORF6 led to a significant improvement in productivity for subgroup B and D adenoviruses (Angelique A C. J Gen Virol 2006; 87:2891-2899; Abbink P. J. Virol. 2007;

81:4654-4663). Replacement of Ad35 E4ORF6, or AD49E4ORF6 with Ad5 E4ORF6, respectively, increased the yield of recombinant hAd35 and hAd49 vectors produced in Per.C6 cells significantly, presumably due the formation of a functional complex of Ad5 E1B-55K and Ad5 E4ORF6 increasing the mRNA export in said producer cell. This finding contributed to a solution for scale up and production of the subgroup B adenovirus vector Ad35 which is actually in clinical testing as vaccine vector for various indications.

Adenovirus pIX has been described to have many roles (Parks R J. Mol Ther. 2005; 11:19-25) including genome packaging, transcriptional activator, whereby pIX is thought to be dispensable for viral replication. The major role for pIX is stabilization of the capsid leading to improved temperature resistance (Colby W. W., and Shenk T. J. Virol 1981; 39:977-980). Consequently, the inclusion of sequences allowing for expression of pIX protein in Per.C6 cells further enhances the thermostability of the adenovirus vectors produced. The inclusion of the promoter providing sufficient expression of pIX protein in production cells confers increased stability of viral vectors, whereas exchange of the Ad35 E4ORF6 with Ad5 E4ORF6 increases the virus yield and lowers the virus particle:p.f.u. ratio (Havenga M. et al. J. Gen. Virol. 2006; 87:2135-2143). The genomes of human Mastadenoviruses are arranged with the coding sequence for pIX preceded from the E1B-55K open reading frame. The protein sequence is highly conserved and start codons thus can be identified in adenoviruses such as human and chimpanzee adenovirus by sequence alignment. The sequence extending 100 bp upstream of the pIX start codon contains a promoter in several of the analyzed adenovirus vectors (hAd5, hAd19a, hAd35, hAd49) according to a bioinformatic sequence analysis (Reese, M. G., Harris, N. L. and Eeckman, F. H. (1996) "Large Scale Sequencing Specific Neural Networks for Promoter and Splice Site Recognition" Biocomputing: Proceedings of the 1996 Pacific Symposium edited by Lawrence Hunter and Terri E. Klein, World Scientific Publishing Co, Singapore, 1996, Jan. 2-7, 1996, available at www.fruitfly.org). This promoter sequence is able to mediate a detectable expression of pIX protein in production cells. For an application of novel human and chimpanzee adenovirus vectors as therapeutic vaccine and gene delivery vector, production to high titer must be achieved in large scale with up to 10.000 l cell culture fermentation volume. Currently, serotype D adenovirus vectors, i.e. hAd19a, and chimpanzee adenovirus vectors in clinical development can be produced with titers up to 1010 IU/ml. In order to allow for large scale amplification and production improvements need to be achieved (Ruzsics Z. et al., J. Virol. 80:8100-8113, 2006). The human 19a adenovirus serotype vector contains a pIX open reading frame with the first ATG starting at nt 3454 (human adenovirus type 19a genomic sequence accession number GI:109115055). The hAd19a vector used by Ruszics et al. contained the 150 bp sequence upstream from the start codon of pIX.

The technical problem underlying the present invention was to identify alternative and/or improved means and methods for the production of adenoviruses.

The solution to this technical problem is achieved by providing the embodiments characterized in the claims.

Accordingly, the present invention relates in a first embodiment to a method for increasing the yield of replication-incompetent adenoviruses having at least a partial deletion in the E1-region, wherein said adenoviruses are generated in a production cell, the method comprising the steps of: (a) expressing in said production cell an adenoviral pIX polypeptide from a nucleic acid sequence encoding said adenoviral pIX polypeptide under the control of (i) at least a minimal endogenous pIX promoter and a heterologous promoter; or (ii) a heterologous promoter; and (b) expressing in said production cell the elements necessary for the production and assembly of said adenoviruses from corresponding coding sequences, thereby increasing the yield of said adenoviruses generated in said production cell, preferably, in comparison to the yield of replication-incompetent adenoviruses having at least a partial deletion in the E1-region generated in said production cell in the absence of said nucleic acid sequence encoding said adenoviral pIX polypeptide.

The term "yield" as used in the context of producing viruses in production cells is known in the art to relate to the number of infectious viruses that are harvested from said production cells. Virus quantification to determine the yield can be achieved via various methods providing relative or absolute virus titers. For example, plaque-based assays are well-known methods to determine virus concentration. Further methods include, e.g. determining the 50% tissue culture infective dose ($TCID_{50}$), performing fluorescent focus assays, protein assays (e.g., hemaggutination assay, bicinchoninic assay, single radial immunodiffusion assay), transmission electron microscopy (TEM), flow cytometry, qPCR, or enzyme-linked immunosorbent assays (ELISA). All of these methods are well-known in the art and described, e.g., Kaufmann, S. H.; Kabelitz, D. (2002). Methods in Microbiology Vol. 32: Immunology of Infection. Academic Press. ISBN 0-12-521532-0. Preferably, quantification is performed by limited dilution of virus stocks and infection of 293 cells followed by immunohistochemical staining for the hexon protein or counting of fluorescent cells (FFU fluorescence forming units) to determine the yield (Mittereder N. et al. J. Virol. (1996) 70:7498-509).

An "increase" in yield as can be achieved with the method of the invention, wherein the increase is to be determined relative to the yield obtained in, preferably, the same experimental setup, when the pIX polypeptide is not expressed in accordance with the method of the invention. In other words, when a production method essentially only differs from the method of the invention in the absence in that the pIX polypeptide is not expressed in accordance with the method of the invention, the experimental setup is the same and the virus yield will be lower. Typically the yield of adenovirus vector genomes (vg) produced per cells ranges from 1E+03 to 1E+4 genomes per cell. In the final purified adenovirus preparation the titer achieved with state of the art methods ranges from typically 1E+10 to 1E+12 vg/ml. It is acknowledged that adenovirus preparations can be further concentrated by applying methods know in the art. As evident from the example section, these values could be significantly increased (cf. Table 3b). In accordance with the method of the invention, the yield will in comparison be at least 10% such as at least (for each value) 15%, 20%, 30%, 40%, 50, 60%, 70%, 80%, 90%, or 100% increased. More preferred, the yield will in comparison be at least (for each value) 110% increased, such as 150%, 200%, 250%, 300%, 400%, 500% or 750%. Most preferred are increases in yield of at least (for each value) 1000%, 2000%, 3000% or 4000%. Also envisaged are higher increases in yield.

The term "replication-incompetent" in the context of adenoviruses is known in the art to relate to adenoviruses that cannot replicate in a host cell upon infection by said virus. This can be achieved by various means such as deleting at least parts of the E1 region, further deleting at least parts of the E1 and the E3 region, or at least parts of the E2 and E4 regions (reviewed in Russell W. C. J. Gen. Virol. (2000) 81:2573-2604). In accordance with the invention, the adenoviruses are rendered replication-incompetent by having at least a part of the E1-region deleted. This part is critical for replication in a host cell so that in its absence the virus cannot replicate in a host cell. The deletion encompasses at least a part of the E1A gene region, resulting in a protein that renders the adenovirus replication-incompetent. Preferably, the entire E1 region encompassing the E1A and E1B gene regions is deleted. The deleted genes are functionally complemented by a production cell. Thereby the pIX coding sequences are preferably maintained in the genome of the virus.

Adenoviruses have been studied extensively for a few decades with the consequence that their genome structure, organization, and sequence has been described in detail (Fields B N, Knipe D M, Howley P M, eds. Fields Virology. 6th eds. 2007, Philadelphia: Lippincott-Raven). Briefly, adenoviruses are non-enveloped icosahedral viruses composed of a nucleocapsid and a double-stranded linear genome. The family contains the genera Atadenovirus, Aviadenovirus, Ichtadenovirus, Mastadenovirus, and Siadenovirus. Preferably, the adenovirus belongs to the genus Mastadenovirus and is a human adenovirus. Human adenoviruses are grouped into the subgroups (also referred to as species herein) A to F, currently comprising 57 serotypes. Within the human adenoviruses, it is preferred that the adenovirus is a subgroup D adenovirus.

Genome organization is similar throughout the various adenovirus genera. The genome comprises up to 40 genes which have been classified as early and late genes. The genome organization of human adenoviruses belonging to the genus Mastadenoviruses is conserved with the E1A and E1B region located directly after the left inverted terminal-repeat (ITR). The delayed early gene of protein IX is found only in Mastadenoviruses and located in all adenviruses belonging to this genus directly after the E1B gene (BenköM and Harrach B, pp 3-36 in Adenoviruses: Model and vector in Virus-host interactions. Dörfler W., Böhm P. editors, Springer Verlag 2003).

The term "production cell" as used in accordance with the invention refers to a cell that is used for producing the adenoviruses in accordance with the invention. Corresponding cells are also referred to in the art as packaging cells. As production cells, cells can be used that can be infected by adenoviruses. For production of adenovirus vectors used in humans, a master cell bank for production under GMP must be available. Currently this is the case for 3 commercially available production cells including 293, Per.C6, and CAP cells (Kovesdi I and Hedley S J. Viruses 2010; 2:1681-1703). Preferably, mammalian cells are used such as human cells. The genetic setup of a production cell depends from the strategy employed for generating viruses. In accordance with the invention, adenoviruses are produced by complementation of adenoviral elements encoded by nucleic acid sequences introduced into the production cell with adenoviral elements present within said production cell.

Thus, production cells in accordance with the invention are cells that have been manipulated so that replication-incompetent adenoviruses having at least a partial deletion in the E1-region can be produced. Said manipulation relates to the expression of the deleted E1-gene adenoviral elements in the production of E1 or E1 and E3-deleted first generation adenoviruses, and optionally further elements of the E2 and E4 region in second generation adenovirus vectors. The coding sequences of said adenoviral elements have either been incorporated in expressible form into the genomic DNA of the production cell or are episomally present within said production cell. Said adenoviral elements complement the adenoviral elements encoded by the partial adenoviral genome that is introduced into said production cell via transduction or via transfection. As a result of said complementation, all the adenoviral elements necessary for production and assembly of replication-incompetent adenoviruses having the E1-region deleted are expressed in the production cells in accordance with the invention. As a consequence of all elements including the pIX polypeptide being expressed in the production cells in culture, replication-incompetent adenoviruses having the E1-region deleted assemble to form viruses and are thus produced. Thus, the method in accordance with the invention may explicitly refer to a further step (c) after step (b) of culturing the production cells under conditions suitable for assembly and production. Corresponding conditions are well-known in the art (Armendáriz-Borunda J. et al., J. Biosci. Bioeng. 2011; 112:415-21). The method may comprise a further step following the above mentioned steps of harvesting the produced adenoviruses. Harvesting techniques are well-known in the art and typically involve release of intracellular adenovirus vectors, and purification using chromatographic or CsCl ultracentrifugation, as well as repeated thawing and freezing of the production cells as evident from the example section. Corresponding production strategies are known in the art and described, e.g., in Adenovirus Methods and Protocols (1998), Editor William S. Wold, Methods in Molecular Medicine Volume No.: 21. Preferably, a method as described in Ann E. Tollefson et al. Preparation and Titration of CsCl-Banded Adenovirus Stock in Adenovirus Methods and Protocols (1998), Editor William S. Wold, Methods in Molecular Medicine Volume No.: 21 is employed which relies on the deletion of the E1A and E1B gene regions from the adenoviral sequences introduced into the production cells, wherein the production cells express the E1A, E1B and pIX protein. Preferably 293 and CAP cells are used.

The elements necessary for the production and assembly of replication-incompetent adenoviruses having at least a part of the E1-region deleted are the gene products encoded by the following early and late genes: E2, E3, E4, late genes L1-L5 and other non-deleted adenovirus gene products such as VA RNAs and sequences encompassing the left and right inverted terminal repeats, as well as the downstream region of the left ITR encompassing the adenovirus packaging sequence. It is known in the art which adenoviral gene products are necessary for the assembly and production of adenoviruses as defined herein. As laid out above, steps (a) and (b) of the method of the invention provide the assembly and thus production of the replication-incompetent adenoviruses having at least a partial deletion in the E1-region in the production cells with an increased yield in comparison to the yield of replication-incompetent adenoviruses having at least a partial deletion in the E1-region generated in said production cell in the absence of said nucleic acid sequence comprising the coding sequence for said adenoviral pIX polypeptide.

Preferably, the adenovirus as generated in accordance with the method of the invention also comprises a transgene or transcription unit for expression of the adenovirus genes to be complemented and expressed. Thus, the production cell also comprises a transgenic sequence either as part of a nucleic acid sequence that has been introduced into said cell by way of transduction or transfection, e.g. as part of the same construct encoding the adenoviral elements, or as part of the production cell being present within the genomic DNA of said cell or on an episomal nucleic acid molecule (Lassam N J. Cell. 1979; 18:781-91; Kovesdi I and Hedley S J. Viruses 2010; 2:1681-1703).

The "nucleic acid sequence encoding the pIX polypeptide", i.e. the coding sequence for the adenoviral pIX polypeptide, comprises the genetic information so that upon expression an adenoviral pIX polypeptide is obtained. Said coding sequence may comprise coding sequences naturally found in adenoviruses, i.e. the pIX gene, as well as the cDNA sequence and mutated pIX coding sequences (comprising, e.g., deletions, additions or substitutions) provided that said mutants remain functional in the sense of the invention, i.e. increase virus yield. Thus, the invention also includes fragments of the pIX coding sequence and therefore also fragments of the pIX polypeptide (partial pIX polypeptides), as long as said pIX polypeptide fragments remain functional in the sense described herein. The skilled person is in the position to experimentally ascertain whether a mutated pIX sequence is in this sense functional, e.g., by comparing yields obtained with a mutated pIX coding sequence and a non-mutated pIX coding sequence. The location of the pIX gene within the genome of an adenovirus is downstream of the E1B gene region and upstream of the major late late L1-52K gene region. In adenovirus Ad19a, the pIX coding sequence extends from the start codon at position 3454 to position 3858 of the DNA sequence of Ad19a as deposited with the National Center for Biotechnology Information (NCBI), 8600 Rockville Pike, Bethesda Md., 20894 USA, under the accession number CS301726 (version number GI:109115055), retrievable using the world wide web address www.ncbi.nlm.nih.gov, and said accession number. The person in the art is in the position to identify the pIX coding sequence in other adenoviruses on the basis of well-established methods such as, e.g., sequence alignments of putative pIX coding sequences with known pIX coding sequences. In this regard and to evaluate the identity level between two nucleotide or protein sequences, they can be aligned electronically using suitable computer programs known in the art. Such programs comprise BLAST (Altschul et al., J. Mol. Biol. 1990, 215: 403), variants thereof such as WU-BLAST (Altschul & Gish, Methods Enzymol. 1996, 266: 460), FASTA (Pearson & Lipman, Proc. Natl. Acad. Sci. USA 1988, 85: 2444) or implementations of the Smith-Waterman algorithm (SSEARCH, Smith & Waterman, J. Mol. Biol. 1981, 147: 195). These programs, in addition to providing a pairwise sequence alignment, also report the sequence identity level (usually in percent identity) and the probability for the occurrence of the alignment by chance (P-value). Programs such as CLUSTALW (Higgins et al., Nucleic Acids Res. 1994, 22: 4673) can be used to align more than two sequences. The same is true also for the sequence required for pIX promoter activity located upstream of the start codon of the pIX coding sequence.

The term "polypeptide" in accordance with the present invention describes a group of molecules consisting of more than 30 amino acids. Polypeptides may further form dimers, trimers and higher oligomers, i.e. consisting of more than one polypeptide molecule. Polypeptide molecules forming such dimers, trimers etc. may be identical or non-identical. The corresponding higher order structures are, consequently, termed homo- or heterodimers, homo- or heterotrimers etc. Homo- or heterodimers etc. also fall under the definition of the term "polypeptide". The terms "polypeptide" and "protein" are used interchangeably herein and also refer to naturally modified polypeptides wherein the modification is effected e.g. by gly cosylation, acetylation, phosphorylation and the like. Such modifications are well known in the art.

Nucleic acid sequences (including coding sequences, promoter sequences, genomic sequences, etc. referred to herein), in accordance with the present invention, include DNA, such as cDNA or genomic DNA, and RNA. Further included are nucleic acid mimicking molecules known in the art such as synthetic or semisynthetic derivatives of DNA or RNA and mixed polymers, both sense and antisense strands. They may contain additional non-natural or derivatized nucleotide bases, as will be readily appreciated by those skilled in the art. In a preferred embodiment the polynucleotide or the nucleic acid molecule(s) is/are DNA. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA), peptide nucleic acid (PNA) and locked nucleic acid (LNA) (see, for example, Braasch and Corey, Chemistry & Biology 8, 1-7 (2001)). LNA is an RNA derivative in which the ribose ring is constrained by a methylene linkage between the 2'-oxygen and the 4'-carbon.

In accordance with the invention, the promoter driving the expression of the pIX polypeptide, in one embodiment, is a combination of at least an endogenous adenoviral minimal pIX promoter, i.e. the pIX promoter of the adenovirus species whose yield is to be increased, and a heterologous promoter, i.e. originating from a different species of adenovirus or originating not from an adenovirus at all. In its minimal setup, the pIX promoter, consists of the sequence required for pIX promoter activity. Preferably, said sequence is located immediately upstream, i.e. without intermitting sequences, of the start codon of the pIX coding sequence, wherein the sequence is the sequence present on the genomic DNA of the respective adenovirus. In other words, a corresponding promoter comprises at least or consists of the sequence required for pIX promoter activity located upstream of the start codon of the pIX coding sequence in relation to the genomic viral DNA. The pIX promoter has been analyzed in detail and the minimal active sequence has been identified by using the NNPP method to find eukaryotic and prokaryotic promoters in a DNA sequence sequence (Reese, M. G. Diploma Thesis, 1994, German Cancer Research Center, Heidelberg; Reese, M. G. and Eeckman, F. H. (1995) "Novel Neural Network Algorithms for Improved Eukaryotic Promoter Site Recognition". The Seventh International Genome Sequencing and Analysis Conference, Hilton Head Island, S. C.; Reese, M. G., Harris, N. L. and Eeckman, F. H. (1996) "Large Scale Sequencing Specific Neural Networks for Promoter and Splice Site Recognition" Biocomputing: Proceedings of the 1996 Pacific Symposium edited by Lawrence Hunter and Terri E. Klein, World Scientific Publishing Co, Singapore, 1996, Jan. 2-7, 1996). It is understood that that the invention is not confined to a minimal pIX promoter, but that at least a minimal pIX promoter must be present. Thus, the pIX promoter may include further adenoviral pIX promoter sequences. For example, and with regard to the sequence of human adenovirus serotype 19a of subgroup D, the pIX promoter sequence required for pIX promoter activity starts at position 3390, i.e. immediately upstream of the start codon of the pIX coding sequence, and includes at least the sequence up to position 3439 with regard to the DNA sequence of serotype 19a available under the accession number CS301726 (version number GI:109115055). The pIX promoter sequence may extend further upstream such as, up to 100 bp downstream of the start codon of the E1B-55K protein corresponding to position 1982 of the entire genomic sequence of serotype 19a, or up to (for each value) 500, 750, 1000, 1250 or 1500 bp downstream of said position. The skilled person is in the position to identify the promoter sequence required for pIX promoter activity in any adenovirus by routine methods, such as those outlined herein above including sequence alignments. The endogenous pIX promoter is located downstream of a heterologous promoter capable of increasing the level of expression of the pIX polypeptide above the expression level achieved when only endogenous pIX promoter drives expression of the pIX polypeptide. Preferably, the increase is an increase of at least (for each value) 10%, such as 20%, 30%, 40% and 50%. More preferred are increases of at least (for each value) 60%, 80%, 100%, 200%, 500% and most preferred increases of at least 1000%, wherein higher increases are also envisaged. In other words, the heterologous promoter is an expression promoter capable of increasing the pIX polypeptide expression level in combination with the endogenous pIX promoter and in comparison to the latter promoter alone. Various expression promoters capable of mediating expression in a given production cell are known in the art. These expression promoters can be tested in accordance with the method of the invention as to whether they can increase the level of expression of the pIX polypeptide above the expression level achieved when only endogenous pIX promoter drives expression of the pIX polypeptide. For example, the heterologous promoter may be a heterologous pIX promoter, wherein the definitions above for the endogenous pIX promoter fully apply to the heterologous pIX promoter. Preferably, heterologous pIX promoters are only used as heterologous promoters in combination with endogenous pIX promoters, in which case the heterologous promoter in item (ii) of this embodiment is not a heterologous pIX promoter.

As an alternative to the above described combination of endogenous pIX promoter and heterologous promoter, a heterologous promoter alone can be used to drive the expression of the pIX polypeptide. It is understood that the same requirements as regards the increase in the pIX polypeptide expression levels must be achieved as stipulated for the combination of endogenous pIX promoter and heterologous promoter defined herein above. As such, some heterologous promoters that can be used in combination with the endogenous pIX promoter cannot be used in isolation. The heterologous promoter may be a constitutive or inducible promoter. Heterologous promoters are, e.g., selected from the group consisting of CAG, CMV, PKG, SV40, EF1alpha and RSV.

The pIX coding sequence and the promoter are part of a nucleic acid sequence, wherein the nucleic acid sequence may be part of the adenoviral sequences introduced into the production cells by way of adenoviral transduction or transfection, or, alternatively, may be present in the production cell. Preferably, the nucleic acid sequence encoding said adenoviral pIX polypeptide under the control of the promoter is part of the adenoviral genome.

Steps (a) and (b) are, preferably, performed simultaneously so as to guarantee the presence of polypeptide pIX during adenovirus assembly and production. If the latter requirement is met, step (a) can be performed prior to step (b). Generally, the expression of the pIX polypeptide is to be maintained as long as adenoviruses are to be produced.

The adenovirus pIX polypeptide has been described to have many roles (Parks R J. Mol Ther. 2005; 11:19-25) including in genome packaging and as transcriptional activator, whereby pIX is thought to be dispensable for viral replication. The major role for pIX is stabilization of the capsid leading to improved temperature resistance (Colby W. W., and Shenk T. J. Virol 1981; 39:977-980). Several adenovirus production cell lines, e.g., 293 cells contain contiguous E1A/E1B sequences encompassing the human adenovirus type 5 pIX, whereas other cell lines (Per.C6) lack pIX sequences (Kovesdi I., and Hedley S. J. Viruses 2:1681-1703, 2010) Production of non-type 5 adenovirus vectors on 293 cells has been demonstrated for human Ad19a (Ruzsics Z et al., J. Virol. 80:8100-8113, 2006) and chimpanzee C68 adenovirus vectors to variable yield.

Surprisingly, it was found that the pIX polypeptide when expressed during adenovirus production in accordance with the present invention results in an increase in adenovirus yield. As evident from the example section, significant increases could be observed in experiments performed in human adenovirus serotype 19a. The increases in yield could be observed independent from the method to introduce adenoviral sequences into the production cells. This finding is important in view of the continuing interest in adenovirus vectors and vaccines as it allows establishing reliable and high yield production methods. Expressing pIX according to the present invention also increased the efficiency for adenovirus vector reconstitution following transfection of the virus genome into 293 cells. Applications of this invention includes the generation of adenovirus-based libraries, such as an expression library, that can now be generated more efficiently. It is understood that the increase in yield may play a particularly important part in large scale adenovirus production, where even minimal increases in yield can provide significant (e.g., financial) advantages. Such large-scale production refers to adenovirus production in at least 2000 l fermenters such as at least (for each value) 3000 l, 4000 l, 5000 l, 6000 l, 7000 l, 8000 l, 9000 l or more than 10000 l fermenters.

The definitions in relation to the main embodiment given herein above, also apply mutatis mutandis to the embodiments herein below unless explicitly stated otherwise.

In a further embodiment, the invention relates a method for the construction of a replication-incompetent adenovirus library, wherein the adenoviruses have at least a partial deletion in the E1-region, comprising the steps of: (a) providing one or more nucleic acid sequences in expressible form comprising at least two partial adenoviral genomes, each partial adenoviral genome further comprising at least one transgene, wherein the at least two partial adenovirus genomes and/or the two transgenes differ from each other; (b) introducing the one or more nucleic acid sequences of step (a) into production cells comprising one or more nucleic acid sequences in expressible form comprising a partial adenoviral genome which complements each partial adenoviral genome comprised by the one or more nucleic acid sequences of step (a) by transfection, wherein each complemented adenoviral genome encodes the elements necessary for the production and assembly of said different adenoviruses and comprises the coding sequence for an adenoviral pIX polypeptide under the control of (i) at least a minimal endogenous pIX promoter and a heterologous promoter; or (ii) a heterologous promoter; and (c) culturing the production cells under conditions suitable for the assembly and production of said differing adenoviruses, thereby constructing said replication-incompetent adenovirus library.

The definitions of the main embodiment also apply to this embodiment mutatis mutandis, in particular and without limitation those relating the pIX coding sequences, pIX promoter sequences, heterologous promoter, transgene, production cells, adenovirus production strategy, culture conditions suitable for assembly and production of adenoviruses.

Adenovirus libraries are known in the art to refer to a collection of viruses differing from each other, wherein the library may take the form of production cells harbouring said viruses, isolated viruses or adenovirus nucleic acid sequences encoding said adenoviruses making up the library. In accordance with the present invention, an adenovirus library refers to the collection of at least two different replication-incompetent adenoviruses having at least a deletion in the E1-region, preferably at least 10, 100, $10^3$, $10^4$, $10^5$, or at least $10^6$, generated in production cells.

As laid out above for the main claim, production of an adenovirus relies on the introduction of adenoviral sequences into production cells which already comprise adenoviral sequences so that after introduction, all elements necessary for the assembly and production of adenoviruses can be expressed from the adenoviral sequences present in the cell. As such, the partial adenoviral genome as referred to in step (a) of this embodiment will be complemented by the production cell. The partial adenoviral genome need not resemble a contiguous stretch of the adenovirus genome but may comprise intermittent additional sequences, such as the transgene, additional regulatory sequences, or may comprise deletions or terminal additions. The at least two partial adenovirus genomes can be encoded by the same nucleic acid sequence or can each be comprised on a separate nucleic acid sequence. Said nucleic acid sequence must be in expressible form so that the elements encoded by said sequence can be expressed upon introduction in the production cell. This can be achieved by methods well-known in the art and usually includes the presence of promoters, wherein the promoters may be the endogenous adenoviral promoters each driving the expression of the endogenously associated gene or heterologous expression vectors.

The at least two adenoviruses making up the library generated in accordance with the method of the invention must be different. This is achieved by providing sequences making up the partial adenoviral genome that are different and preferably result in a different phenotype of the respective adenovirus. Alternatively or in addition, the transgene may be different. Conceivably, if the adenoviral genome is different to the effect that different complementing sequences in the production cells are required for virus assembly and production, the production cell for each nucleic acid sequence comprising a partial adenoviral genome must be different and introduction in step (b) must be performed selectively. Preferably, the requirements for the production cells are the same for the at least two adenoviral genomes, thus allowing the construction of the adenovirus library on the basis of one kind of production cell.

In accordance with step (b) of the method of the invention, the nucleic acid sequences of step (a) are introduced by way of transfection. The term "transfection" in accordance with the invention refers to the introduction of nucleic acid sequences into a eukaryotic cell by way of non-viral methods such as, e.g., chemical based methods (calcium phosphate, liposomes, DEAE-dextrane, polyethylenimine, nucleofection), non-chemical methods (electroporation, sonoporation, optical transfection, gene electrotransfer, hydrodynamic delivery), and particle-based methods (gene gun, magnetofection, impalefection).

The method can comprise the further step of harvesting the at least two different adenoviruses after step (c).

The finding that expression of the adenoviral pIX polypeptide as defined herein increases the yield, in particular when adenoviral sequences are transfected, is especially advantageous when constructing adenoviral libraries which rely on the introduction of the differing adenoviral nucleic acid constructs by way of transfection. This way, the yield of the generated different adenoviruses can be significantly enhanced and the complexity of a library increased. The complexity of a library is determined by the number of different adenoviruses present in the resulting complex adenovirus mixture compared to the initially transfected number of different adenoviral nucleic acid constructs. Without being bound to or limited by a specific scientific theory, it is presumed that the pIX polypeptide advantageously affects the reconstitution of the adenovirus in the production cells. In an alternative version of this embodiment, the one or more nucleic acid sequences of step (a) are introduced by transduction.

In a preferred embodiment of the first mentioned method of the invention, the one or more of said coding sequences of step (b) are introduced into the production cell for expression (a) by transduction using the replication-incompetent adenoviruses having at least a partial deletion in the E1-region that are to be produced in the cell; or (b) by transfection.

The term "transduction" as used in accordance with the method of the invention refers to the introduction of coding sequences of step (b) into said production cell by infection with the adenovirus that is to be produced in said production cell. The term "transfection" has been defined herein above, said definition applying mutatis mutandis also to this embodiment.

As can be seen from the example section, an increase in yield is achievable with both methods for introducing the one or more coding sequences, however, with a differing magnitude. When nucleic acids coding for a replication-incompetent adenovirus as defined herein are introduced by means of transfection into production cells, the resulting yield of adenoviruses was strongly increased by up to 39-fold when in addition to the endogenous proximal pIX promoter sequence at least one additional heterologous promoter was present. The combination of the human adenovirus type 5 pIX minimal promoter and/or the SV40 promoter was used. In a different setting, a fermentation process was mimicked and production cells transduced with a defined amount of virus inoculum. In this example the presence of promoter sequences in addition to the endogenous proximal promoter sequence upstream of the start codon of pIX increased virus yield and shortened the time until harvesting. This has implications for effective and productive fermentation in large scale.

In a further preferred embodiment of the method of the invention, the adenovirus is a human adenovirus of subgroup D, such as serotype 19a.

In another preferred embodiment of the invention, the method further comprises the step of assessing the expression level of said pIX protein in the production cell and/or the increase in yield of said adenoviruses.

It is understood that depending on which result is to be assessed said further step may be performed only after adenoviruses have been produced. Assessment of the increase in yield of the replication-incompetent adenoviruses having at least a partial deletion in the E1-region will be performed after said viruses have been harvested, whereas the assessment of the expression level of said pIX protein in the production cell can be performed after step (a) of the method of the invention. Assessment of said parameters, in particular in combination, can be advantageous in (further) optimizing the production of adenoviruses as defined herein.

In a further embodiment, the invention relates to a production cell for generating replication-incompetent human adenoviruses of subgroup D with the exception of serotype 19a having at least a partial deletion in the E1-region, comprising nucleotide sequences encoding an adenoviral pIX polypeptide under the control of (a) at least an endogenous minimal pIX promoter and a heterologous promoter; or (b) a heterologous promoter; and coding sequences for the elements necessary for the production and assembly of said subgroup D adenoviruses.

The definitions of the main embodiment also apply to this embodiment mutatis mutandis, in particular and without limitation those relating the pIX coding sequences, pIX promoter sequences, heterologous promoter, transgene, production cell, adenovirus production strategy, culture conditions suitable for assembly and production of adenoviruses.

In accordance with the invention, a production cell as defined in this embodiment can be used, e.g., in accordance with the method of the invention, to achieve an increase in the yield of replication-incompetent human adenoviruses of subgroup D with the exception of serotype 19a.

In a preferred embodiment of the method or the production cell of the invention, the subgroup D adenovirus is selected from the group consisting of serotypes 8, 9, 13, 15, 17, 19, 20, 22 to 25, 27 to 30, 32, 33, 36 to 39, 42 to 49 and 51.

In another preferred embodiment of the method or the production cell of the invention, the production cell is selected from the group consisting of a HEK293 production cell, a Per.C6 production cell, a CAP cell, a GH329 production cell and a pTG6559 production cell.

As has been outlined herein above, the setup of the production cell dictates which adenoviral sequences have to be introduced into the production cell in order to have all adenoviral elements necessary for assembly and production expressed in said production cell.

When using the HEK293 cell, adenovirus vectors can be deleted for the E1A and E1B gene regions as well as optionally for the pIX gene. The HEK 293 cell was transformed by insertion of the E1A and E1B sequences from human adenovirus type 5 from nucleotide 1 to 4344 into chromosome 19 at 19q13.2 (Graham F. L. et al. J. Gen. Virol. 1977; 36:59-74). The PER.C6 cell was derived from human embryonic retinoblasts and contains the E1A and E1B sequences from human adenovirus type 5 from nucleotide 459 to 3510. Consequently, the respective adenovirus genomes to be introduced into PER.C6 cells may be deleted for the E1A and E1B gene regions (Fallaux F. J. et al., Hum. Gene Ther. 1998; 9:1909-1917). CAP cells are similar to the human amniocyte-derived N52.E6 cells transformed by human adenovirus type 5 E1A and E1B genes. The cells have the e1A and E1B gene regions from nucleotide 459-3510 inserted into the genome, and in addition a separate expression cassette for pIX expression (Schiedner G. et al., Hum. Gene Ther. 2000; 11:2105-2116). Consequently for HEK293, PER.C6, and CAP cells the respective adenovirus genomes to be introduced may be deleted for the E1A and E1B gene regions. These cells can be generated according to the instructions given in the above-recited scientific articles and are, moreover, commercially available.

Preferably, HEK293, Per-C6 or CAP production cells are used in accordance with the invention.

In a further preferred embodiment of the method or the production cell of the invention, the heterologous promoter is (a) a heterologous minimal pIX promoter; or (b) selected from the group consisting of a viral promoter, a cellular promoter, synthetic promoter and a hybrid promoter.

The definitions as laid out herein above regarding the heterologous minimal pIX promoter and the heterologous promoter apply mutatis mutandis to this embodiment. Viral, cellular, synthetic and hybrid promoters are known in the art and can be used in accordance with the method of the invention provided that they are capable of increasing the level of expression of the pIX polypeptide above the expression level achieved when only an endogenous pIX promoter drives the expression of the pIX polypeptide. All heterologous promoters, including synthetic or hybrid promoters comprising elements from more than one promoter can be tested for their capability to increase the level of expression of the pIX polypeptide above the expression level achieved when only an endogenous pIX promoter drives the expression of the pIX polypeptide. Examples of cellular promoters include without limitation PKG, methallothionein, EF1-alpha and beta-actin.

In a further preferred embodiment of the method or the production cell of the invention, the heterologous minimal pIX promoter of (a) originates from a human adenovirus serotype 5.

As evident from the example section, the combination of the pIX promoter from human adenovirus serotype 5 was sufficient to achieve a significant increase in virus yield in a protocol for virus reconstitution.

In another preferred embodiment of the method or the production cell of the invention, the heterologous promoter of (b) is selected from the group consisting of CAG, CMV, PKG, SV40, EF1alpha and RSV.

The use of viral expression promoters is well-established in the art and each of the above promoters is well-characterized with regard to its activity and structural setup. Furthermore, they comply with the functional requirements of the invention with regard to increasing the expression level of pIX polypeptide. As such, they are well suited to be used as heterologous promoters in accordance with the invention.

In a preferred embodiment of the method or the cell of the invention, the coding sequence for said adenoviral pIX polypeptide is also under the control of an additional heterologous promoter.

The definitions given herein above with regard to heterologous promoters apply mutatis mutandis to this preferred embodiment, in particular with regard to the nature of heterologous promoters and their combinations of heterologous promoters with each other or with endogenous pIX promoters. In this embodiment, a further heterologous promoter drives the expression of the pIX coding sequence in addition to the promoters referred to, e.g., in items (i) and (ii) of step (a) of the method of the invention in the main embodiment. In other words, in step (a) item (i) the endogenous pIX promoter may be located downstream of two heterologous promoters and the heterologous promoter according to item (ii) may be located downstream of a further promoter. Even more preferred is that at least one of the two heterologous promoters according to items (i) and (ii) is a heterologous pIX promoter in this embodiment. For example, the promoters according to item (i) driving the expression of the pIX coding sequence are the endogenous pIX promoter, the heterologous human adenovirus serotype 5 pIX promoter and an SV40 promoter; for example, the promoters according to item (ii) driving the expression of the pIX coding sequence are a heterologous human adenovirus serotype 5 pIX promoter and an SV40 promoter. The above has been described with regard to the main embodiment, but explicitly applies mutatis mutandis to the other embodiments of the invention.

As can be seen from the example section, a corresponding triple promoter setup of endogenous pIX promoter and two heterologous promoters has been shown to be very effective in increasing the yield in different scenarios of adenovirus generation. The presence of two heterologous promoters is expected to also achieve a significant increase in yield.

In a further embodiment, the invention relates to the use of an adenoviral pIX polypeptide for increasing the yield of replication-incompetent adenoviruses having at least a partial deletion in the E1-region in a production cell, wherein said adenoviruses are generated according to the method of the invention.

As has been explained herein above in detail as well as documented in the example section, the use of the adenoviral polypeptide pIX is advantageous in that it significantly increases the yield of adenoviruses produced in said production cells.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The FIGURE shows:
FIG. 1:

A schematic representation including vectors maps for the construction of recombinant adenovirus type 19a genome harbouring a GFP expression cassette with or without a heterologous promoter upstream of their respective Ad19a pIX coding sequence is shown in FIGS. 1A-D.

The examples illustrate the invention:

Example 1: Construction of Recombinant Adenovirus Type 19a BACs Using Site-Specific Recombination in *E. coli* Expressing Flp Recombinase For construction of a human type 19a recombinant adenovirus genome, a first Ad19a nucleic acid pDonorSir19aGFP containing a GFP expression cassette (pDonorSir19aGFP (SEQ ID NO.: 1), and the acceptor Ad19a nucleic acid molecule pBACSir19a_SV40 (SEQ ID NO.: 2), were combined and reacted in DH10B *E. coli* cells harbouring pBACSir19a-_SV40 and the plasmid pCP20 for conditional expression of FLP recombinase. The plasmid pDonorSir19aGFP was introduced into the DH10B *E. coli* cells by means of electroporation using a standard protocol. The nucleic acid Ad19a molecule pBACSir19a_SV40 was maintained in *E. coli* DH10B (or equivalent *E. coli* K12-derived strains lacking the F-factor) harbouring a conditional expression system for Flp. Here, in example 1, the DH10B cells harboured the adenovirus type 19a BAC pBACSir19a_SV40, and the Flp recombinase was provided by the plasmid pCP20, which replication is controlled by a temperature-sensitive origin of replication. DH10B cells harbouring pBACSir19a_SV40 and the pCP20 were maintained at 30° C. in the presence of ampicillin (50 μg/ml) and chloramphenicol (25 μg/ml). Next, these DH10B cells were electro-transformed with pDonorSir19aGFP and cultured for 60 minutes at 42° C. in the absence of any antibiotics. The expressed Flp induced site-specific recombination between FRT sites present on pDonorSir19aGFP and pBACSir19a_SV40, respectively. At the same time the elimination of Flp expression also started, since pCP20 cannot replicate in *E. coli* at elevated temperature. The transformed culture was plated onto agar plates which contained kanamycin (25 μg/ml) and chloramphenicol (25 μg/ml) as selecting agents. Under these conditions *E. coli* containing recombined recombinant adenovirus type 19a BACs (pRAB19aGFP_SV40 SEQ ID NO.: 3) were selected in which at least one pDonorSir19aGFP plasmid had recombined with pBACSir19a_SV40. DNA from growing cultures of DH10B cells was isolated and the integrity of the reaction products analysed by restriction digestion with Kpnl. All the recombination products analysed contained one copy of a contiguous Ad19a vector sequence flanked by the Ad19a ITRs (data not shown). A schematic representation and vectors maps for the construction of recombinant adenovirus type 19a genome harbouring a GFP expression cassette and a heterologous SV40 promoter is shown in FIG. 1A.

Example 2: Reconstitution of and Production of Recombinant Human Adenovirus Type 19a Vectors in 293 Cells DNA from cultures of DH10B cells containing the pRAB19aGFP_SV40 was isolated and purified from saturated *E. coli* overnight cultures (100 ml) in LB medium using a kit for plasmid preparation. Here, the NUCLEOBOND® PC-100 kit from Macherey and Nagel, Germany was used according to the manufacturer's recommendations. For virus reconstitution purified pRAB19aGFP_SV40 DNA was treated with 10 U PacI per μg DNA for 2 h according to the manufacture's recommendations. Subsequently the PacI-digested DNA was purified using phenol-chloroform according to standard protocols prior to transfection into 293 cells. In brief, 10 μg pRAB19a DNA was digested in a volume of 100 μl for 1.5 h at 37° C. in a water bath. Subsequently 50 μl phenol/chloroform (1:1 mixture) was added to the reaction tube (Eppendorff cup size 1.5 ml, Eppendorf AG, Hamburg, Germany) and vortexed for 20 sec. Here, the Vortexer MS-3 basic was used (IKA® Werke GmbH & Co. KG, Staufen, Germany). The tube was centrifuged in a table top centrifuge at maximum speed (20000.times.g) for 5 min at room temperature and 80 μl of the aqueous upper phase was transferred into a fresh tube and 10 μl 3 M NaAc (pH 4.5) and 200 μl EtOH was added. All reagents and chemicals were purchased from CARL ROTH GMBH+CO. KG, Karlsruhe. The tube was mixed with the finger tips until the precipitated DNA became visible. Moreover, the tube was incubated for 5 min at room temperature and the DNA was pelleted in a table top centrifuge at maximum speed for 15 min at room temperature. The supernatant was quantitatively removed and the pellet immediately dissolved in 20 μl sterile deionized water.

HEK-293 cells plated in DMEM (PAA)+10% FCS+2 mM L-Glutamine+1% PS (standard culture media) in Ewell plates the day before were transfected with the adenoviral DNA by using JETPEI® (Polyplus, Illkirch Cedex, France) according to manufacturer's guidelines and incubated for 3 days at 37° C.

Cells were then flushed off using standard culture media, centrifuged for 5 min at 100 g and resuspended in 400 μl standard culture media. The viral particles were released by 3 rounds of freeze-thaw. Briefly the cell suspension was frozen in liquid nitrogen for 2 min until the suspension solidified and then thawed in a water bath at 37° C. for 2 min. This procedure was repeated 3 times and cell debris was removed by centrifugation at 3500 g for 10 minutes at 4° C.

Fresh HEK-293 cells plated the day before on 6 well plates were then infected with the resulting cell lysate and incubated at 37° C. When cells became confluent they were expanded from Ewell to 10 cm dishes. Infected cells were cultivated until the cytopathic effect was completed (CPE). Harvest was performed as previously described. The cell pellet was resuspended in 1000 μl culture media. Subsequently, 3 rounds of freeze-thaw was performed as described above.

5E+06 HEK293 cells were seeded in a 15 cm dish and infected the next day with 150 μl of the virus inoculum received from the second 6 well plate. Harvest was performed when cpe was almost completed. Finally cells were harvested as described above and cell pellet was resuspended in 400 μl culture media. The titer of the obtained recombinant human Ad19a adenovirus vector expressing GFP (hAd19aGFP_SV40) was determined as fluorescence forming units (IU) 48 h after 293 cells had been infected with limited dilutions with purified adenovirus. The genomic titer in vector genomes was determined by means of QPCR according. The titer was 1.36E+08 IU/ml and the yield 6.79E+07 IU in total.

Example 3: Effect of Promoter Choice for pIX Expression on Virus Reconstitution

A series of recombinant human Ad19a adenovirus vector genomes containing an expression cassette for GFP were constructed applying the same method as described in example 1. The first recombinant adenovirus vector genome contained a heterologous human adenovirus type 5 pIX promoter upstream of the pIX coding sequence and a GFP expression cassette (pRAB__ pRAB19aGFP_5pIX, SEQ ID NO.: 4). This vector was constructed by combining the donor plasmid pDonorSir19aGFP_5pIX (SEQ ID NO.: 5) and the acceptor vector pBACSir19aGFP (SEQ ID NO.: 7). The second recombinant adenovirus vector genome contained a heterologous SV40 promoter upstream of the pIX coding sequence and a GFP expression cassette (pRAB__ pRAB19aGFP_SV40 (SEQ ID NO.: 3)). This vector was constructed by combining the donor plasmid pDonorSir19aGFP (SEQ ID NO.: 1) and the acceptor vector pBACSir19a_SV40 (SEQ ID NO.: 2) containing an SV40 promoter sequence upstream of pIX coding sequence. The third recombinant adenovirus vector genome contained no heterologous promoter upstream of the pIX coding sequence (pRAB19aGFP, SEQ ID NO.: 7). This vector was constructed by combining the donor plasmid pDonorSir19aGFP and the acceptor vector pBACSir19a (SEQ ID NO.: 6). The fourth recombinant adenovirus vector genome contained both the adenovirus type 5 pIX promoter and the SV40 promoter upstream of the pIX coding sequence pRAB19aGFP_p5IX+SV40 (SEQ ID NO.: 8). This vector was constructed by combining the donor plasmid pDonorSir19aGFP_5pIX (SEQ ID NO.: 5) and the acceptor vector pBACSir19a_SV40 (SEQ ID NO.: 2). A schematic representation including vectors maps for the construction of recombinant adenovirus type 19a genome harboring a GFP expression cassette with or without a heterologous promoter upstream of their respective Ad19a pIX coding sequence is shown in FIGS. 1A-D.

Subsequently the four recombinant adenovirus type 19a vector genomes were reconstituted and produced in 293 cells according to the method provided in example 2. To define the effect of the presence of heterologous promoters upstream of the pIX open reading frame on reconstitution all vectors were harvested at the same timepoint independently on the cpe state. 300 μl of the 6 well lysate was used to transduce 5E+06 cells seeded in 15 cm dishes. When cells became confluent, a 1:2 split was performed. The total yield of recombinant adenovirus vectors was dependent on the presence of heterologous promoters, and increased by 39-fold for the adenovirus with the combined 5pIX+SV40 promoter (hAd19aGFP_5pIX+SV40) compared to the adenovirus vector without any promoter hAd19aGFP_delta. The yield of adenoviruses with the SV40 promoter only hAd19aGFP_SV40 was increased 22-fold over hAd19aGFP_delta, and the yield of the adenovirus vector with the 5pIX promoter hAd19aGFP_5pIX was increased 13-fold over hAd19aGFP_delta (Table 1). The adenovirus serotype 19a vectors all contained a minimal endogenous pIX promoter sequence.

TABLE 1

Effect of promoter choice for pIX expression on virus reconstitution

| Virus | Promoter | Titer (ifu/ml) | Total ifu | Factor relative to no promoter |
|---|---|---|---|---|
| hAd19aGFP_ 5pIX + SV40 | SV40 + 5pIX | 1.97E+09 | 1.57E+09 | 38.88 |
| hAd19aGFP_delta | no promoter | 5.06E+07 | 4.04E+07 | 1.00 |
| hAd19aGFP_5pIX | 5pIX | 6.76E+08 | 5.41E+08 | 13.37 |
| hAd19aGFP_SV40 | SV40 | 1.10E+09 | 8.81E+08 | 21.79 |

Table 1: The duration until the $2^{nd}$ rescue was harvested was 6 days. Cells were seeded in 15 cm dishes at 5.00E+06 and an inoculum of 300 μl was used per 15 cm dish. Duration for virus amplification on 15 cm dish until cpe completed was 6 days with partial cpe on all dishes observed for all virus constructs. The 15 cm dishes were split 1:2 and the total duration of the experiment was 15 days.

Example 4: Effect of Promoter Choice For pIX Expression on Virus Amplification

To define the effect of promoter choice on the virus amplification, the adenovirus vectors described in Example 3 were produced in HEK293 the same way as described there but harvest was performed when all cells showed complete cpe which resulted in various harvest times. The improving effect of SV40 promotor in hAd19aGFP_SV40 and hAd19aGFP_5pIX+SV40 compared to hAd19aGFP_delta was 2.69 for the presence of the SV40 promoter alone, and 2.44-fold for the SV40 promoter in combination with the 5pIX promoter. hAd19aGFP_5pIX+SV40 and hAd19aGFP_SV40 were harvested after 2 days, hAd19aGFP_delta was harvested after 5 days (Table 2).

TABLE 2

| Effect of promoter choice for pIX expression on virus amplification | | | | | | |
|---|---|---|---|---|---|---|
| Virus | Promoter | Duration for virus amplification on 15 cm dish until cpe completed | Total duration | Titer (ifu/ml) | Total ifu | Factor relative to no promoter |
| hAd19aGFP_5pIX + SV40 | SV40 + 5pIX | 2 days | 13 days | 1.23E+08 | 6.16E+07 | 2.44 |
| hAd19aGFP_delta | no promoter | 5 days | 16 days | 5.06E+07 | 2.53E+07 | 1.00 |
| hAd19aGFP_SV40 | SV40 | 2 days | 13 days | 1.36E+08 | 6.79E+07 | 2.69 |

Table 2: The duration until the $2^{nd}$ rescue was harvested was 8 days. Cells were seeded in 15 cm dishes at 5.00E+06 and an inoculum of 250 μl was used per 15 cm dish. Complete cpe on all dishes was observed for all virus constructs. The 15 cm dishes were not split.

Example 5: Effect of Promoter Choice for pIX Expression on Virus Yield after Inoculation with a Defined Virus Amount To simulate virus batch production, 2.5E+06 HEK293 cells were seeded in 15 cm dishes and inoculated with the vectors hAd19aGFP_delta, hAd19aGFP_5pIX, hAd19aGFP_SV40, hAd19aGFP_5pIX+SV40 with a defined amount of infectious viral particles. A multiplicity of infection of 5 (MOI) was used. Harvest was performed at the time point when cells showed a CPE associated with rounding up of cells and beginning cell detachment. Accordingly, hAd19aGFP_5pIX+SV40 and hAd19aGFP_SV40 were harvested 4 days after inoculation, and the viruses hAd19aGFP_delta and hAd19aGFP_5pIX harvested after 5 days with only partially completed cpe. The total yield of recombinant virus was increased in the presence of heterologous promotor 5pIX+SV40 by 2.26 fold compared to the promotor of hAd19aGFP_delta. The hAd19aGFP_5pIX resulted in a less significant increase of 1.89 followed by an 1.59 increase of the hAd19aGFP_SV40 promotor (Table 3a). The total yield of recombinant virus particles was increased in the presence of heterologous promotor 5pIX+SV40 by 6.89-fold compared to the promotor of hAd19aGFP_delta. The hAd19aGFP_5pIX resulted in a less significant increase of 6.17-fold followed by an 6-fold increase of the hAd19aGFP_SV40 promotor (Table 3b).

TABLE 3a

| Effect of promoter choice for pIX expression on virus yield after defined virus amplification | | | | | | |
|---|---|---|---|---|---|---|
| Virus | Promoter | Cells seeded in 15 cm dish | Duration for virus amplification on 15 cm dish until cpe completed | Titer (ifu/ml) | Total ifu | Factor relative to no promoter |
| hAd19aGFP_5pIX + SV40 | SV40 + 5pIX | 2.50E+06 | 4 days | 1.93E+08 | 7.71E+07 | 2.26 |
| hAd19aGFP_delta | no promoter | 2.50E+06 | 5 days | 8.53E+07 | 3.41E+07 | 1.00 |
| hAd19aGFP_5pIX | 5pIX | 2.50E+06 | 5 days | 1.61E+08 | 6.45E+07 | 1.89 |
| hAd19aGFP_SV40 | SV40 | 2.50E+06 | 4 days | 1.36E+08 | 5.44E+07 | 1.59 |

Cells were seeded in 15 cm dishes at 2.50E+06 and a volume inoculum of MOI5 was used per 15 cm dish. Partial cpe on dishes was observed for all virus constructs, except for construct hAd19aGFP_5pIX + SV40 which showed complete cpe. The 15 cm dishes were not split.

TABLE 3b

| Virus | Promoter | Cells seeded in 15 cm dish | Duration for virus amplification on 15 cm dish until cpe completed | vg/ml | Factor increase vg relative to no promoter |
|---|---|---|---|---|---|
| hAd19aGFP_5pIX + SV40 | SV40 + 5pIX | 2.50E+06 | 4 days | 8.13E+10 | 6.89 |
| hAd19aGFP_delta | no promoter | 2.50E+06 | 5 days | 1.18E+10 | 1 |
| hAd19aGFP_5pIX | 5pIX | 2.50E+06 | 5 days | 7.28E+10 | 6.17 |
| hAd19aGFP_SV40 | SV40 | 2.50E+06 | 4 days | 7.09E+10 | 6.00 |

Cells were seeded in 15 cm dishes at 2.50E+06 and a volume inoculum of MOI5 was used per 15 cm dish. Partial cpe on dishes was observed for all virus constructs, except for construct hAd19aGFP_5pIX + SV40 which showed complete cpe. The 15 cm dishes were not split.

The invention claimed is:

1. A method for increasing the yield of replication-incompetent adenoviruses having at least a partial deletion in the E1-region, wherein said adenoviruses are generated in a production cell, the method comprising the steps of:

(a) expressing in said production cell an adenoviral pIX polypeptide from a nucleic acid sequence encoding said adenoviral pIX polypeptide under the control of at least a minimal endogenous pIX promoter and at least one heterologous promoter, wherein said minimal endogenous pIX promoter is located downstream of said heterologous promoter; and (b) expressing in said production cell the elements necessary for the production and assembly of said adenoviruses from corresponding coding sequences, thereby increasing the yield of said adenoviruses generated in said production cell in comparison to the yield of replication-incompetent adenoviruses having at least a partial deletion in the E1-region generated in said production cell in the absence of said nucleic acid sequence encoding said adenoviral pIX polypeptide, wherein the adenovirus is a human adenovirus of subgroup D.

2. A method for the construction of a replication-incompetent adenovirus library, wherein the adenoviruses have at least a partial deletion in the E1-region, comprising the steps of:

(a) providing one or more nucleic acid sequences in expressible form comprising at least two partial adenoviral genomes, wherein each nucleic acid sequence of said one or more nucleic acid sequences comprises at least one partial adenoviral genome, each partial adenoviral genome further comprising at least one transgene, wherein the at least two partial adenovirus genomes and/or the two transgenes differ from each other;

(b) introducing the one or more nucleic acid sequences of step (a) into production cells comprising one or more nucleic acid sequences in expressible form comprising a partial adenoviral genome which complements each partial adenoviral genome comprised by the one or more nucleic acid sequences of step (a) by transfection, wherein each complemented adenoviral genome encodes the elements necessary for the production and assembly of said different adenoviruses and comprises the coding sequence for an adenoviral pIX polypeptide under the control of at least a minimal endogenous pIX promoter and a heterologous promoter, wherein said minimal endogenous pIX promoter is located downstream of said heterologous promoter; and (c) culturing the production cells under conditions suitable for the assembly and production of said differing adenoviruses, thereby constructing said replication-incompetent adenovirus library.

3. The method of claim 1, wherein one or more of said coding sequences of step (b) are introduced into the production cell for expression (a) by transduction using the replication-incompetent adenoviruses having at least a partial deletion in the E1-region that are to be produced in the cell; or (b) by transfection.

4. The method of claim 1, wherein the subgroup D adenovirus is of serotype 19a.

5. The method of claim 1, further comprising the step of assessing the expression level of said pIX protein in the production cell and/or the increase in yield of said adenoviruses.

6. The method of claim 1, wherein the subgroup D adenovirus is selected from the group consisting of serotypes 8, 9, 13, 15, 17, 19, 20, 22 to 25, 27 to 30, 32, 33, 36 to 39, 42 to 49 and 51.

7. The method of claim 1, wherein the production cell is selected from the group consisting of a HEK293 production cell, a Per.C6 production cell, a CAP cell, a GH329 production cell and a pTG6559 production cell.

8. The method of claim 1, wherein the heterologous promoter is (a) a heterologous minimal pIX promoter; or (b) selected from the group consisting of a viral promoter, a cellular promoter, synthetic promoter and a hybrid promoter.

9. The method of claim 8, wherein the heterologous minimal pIX promoter of (a) originates from a human adenovirus serotype 5.

10. The method of claim 8, wherein the heterologous promoter of (b) is selected from the group consisting of CAG, CMV, PKG, SV40, EF1 alpha and RSV.

11. The method of claim 1, wherein the coding sequence for said adenoviral pIX polypeptide is under the control of an additional heterologous promoter.

12. The method of claim 4, wherein the heterologous promoter is (a) a heterologous minimal pIX promoter that originates from a human adenovirus serotype 5; or (b) an SV40 viral promoter.

* * * * *

SEQUENCE LISTING

<160> NUMBER OF SEQ ID NOS: 8

<210> SEQ ID NO 1
<211> LENGTH: 3350
<212> TYPE: DNA
<213> ORGANISM: Artificial sequence
<220> FEATURE:
<223> OTHER INFORMATION: /note="Description of artificial sequence: pDonorSir19aGFP"

<400> SEQUENCE: 1
taactatcta ataatatacc ccacaaagta aacaaaagtt aatatgcaaa tgagcttttg 60
aattttaacg gttttggggc ggagccaacg ctgattggac gagaagcggt gatgcaaata 120
acgtcacgac gcacggctaa cggccggcgc ggaggcgtgg cctaggccgg aagcaagtcg 180
cggggctaat gacgtataaa aaagcggact ttagacccgg aaacggccga ttttcccgcg 240
gccacgcccg gatatgaggt aattctgggc ggatgcaagt gaaattaggt cattttggcg 300
ccaaaactga atgaggaagt gaaaagtgaa aaatacctgt cccgcccagg gcggaatatt 360
taccgagggc cgagagactt tgaccgatta cgtggggttt cgattgcggt gttttttttcg 420 cgagaaggta aactgcccac ttggcagtac atcaagtgta tcatatgcca agtacgcccc 480
ctattgacgt caatgacggt aaatggcccg cctggcatta tgcccagtac atgaccttat 540
gggactttcc tacttggcag tacatctacg tattagtcat cgctattacc atggtgatgc 600
ggttttggca gtacatcaat gggcgtggat agcggtttga ctcacgggga tttccaagtc 660
tccaccccat tgacgtcaat gggagtttgt tttggcacca aaatcaacgg gactttccaa 720
aatgtcgtaa caactccgcc ccattgacgc aaatgggcgg taggcgtgta cggtgggagg 780
tctatataag cagagctggt ttagtgaacc gtcagatccg ctagcgctac cggactcaga 840
tctcgagctc aagcttcgaa ttctgcagtc gacggtaccg cgggcccggg atccaccggt 900
cgccaccatg gtgagcaagg gcgaggagct gttcaccggg gtggtgccca tcctggtcga 960
gctggacggc gacgtaaacg gccacaagtt cagcgtgtcc ggcgagggcg agggcgatgc 1020
cacctacggc aagctgaccc tgaagttcat ctgcaccacc ggcaagctgc ccgtgccctg 1080
gcccaccctc gtgaccaccc tgacctacgg cgtgcagtgc ttcagccgct accccgacca 1140
catgaagcag cacgacttct tcaagtccgc catgcccgaa ggctacgtcc aggagcgcac 1200
catcttcttc aaggacgacg gcaactacaa gacccgcgcc gaggtgaagt tcgagggcga 1260
caccctggtg aaccgcatcg agctgaaggg catcgacttc aaggaggacg gcaacatcct 1320
ggggcacaag ctggagtaca actacaacag ccacaacgtc tatatcatgg ccgacaagca 1380
gaagaacggc atcaaggtga acttcaagat ccgccacaac atcgaggacg gcagcgtgca 1440
gctcgccgac cactaccagc agaacacccc catcggcgac ggccccgtgc tgctgcccga 1500
caaccactac ctgagcaccc agtccgccct gagcaaagac cccaacgaga agcgcgatca 1560
catggtcctg ctggagttcg tgaccgccgc cgggatcact ctcggcatgg acgagctgta 1620
caagtaaagc ggccgcgact ctagatcata atcagccata ccacatttgt agaggtttta 1680
cttgctttaa aaaacctccc acacctcccc ctgaacctga aacataaaat gaatgcaatt 1740
gttgttgtta acttgtttat tgcagcttat aatggttaca aataaagcaa tagcatcaca 1800
aatttcacaa ataaagcatt tttttcactg cattctagtt gtggtttgtc caaactcatc 1860
aatgtatctt aaatcgaatt caagcttgtc gactcgaaga tctgagctca cgcgtgaagt 1920
tcctattctc tagaaagtat aggaacttca attcccatgt cagccgttaa gtgttcctgt 1980
gtcactcaaa attgctttga gaggctctaa gggcttctca gtgcgttaca tccctggctt 2040
gttgtccaca accgttaaac cttaaaagct ttaaaagcct tatatattct ttttttctt 2100 ataaaactta aaaccttaga ggctatttaa gttgctgatt tatattaatt ttattgttca 2160
aacatgagag cttagtacgt gaaacatgag agcttagtac gttagccatg agagcttagt 2220
acgttagcca tgagggttta gttcgttaaa catgagagct tagtacgtta aacatgagag 2280
cttagtacgt gaaacatgag agcttagtac gtactatcaa caggttgaac tgctgatctt 2340
cagatcctct acgccggacg catcgtggcc ggatccgatt tattcaacaa agccacgttg 2400
tgtctcaaaa tctctgatgt tacattgcac aagataaaaa tatatcatca tgaacaataa 2460
aactgtctgc ttacataaac agtaatacaa ggggtgttat gagccatatt caacgggaaa 2520
cgtcttgctc gaggccgcga ttaaattcca acatggatgc tgatttatat gggtataaat 2580
gggctcgcga taatgtcggg caatcaggtg cgacaatcta tcgattgtat gggaagcccg 2640
atgcgccaga gttgtttctg aaacatggca aaggtagcgt tgccaatgat gttacagatg 2700
agatggtcag actaaactgg ctgacggaat ttatgcctct tccgaccatc aagcatttta 2760
tccgtactcc tgatgatgca tggttactca ccactgcgat ccccgggaaa acagcattcc 2820
aggtattaga agaatatcct gattcaggtg aaaatattgt tgatgcgctg gcagtgttcc 2880
tgcgccggtt gcattcgatt cctgtttgta attgtccttt taacagcgat cgcgtatttc 2940
gtctcgctca ggcgcaatca cgaatgaata acggtttggt tgatgcgagt gattttgatg 3000
acgagcgtaa tggctggcct gttgaacaag tctggaaaga aatgcataag cttttgccat 3060
tctcaccgga ttcagtcgtc actcatggtg atttctcact tgataacctt atttttgacg 3120
aggggaaatt aataggttgt attgatgttg gacgagtcgg aatcgcagac cgataccagg 3180
atcttgccat cctatggaac tgcctcggtg agttttctcc ttcattacag aaacggcttt 3240
ttcaaaaata tggtattgat aatcctgata tgaataaatt gcagtttcat ttgatgctcg 3300
atgagttttt ctaatcagaa ttggttaatt ggttgtaaca ctggcttaat 3350

<210> SEQ ID NO 2
<211> LENGTH: 34809
<212> TYPE: DNA
<213> ORGANISM: Artificial sequence
<220> FEATURE:
<223> OTHER INFORMATION: /note="Description of artificial sequence: pBACSir19A_SV40"

<400> SEQUENCE: 2
gaagttccta ttccgaagtt cctattctct agaaagtata ggaacttcgc gtaaattgta 60
agcgttaata ttttgttaaa attcgcgtta aatttttgtt aaatcagctc atttttaac 120 caataggccg aaatcggcaa aatcccttat aaatcaaaag aatagaccga gatagggttg 180
agtgttgttc cagtttggaa caagagtcca ctattaaaga acgtggactc caacgtcaaa 240
gggcgaaaaa ccgtctatca gggcgatggc ccactacgtg aaccatcacc ctaatcaagt 300 ttttggggt cgaggtgccg taaagcacta aatcggaacc ctaaagggag cccccgattt 360
agagcttgac ggggaaagcc ggcgaacgtg gcgagaaagg aagggaagaa agcgaaagga 420
gcgggcgcta gggcgctggc aagtgtagcg gtcacgctgc gcgtaaccac cacacccgcc 480
gcgcttaatg cgccgctaca gggcgcgtca ggtggcactt ttcggggaaa tgtgcgcgga 540
acccctattt gtttattttt ctaaatacat tcaaatatgt atccgctcat gagacaataa 600
ccctgataaa tgcttcaata atattgaaaa aggaagagtc ctgaggcgga aagaaccagc 660

-continued

```
tgtggaatgt gtgtcagtta gggtgtggaa agtccccagg ctccccagca ggcagaagta    720
tgcaaagcat gcatctcaat tagtcagcaa ccaggtgtgg aaagtcccca ggctccccag    780
caggcagaag tatgcaaagc atgcatctca attagtcagc aaccatagtc ccgcccctaa    840
ctccgcccat cccgcccta actccgccca gttccgccca ttctccgccc catggctgac    900
taattttttt tatttatgca gaggccgagg ccgcctcggc ctctgagcta ttccagaagt    960
agtgaggagg cttttttgga ggggggtgggg taccaggtaa gtgtacccaa ttcgccctat   1020
agtgagtcgt attacaattc actggccgtc gttttacaac gtcgtgactg ggaaaaccct   1080
ggcgttaccc aacgtgagac cagaccacct ggtgatggcc tgtaccggga ccgagttcag   1140
ctccagtggg gaggacacag attagaggta ggtttgagta gtgggcgtgg ctaatgtgag   1200
tataaaggcg ggtgtcttac gagggtcttt ttgcttttct gcagacatca tgaacgggac   1260
cggcggggcc ttcgaagggg ggctttttag cccttatttg acaacccgcc tgccgggatg   1320
ggccggagtt cgtcagaatg tgatgggatc tacggtggat gggcgtccag tgcttccagc   1380
aaattcctcg accatgacct acgcgaccgt ggggagctcg tcgcttgaca gcaccgccgc   1440
agccgcggca gccgcagccg ccatgacagc gacgagactg gcctcgagct atatgcccag   1500
cagcggtagc agcccctctg tgcccagttc catcatcgcc gaggagaaac tgctggccct   1560
gctggccgag ctggaagccc tgagccgcca gctggccgcc ctgacccagc aggtgtccga   1620
tctccgcgag caacagcagc agcaaaataa atgaattcaa taaacacaga ttctgattca   1680
aacagcaaag catctttatt atttattttt tcgcgcgcgg taggccctgg tccacctctc   1740
ccgatcattg agagtgcggt ggattttttc caggacccgg tagaggtggg attggatgtt   1800
gaggtacatg ggcatgagcc cgtcccgggg gtggaggtag caccactgca tggcctcgtg   1860
ctctggggtc gtgttgtaga taatccagtc atagcagggg cgctgggcgt ggtgctggat   1920
gatgtccttg aggaggagac tgatggccac ggggagcccc ttggtgtagg tgttggcaaa   1980
gcggttaagc tgggagggat gcatgcgggg ggagatgatg tgcagtttgg cctggatctt   2040
gaggttggcg atgttgccac ccagatcccg ccgggggttc atattgtgca ggaccaccag   2100
aacggtgtag cccgtgcact tggggaactt atcatgcaac ttggaaggga atgcgtggaa   2160
gaatttggag acgcccttgt gcccgcccag gttttccatg cactcatcca tgatgatggc   2220
aatgggcccg tgggctgcgg ctttggcaaa aacgtttctg ggtcagaga catcataatt   2280
atgctcctgg gtgagatcat cataagacat tttaatgaat ttggggcgaa gggtgccaga   2340
ttgggggacg atcgttccct cgggccccgg ggcgaagttc cctcgcaga tctgcatctc    2400
ccaggctttc atctcggagg gggggatcat gtccacctgc ggggcgatga aaaaaacggt   2460
ttccggggcg ggggtgatga gctgcgagga gagcaggttt cttaacagct gggacttgcc   2520
gcacccggtc gggccgtaga tgaccccgat gacgggttgc aggtggtagt tcaaggagat   2580
gcagctgccg tcgtcccgga ggagggggc cacctcgttg agcatgtctc tcacttggag    2640
gttttcccgg acgagctcgc cgaggaggcg gtccccgccc agcgagagca gctcttgcag   2700
ggaagcaaag tttttcaggg gcttgagccc gtcggccatg ggcatcttgg caagggtctg   2760
cgagaggagc tccaggcggt cccatagctc ggtgacgtgc tctacggcat ctcgatccag   2820
cagacttcct cgtttcgggg gttgggacga ctgcgactgt agggcacgag acgatgggcg   2880
tccagcgcgg ccagcgtcat gtccttccag ggtctcaggg tccgagtgag ggtggtctcc   2940
gtcacggtga aggggtgggc cccgggctgg gcgcttgcaa gggtgcgctt gagactcatc   3000
ctgctggtgc tgaaacgggc acggtcttcg ccctgcgcgt cggcgagata gcagttgacc   3060
```

-continued

```
atgagcttgt agttaagggc ctcggcggcg tggcccttgg cacggagctt gcctttggaa   3120
gagcgcccgc aggcgggaca gaggagggat tgcagggcgt agagcttggg tgcgagaaag   3180
acggactcgg gagcgaaggc gtccgctccg cagtgggcgc agacggtctc gcactcgacg   3240
agccaggtga gctcgggctg ctcggggtca aaaaccagtt ttcccccgtt ctttttgatg   3300
cgcttcttac ctcgcgtctc catgagtctg tgtccgcgtt cggtgacaaa caggctgtct   3360
gtgtccccgt agacggactt gattggcctg tcctgcaggg gcgtcccgcg gtcctcctcg   3420
tagagaaact cggaccactc tgagacaaag gcgcgcgtcc acgccaagac aaaggaggcc   3480
acgtgcgagg ggtagcggtc gttgtccacc agggggtcca ccttttccac cgtgtgcaga   3540
cacatgtccc cctcctccgc atccaagaag gtgattggct tgtaggtgta ggccacgtga   3600
ccgggggtcc ccgacggggg ggtataaaag ggggcgggtc tgtgctcgtc ctcactctct   3660
tccgcgtcgc tgtccacgag cgccagctgt tggggtaggt attccctctc gagagcgggc   3720
atgacctcgg cactcaggtt gtcagtttct agaaacgagg aggatttgat gttggcctgc   3780
cctgccgcaa tgctttttag gagactttca tccatctggt cagaaaagac tattttttta   3840
ttgtcaagct tggtggcaaa ggagccatag agggcgttgg agagaagctt ggcgatggat   3900
ctcatggtct gatttttgtc acggtcggcg cgctccttgg ccgcgatgtt gagctggaca   3960
tactcgcgcg cgacacactt ccattctggg aagacggtgg tgcgctcgtc gggcacgatc   4020
ctgacgcgcc agccgcgatt atgcagggtg accaggtcca cgctggtggc cacctcgccg   4080
cgcaggggct cgttggtcca gcagaggcgt ccgcccttgc gcgagcagaa cgggggcagc   4140
acatcaagca gatgctcgtc agggggggtcc gcatcgatgg tgaagatgcc cggacagagt   4200
tccttgtcaa aataatcgat ttttgaggat gcatcatcca aggccatctg ccactcgcgg   4260
gcggccagcg ctcgctcgta ggggttgagg ggcggacccc agggcatggg atgcgtgagg   4320
gcggaggcgt acatgccgca gatgtcgtag acatagatgg gctccgagag gatgccgatg   4380
taggtgggat aacagcgccc cccgcggatg ctggcgcgca catagtcata caactcgtgc   4440
gagggggcca agaaagcggg gccgagattg gtgcgctggg gctgctcggc gcggaagacg   4500
atctggcgaa agatggcatg cgagttggag gagatggtgg gccgttggaa gatgttaaag   4560
tgggcgtggg gcaagcggac cgagtcgcgg atgaagtgcg cgtaggagtc ttgcagcttg   4620
gcaacgagct cggcggtgac aaggacgtcc atggcgcagt agtccagcgt ttcacggatg   4680
atgtcataac ccgcctcttc tttcttctcc cacagcgcgc ggttgagggc gtactcctcg   4740
tcatccttcc agtactcccg gagcgggaat cctcgatcgt ccgcacggta agagcccagc   4800
atgtagaaat ggttcacggc cttgtaggga cagcagccct tctccacggg gagggcgtaa   4860
gcttgagcgg ccttgcggag cgaggtgtgc gtcagggcga aggtatccct aaccatgact   4920
ttcaagaact ggtacttgaa atccgagtcg tcgcagccgc cgtgctccca gagctcgaaa   4980
tcggtgcgct tcttcgagag gggggttaggc agagcgaaag tgacgtcatt gaagagaatc   5040
ttgcctgccc gcggcatgaa attgcgggtg atgcggaaag ggcccggaac ggaggctcgg   5100
ttgttgatga cctgggcggc gaggacgatc tcgtcgaagc cgttgatgtt gtgcccgacg   5160
atgtagagtt ccatgaatcg cgggcggcct ttgatgtgcg gcagcttttt gagttcctcg   5220
taggtgaggt cctcggggca ttgcaggccg tgctgctcga gcgcccactc ctggagatgt   5280
gggttggctt gcatgaatga agcccagagc tcgcgggcca tgagggtctg gagctcgtcg   5340
cgaaagaggc ggaactgctg gcccacggcc atcttttctg ggtgacgca gtagaaggtg   5400
```

-continued

```
aggggggtccc gctcccagcg atcccagcgt aagcgcacgg cgagatcgcg agcgagggcg   5460
accagctcgg ggtccccgga gaatttcatg accagcatga aggggacgag ctgcttgccg   5520
aaggacccca tccaggtgta ggtttctaca tcgtaggtga caaagagccg ctccgtgcga   5580
ggatgagagc cgattgggaa gaactggatt tcctgccacc agttggtcga gtggctgttg   5640
atgtgatgaa agtagaaatc ccgccggcga accgagcact cgtgctgatg cttgtaaaag   5700
cgtccgcagt actcgcagcg ctgcacgggc tgtacctcat ccacgagata cacagcgcgt   5760
cccttgagga ggaacttcag gagtggcggc cctggctggt ggttttcatg ttcgcctgcg   5820
tgggactcac cctggggctc ctcgaggacg gagaggctga cgagcccgcg cgggagccag   5880
gtccagattt cggcgcggcg ggggcggaga gcgaaaacga gggcgcgcag ttgggagctg   5940
tccatggtgt cgcggagatc caggtccggg ggcagggttc tgaggttgac ctcgtagagg   6000
cgggtgaggg cgtgcttgag atgcagatgg tacttgatct ccacgggtga gttggtggtc   6060
gtgtccacgc attgcatgag cccgtagctg cgcggggcca cgaccgtgcc gcggtgcgct   6120
tttagaagcg gtgtcgcgga cgcgctcccg gcggcagcgg cggttccggc cccgcgggca   6180
gtggcggtag aggcacgtcg gcgtggcgct cgggcaggtc ccggtgctgc gccctgagag   6240
cgctggcgtg cgcgacgacg cggcggttga catcctggat ctgccgcctt tgcgtgaaga   6300
ccacgggccc cgtgactttg aacctgaaag acagttcaac agaatcaatc tcggcgtcat   6360
tgacggcggc ctgacgcagg atctcttgca cgtcgcccga gttgtcctgg taggcgatct   6420
cggacatgaa ctgctcgatt tcctcctcct ggagatcgcc gcggcccgcg cgctctacgg   6480
tggcggcaag gtcattcgag atgcgaccca tgagctgcga gaaggcgccc aggccgctct   6540
cgttccagac gcggctgtaa accacgtccc cgtcggcgtc gcgcgcgcgc atgaccacct   6600
gcgcgaggtt gagctccacg tgccgcgtaa agacggcgta gttgcgcagg cgctggaaga   6660
ggtagttgag ggtggtggcg atgtgctcgg tgacgaagaa gtacataatc cagcggcgca   6720
ggggcatttc gctgatgtcg ccaatggcct ccagcctttc catggcctcg tagaaatcca   6780
cggcgaagtt gaaaaactgg gcgttgcggg ccgagaccgt gagctcgtct tccaggagcc   6840
tgatgagttc ggcgatggtg gcgcgcacct cgcgctcgaa atcccagggg gcctcctcct   6900
cttcctcttc ttccatgacg acctcttctt ctatttcttc ctctgggggc ggtggtggtg   6960
gcggggcccg acgacgacgg cgacgcaccg ggagacggtc gacgaagcgc tcgatcatct   7020
ccccgcggcg gcgacgcatg gtttcggtga cggcgcgacc ccgttcgcga ggacgcagcg   7080
tgaagacgcc gccggtcatc tcccggtaat ggggtgggtc cccgttgggc agcgataggg   7140
cgctgacaat gcatcttatc aattgcggtg tagggcacgt gagcgcgtcg agatcgaccg   7200
gatcggagaa tctttcgagg aaagcgtcta gccaatcgca gtcgcaaggt aagctcaaac   7260
acgtagcagc cctgtggacg ctgttagaat tgcggttgct gatgatgtaa ttgaagtagg   7320
cgtttttgag gcggcggatg gtggcgagga ggaccaggtc cttgggtccc gcttgctgga   7380
tgcggagccg ctcggccatg ccccaggcct ggccctgaca ccggctcagg ttcttgtagt   7440
agtcatgcat gagcctctcg atgtcatcac tggcggaggc ggagtcttcc atgcgggtga   7500
ccccgacgcc cctgaacggc tgcacgagcg ccaggtcggc gacgacgcgc tcggcgagga   7560
tggcctgttg cacgcgggtg agggtgtcct ggaagtcgtc catgtcgacg aagcggtggt   7620
aggcccctgt gttgatggtg taagtgcagt tggccataag cgaccagttg acggtctgca   7680
ggccgggttg cacgacctcg gagtacctga gccgcgagaa ggcgcgcgag tcgaagacat   7740
agtcgttgca ggtgcgcacg aggtactggt atccgactag aaagtgcggc ggcggctggc   7800
```

```
ggtagagcgg ccagcgctgg gtggccggcg cgcccggggc caggtcctca agcatgagtc   7860
ggtggtagcc gtagaggtag cgggacatcc aggtgatgcc ggcggcggtg gtggaggcgc   7920
gcgggaactc gcggacgcgg ttccagatgt tgcgcagggg caggaaatag tccatggtcg   7980
gcacggtctg gccggtgaga cgcgcgcagt cattgatgct ctagaggcaa aaacgaaagc   8040
ggttgagcgg gctcttcctc cgtagcctgg cggaacgcaa acgggttagg ccgcgtgtgt   8100
accccggttc gagtcccctc gaatcaggct ggagccgcga ctaacgtggt attggcactc   8160
ccgtctcgac ccaagcccga tagccgccag gatacggcgg agagcccttt ttgtcggccg   8220
aggggagtcg ctagacttga aagcggccga aaaccctgcc gggtagtggc tcgcgcccgt   8280
agtctggaga agcatcgcca gggttgagtc gcggcagaac ccggttcaag gacggccgcg   8340
gcgagcggga cttggtcacc ccgccgattt aaagacccac agccagccga cttctccagt   8400
tacgggagcg agcccccttt tttctttttg ccagatgcat cccgtcctgc gccaaatgcg   8460
tcccaccccc ccggcgacca ccgcgaccgc ggccgtagca ggcgccggcg ctagccagcc   8520
acagccacag acagagatgg acttggaaga gggcgaaggg ctggcgagac tgggggcgcc   8580
gtccccggag cgacatcccc gcgtgcagct gcagaaggac gtgcgcccgg cgtacgtgcc   8640
tgcgcagaac ctgttcaggg accgcagcgg ggaggagccc gaggagatgc gcgactgccg   8700
gtttcgggcg ggcagggagc tgcgcgaggg cctggaccgc cagcgcgtgc tgcgcgacga   8760
ggatttcgag ccgaacgagc agacggggat cagccccgcg cgcgcgcacg tggcggcggc   8820
caacctggtg acagcctacg agcagacggt gaagcaggaa cgcaactttc aaaagagttt   8880
caacaaccac gtgcgcaccc tgatcgcgcg cgaggaggtg gccctgggcc tgatgcacct   8940
gtgggacctg gcggaggcca ttgtgcagaa cccggacagc aagcctctga cggcacaact   9000
gttcctggtg gtgcagcaca gcagggacaa cgaggcgttc agggaggcgc tgctaaacat   9060
cgccgagccc gagggccgct ggctgctgga gctgatcaac atcttgcaaa gcatcgtagt   9120
gcaggagcgc agcctgagct tggccgagaa ggtggcggcg atcaactact cggtgctaag   9180
cctgggcaag ttttacgcgc gcaagattta caagacgccg tacgtgccca tagacaagga   9240
ggtgaaaata gacagctttt acatgcgcat ggcgctcaag gtgctgacgc tgagcgacga   9300
cctgggcgtg taccgcaacg accgcatcca caaggccgtg agcacgagcc ggcggcgcga   9360
gctgagcgac cgcgagctga tgctaagcct gcgccgggcg ctggtaggtg gcgccgccgg   9420
cggcgaggag tcctacttcg acatgggggc ggacctgcat tggcagccga gccggcgcgc   9480
cttggaggcc gcctacggtc cagaggactt ggatgaggat gaggaagagg aggaggatgc   9540
acccgttgcg ggtactgac gcctccgtga tgtgttttta gatgtcccag cagcaagccc   9600
cggaccccgc cataagggcg gcgctgcaaa gccagccgtc cggtctagca tcggacgact   9660
gggaggccgc gatgcaacgc atcatggccc tgacgacccg caaccccgag tcctttagac   9720
aacagccgca ggccaacaga ctttcgacca ttctggaggc ggtggtcccc tctcggacca   9780
accccacgca cgagaaggtg ctggcgatcg tgaacgcgct ggcggagaac aaggctattc   9840
gtcccgacga ggctgggctg gtatacaacg ccctgctgga gcgcgtgggc cgctacaaca   9900
gcacgaacgt gcagtccaac ctggaccggc tggtgacgga cgtgcgcgag gccgtggcgc   9960
agcgcgagcg gttcaagaac gagggcctgg gctcgctggt ggcgctgaac gccttcctgg  10020
cgacgcagcc ggcgaacgtg ccgcgcgggc aggacgatta taccaacttt atcagcgcgc  10080
tgcggctgat ggtgaccgag gttccccaga gcgaggtgta ccagtcgggc ccggactact  10140
```

-continued

```
ttttccagac tagcagacag ggcctgcaga cggtgaacct gagccaggct ttcaagaacc  10200
tgcgcgggct gtggggcgtg caggcgcccg tgggcgaccg gtcgacggtg agcagcttgc  10260
tgacgcccaa ctcgcggctg ctgctgctgc tgatcgcgcc cttcaccgac agcggcagcg  10320
tgaaccgcaa ctcgtacctg ggtcacctgc tgacgctgta ccgcgaggcc ataggccagg  10380
cacaggtgga cgagcagacc ttccaggaga tcactagtgt aagccgcgcg ctgggtcaga  10440
acgacaccga cagtctgagg gccaccctga acttcttgct gaccaataga cagcagaaga  10500
tcccggcgca gtatgcgctg tcggccgagg aggagcgcat cctgagatat gtgcagcaga  10560
gcgtagggct gtttctgatg caggaggggg ccaccccag cgccgcgctg gacatgaccg  10620
cgcgcaacat ggaacctagc atgtacgccg ccaaccggcc gtttatcaat aagctgatgg  10680
actacctgca ccgcgcggcg tccatgaact cggactactt taccaatgcc attttgaacc  10740
cgcactggct cccgccgccg gggttctaca cgggcgagta cgacatgcct gaccccaacg  10800
acgggttttt gtgggacgac gtggacagcg cggtgttctc accgaccttg caaaagcgcc  10860
aggaggcggt gcgcacgccc gcgagcgagg gcgcggtggg tcggagcccc tttcctagct  10920
tagggagttt gcatagcttg ccgggctcgg tgaacagcgg cagggtgagc cggccgcgct  10980
tgctgggcga ggacgagtac ctaaacgact cgctgctgca gccgccgcgg gtcaagaacg  11040
ccatggccaa taacgggata gagagtctgg tggacaaact gaaccgctgg aagacctacg  11100
ctcaggacca tagggagcct gcgcccgcgc cgcggcgaca gcgccacgac cggcagcggg  11160
gcctggtgtg ggacgacgag gactcggccg acgatagcag cgtgttggac ttgggcggga  11220
gcggtggggt caacccgttc gcgcatctgc agcccaaact ggggcgacgg atgttttgaa  11280
tgcaaaataa aactcaccaa ggccatagcg tgcgttctct tccttgttag agatgaggcg  11340
tgcggtggtg tcttcctctc ctcctccctc gtacgagagc gtgatggcgc aggcgaccct  11400
ggaggttccg tttgtgcctc cgcggtatat ggctcctacg gagggcagaa acagcattcg  11460
ttactcagag ctggctccgc tgtacgacac cactcgcgtg tacttggtgg acaacaagtc  11520
ggcggacatc gcttccctga actaccaaaa cgaccacagc aactttctga ccacggtggt  11580
gcaaaacaac gatttcaccc ccgccgaggc tagcacgcag acgataaatt ttgacgagcg  11640
gtcgcggtgg ggcggtgatc tgaagaccat tctgcacacc aacatgccca atgtgaacga  11700
gtacatgttt accagcaagt ttaaggcgcg ggtgatggtg gctaggaaac acccacaggg  11760
ggtagaagca acagatttaa gcaaggatat cttagagtac cagtggtttg agtttaccct  11820
gcccgagggc aacttttccg agaccatgac catagacctg atgaacaacg ccatcttgga  11880
aaactacttg caagtggggc ggcaaaatgg cgtgctggag agcgatatcg gagtcaagtt  11940
tgacagcagg aatttcaagc tgggctggga ccccgtgacc aagctggtga tgccaggggt  12000
ctacacctat gaggccttcc acccggacgt ggtgctgctg cctggctgcg gggtggactt  12060
caccgagagc cgcctaagca accttctggg cattcgcaag aagcaacctt tccaagaggg  12120
cttcagaatc atgtatgagg atctcgaagg gggcaacatt cccgcacttc tgaatgtgac  12180
caagtacctg gaaagcaaga agaagctaga ggagaatgcc gctaaggcta atggtcctgc  12240
aagaggagac agtagtgtct caagagaggt ggaaaaggca gctgaaaaag agcttgtcat  12300
tgagcccatc aagcaagatg atagcaagag aagttacaac ctcattgagg gtacccatga  12360
caccctgtac cgaagctggt acctgtccta tacctacggg gaccccgaga agggggtgca  12420
gtcgtggacg ctgctcacca ccccggacgg tcactgcggc gcggagcaag tctactggtc  12480
gctgccggac ctcatgcaag accccgtcac cttccgctct acccagcaag tcagcaacta  12540
```

ccccgtggtc ggcgccgagc tcatgccttt ccgcgccaag agcttttaca acgacctcgc 12600
cgtctactcc cagctcatcc gcagctacac ctccctcacc cacgtcttca accgcttccc 12660
cgacaaccag atcctctgcc gcccgcccgc gcccaccatc accaccgtca gtgaaaacgt 12720
gcctgctctc acagatcacg ggacgctacc gctgcgcagc agtatccgcg gagtccagcg 12780
agtgaccgtc actgacgccc gtcgccgcac ctgtccctac gtctacaagg ccctgggcat 12840
agtcgcgccg cgcgtgcttt ccagtcgcac cttctaaaaa atgtctattc tcatctcgcc 12900
cagcaataac accggctggg gtcttactag gcccagcacc atgtacggag gagccaagaa 12960
acgctcccag cagcaccccg tccgcgtccg cggccacttt cgcgctccct ggggcgcata 13020
caagcgcggg cggacttcca ccgccgccgc cgtgcgcacc accgtcgacg acgtcatcga 13080
ctcggtggtc gccgatgcgc gcaactatac ccccgccccc tccaccgtgg acgcggtcat 13140
tgacagcgtg gtggccgacg cgcgcgacta tgccagacgc aagagccggc ggcgacggat 13200
cgccaggcgc caccggagca cgcccgccat gcgcgccgcc cgggctctgc tgcgccgcgc 13260
cagacgcacg ggccgccggg ccatgatgcg agccgcgcgc cgcgctgcca ctgcacccac 13320
ccccgcaggc aggactcgca gacgagcggc cgctgccgcc gccgcggcca tctctagcat 13380
gaccagaccc aggcgcggaa acgtgtactg ggtgcgcgac tccgtcacgg gcgtgcgcgt 13440
gcccgtgcgc actcgtcctc ctcgtccctg atctaatgct tgtgtcctcc cccgcaagcg 13500
acgatgtcaa agcgcaaaat caaggaggag atgctccagg tcgtcgcccc ggagatttac 13560
ggacccccgg accagaaacc ccgcaaaatc aagcgggtta aaaaaaagga tgaggtggac 13620
gagggggcag tagagtttgt gcgcgagttc gctccgcggc ggcgcgtaaa ttggaagggg 13680
cgcagggtgc agcgtgtgtt gcggcccggc acggcggtgg tgttcacgcc cggcgagcgg 13740
tcctcggtca ggagcaagcg tagctatgac gaggtgtacg gcgacgacga catcctggac 13800
caggcggcgg agcgggcggg cgagttcgcc tacgggaagc ggtcgcgcga agaggagctg 13860
atctcgctgc cgctggacga aagcaacccc acgccgagcc tgaagcccgt gaccctgcag 13920
caggtgctgc cccaggcggt gctgctgccg agccgcgggg ttaagcgcga gggcgagagc 13980
atgtacccga ccatgcagat catggtgccc aagcgccggc gcgtggagga cgtgctggac 14040
accgtgaaaa tggatgtgga gcccgaggtc aaggtgcgcc ccatcaagca ggtggcgccg 14100
ggcctgggcg tgcaaaccgt ggacattcag atccccaccg acatggatgt cgacaaaaaa 14160
ccctcgacca gcatcgaggt gcaaaccgac ccctggctcc cagcctccac cgctaccgcc 14220
gccacggcca ccgagcctcc caggaggcga agatggggcc ctgccaaccg gctgatgccc 14280
aactacgtgt tgcatccttc catcatcccg acgccgggct accgcggcac ccggtactac 14340
gccagccgca ggcgcccagc cagtaaacgc cgccgccgca ccgccacccg ccgccgtctg 14400
gcccccgccc gcgtgcgccg cgtgaccacg cgccggggcc gctcgctcgt tctgcccacc 14460
gtgcgctacc accccagcat cctttaatcc gtgtgctgtg atactgttgc agagagatgg 14520
ctctcacttg ccgcctgcgc atccccgtcc cgaattaccg aggaagatcc cgccgcagga 14580
gaggcatggc aggcagtggc ctgaaccgcc gccggcggcg ggccatgcgc aggcgcctga 14640
gtggcggctt tctgcccgcg ctcatcccca taatcgccgc ggccatcggc acgatcccgg 14700
gcatagcttc cgttgcgctg caggcgtcgc agcgccgttg atgtgcgaat aaagcctctt 14760
tagactctga cacacctggt cctgtatatt tttagaatgg aagacatcaa ttttgcgtcc 14820
ctggctccgc ggcacggcac gcggccgttc atgggcacct ggaacgagat cggcaccagc 14880

```
cagctgaacg ggggcgcctt caattggagc agtgtctgga gcgggcttaa aaatttcggc  14940
tcgacgctcc ggacctatgg gaacaaggcc tggaatagta gcactgggca gttgttaagg  15000
gaaaagctca aagaccagaa cttccagcaa aaggtggtgg acgggctggc ctcgggcatt  15060
aacggggtgg tggacatcgc gaacccaggc cgtgcagcgc gagataaaca accgcctgga  15120
cccgcggccg cccacggtgg tggagatgga agatgcaact cctccgccgc ccaagggcga  15180
gaagcgaccg cggcccgacg cggaggagac gatcctgcag gtggacgagc cgccctcgta  15240
cgaggaggcc gtaaaggccg gcatgcccac cacgcgcatc atcgcgccac tggccacggg  15300
tgtaatgaaa cccgccaccc ttgacctgcc tccaccaccc acgcccgctc caccgaaggc  15360
agctccggta gtgcagcccc ctccggtggc gaccgccgtg cgccgcgtcc ccgcccgccg  15420
ccaggcccaa aactggcaaa gcacgctgca cagtattgtg ggcctgggag tgaaaagtct  15480
gaagcgccgc cgatgctatt gaaagagagg aaggaagaca ctaaagggag agcttaactt  15540
gtatgtgcct taccgccaga gaacgcgcga agatggccac cccctcgatg atgccgcagt  15600
gggcgtacat gcacatcgcc gggcaggacg cctcggagta cctgagcccg ggtctggtgc  15660
agtttgcccg cgccaccgac acgtacttca gcctgggcaa caagtttagg aaccccacgg  15720
tggccccaac ccacgatgtg accacggacc ggtcccagcg tctgacgctg cgcttcgtgc  15780
ccgtggatcg cgaggacacc acgtactcgt acaaggcgcg cttcactctg gccgtgggcg  15840
acaaccgggt gctagacatg gccagcactt actttgacat ccgcggcgtt ctggaccgcg  15900
gccccagctt caaaccctac tcgggcacgg cttacaacag cctggccccc aagggcgccc  15960
ccaattccag tcagtgggat gctcaagaaa aaaatggaca aggaggaaat gacatggtta  16020
ccaaaactca cacatttggc gtggctgcta tgggaggaac aaatattaca aaccagggtt  16080
tgttaattgg aactgaagaa acagccgata atcctccaaa ggaaatcttt gcagacaaat  16140
tattccagcc agaacctcaa gtaggagagg aaaactggca agacagcaat gcattctatg  16200
gaggcagggc tcttaagaag gaaactaaaa tgaaaccatg ctatggatct tatgctagac  16260
caacaaacac aagtggcgga caggctaagc ttaaaactgg tgacaatatc gatcctacca  16320
aggatttcga catagatctt gctttcttcg atactcctgg cggaaatcct ccagcaggtg  16380
gtagtggaac ggaagaatac aaagcagata ttgttatgta cactgaaaat gtcaaccttg  16440
aaacacctga cactcatgtg gtgtacaaac cagccaaaga ggatgaaagt tctcaggcca  16500
acttggttca gcagtccatg cccaacagac ccaactacat tggcttcaga gacaattttg  16560
tggggctcat gtattacaac agcactggca acatgggagt gctggctggt caggcctctc  16620
agttgaatgc tgtggtggac ttgcaagaca gaaacacaga gctgtcttac cagctcttgc  16680
tagattctct gggtgacaga accagatact ttagcatgtg gaactctgcg gtggacagct  16740
atgatccaga tgtcagaatc attgaaaatc acggtgtgga agatgagctt ccaaactatt  16800
gctttccatt ggatggctct ggtaccaatg ctgcctacca aggtgtaaag gttcaagatg  16860
gtgaagacgg ggataaagaa actgaatggg aaaaagatac caaagtcgca gatcgtaacc  16920
aactgtgcaa gggtaacatc ttcgccatgg agatcaacct ccaggccaac ctgtggaaga  16980
gttttctgta ctcgaacgtg gccctgtacc tgcccgactc ctacaagtac acgccggcca  17040
acatcacgct gcccgccaac accaacacct acgagtacat gaacggccgc gtggtagccc  17100
cctcgctggt ggacgcatac gtcaacatcg gtgcgcgctg gtcgctggac cccatggaca  17160
acgtcaaccc cttcaaccac caccgcaacg cgggcctgcg ctaccgctcc atgcttctcg  17220
gcaacggccg ctacgtgccc ttccacatcc aagtgcccca aaagttcttt gccattaaga  17280
```

```
acctgctcct gctccccggc tcctacacct acgagtggaa cttccgcaag gatgtcaaca  17340
tgatcctgca gagttccctc ggaaacgacc tgcgcgtcga cggcgcctcc gtgcgcttcg  17400
acagcgtcaa cctctacgct accttcttcc ccatggcgca caacaccgcc tccaccctgg  17460
aagccatgct gcgcaacgac accaacgacc agtcctttaa cgactacctc tcggccgcca  17520
acatgctcta ccccataccg gccaaggcca ccaacgtgcc catctccatc ccctcgcgca  17580
actgggctgc cttccgcggc tggagtttca cccggctcaa gaccaaggaa actccttccc  17640
ttggctcggg tttcgacccc tactttgtct actcgggctc catcccctac ctcgacggga  17700
ccttctacct caaccacacc ttcaaaaagg tgtccattat gttcgactcc tcggtcagct  17760
ggcccggcaa cgaccggctg ctcacgccga atgagttcga gatcaagcgc agcgtcgacg  17820
gggagggcta caacgtggcc caatgcaaca taaccaagga ctggttcctc gtccagatgc  17880
tctcccacta caacatcggc taccagggct tccacgtgcc cgagggctac aaggaccgca  17940
tgtactcctt tttccgcaac ttccagccca tgagcaggca ggtggtggat gagatcaact  18000
acaaggacta caaggccgtc accctgccct tccagcacaa caactctggc ttcaccggct  18060
acctcgcacc caccatgcgt caggggcagc cttaccccgc caacttccct tacccgctca  18120
tcggctccac cgcagtcccc tccgtcaccc agaaaaagtt cctctgcgac agggtcatgt  18180
ggcgcatccc cttctccagc aacttcatgt ccatgggtgc cctcaccgac ctgggtcaga  18240
acatgctcta tgccaactcg gcccacgcgc tcgacatgac cttcgaggtg gaccccatgg  18300
atgagcccac cctcctctat cttctcttcg aagttttcga cgtggtcaga gtgcaccagc  18360
cgcaccgcgg cgtcatcgag gccgtctacc tgcgcacacc cttctccgcc ggcaacgcca  18420
ccacctaagc atgagcggtt ccagcgaacg agaactcgcg gccatcgtgc gcgacctggg  18480
ctgcgggccc tactttttgg gcacccacga caagcgcttc ccgggcttcc tagccggcga  18540
caagctggcc tgcgccatcg tcaacacggc cggccgcgag accggaggcg tgcactggct  18600
cgccttcggc tggaacccgc gctcgcgcac ctgctacatg ttcgacccct ttgggttctc  18660
ggaccgccgg ctcaagcaga tttacagctt cgagtacgag gccatgctgc gccgaagcgc  18720
cctggcctcc tcgcccgacc gctgtctcag cctcgaacag tccacccaga ccgtgcaggg  18780
gcccgactcc gccgcctgcg gactttttttg ttgcatgttc ttgcatgcgt tcgtgcactg  18840
gcccgaccga cccatggacg gaaaccccac catgaacttg ctgacggggg tgcccaacgg  18900
catgctacaa tcgccacagg tgctgcccac cctccggcgc aaccaggagg agctctaccg  18960
cttcctcgcg cgccactccc cttacttccg atcccaccgc gccgccatcg aacacgccac  19020
cgcttttgac aaaatgaaac aactgcgtgt atctcaataa acagcacttt ttattttaca  19080
tgcactggag tatatgcaag ttatttaaaa gtcgaagggg ttctcgcgct cgtcgttgtg  19140
cgccgcgctg gggagggcca cgttgcggta ctggtacttg gaaagccact tgaactcggg  19200
gatcaccagt ttgggcactg gggtctcggg gaaggtctcg ctccacatgc gccggctcat  19260
ctgcagggcg cccagcatgt cagggccgga gatcttgaaa tcacagttgg ggccggtgct  19320
ctgcgcgcgc gagttgcggt acacggggtt gcagcactgg aacaccatca gactggggta  19380
cttcacactg gcaagcacgc tcttgtcgct aatctgatcc ttgtccaggt cctcggcgtt  19440
gctcaggccg aacggggtca tcttgcacag ctggcggccc aggaagggca cgctctgagg  19500
cttgtggtta cactcgcagt gcacgggcat cagcatcatc cccgcgccgc gctgcatatt  19560
cgggtagagg gccttgacga aggccgcgat ctgcttgaaa gcttgctggg ccttggcccc  19620
```

-continued

```
ctcgctgaag aacagaccgc agctcttccc gctgaactgg ttattcccgc acccggcatc  19680
atgcacgcag cagcgcgcgt catggctggt cagttgcacc acgctccgtc cccagcggtt  19740
ctgggtcacc ttagccttgc tgggctgctc cttcagcgcg cgctgtccgt tctcgctggt  19800
cacatccatc tccaccacgt ggtccttgtg aatcatcacc gttccatgca gacacttgag  19860
ctgaccttcc acctcggtgc agccgtgatc ccacaggacg cagccggtgc actcccaatt  19920
cttgtgcgcg atcccgctgt ggctgaaaat gtaaccttgc aacaggcgac ccataatggt  19980
gctaaatgat ttctgggtgg tgaatgtcag ttgcatcccg cgggcctcct cgttcatcca  20040
ggtctggcac atcttctgga agatctcggt ctgctccggc atgagcttgt aagcatcgcg  20100
caagccgctg tcgacgcggt agcgttccat cagcacgttc atggtatcca tgcccttctc  20160
ccatgacgag accagaggca gactcagggg gttgcgcacg ttcaggacac caggggtcgc  20220
gggctcgacg atgcgttttc cgtccttgcc ttccttcaac agaaccggag gctggctgaa  20280
tcccactccc acgatcacgg cgtcttcctg gggcatctct tcgtcggggt ctaccttggt  20340
cacatgcttg gtctttctgg cttgcttctt ttttggaggg ctgtccacgg ggaccacgtc  20400
ctcctcggaa gacccggagc ccacccgctg atactttcgg cgcttggtgg gcagaggagg  20460
tggcggcggc gaggggctcc tctcctgctc cggcggatag cgcgccgacc cgtggccccg  20520
gggcggagtg gcctctcgct ccatgaaccg gcgcacgtcc tgactgccgc cggccattgt  20580
ttcctagggg aagatggagg agcagccgcg taagcaggag caggaggagg acttaaccac  20640
ccacgagcaa cccaaaatcg agcaggacct gggcttcgaa gagccggctc gtctaaaacc  20700
cccacaggat gaacaggagc acgagcaaga cgcaggccag gaggagaccg acgctgggct  20760
cgagcatggc tacctgggag gagaggagga tgtgctgcta aaacacctgc agcgccagtc  20820
cctcatcctc cgggacgccc tggccgaccg gagcgaaacc cccctcagcg tcgaggagct  20880
gtgtcgggcc tacgagctca acctcttctc gccgcgcgtg ccccccaaac gccagcccaa  20940
cggcacctgc gagcccaacc cgcgtctcaa cttctatccc gtctttgcgg tccccgaggc  21000
ccttgccacc tatcacatct ttttcaagaa ccaaaagatc cccatctcct gtcgcgccaa  21060
tcgcactcgc gccgacgcgc tcctcgctct ggggcccggc gcgcgcatac ctgatatcgc  21120
ttccctggaa gaggtgccca agatcttcga agggctcggt cgggacgaga cgcgcgcggc  21180
aaacgctctg aaagaaacag cagaggaaga gggttacact agcgccctgg tagagttgga  21240
aggcgacaac gccaggctgg ccgtgcttaa gcgcagcgtc gagctcaccc atttcgccta  21300
ccccgccgtc aacctcccgc ccaaggtcat gcgtcgcatc atggatcagc tcatcatgcc  21360
ccacatcgag gcccttgatg aaagtcagga acagcgcccc gagaacgccc agcccgtggt  21420
cagcgacgag atgctcgcgc gctggctcgg gacccgcgac ccccaggccc tggagcagcg  21480
gcgcaagctc atgctggccg tggtcctggt caccettgag ctcgaatgca tgcgccgctt  21540
ttttaccgac cccgagaccc tgcgcaaggt cgaggagacc ctgcactaca ctttcagaca  21600
cggtttcgtc aggcaggcct gcaagatctc caacgtggag ctgaccaacc tggtctcctg  21660
cctggggatc ctacacgaga accgcttggg acagaccgtg ctccactcta ccctgaaggg  21720
cgaggcgcgg cgggactaca tccgcgactg cgtctttctc tttctctgcc acacatggca  21780
agcggccatg ggcgtgtggc agcagtgtct cgaggacgag aacctgaagg agctggacaa  21840
gcttcttgct agaaacctta aaaagctgtg gacgggcttc gacgagcgca ccgtcgcctc  21900
ggacctggcc gagatcgtct tccccgagcg cctgaggcag acgctgaaag gagggctgcc  21960
cgacttcatg agccagagca tgttgcaaaa ctaccgcact ttcattctcg agcgatctgg  22020
```

```
gatgctgccc gccacctgca acgccttccc ctccgacttt gtcccgctga gctaccgcga  22080
gtgtcccccg ccgctgtgga gccactgcta cctcttgcag ctggccaact acattgccca  22140
ccactcggat gtgatcgagg acgtgagcgg cgaggggctg ctcgagtgcc actgtcgctg  22200
caacctatgc tccccgcacc gctccctggt ctgcaacccc cagctactga gcgagaccca  22260
ggtcatcggt acctttgagc tgcaaggtcc gcaggagtcc accgctccgc tgaaactcac  22320
gccggggttg tggacttccg cgtacctgcg caaatttgta cccgaggact actacgccca  22380
tgagataaag ttcttcgagg accaatcgcg tccgcagcac gcggatctca cggcctgcgt  22440
catcacccag ggcgcgatcc tcgcccaatt gcacgccatc caaaaatccc gccaagagtt  22500
tcttctgaaa aagggtagag ggtctacct ggacccccag acgggcgagg tgctcaaccc  22560
gggtctcccc cagcatgccg aggaagaagc aggagccgct agtggaggag atggaagaag  22620
aatgggacag ccaggcagag gaggacgaat gggaggagga gacagaggag gaagacttgg  22680
aagaggtgga agaggagcag gcaacagagc agcccgtcgc cgcaccatcc gcgccggcag  22740
cccctccggt cacggataca acctccgcag ctccggccaa gcctcctcgt agatgggatc  22800
gagtgaaggg tgacggtaag cacgagcgac agggctaccg atcatggagg gcccacaaag  22860
ccgcgatcat cgcctgcttg caagactgcg gggggaacat cgctttcgcc cgccgctacc  22920
tgctcttcca ccgcggggtg aacatccccc gcaacgtgtt gcattactac cgtcaccttc  22980
acagctaaga aaaagcaagt caaaggagtc gccggaggag gaggcctgag gatcgcggcg  23040
aacgagccct tgaccaccag ggagctgagg aaccggatct tccccactct ttatgccatt  23100
tttcagcaaa gtcgaggtca gcagcaagag ctcaaagtaa aaaaccggtc tctgcgctcg  23160
ctcacccgca gttgcttgta ccacaaaaac gaagatcagc tgcagcgcac tctcgaagac  23220
gccgaggctc tgttccacaa gtactgcgcg ctgactctta aagactaagg cgcgcccacc  23280
cggaaaaaag gcgggaatta cctcatcgcc accatgagca aggagattcc cacccccttac  23340
atgtggagct atcagcccca gatgggcctg gccgcgggcg cctcccagga ctactccacc  23400
cgcatgaact ggcttagtgc cggcccctcg atgatctcac gggtcaacgg ggtccgtaac  23460
catcgaaacc agatattgtt gcagcaggcg gcggtcacct ccacgcccag ggcaaagctc  23520
aacccgcgta attggccctc caccctggtg tatcaggaaa tccccgggcc gactaccgta  23580
ctacttccgc gtgacgcact ggccgaagtc cgcatgacta actcaggtgt ccagctggcc  23640
ggcggcgctt cccggtgccc gctccgccca caatcgggta taaaaaccct ggtgatccga  23700
ggcagaggca cacagctcaa cgacgagttg gtgagctctt acaatcgtct gcgaccggac  23760
ggagtgttcc aactagccgg agccgggaga tcgtccttca ctcccaacca ggcctacctg  23820
accttgcaga gcagctcttc ggagcctcgc tcgggaggca tcggaaccca ccagttcgtg  23880
gaggagtttg tgccctcggt ctacttcaac cccttctcgg gctcgccagg cctctacccg  23940
gacgagttta taccgaactt cgacgcagtg agagaagcgg tggacggcta cgactgaagc  24000
ttgttgatta aaagcccaga aaccaatcag acccttcctc atttccccat cccaatactc  24060
ataagaataa atcattggaa ttaatcattc aataaagatc acttacttga aatctgaaag  24120
tatgtctctg gtgtagttgc tcagcaacac ctcggtaccc tcctcccagc tctggtactc  24180
cagtccccgg cgggcggcga acttcctcca caccttgaaa gggatgtcaa agaggctccg  24240
ggtggaagat gacttcaacc ccgtctaccc ctatggctac gcgcggaatc agaatatccc  24300
cttcctcact ccccccttttg tctcctccga tggattcaaa aacttccccc ctggggtact  24360
```

-continued

```
gtcactcaaa ctggctgatc caatcaccat taccaatggg gatgtatccc tcaaggtggg  24420
aggtggtctc actttgcaag atggaagcct aactgtaaac cctaaggctc cactgcaagt  24480
taatactgat aaaaaacttg agcttgcata tgataatcca tttgaaagta gtgctaataa  24540
acttagttta aaagtaggac atggattaaa agtattagat gaaaaaagtg ctgcggggtt  24600
aaaagattta attggcaaac ttgtggtttt aacaggaaaa ggaataggca ctgaaaattt  24660
agaaaataca gatggtagca gcagaggaat tggtataaat gtaagagcaa gagaagggtt  24720
gacatttgac aatgatggat acttggtagc atggaaccca aagtatgaca cgcgcacact  24780
ttggacaaca ccagacacat ctccaaactg cacaattgct caagataagg actctaaact  24840
cactttggta cttacaaagt gtggaagtca aatattagct aatgtgtctt tgattgtggt  24900
cgcaggaaag taccacatca taaataataa gacaaatcca aaaataaaaa gttttactat  24960
taaactgcta tttaataaga acggagtgct tttagacaac tcaaatcttg gaaaagctta  25020
ttggaacttt agaagtggaa attccaatgt ttcgacagct tatgaaaaag caattggttt  25080
tatgcctaat ttggtagcgt atccaaaacc cagtaattct aaaaaatatg caagagacat  25140
agtttatgga actatatatc ttggtggaaa acctgatcag ccagcagtca ttaaaactac  25200
ctttaaccaa gaaactggat gtgaatactc tatcacattt aactttagtt ggtccaaaac  25260
ctatgaaaat gttgaatttg aaaccacctc ttttaccttc tcctatattg cccaagaatg  25320
aaagaccaat aaacgtgttt ttcatttgaa attttcatgt atctttattg atttttacac  25380
cagcacgagt agacagtctc ccaccaccag cccattttac agtgtacacg gttctctcag  25440
cacgggtagc cttaaatagg gaaatattct cattagtgcg ggaattggac ttggggtcta  25500
taatccacac agtttcctgg cgagccaaac gggggtcggt gattgaaata aagccgtcct  25560
ctgaaaagtc atccaagcgg gcctcacagt ccaaggtcac agtctggtgg aacgagaaga  25620
acgcacagat tcatactcgg aaaacaggat gggtctgtgc ctctccatca gcgccctcag  25680
cagtctctgc cgccggggct cggtgcggct gctgcaaatg ggatcgggat cacaagtctc  25740
tctgactatg atcccaacag ccttcagcat cagtctcctg gtgcgacggg cacagcaccg  25800
catcctgatc tctgccatgt tctcacagta agtgcagcac ataatcacca tgttattcag  25860
cagcccataa ttcagggcgc tccagccaaa gctcatgttg ggaatgatgg aacccacgtg  25920
accatcgtac cagatgcgac agtatatcag atgcctgccc ctcatgaaca cactgcccat  25980
gtacatgatc tctttgggca tgtttctgtt tacaatctgg cggtaccagg ggaagcgctg  26040
gttgaacatg cacccgtaaa tgactctcct gaaccacacg gccagcaggg tgcctcccgc  26100
ccgacactgc agggagccag gggatgaaca gtggcaatgc aggatccagc gctcgtaccc  26160
gctcaccatt tgagctctta ccaagtccag ggtagcgggg cacaggcaca ctgacataca  26220
tctttttaaa atttttattt cctctgtggt gaggatcata tcccagggga ctggaaactc  26280
ttggagcagg gtaaagccag cagcacatgg taatccacgg acagaactta cattatgata  26340
atctgcatga tcacaatcgg gcaacagggg atgttgttca gtcagtgaag ccctggtttc  26400
ctcatcagat cgtggtaaac gggccctgcg atatggatga tggcggagcg agctggattg  26460
aatctcggtt tgcattgtag tggattctct tgcgtacctt gtcgtacttc tgccagcaga  26520
aatgggccct tgaacagcat ataccctcc tacggccgtc ctttcgctgc tgccgctcag  26580
tcatccaact aaagtacatc cattctcgaa gattctggag aagttcctct gcatctgata  26640
aaataaaaaa cccgtccatg cgaattcccc tcatcacatc agccaggact ctgtaggcca  26700
tccccatcca gttaatgctg ccttgtctat cattcagagg gggcggtggc aggactggaa  26760
```

```
gaaccatttt tattccaaac ggtctcgaag gacgataaag tgcaagtcac gcaggtgaca  26820
gcgttcccct ccgctgtgct ggtggaaaca gacagccagg tcaaaaccca ctctattttc  26880
aaggtgctcg accgtggctt cgagcagtgg ctctacgcgc acatccagca taagaatcac  26940
attaaaggct ggccctccat cgatttcatc aatcatcagg ttacattcct gcaccatccc  27000
caggtaattc tcatttttcc agccttggat tatctctaca aattgttggt gtaagtccac  27060
tccgcacatg tggaaaagct cccacagtgc cccctccact ttcataatca ggcagacctt  27120
cataatagaa acagatcctg ctgctccacc acctgcagcg tgttcaaaac aacaagattc  27180
aataaggttc tgccctccgc cctgagctcg cgcctcaatg tcagctgcaa aaagtcactt  27240
aagtcctggg ccactacagc tgacaattca gagccagggc taagcgtggg actggcaagc  27300
gtaagggaaa actttaatgc tccaaagcta gcacccaaaa actgcatgct ggaataagct  27360
ctctttgtgt ctccggtgat gccttccaaa atgtgagtga taaagcgtgg tagtttttct  27420
ttaatcattt gcgtaataga aaagtcctct aaataagtca ctaggacccc agggaccaca  27480
atgtggtagc ttacaccgcg tcgctgaagc atggttagta gagatgagag tctgaaaaac  27540
agaaagcatg cactaaacta aggtggctat tttcactgaa ggaaaaatca ctctctccag  27600
cagcagggta cccactgggt ggcccttgcg gacatacaaa aatcggtccg tgtgattaaa  27660
aagcagcaca gtaagttcct gtcttcttcc ggcaaaaatc acatcagact gggttagtat  27720
gtccctggca tggtagtcat tcaaggccat aaatctgccc tgatatccag taggaaccag  27780
cacactcact tttaggtgaa gcaataccac cccatgcgga ggaatgtgga aagattcagg  27840
gcaaaaaaat tatatctatt gctagcccct tcctggacgg gagcaatccc tccaggacta  27900
tctataaaag catacagaga ttcagccata gcttagcccg cttaccagta gacagaaagc  27960
acagcagtac aagcgccaac agcagcaact gactacccac tgacccagct ccctatttaa  28020
aggcacctta cactgacgta atgaccaaag gtctaaaaac ccgccaaaa aaaacacaca  28080
cgccctgggt gtttttcaca aaaacacttc cgcgttctca cttcctcgta tcgattttgt  28140
gactcaactt ccgggttccc acgttacgtc acttctgccc ttacatgtaa cttggccgta  28200
tggcgccatc ttgcccacgt ccaaaatggc tttcatgacc ggccacgcct ccgcgccggc  28260
cgttagccgt gcgtcgtgac gttatttgca tcaccgcttc tcgtccaatc agcgttggct  28320
ccgccccaaa accgttaaaa ttcaaaagct catttgcata ttaacttttg tttactttgt  28380
ggggtatatt attagatagt taattaagga tgcatgttta aactcgacag cgacacactt  28440
gcatcggatg cagcccggtt aacgtgccgg cacggcctgg gtaaccaggt attttgtcca  28500
cataaccgtg cgcaaaatgt tgtggataag caggacacag cagcaatcca cagcaggcat  28560
acaaccgcac accgaggtta ctccgttcta caggttacga cgacatgtca atacttgccc  28620
ttgacaggca ttgatggaat cgtagtctca cgctgatagt ctgatcgaca atacaagtgg  28680
gaccgtggtc ccagaccgat aatcagaccg acaacacgag tgggatcgtg gtcccagact  28740
aataatcaga ccgacgatac gagtgggacc gtggtcccag actaataatc agaccgacga  28800
tacgagtggg accgtggttc cagactaata atcagaccga cgatacgagt gggaccgtgg  28860
tcccagacta ataatcagac cgacgatacg agtgggacca tggtcccaga ctaataatca  28920
gaccgacgat acgagtggga ccgtggtccc agtctgatta tcagaccgac gatacgagtg  28980
ggaccgtggt cccagactaa taatcagacc gacgatacga gtgggaccgt ggtcccagac  29040
taataatcag accgacgata cgagtgggac cgtggtccca gtctgattat cagaccgacg  29100
```

atacaagtgg aacagtgggc ccagagagaa tattcaggcc agttatgctt tctggcctgt 29160
aacaaaggac attaagtaaa gacagataaa cgtagactaa aacgtggtcg catcagggtg 29220
ctggcttttc aagttcctta agaatggcct caattttctc tatacactca gttggaacac 29280
gagacctgtc caggttaagc accattttat cgcccttata caatactgtc gctccaggag 29340
caaactgatg tcgtgagctt aaactagttc ttgatgcaga tgacgtttta agcacagaag 29400
ttaaaagagt gataacttct tcagcttcaa atatcacccc agcttttttc tgctcatgaa 29460
ggttagatgc ctgctgctta agtaattcct ctttatctgt aaaggctttt tgaagtgcat 29520
cacctgaccg ggcagatagt tcaccggggt gagaaaaaag agcaacaact gatttaggca 29580
atttggcggt gttgatacag cgggtaataa tcttacgtga aatattttcc gcatcagcca 29640
gcgcagaaat atttccagca aattcattct gcaatcggct tgcataacgc tgaccacgtt 29700
cataagcact tgttgggcga taatcgttac ccaatctgga taatgcagcc atctgctcat 29760
catccagctc gccaaccaga acacgataat cactttcggt aagtgcagca gctttacgac 29820
ggcgactccc atcggcaatt tctatgacac cagatactct tcgaccgaac gccggtgtct 29880
gttgaccagt cagtagaaaa gaagggatga gatcatccag tgcgtcctca gtaagcagct 29940
cctggtcacg ttcattacct gaccataccc gagaggtctt ctcaacacta tcaccccgga 30000
gcacttcaag agtaaacttc acatcccgac cacatacagg caaagtaatg gcattaccgc 30060
gagccattac tcctacgcgc gcaattaacg aatccaccat cggggcagct ggtgtcgata 30120
acgaagtatc ttcaaccggt tgagtattga gcgtatgttt tggaataaca ggcgcacgct 30180
tcattatcta atctcccagc gtggtttaat cagacgatcg aaaatttcat tgcagacagg 30240
ttcccaaata gaaagagcat ttctccaggc accagttgaa gagcgttgat caatggcctg 30300
ttcaaaaaca gttctcatcc ggatctgacc tttaccaact tcatccgttt cacgtacaac 30360
attttttaga accatgcttc cccaggcatc ccgaatttgc tcctccatcc acggggactg 30420
agagccatta ctattgctgt atttggtaag caaaatacgt acatcaggct cgaacccttt 30480
aagatcaacg ttcttgagca gatcacgaag catatcgaaa aactgcagtg cggaggtgta 30540
gtcaaacaac tcagcaggcg tgggaacaat cagcacatca gcagcacata cgacattaat 30600
cgtgccgata cccaggttag gcgcgctgtc aataactatg acatcatagt catgagcaac 30660
agtttcaatg gccagtcgga gcatcaggtg tggatcggtg ggcagtttac cttcatcaaa 30720
tttgcccatt aactcagttt caatacggtg cagagccaga caggaaggaa taatgtcaag 30780
ccccggccag caagtgggct ttattgcata agtgacatcg tccttttccc caagatagaa 30840
aggcaggaga gtgtcttctg catgaatatg aagatctggt acccatccgt gatacattga 30900
ggctgttccc tgggggtcgt taccttccac gagcaaaaca cgtagcccct tcagagccag 30960
atcctgagca agatgaacag aaactgaggt tttgtaaacg ccacctttat gggcagcaac 31020
cccgatcacc ggtggaaata cgtcttcagc acgtcgcaat cgcgtaccaa acacatcacg 31080
catatgatta atttgttcaa ttgtataacc aacacgttgc tcaacccgtc ctcgaatttc 31140
catatccggg tgcggtagtc gccctgcttt ctcggcatct ctgatagcct gagaagaaac 31200
cccaactaaa tccgctgctt cacctattct ccagcgccgg gttattttcc tcgcttccgg 31260
gctgtcatca ttaaactgtg caatggcgat agccttcgtc atttcatgac cagcgtttat 31320
gcactggtta agtgtttcca tgagtttcat tctgaacatc ctttaatcat tgctttgcgt 31380
ttttttatta aatcttgcaa tttactgcaa agcaacaaca aaatcgcaaa gtcatcaaaa 31440
aaccgcaaag ttgtttaaaa taagagcaac actacaaaag gagataagaa gagcacatac 31500
ctcagtcact tattatcact agcgctcgcc gcagccgtgt aaccgagcat agcgagcgaa 31560
ctggcgagga agcaaagaag aactgttctg tcagatagct cttacgctca gcgcaagaag 31620
aaatatccac cgtgggaaaa actccaggta gaggtacaca cgcggatagc caattcagag 31680
taataaactg tgataatcaa ccctcatcaa tgatgacgaa ctaacccccg atatcaggtc 31740
acatgacgaa gggaaagaga aggaaatcaa ctgtgacaaa ctgccctcaa atttggcttc 31800
cttaaaaatt acagttcaaa aagtatgaga aaatccatgc aggctgaagg aaacagcaaa 31860
actgtgacaa attaccctca gtaggtcaga acaaatgtga cgaaccaccc tcaaatctgt 31920
gacagataac cctcagacta tcctgtcgtc atggaagtga tatcgcggaa ggaaaatacg 31980
atatgagtcg tctggcggcc tttctttttc tcaatgtatg agaggcgcat tggagttctg 32040
ctgttgatct cattaacaca gacctgcagg aagcggcggc ggaagtcagg catacgctgg 32100
taactttgag gcagctggta acgctctatg atccagtcga ttttcagaga gacgatgcct 32160
gagccatccg gcttacgata ctgacacagg gattcgtata aacgcatggc atacggattg 32220
gtgatttctt ttgtttcact aagccgaaac tgcgtaaacc ggttctgtaa cccgataaag 32280
aagggaatga gatatgggtt gatatgtaca ctgtaaagcc ctctggatgg actgtgcgca 32340
cgtttgataa accaaggaaa agattcatag cctttttcat cgccggcatc ctcttcaggg 32400
cgataaaaaa ccacttcctt ccccgcgaaa ctcttcaatg cctgccgtat atccttactg 32460
gcttccgcag aggtcaatcc gaatatttca gcatatttag caacatggat ctcgcagata 32520
ccgtcatgtt cctgtagggt gccatcagat tttctgatct ggtcaacgaa cagatacagc 32580
atacgttttt gatcccggga gagactatat gccgcctcag tgaggtcgtt tgactggacg 32640
attcgcgggc tatttttacg tttcttgtga ttgataaccg ctgtttccgc catgacagat 32700
ccatgtgaag tgtgacaagt ttttagattg tcacactaaa taaaaaagag tcaataagca 32760
gggataactt tgtgaaaaaa cagcttcttc tgagggcaat ttgtcacagg gttaagggca 32820
atttgtcaca gacaggactg tcatttgagg gtgatttgtc acactgaaag ggcaatttgt 32880
cacaacacct tctctagaac cagcatggat aaaggcctac aaggcgctct aaaaaagaag 32940
atctaaaaac tataaaaaaa ataattataa aaatatcccc gtggataagt ggataacccc 33000
aagggaagtt ttttcaggca tcgtgtgtaa gcagaatata taagtgctgt tccctggtgc 33060
ttcctcgctc actcgagggc ttcgccgtcg ctcgactgcg gcgagcctac tggctgtaaa 33120
aggacagacc acatcatggt tctgtgttca ttaggttgtt ctgtccattg ctgacataat 33180
ccgctccact tcaacgtaac accgcacgaa gatttctatt gttcctgaag gcatattcaa 33240
atcgttttcg ttaccgcttg caggcatcat gacagaacac tacttcctat aaacgctaca 33300
caggctcctg agattaataa tgcggatctc tacgataatg ggagattttc ccgactgttt 33360
cgttcgcttc tcagtggata acagccagct tctctgttta acagacaaaa acagcatatc 33420
cactcagttc cacatttcca tataaaggcc aaggcattta ttctcaggat aattgtttca 33480
gcatcgcaac cgcatcagac tccggcatcg caaactgcac ccggtgccgg gcagccacat 33540
ccagcgcaaa aaccttcgtg tagacttccg ttgaactgat ggacttatgt cccatcaggc 33600
tttgcagaac tttcagcggt ataccggcat acagcatgtg catcgcatag gaatggcgga 33660
acgtatgtgg tgtgaccgga acagagaacg tcacaccgtc agcagcagcg gcggcaaccg 33720
cctccccaat ccaggtcctg accgttctgt ccgtcacttc ccagatccgc gctttctctg 33780
tccttcctgt gcgacggtta cgccgctcca tgagcttatc gcgaataaat acctgtgacg 33840

-continued gaagatcact tcgcagaata aataaatcct ggtgtccctg ttgataccgg gaagccctgg 33900
gccaactttt ggcgaaaatg agacgttgat cggcacgtaa gaggttccaa ctttcaccat 33960
aatgaaataa gatcactacc gggcgtattt tttgagttat cgagattttc aggagctaag 34020
gaagctaaaa tggagaaaaa aatcactgga tataccaccg ttgatatatc ccaatggcat 34080
cgtaaagaac attttgaggc atttcagtca gttgctcaat gtacctataa ccagaccgtt 34140
cagctggata ttacggcctt tttaaagacc gtaaagaaaa ataagcacaa gttttatccg 34200
gcctttattc acattcttgc ccgcctgatg aatgctcatc cggaattccg tatggcaatg 34260
aaagacggtg agctggtgat atgggatagt gttcaccctt gttacaccgt tttccatgag 34320
caaactgaaa cgttttcatc gctctggagt gaataccacg acgatttccg gcagtttcta 34380
cacatatatt cgcaagatgt ggcgtgttac ggtgaaaacc tggcctattt ccctaaaggg 34440
tttattgaga atatgttttt cgtctcagcc aatccctggg tgagtttcac cagttttgat 34500
ttaaacgtgg ccaatatgga caacttcttc gcccccgttt tcaccatggg caaatattat 34560
acgcaaggcg acaaggtgct gatgccgctg gcgattcagg ttcatcatgc cgtctgtgat 34620
ggcttccatg tcggcagaat gcttaatgaa ttacaacagt actgcgatga gtggcagggc 34680
ggggcgtaat ttttttaagg cagttattgg tgcccttaaa cgcctggttg ctacgcctga 34740
ataagtgata ataagcggat gaatggcaga aattcgatga taagctgtca aacatgagaa 34800
tgggtcgag 34809

<210> SEQ ID NO 3
<211> LENGTH: 38159
<212> TYPE: DNA
<213> ORGANISM: Artificial sequence
<220> FEATURE:
<223> OTHER INFORMATION: /note="Description of artificial sequence: pRAB19aGFP_SV40"

<400> SEQUENCE: 3
gaagttccta ttccgaagtt cctattctct agaaagtata ggaacttcaa ttcccatgtc 60
agccgttaag tgttcctgtg tcactcaaaa ttgctttgag aggctctaag ggcttctcag 120
tgcgttacat ccctggcttg ttgtccacaa ccgttaaacc ttaaaagctt taaaagcctt 180
atatattctt ttttttctta taaaacttaa aaccttagag gctatttaag ttgctgattt 240
atattaattt tattgttcaa acatgagagc ttagtacgtg aaacatgaga gcttagtacg 300
ttagccatga gagcttagta cgttagccat gagggtttag ttcgttaaac atgagagctt 360
agtacgttaa acatgagagc ttagtacgtg aaacatgaga gcttagtacg tactatcaac 420
aggttgaact gctgatcttc agatcctcta cgccggacgc atcgtggccg gatccgattt 480
attcaacaaa gccacgttgt gtctcaaaat ctctgatgtt acattgcaca agataaaaat 540
atatcatcat gaacaataaa actgtctgct tacataaaca gtaatacaag gggtgttatg 600
agccatattc aacgggaaac gtcttgctcg aggccgcgat taaattccaa catggatgct 660
gatttatatg ggtataaatg ggctcgcgat aatgtcgggc aatcaggtgc gacaatctat 720
cgattgtatg ggaagcccga tgcgccagag ttgtttctga aacatggcaa aggtagcgtt 780
gccaatgatg ttacagatga gatggtcaga ctaaactggc tgacggaatt tatgcctctt 840
ccgaccatca agcattttat ccgtactcct gatgatgcat ggttactcac cactgcgatc 900
cccgggaaaa cagcattcca ggtattagaa gaatatcctg attcaggtga aaatattgtt 960
gatgcgctgg cagtgttcct gcgccggttg cattcgattc ctgtttgtaa ttgtcctttt 1020

-continued

```
aacagcgatc gcgtatttcg tctcgctcag gcgcaatcac gaatgaataa cggtttggtt   1080
gatgcgagtg attttgatga cgagcgtaat ggctggcctg ttgaacaagt ctggaaagaa   1140
atgcataagc ttttgccatt ctcaccggat tcagtcgtca ctcatggtga tttctcactt   1200
gataacctta tttttgacga ggggaaatta ataggttgta ttgatgttgg acgagtcgga   1260
atcgcagacc gataccagga tcttgccatc ctatggaact gcctcggtga gttttctcct   1320
tcattacaga aacggctttt tcaaaaatat ggtattgata atcctgatat gaataaattg   1380
cagtttcatt tgatgctcga tgagtttttc taatcagaat tggttaattg gttgtaacac   1440
tggcttaatt aactatctaa taatataccc cacaaagtaa acaaaagtta atatgcaaat   1500
gagcttttga attttaacgg ttttggggcg gagccaacgc tgattggacg agaagcggtg   1560
atgcaaataa cgtcacgacg cacggctaac ggccggcgcg gaggcgtggc ctaggccgga   1620
agcaagtcgc ggggctaatg acgtataaaa aagcggactt tagacccgga aacggccgat   1680
tttcccgcgg ccacgcccgg atatgaggta attctgggcg gatgcaagtg aaattaggtc   1740
attttggcgc caaaactgaa tgaggaagtg aaaagtgaaa aatacctgtc ccgcccaggg   1800
cggaatattt accgagggcc gagagacttt gaccgattac gtggggtttc gattgcggtg   1860
tttttttcgc gagaaggtaa actgcccact tggcagtaca tcaagtgtat catatgccaa   1920
gtacgccccc tattgacgtc aatgacggta aatggcccgc ctggcattat gcccagtaca   1980
tgaccttatg ggactttcct acttggcagt acatctacgt attagtcatc gctattacca   2040
tggtgatgcg gttttggcag tacatcaatg ggcgtggata gcggtttgac tcacggggat   2100
ttccaagtct ccaccccatt gacgtcaatg ggagtttgtt ttggcaccaa aatcaacggg   2160
actttccaaa atgtcgtaac aactccgccc cattgacgca aatgggcggt aggcgtgtac   2220
ggtgggaggt ctatataagc agagctggtt tagtgaaccg tcagatccgc tagcgctacc   2280
ggactcagat ctcgagctca agcttcgaat tctgcagtcg acggtaccgc gggcccggga   2340
tccaccggtc gccaccatgg tgagcaaggg cgaggagctg ttcaccgggg tggtgcccat   2400
cctggtcgag ctggacggcg acgtaaacgg ccacaagttc agcgtgtccg gcgagggcga   2460
gggcgatgcc acctacggca agctgaccct gaagttcatc tgcaccaccg gcaagctgcc   2520
cgtgccctgg cccaccctcg tgaccaccct gacctacggc gtgcagtgct tcagccgcta   2580
ccccgaccac atgaagcagc acgacttctt caagtccgcc atgcccgaag gctacgtcca   2640
ggagcgcacc atcttcttca aggacgacgg caactacaag acccgcgccg aggtgaagtt   2700
cgagggcgac accctggtga accgcatcga gctgaagggc atcgacttca aggaggacgg   2760
caacatcctg gggcacaagc tggagtacaa ctacaacagc cacaacgtct atatcatggc   2820
cgacaagcag aagaacggca tcaaggtgaa cttcaagatc cgccacaaca tcgaggacgg   2880
cagcgtgcag ctcgccgacc actaccagca gaacaccccc atcggcgacg gccccgtgct   2940
gctgcccgac aaccactacc tgagcaccca gtccgccctg agcaaagacc ccaacgagaa   3000
gcgcgatcac atggtcctgc tggagttcgt gaccgccgcc gggatcactc tcggcatgga   3060
cgagctgtac aagtaaagcg gccgcgactc tagatcataa tcagccatac cacatttgta   3120
gaggttttac ttgctttaaa aaacctccca cacctccccc tgaacctgaa acataaaatg   3180
aatgcaattg ttgttgttaa cttgtttatt gcagcttata atggttacaa ataaagcaat   3240
agcatcacaa atttcacaaa taaagcattt ttttcactgc attctagttg tggtttgtcc   3300
aaactcatca atgtatctta aatcgaattc aagcttgtcg actcgaagat ctgagctcac   3360
gcgtgaagtt cctattctct agaaagtata ggaacttcgc gtaaattgta agcgttaata   3420
```

-continued

```
ttttgttaaa attcgcgtta aatttttgtt aaatcagctc atttttaac caataggccg   3480
aaatcggcaa aatcccttat aaatcaaaag aatagaccga gatagggttg agtgttgttc   3540
cagtttggaa caagagtcca ctattaaaga acgtggactc caacgtcaaa gggcgaaaaa   3600
ccgtctatca gggcgatggc ccactacgtg aaccatcacc ctaatcaagt tttttggggt   3660
cgaggtgccg taaagcacta aatcggaacc ctaaagggag cccccgattt agagcttgac   3720
ggggaaagcc ggcgaacgtg gcgagaaagg aagggaagaa agcgaaagga gcgggcgcta   3780
gggcgctggc aagtgtagcg gtcacgctgc gcgtaaccac cacacccgcc gcgcttaatg   3840
cgccgctaca gggcgcgtca ggtggcactt ttcggggaaa tgtgcgcgga acccctattt   3900
gtttattttt ctaaatacat tcaaatatgt atccgctcat gagacaataa ccctgataaa   3960
tgcttcaata atattgaaaa aggaagagtc ctgaggcgga aagaaccagc tgtggaatgt   4020
gtgtcagtta gggtgtggaa agtccccagg ctccccagca ggcagaagta tgcaaagcat   4080
gcatctcaat tagtcagcaa ccaggtgtgg aaagtcccca ggctccccag caggcagaag   4140
tatgcaaagc atgcatctca attagtcagc aaccatagtc ccgcccctaa ctccgcccat   4200
cccgccccta actccgccca gttccgccca ttctccgccc catggctgac taattttttt   4260
tatttatgca gaggccgagg ccgcctcggc ctctgagcta ttccagaagt agtgaggagg   4320
ctttttgga ggggggtgggg taccaggtaa gtgtacccaa ttcgccctat agtgagtcgt   4380
attacaattc actggccgtc gttttacaac gtcgtgactg ggaaaaccct ggcgttaccc   4440
aacgtgagac cagaccacct ggtgatggcc tgtaccggga ccgagttcag ctccagtggg   4500
gaggacacag attagaggta ggtttgagta gtgggcgtgg ctaatgtgag tataaaggcg   4560
ggtgtcttac gagggtcttt ttgcttttct gcagacatca tgaacgggac cggcggggcc   4620
ttcgaagggg ggctttttag cccttatttg acaacccgcc tgccgggatg ggccggagtt   4680
cgtcagaatg tgatgggatc tacggtggat gggcgtccag tgcttccagc aaattcctcg   4740
accatgacct acgcgaccgt ggggagctcg tcgcttgaca gcaccgccgc agccgcggca   4800
gccgcagccg ccatgacagc gacgagactg gcctcgagct atatgcccag cagcggtagc   4860
agcccctctg tgcccagttc catcatcgcc gaggagaaac tgctggccct gctggccgag   4920
ctggaagccc tgagccgcca gctggccgcc ctgacccagc aggtgtccga tctccgcgag   4980
caacagcagc agcaaaataa atgaattcaa taaacacaga ttctgattca aacagcaaag   5040
catctttatt atttattttt tcgcgcgcgg taggccctgg tccacctctc ccgatcattg   5100
agagtgcggt ggatttttc caggacccgg tagaggtggg attggatgtt gaggtacatg   5160
ggcatgagcc cgtcccgggg gtggaggtag caccactgca tggcctcgtg ctctggggtc   5220
gtgttgtaga taatccagtc atagcagggg cgctgggcgt ggtgctggat gatgtccttg   5280
aggaggagac tgatggccac ggggagcccc ttggtgtagg tgttggcaaa gcggttaagc   5340
tgggagggat gcatgcgggg ggagatgatg tgcagtttgg cctggatctt gaggttggcg   5400
atgttgccac ccagatcccg ccgggggttc atattgtgca ggaccaccag aacggtgtag   5460
cccgtgcact tggggaactt atcatgcaac ttggaaggga atgcgtggaa gaatttggag   5520
acgcccttgt gcccgcccag gttttccatg cactcatcca tgatgatggc aatgggcccg   5580
tgggctgcgg ctttggcaaa aacgtttctg ggtcagaga catcataatt atgctcctgg   5640
gtgagatcat cataagacat tttaatgaat ttggggcgaa gggtgccaga ttgggggacg   5700
atcgttccct cgggccccgg ggcgaagttc ccctcgcaga tctgcatctc ccaggctttc   5760
```

-continued atctcggagg gggggatcat gtccacctgc ggggcgatga aaaaaacggt ttccggggcg 5820
ggggtgatga gctgcgagga gagcaggttt cttaacagct gggacttgcc gcacccggtc 5880
gggccgtaga tgaccccgat gacgggttgc aggtggtagt tcaaggagat gcagctgccg 5940
tcgtcccgga ggaggggggc cacctcgttg agcatgtctc tcacttggag gttttcccgg 6000
acgagctcgc cgaggaggcg gtccccgccc agcgagagca gctcttgcag ggaagcaaag 6060
tttttcaggg gcttgagccc gtcggccatg ggcatcttgg caagggtctg cgagaggagc 6120
tccaggcggt cccatagctc ggtgacgtgc tctacggcat ctcgatccag cagacttcct 6180
cgtttcgggg gttgggacga ctgcgactgt agggcacgag acgatgggcg tccagcgcgg 6240
ccagcgtcat gtccttccag ggtctcaggg tccgagtgag ggtggtctcc gtcacggtga 6300
aggggtgggc cccgggctgg gcgcttgcaa gggtgcgctt gagactcatc ctgctggtgc 6360
tgaaacgggc acggtcttcg ccctgcgcgt cggcgagata gcagttgacc atgagcttgt 6420
agttaagggc ctcggcggcg tggcccttgg cacggagctt gcctttggaa gagcgcccgc 6480
aggcgggaca gaggagggat tgcagggcgt agagcttggg tgcgagaaag acggactcgg 6540
gagcgaaggc gtccgctccg cagtgggcgc agacggtctc gcactcgacg agccaggtga 6600
gctcgggctg ctcggggtca aaaaccagtt ttcccccgtt ctttttgatg cgcttcttac 6660
ctcgcgtctc catgagtctg tgtccgcgtt cggtgacaaa caggctgtct gtgtccccgt 6720
agacggactt gattggcctg tcctgcaggg gcgtcccgcg gtcctcctcg tagagaaact 6780
cggaccactc tgagacaaag gcgcgcgtcc acgccaagac aaaggaggcc acgtgcgagg 6840
ggtagcggtc gttgtccacc aggggggtcca ccttttccac cgtgtgcaga cacatgtccc 6900
cctcctccgc atccaagaag gtgattggct tgtaggtgta ggccacgtga ccgggggtcc 6960
ccgacggggg ggtataaaag gggcgggtc tgtgctcgtc ctcactctct tccgcgtcgc 7020
tgtccacgag cgccagctgt tggggtaggt attccctctc gagagcgggc atgacctcgg 7080
cactcaggtt gtcagtttct agaaacgagg aggatttgat gttggcctgc cctgccgcaa 7140
tgctttttag gagactttca tccatctggt cagaaaagac tattttttta ttgtcaagct 7200
tggtggcaaa ggagccatag agggcgttgg agagaagctt ggcgatggat ctcatggtct 7260
gatttttgtc acggtcggcg cgctccttgg ccgcgatgtt gagctggaca tactcgcgcg 7320
cgacacactt ccattctggg aagacggtgg tgcgctcgtc gggcacgatc ctgacgcgcc 7380
agccgcgatt atgcagggtg accaggtcca cgctggtggc cacctcgccg cgcaggggct 7440
cgttggtcca gcagaggcgt ccgcccttgc gcgagcagaa cgggggcagc acatcaagca 7500
gatgctcgtc agggggtcc gcatcgatgg tgaagatgcc cggacagagt tccttgtcaa 7560
aataatcgat tttgaggat gcatcatcca aggccatctg ccactcgcgg gcggccagcg 7620
ctcgctcgta ggggttgagg ggcggacccc agggcatggg atgcgtgagg gcggaggcgt 7680
acatgccgca gatgtcgtag acatagatgg gctccgagag gatgccgatg taggtgggat 7740
aacagcgccc cccgcggatg ctggcgcgca catagtcata caactcgtgc gagggggcca 7800
agaaagcggg gccgagattg gtgcgctggg gctgctcggc gcggaagacg atctggcgaa 7860
agatggcatg cgagttggag gagatggtgg gccgttggaa gatgttaaag tgggcgtggg 7920
gcaagcggac cgagtcgcgg atgaagtgcg cgtaggagtc ttgcagcttg gcaacgagct 7980
cggcggtgac aaggacgtcc atggcgcagt agtccagcgt ttcacggatg atgtcataac 8040
ccgcctcttc tttcttctcc cacagcgcgc ggttgagggc gtactcctcg tcatccttcc 8100
agtactcccg gagcgggaat cctcgatcgt ccgcacggta agagcccagc atgtagaaat 8160

-continued

```
ggttcacggc cttgtaggga cagcagccct tctccacggg gagggcgtaa gcttgagcgg   8220
ccttgcggag cgaggtgtgc gtcagggcga aggtatccct aaccatgact ttcaagaact   8280
ggtacttgaa atccgagtcg tcgcagccgc cgtgctccca gagctcgaaa tcggtgcgct   8340
tcttcgagag gggttaggc agagcgaaag tgacgtcatt gaagagaatc ttgcctgccc   8400
gcggcatgaa attgcgggtg atgcggaaag ggcccggaac ggaggctcgg ttgttgatga   8460
cctgggcggc gaggacgatc tcgtcgaagc cgttgatgtt gtgcccgacg atgtagagtt   8520
ccatgaatcg cgggcggcct ttgatgtgcg gcagcttttt gagttcctcg taggtgaggt   8580
cctcggggca ttgcaggccg tgctgctcga gcgcccactc ctggagatgt gggttggctt   8640
gcatgaatga agcccagagc tcgcgggcca tgagggtctg gagctcgtcg cgaaagaggc   8700
ggaactgctg gcccacggcc atcttttctg gggtgacgca gtagaaggtg agggggtccc   8760
gctcccagcg atcccagcgt aagcgcacgg cgagatcgcg agcgagggcg accagctcgg   8820
ggtccccgga gaatttcatg accagcatga aggggacgag ctgcttgccg aaggacccca   8880
tccaggtgta ggtttctaca tcgtaggtga caaagagccg ctccgtgcga ggatgagagc   8940
cgattgggaa gaactggatt tcctgccacc agttggtcga gtggctgttg atgtgatgaa   9000
agtagaaatc ccgccggcga accgagcact cgtgctgatg cttgtaaaag cgtccgcagt   9060
actcgcagcg ctgcacgggc tgtacctcat ccacgagata cacagcgcgt cccttgagga   9120
ggaacttcag gagtggcggc cctggctggt ggttttcatg ttcgcctgcg tgggactcac   9180
cctggggctc ctcgaggacg gagaggctga cgagcccgcg cgggagccag gtccagattt   9240
cggcgcggcg gggcggaga gcgaaaacga gggcgcgcag ttgggagctg tccatggtgt   9300
cgcggagatc caggtccggg ggcagggttc tgaggttgac ctcgtagagg cgggtgaggg   9360
cgtgcttgag atgcagatgg tacttgatct ccacgggtga gttggtggtc gtgtccacgc   9420
attgcatgag cccgtagctg cgcggggcca cgaccgtgcc gcggtgcgct tttagaagcg   9480
gtgtcgcgga cgcgctcccg gcggcagcgg cggttccggc cccgcgggca gtggcggtag   9540
aggcacgtcg gcgtggcgct cgggcaggtc ccggtgctgc gccctgagag cgctggcgtg   9600
cgcgacgacg cggcggttga catcctggat ctgccgcctt tgcgtgaaga ccacgggccc   9660
cgtgactttg aacctgaaag acagttcaac agaatcaatc tcggcgtcat tgacggcggc   9720
ctgacgcagg atctcttgca cgtcgcccga gttgtcctgg taggcgatct cggacatgaa   9780
ctgctcgatt tcctcctcct ggagatcgcc gcggcccgcg cgctctacgg tggcggcaag   9840
gtcattcgag atgcgaccca tgagctgcga gaaggcgccc aggccgctct cgttccagac   9900
gcggctgtaa accacgtccc cgtcggcgtc gcgcgcgcgc atgaccacct gcgcgaggtt   9960
gagctccacg tgccgcgtaa agacggcgta gttgcgcagg cgctggaaga ggtagttgag  10020
ggtggtggcg atgtgctcgg tgacgaagaa gtacataatc cagcggcgca ggggcatttc  10080
gctgatgtcg ccaatggcct ccagcctttc catggcctcg tagaaatcca cggcgaagtt  10140
gaaaaactgg gcgttgcggg ccgagaccgt gagctcgtct tccaggagcc tgatgagttc  10200
ggcgatggtg gcgcgcacct cgcgctcgaa atcccagggg gcctcctcct cttcctcttc  10260
ttccatgacg acctcttctt ctatttcttc ctctgggggc ggtggtggtg gcggggcccg  10320
acgacgacgg cgacgcaccg ggagacggtc gacgaagcgc tcgatcatct ccccgcggcg  10380
gcgacgcatg gtttcggtga cggcgcgacc ccgttcgcga ggacgcagcg tgaagacgcc  10440
gccggtcatc tcccggtaat ggggtgggtc cccgttgggc agcgataggg cgctgacaat  10500
```

-continued

```
gcatcttatc aattgcggtg tagggcacgt gagcgcgtcg agatcgaccg gatcggagaa  10560
tctttcgagg aaagcgtcta gccaatcgca gtcgcaaggt aagctcaaac acgtagcagc  10620
cctgtggacg ctgttagaat tgcggttgct gatgatgtaa ttgaagtagg cgtttttgag  10680
gcggcggatg gtggcgagga ggaccaggtc cttgggtccc gcttgctgga tgcggagccg  10740
ctcggccatg ccccaggcct ggccctgaca ccggctcagg ttcttgtagt agtcatgcat  10800
gagcctctcg atgtcatcac tggcggaggc ggagtcttcc atgcgggtga ccccgacgcc  10860
cctgaacggc tgcacgagcg ccaggtcggc gacgacgcgc tcggcgagga tggcctgttg  10920
cacgcgggtg agggtgtcct ggaagtcgtc catgtcgacg aagcggtggt aggcccctgt  10980
gttgatggtg taagtgcagt tggccataag cgaccagttg acggtctgca ggccgggttg  11040
cacgacctcg gagtacctga gccgcgagaa ggcgcgcgag tcgaagacat agtcgttgca  11100
ggtgcgcacg aggtactggt atccgactag aaagtgcggc ggcggctggc ggtagagcgg  11160
ccagcgctgg gtggccggcg cgcccggggc caggtcctca agcatgagtc ggtggtagcc  11220
gtagaggtag cgggacatcc aggtgatgcc ggcggcggtg gtggaggcgc gcgggaactc  11280
gcggacgcgg ttccagatgt tgcgcagggg caggaaatag tccatggtcg gcacggtctg  11340
gccggtgaga cgcgcgcagt cattgatgct ctagaggcaa aaacgaaagc ggttgagcgg  11400
gctcttcctc cgtagcctgg cggaacgcaa acgggttagg ccgcgtgtgt accccggttc  11460
gagtcccctc gaatcaggct ggagccgcga ctaacgtggt attggcactc ccgtctcgac  11520
ccaagcccga tagccgccag gatacggcgg agagcccttt ttgtcggccg aggggagtcg  11580
ctagacttga aagcggccga aaaccctgcc gggtagtggc tcgcgcccgt agtctggaga  11640
agcatcgcca gggttgagtc gcggcagaac ccggttcaag gacggccgcg gcgagcggga  11700
cttggtcacc ccgccgattt aaagacccac agccagccga cttctccagt tacgggagcg  11760
agccccctttt tttcttttttg ccagatgcat cccgtcctgc gccaaatgcg tcccaccccc  11820
ccggcgacca ccgcgaccgc ggccgtagca ggcgccggcg ctagccagcc acagccacag  11880
acagagatgg acttggaaga gggcgaaggg ctggcgagac tgggggcgcc gtccccggag  11940
cgacatcccc gcgtgcagct gcagaaggac gtgcgcccgg cgtacgtgcc tgcgcagaac  12000
ctgttcaggg accgcagcgg ggaggagccc gaggagatgc gcgactgccg gtttcgggcg  12060
ggcagggagc tgcgcgaggg cctggaccgc cagcgcgtgc tgcgcgacga ggatttcgag  12120
ccgaacgagc agacggggat cagccccgcg cgcgcgcacg tggcggcggc caacctggtg  12180
acagcctacg agcagacggt gaagcaggaa cgcaactttc aaaagagttt caacaaccac  12240
gtgcgcaccc tgatcgcgcg cgaggaggtg gccctgggcc tgatgcacct gtgggacctg  12300
gcggaggcca ttgtgcagaa cccggacagc aagcctctga cggcacaact gttcctggtg  12360
gtgcagcaca gcagggacaa cgaggcgttc agggaggcgc tgctaaacat cgccgagccc  12420
gagggccgct ggctgctgga gctgatcaac atcttgcaaa gcatcgtagt gcaggagcgc  12480
agcctgagct tggccgagaa ggtggcggcg atcaactact cggtgctaag cctgggcaag  12540
ttttacgcgc gcaagattta caagacgccg tacgtgccca tagacaagga ggtgaaaata  12600
gacagctttt acatgcgcat ggcgctcaag gtgctgacgc tgagcgacga cctgggcgtg  12660
taccgcaacg accgcatcca caaggccgtg agcacgagcc ggcggcgcga gctgagcgac  12720
cgcgagctga tgctaagcct gcgccgggcg ctggtaggtg gcgccgccgg cggcgaggag  12780
tcctacttcg acatgggggc ggacctgcat tggcagccga gccggcgcgc cttggaggcc  12840
gcctacggtc cagaggactt ggatgaggat gaggaagagg aggaggatgc acccgttgcg  12900
```

gggtactgac gcctccgtga tgtgttttta gatgtcccag cagcaagccc cggaccccgc 12960
cataagggcg gcgctgcaaa gccagccgtc cggtctagca tcggacgact gggaggccgc 13020
gatgcaacgc atcatggccc tgacgacccg caaccccgag tcctttagac aacagccgca 13080
ggccaacaga ctttcgacca ttctggaggc ggtggtcccc tctcggacca accccacgca 13140
cgagaaggtg ctggcgatcg tgaacgcgct ggcggagaac aaggctattc gtcccgacga 13200
ggctgggctg gtatacaacg ccctgctgga gcgcgtgggc cgctacaaca gcacgaacgt 13260
gcagtccaac ctggaccggc tggtgacgga cgtgcgcgag gccgtggcgc agcgcgagcg 13320
gttcaagaac gagggcctgg gctcgctggt ggcgctgaac gccttcctgg cgacgcagcc 13380
ggcgaacgtg ccgcgcgggc aggacgatta taccaacttt atcagcgcgc tgcggctgat 13440
ggtgaccgag gttccccaga gcgaggtgta ccagtcgggc ccggactact ttttccagac 13500
tagcagacag ggcctgcaga cggtgaacct gagccaggct ttcaagaacc tgcgcgggct 13560
gtggggcgtg caggcgcccg tgggcgaccg gtcgacggtg agcagcttgc tgacgcccaa 13620
ctcgcggctg ctgctgctgc tgatcgcgcc cttcaccgac agcggcagcg tgaaccgcaa 13680
ctcgtacctg ggtcacctgc tgacgctgta ccgcgaggcc ataggccagg cacaggtgga 13740
cgagcagacc ttccaggaga tcactagtgt aagccgcgcg ctgggtcaga acgacaccga 13800
cagtctgagg gccaccctga acttcttgct gaccaataga cagcagaaga tcccggcgca 13860
gtatgcgctg tcggccgagg aggagcgcat cctgagatat gtgcagcaga gcgtagggct 13920
gtttctgatg caggaggggg ccacccccag cgccgcgctg gacatgaccg cgcgcaacat 13980
ggaacctagc atgtacgccg ccaaccggcc gtttatcaat aagctgatgg actacctgca 14040
ccgcgcggcg tccatgaact cggactactt taccaatgcc attttgaacc cgcactggct 14100
cccgccgccg gggttctaca cgggcgagta cgacatgcct gaccccaacg acgggttttt 14160
gtgggacgac gtggacagcg cggtgttctc accgaccttg caaaagcgcc aggaggcggt 14220
gcgcacgccc gcgagcgagg gcgcggtggg tcggagcccc tttcctagct tagggagttt 14280
gcatagcttg ccgggctcgg tgaacagcgg cagggtgagc cggccgcgct tgctgggcga 14340
ggacgagtac ctaaacgact cgctgctgca gccgccgcgg gtcaagaacg ccatggccaa 14400
taacgggata gagagtctgg tggacaaact gaaccgctgg aagacctacg ctcaggacca 14460
tagggagcct gcgcccgcgc cgcggcgaca gcgccacgac cggcagcggg gcctggtgtg 14520
ggacgacgag gactcggccg acgatagcag cgtgttggac ttgggcggga gcggtggggt 14580
caacccgttc gcgcatctgc agcccaaact ggggcgacgg atgttttgaa tgcaaaataa 14640
aactcaccaa ggccatagcg tgcgttctct tccttgttag agatgaggcg tgcggtggtg 14700
tcttcctctc ctcctccctc gtacgagagc gtgatggcgc aggcgaccct ggaggttccg 14760
tttgtgcctc cgcggtatat ggctcctacg gagggcagaa acagcattcg ttactcagag 14820
ctggctccgc tgtacgacac cactcgcgtg tacttggtgg acaacaagtc ggcggacatc 14880
gcttccctga actaccaaaa cgaccacagc aactttctga ccacggtggt gcaaaacaac 14940
gatttcaccc ccgccgaggc tagcacgcag acgataaatt ttgacgagcg gtcgcggtgg 15000
ggcggtgatc tgaagaccat tctgcacacc aacatgccca atgtgaacga gtacatgttt 15060
accagcaagt ttaaggcgcg ggtgatggtg gctaggaaac acccacaggg ggtagaagca 15120
acagatttaa gcaaggatat cttagagtac cagtggtttg agtttaccct gcccgagggc 15180
aacttttccg agaccatgac catagacctg atgaacaacg ccatcttgga aaactacttg 15240

-continued caagtggggc ggcaaaatgg cgtgctggag agcgatatcg gagtcaagtt tgacagcagg 15300
aatttcaagc tgggctggga ccccgtgacc aagctggtga tgccaggggt ctacacctat 15360
gaggccttcc acccggacgt ggtgctgctg cctggctgcg gggtggactt caccgagagc 15420
cgcctaagca accttctggg cattcgcaag aagcaacctt tccaagaggg cttcagaatc 15480
atgtatgagg atctcgaagg gggcaacatt cccgcacttc tgaatgtgac caagtacctg 15540
gaaagcaaga agaagctaga ggagaatgcc gctaaggcta atggtcctgc aagaggagac 15600
agtagtgtct caagagaggt ggaaaaggca gctgaaaaag agcttgtcat tgagcccatc 15660
aagcaagatg atagcaagag aagttacaac ctcattgagg gtacccatga caccctgtac 15720
cgaagctggt acctgtccta tacctacggg gaccccgaga agggggtgca gtcgtggacg 15780
ctgctcacca ccccggacgg tcactgcggc gcggagcaag tctactggtc gctgccggac 15840
ctcatgcaag accccgtcac cttccgctct acccagcaag tcagcaacta ccccgtggtc 15900
ggcgccgagc tcatgccttt ccgcgccaag agcttttaca acgacctcgc cgtctactcc 15960
cagctcatcc gcagctacac ctccctcacc cacgtcttca accgcttccc cgacaaccag 16020
atcctctgcc gcccgcccgc gcccaccatc accaccgtca gtgaaaacgt gcctgctctc 16080
acagatcacg ggacgctacc gctgcgcagc agtatccgcg gagtccagcg agtgaccgtc 16140
actgacgccc gtcgccgcac ctgtccctac gtctacaagg ccctgggcat agtcgcgccg 16200
cgcgtgcttt ccagtcgcac cttctaaaaa atgtctattc tcatctcgcc cagcaataac 16260
accggctggg gtcttactag gcccagcacc atgtacggag gagccaagaa acgctcccag 16320
cagcaccccg tccgcgtccg cggccacttt cgcgctccct ggggcgcata caagcgcggg 16380
cggacttcca ccgccgccgc cgtgcgcacc accgtcgacg acgtcatcga ctcggtggtc 16440
gccgatgcgc gcaactatac cccgcccccc tccaccgtgg acgcggtcat tgacagcgtg 16500
gtggccgacg cgcgcgacta tgccagacgc aagagccggc ggcgacggat cgccaggcgc 16560
caccggagca cgcccgccat gcgcgccgcc cgggctctgc tgcgccgcgc cagacgcacg 16620
ggccgccggg ccatgatgcg agccgcgcgc cgcgctgcca ctgcacccac ccccgcaggc 16680
aggactcgca gacgagcggc cgctgccgcc gccgcggcca tctctagcat gaccagaccc 16740
aggcgcggaa acgtgtactg ggtgcgcgac tccgtcacgg gcgtgcgcgt gcccgtgcgc 16800
actcgtcctc ctcgtccctg atctaatgct tgtgtcctcc cccgcaagcg acgatgtcaa 16860
agcgcaaaat caaggaggag atgctccagg tcgtcgcccc ggagatttac ggaccccccgg 16920 accagaaacc ccgcaaaatc aagcgggtta aaaaaaagga tgaggtggac gaggggggcag 16980 tagagtttgt gcgcgagttc gctccgcggc ggcgcgtaaa ttggaagggg cgcagggtgc 17040
agcgtgtgtt gcggcccggc acggcggtgg tgttcacgcc cggcgagcgg tcctcggtca 17100
ggagcaagcg tagctatgac gaggtgtacg gcgacgacga catcctggac caggcggcgg 17160
agcgggcggg cgagttcgcc tacgggaagc ggtcgcgcga agaggagctg atctcgctgc 17220
cgctggacga aagcaacccc acgccgagcc tgaagcccgt gaccctgcag caggtgctgc 17280
cccaggcggt gctgctgccg agccgcgggg ttaagcgcga gggcgagagc atgtacccga 17340
ccatgcagat catggtgccc aagcgccggc gcgtggagga cgtgctggac accgtgaaaa 17400
tggatgtgga gcccgaggtc aaggtgcgcc ccatcaagca ggtggcgccg ggcctgggcg 17460
tgcaaaccgt ggacattcag atccccaccg acatggatgt cgacaaaaaa ccctcgacca 17520
gcatcgaggt gcaaaccgac ccctggctcc cagcctccac cgctaccgcc gccacggcca 17580
ccgagcctcc caggaggcga agatggggcc ctgccaaccg gctgatgccc aactacgtgt 17640

```
tgcatccttc catcatcccg acgccgggct accgcggcac ccggtactac gccagccgca  17700
ggcgcccagc cagtaaacgc cgccgccgca ccgccacccg ccgccgtctg gcccccgccc  17760
gcgtgcgccg cgtgaccacg cgccggggcc gctcgctcgt tctgcccacc gtgcgctacc  17820
accccagcat cctttaatcc gtgtgctgtg atactgttgc agagagatgg ctctcacttg  17880
ccgcctgcgc atccccgtcc cgaattaccg aggaagatcc cgccgcagga gaggcatggc  17940
aggcagtggc ctgaaccgcc gccggcggcg ggccatgcgc aggcgcctga gtggcggctt  18000
tctgcccgcg ctcatcccca taatcgccgc ggccatcggc acgatcccgg gcatagcttc  18060
cgttgcgctg caggcgtcgc agcgccgttg atgtgcgaat aaagcctctt tagactctga  18120
cacacctggt cctgtatatt tttagaatgg aagacatcaa ttttgcgtcc ctggctccgc  18180
ggcacggcac gcggccgttc atgggcacct ggaacgagat cggcaccagc cagctgaacg  18240
ggggcgcctt caattggagc agtgtctgga gcgggcttaa aaatttcggc tcgacgctcc  18300
ggacctatgg gaacaaggcc tggaatagta gcactgggca gttgttaagg gaaaagctca  18360
aagaccagaa cttccagcaa aaggtggtgg acgggctggc ctcgggcatt aacggggtgg  18420
tggacatcgc gaacccaggc cgtgcagcgc gagataaaca accgcctgga cccgcggccg  18480
cccacggtgg tggagatgga agatgcaact cctccgccgc ccaagggcga gaagcgaccg  18540
cggcccgacg cggaggagac gatcctgcag gtggacgagc cgccctcgta cgaggaggcc  18600
gtaaaggccg gcatgcccac cacgcgcatc atcgcgccac tggccacggg tgtaatgaaa  18660
cccgccaccc ttgacctgcc tccaccaccc acgcccgctc caccgaaggc agctccggta  18720
gtgcagcccc ctccggtggc gaccgccgtg cgccgcgtcc ccgcccgccg ccaggcccaa  18780
aactggcaaa gcacgctgca cagtattgtg ggcctgggag tgaaaagtct gaagcgccgc  18840
cgatgctatt gaaagagagg aaggaagaca ctaaagggag agcttaactt gtatgtgcct  18900
taccgccaga gaacgcgcga agatggccac cccctcgatg atgccgcagt gggcgtacat  18960
gcacatcgcc gggcaggacg cctcggagta cctgagcccg ggtctggtgc agtttgcccg  19020
cgccaccgac acgtacttca gcctgggcaa caagtttagg aaccccacgg tggccccaac  19080
ccacgatgtg accacggacc ggtcccagcg tctgacgctg cgcttcgtgc ccgtggatcg  19140
cgaggacacc acgtactcgt acaaggcgcg cttcactctg gccgtgggcg acaaccgggt  19200
gctagacatg gccagcactt actttgacat ccgcggcgtt ctggaccgcg gccccagctt  19260
caaaccctac tcgggcacgg cttacaacag cctggccccc aagggcgccc ccaattccag  19320
tcagtgggat gctcaagaaa aaaatggaca aggaggaaat gacatggtta ccaaaactca  19380
cacatttggc gtggctgcta tgggaggaac aaatattaca aaccagggtt tgttaattgg  19440
aactgaagaa acagccgata atcctccaaa ggaaatcttt gcagacaaat tattccagcc  19500
agaacctcaa gtaggagagg aaaactggca agacagcaat gcattctatg gaggcagggc  19560
tcttaagaag gaaactaaaa tgaaaccatg ctatggatct tatgctagac caacaaacac  19620
aagtggcgga caggctaagc ttaaaactgg tgacaatatc gatcctacca aggatttcga  19680
catagatctt gctttcttcg atactcctgg cggaaatcct ccagcaggtg gtagtggaac  19740
ggaagaatac aaagcagata ttgttatgta cactgaaaat gtcaaccttg aaacacctga  19800
cactcatgtg gtgtacaaac cagccaaaga ggatgaaagt tctcaggcca acttggttca  19860
gcagtccatg cccaacagac ccaactacat tggcttcaga gacaattttg tggggctcat  19920
gtattacaac agcactggca acatgggagt gctggctggt caggcctctc agttgaatgc  19980
```

-continued

```
tgtggtggac ttgcaagaca gaaacacaga gctgtcttac cagctcttgc tagattctct  20040
gggtgacaga accagatact ttagcatgtg gaactctgcg gtggacagct atgatccaga  20100
tgtcagaatc attgaaaatc acggtgtgga agatgagctt ccaaactatt gctttccatt  20160
ggatggctct ggtaccaatg ctgcctacca aggtgtaaag gttcaagatg gtgaagacgg  20220
ggataaagaa actgaatggg aaaaagatac caaagtcgca gatcgtaacc aactgtgcaa  20280
gggtaacatc ttcgccatgg agatcaacct ccaggccaac ctgtggaaga gttttctgta  20340
ctcgaacgtg gccctgtacc tgcccgactc ctacaagtac acgccggcca acatcacgct  20400
gcccgccaac accaacacct acgagtacat gaacggccgc gtggtagccc cctcgctggt  20460
ggacgcatac gtcaacatcg gtgcgcgctg gtcgctggac cccatggaca acgtcaaccc  20520
cttcaaccac caccgcaacg cgggcctgcg ctaccgctcc atgcttctcg gcaacggccg  20580
ctacgtgccc ttccacatcc aagtgcccca aaagttcttt gccattaaga acctgctcct  20640
gctccccggc tcctacacct acgagtggaa cttccgcaag gatgtcaaca tgatcctgca  20700
gagttccctc ggaaacgacc tgcgcgtcga cggcgcctcc gtgcgcttcg acagcgtcaa  20760
cctctacgct accttcttcc ccatggcgca caacaccgcc tccaccctgg aagccatgct  20820
gcgcaacgac accaacgacc agtcctttaa cgactacctc tcggccgcca acatgctcta  20880
ccccataccg gccaaggcca ccaacgtgcc catctccatc cctcgcgcga actgggctgc  20940
cttccgcggc tggagtttca cccggctcaa gaccaaggaa actccttccc ttggctcggg  21000
tttcgacccc tactttgtct actcgggctc catcccctac ctcgacggga ccttctacct  21060
caaccacacc ttcaaaaagg tgtccattat gttcgactcc tcggtcagct ggcccggcaa  21120
cgaccggctg ctcacgccga atgagttcga gatcaagcgc agcgtcgacg gggagggcta  21180
caacgtggcc caatgcaaca taaccaagga ctggttcctc gtccagatgc tctcccacta  21240
caacatcggc taccagggct tccacgtgcc cgagggctac aaggaccgca tgtactcctt  21300
tttccgcaac ttccagccca tgagcaggca ggtggtggat gagatcaact acaaggacta  21360
caaggccgtc accctgccct tccagcacaa caactctggc ttcaccggct acctcgcacc  21420
caccatgcgt caggggcagc cttaccccgc caacttccct tacccgctca tcggctccac  21480
cgcagtcccc tccgtcaccc agaaaaagtt cctctgcgac agggtcatgt ggcgcatccc  21540
cttctccagc aacttcatgt ccatgggtgc cctcaccgac ctgggtcaga acatgctcta  21600
tgccaactcg gcccacgcgc tcgacatgac cttcgaggtg gaccccatgg atgagcccac  21660
cctcctctat cttctcttcg aagttttcga cgtggtcaga gtgcaccagc cgcaccgcgg  21720
cgtcatcgag gccgtctacc tgcgcacacc cttctccgcc ggcaacgcca ccacctaagc  21780
atgagcggtt ccagcgaacg agaactcgcg gccatcgtgc gcgacctggg ctgcgggccc  21840
tactttttgg gcacccacga caagcgcttc ccgggcttcc tagccggcga caagctggcc  21900
tgcgccatcg tcaacacggc cggccgcgag accggaggcg tgcactggct cgccttcggc  21960
tggaacccgc gctcgcgcac ctgctacatg ttcgacccct ttgggttctc ggaccgccgg  22020
ctcaagcaga tttacagctt cgagtacgag gccatgctgc gccgaagcgc cctggcctcc  22080
tcgcccgacc gctgtctcag cctcgaacag tccacccaga ccgtgcaggg gcccgactcc  22140
gccgcctgcg gactttttttg ttgcatgttc ttgcatgcgt tcgtgcactg gcccgaccga  22200
cccatggacg gaaaccccac catgaacttg ctgacggggg tgcccaacgg catgctacaa  22260
tcgccacagg tgctgcccac cctccggcgc aaccaggagg agctctaccg cttcctcgcg  22320
cgccactccc cttacttccg atcccaccgc gccgccatcg aacacgccac cgcttttgac  22380
```

aaaatgaaac aactgcgtgt atctcaataa acagcacttt ttattttaca tgcactggag 22440
tatatgcaag ttatttaaaa gtcgaagggg ttctcgcgct cgtcgttgtg cgccgcgctg 22500
gggagggcca cgttgcggta ctggtacttg gaaagccact tgaactcggg gatcaccagt 22560
ttgggcactg gggtctcggg gaaggtctcg ctccacatgc gccggctcat ctgcagggcg 22620
cccagcatgt cagggccgga gatcttgaaa tcacagttgg ggccggtgct ctgcgcgcgc 22680
gagttgcggt acacggggtt gcagcactgg aacaccatca gactggggta cttcacactg 22740
gcaagcacgc tcttgtcgct aatctgatcc ttgtccaggt cctcggcgtt gctcaggccg 22800
aacggggtca tcttgcacag ctggcggccc aggaagggca cgctctgagg cttgtggtta 22860
cactcgcagt gcacgggcat cagcatcatc cccgcgccgc gctgcatatt cgggtagagg 22920
gccttgacga aggccgcgat ctgcttgaaa gcttgctggg ccttggcccc ctcgctgaag 22980
aacagaccgc agctcttccc gctgaactgg ttattcccgc acccggcatc atgcacgcag 23040
cagcgcgcgt catggctggt cagttgcacc acgctccgtc cccagcggtt ctgggtcacc 23100
ttagccttgc tgggctgctc cttcagcgcg cgctgtccgt tctcgctggt cacatccatc 23160
tccaccacgt ggtccttgtg aatcatcacc gttccatgca gacacttgag ctgaccttcc 23220
acctcggtgc agccgtgatc ccacaggacg cagccggtgc actcccaatt cttgtgcgcg 23280
atcccgctgt ggctgaaaat gtaaccttgc aacaggcgac ccataatggt gctaaatgat 23340
ttctgggtgg tgaatgtcag ttgcatcccg cgggcctcct cgttcatcca ggtctggcac 23400
atcttctgga agatctcggt ctgctccggc atgagcttgt aagcatcgcg caagccgctg 23460
tcgacgcggt agcgttccat cagcacgttc atggtatcca tgcccttctc ccatgacgag 23520
accagaggca gactcagggg gttgcgcacg ttcaggacac caggggtcgc gggctcgacg 23580
atgcgttttc cgtccttgcc ttccttcaac agaaccggag gctggctgaa tcccactccc 23640
acgatcacgg cgtcttcctg ggcatctct tcgtcggggt ctaccttggt cacatgcttg 23700
gtctttctgg cttgcttctt ttttggaggg ctgtccacgg ggaccacgtc ctcctcggaa 23760
gacccggagc ccacccgctg atactttcgg cgcttggtgg gcagaggagg tggcggcggc 23820
gaggggctcc tctcctgctc cggcggatag cgcgccgacc cgtggccccg gggcggagtg 23880
gcctctcgct ccatgaaccg gcgcacgtcc tgactgccgc cggccattgt ttcctagggg 23940
aagatggagg agcagccgcg taagcaggag caggaggagg acttaaccac ccacgagcaa 24000
cccaaaatcg agcaggacct gggcttcgaa gagccggctc gtctaaaacc cccacaggat 24060
gaacaggagc acgagcaaga cgcaggccag gaggagaccg acgctgggct cgagcatggc 24120
tacctgggag gagaggagga tgtgctgcta aaacacctgc agcgccagtc cctcatcctc 24180
cgggacgccc tggccgaccg gagcgaaacc cccctcagcg tcgaggagct gtgtcgggcc 24240
tacgagctca acctcttctc gccgcgcgtg ccccccaaac gccagcccaa cggcacctgc 24300
gagcccaacc cgcgtctcaa cttctatccc gtctttgcgg tccccgaggc ccttgccacc 24360
tatcacatct tttcaagaa ccaaaagatc cccatctcct gtcgcgccaa tcgcactcgc 24420
gccgacgcgc tcctcgctct ggggcccggc gcgcgcatac ctgatatcgc ttccctggaa 24480
gaggtgccca agatcttcga agggctcggt cgggacgaga cgcgcgcggc aaacgctctg 24540
aaagaaacag cagaggaaga gggttacact agcgccctgg tagagttgga aggcgacaac 24600
gccaggctgg ccgtgcttaa gcgcagcgtc gagctcaccc atttcgccta ccccgccgtc 24660
aacctcccgc ccaaggtcat gcgtcgcatc atggatcagc tcatcatgcc ccacatcgag 24720

```
gcccttgatg aaagtcagga acagcgcccc gagaacgccc agcccgtggt cagcgacgag   24780

atgctcgcgc gctggctcgg gacccgcgac ccccaggccc tggagcagcg gcgcaagctc   24840

atgctggccg tggtcctggt cacccttgag ctcgaatgca tgcgccgctt ttttaccgac   24900

cccgagaccc tgcgcaaggt cgaggagacc ctgcactaca ctttcagaca cggtttcgtc   24960

aggcaggcct gcaagatctc caacgtggag ctgaccaacc tggtctcctg cctggggatc   25020

ctacacgaga accgcttggg acagaccgtg ctccactcta ccctgaaggg cgaggcgcgg   25080

cgggactaca tccgcgactg cgtctttctc tttctctgcc acacatggca agcggccatg   25140

ggcgtgtggc agcagtgtct cgaggacgag aacctgaagg agctggacaa gcttcttgct   25200

agaaacctta aaaagctgtg gacgggcttc gacgagcgca ccgtcgcctc ggacctggcc   25260

gagatcgtct tccccgagcg cctgaggcag acgctgaaag gagggctgcc cgacttcatg   25320

agccagagca tgttgcaaaa ctaccgcact ttcattctcg agcgatctgg gatgctgccc   25380

gccacctgca acgccttccc ctccgacttt gtcccgctga gctaccgcga gtgtcccccg   25440

ccgctgtgga gccactgcta cctcttgcag ctggccaact acattgccca ccactcggat   25500

gtgatcgagg acgtgagcgg cgaggggctg ctcgagtgcc actgtcgctg caacctatgc   25560

tccccgcacc gctccctggt ctgcaacccc cagctactga gcgagaccca ggtcatcggt   25620

acctttgagc tgcaaggtcc gcaggagtcc accgctccgc tgaaactcac gccggggttg   25680

tggacttccg cgtacctgcg caaatttgta cccgaggact actacgccca tgagataaag   25740

ttcttcgagg accaatcgcg tccgcagcac gcggatctca cggcctgcgt catcacccag   25800

ggcgcgatcc tcgcccaatt gcacgccatc caaaaatccc gccaagagtt tcttctgaaa   25860

aagggtagag gggtctacct ggacccccag acgggcgagg tgctcaaccc gggtctcccc   25920

cagcatgccg aggaagaagc aggagccgct agtggaggag atggaagaag aatgggacag   25980

ccaggcagag gaggacgaat gggaggagga gacagaggag gaagacttgg aagaggtgga   26040

agaggagcag gcaacagagc agcccgtcgc cgcaccatcc gcgccggcag cccctccggt   26100

cacggataca acctccgcag ctccggccaa gcctcctcgt agatgggatc gagtgaaggg   26160

tgacggtaag cacgagcgac agggctaccg atcatggagg gcccacaaag ccgcgatcat   26220

cgcctgcttg caagactgcg gggggaacat cgctttcgcc cgccgctacc tgctcttcca   26280

ccgcggggtg aacatccccc gcaacgtgtt gcattactac cgtcaccttc acagctaaga   26340

aaaagcaagt caaaggagtc gccggaggag gaggcctgag gatcgcggcg aacgagccct   26400

tgaccaccag ggagctgagg aaccggatct tccccactct ttatgccatt tttcagcaaa   26460

gtcgaggtca gcagcaagag ctcaaagtaa aaaaccggtc tctgcgctcg ctcacccgca   26520

gttgcttgta ccacaaaaac gaagatcagc tgcagcgcac tctcgaagac gccgaggctc   26580

tgttccacaa gtactgcgcg ctgactctta aagactaagg cgcgcccacc cggaaaaaag   26640

gcggaatta cctcatcgcc accatgagca aggagattcc caccccttac atgtggagct   26700

atcagcccca gatgggcctg gccgcgggcg cctcccagga ctactccacc cgcatgaact   26760

ggcttagtgc cggcccctcg atgatctcac gggtcaacgg ggtccgtaac catcgaaacc   26820

agatattgtt gcagcaggcg gcggtcacct ccacgcccag ggcaaagctc aacccgcgta   26880

attggccctc caccctggtg tatcaggaaa tccccgggcc gactaccgta ctacttccgc   26940

gtgacgcact ggccgaagtc cgcatgacta actcaggtgt ccagctggcc ggcggcgctt   27000

cccggtgccc gctccgccca caatcgggta taaaaaccct ggtgatccga ggcagaggca   27060

cacagctcaa cgacgagttg gtgagctctt acaatcgtct gcgaccggac ggagtgttcc   27120
```

aactagccgg agccgggaga tcgtccttca ctcccaacca ggcctacctg accttgcaga 27180
gcagctcttc ggagcctcgc tcgggaggca tcggaaccca ccagttcgtg gaggagtttg 27240
tgccctcggt ctacttcaac cccttctcgg gctcgccagg cctctacccg gacgagttta 27300
taccgaactt cgacgcagtg agagaagcgg tggacggcta cgactgaagc ttgttgatta 27360
aaagcccaga aaccaatcag acccttcctc atttccccat cccaatactc ataagaataa 27420
atcattggaa ttaatcattc aataaagatc acttacttga aatctgaaag tatgtctctg 27480
gtgtagttgc tcagcaacac ctcggtaccc tcctcccagc tctggtactc cagtccccgg 27540
cgggcggcga acttcctcca caccttgaaa gggatgtcaa agaggctccg ggtggaagat 27600
gacttcaacc ccgtctaccc ctatggctac gcgcggaatc agaatatccc cttcctcact 27660
ccccccttttg tctcctccga tggattcaaa aacttccccc ctggggtact gtcactcaaa 27720
ctggctgatc caatcaccat taccaatggg gatgtatccc tcaaggtggg aggtggtctc 27780
actttgcaag atggaagcct aactgtaaac cctaaggctc cactgcaagt taatactgat 27840
aaaaaacttg agcttgcata tgataatcca tttgaaagta gtgctaataa acttagttta 27900
aaagtaggac atggattaaa agtattagat gaaaaaagtg ctgcggggtt aaaagattta 27960
attggcaaac ttgtggtttt aacaggaaaa ggaataggca ctgaaaattt agaaaataca 28020
gatggtagca gcagaggaat tggtataaat gtaagagcaa gagaagggtt gacatttgac 28080
aatgatggat acttggtagc atggaaccca aagtatgaca cgcgcacact ttggacaaca 28140
ccagacacat ctccaaactg cacaattgct caagataagg actctaaact cactttggta 28200
cttacaaagt gtggaagtca aatattagct aatgtgtctt tgattgtggt cgcaggaaag 28260
taccacatca taaataataa gacaaatcca aaaataaaaa gttttactat taaactgcta 28320
tttaataaga acggagtgct tttagacaac tcaaatcttg gaaaagctta ttggaacttt 28380
agaagtggaa attccaatgt ttcgacagct tatgaaaaag caattggttt tatgcctaat 28440
ttggtagcgt atccaaaacc cagtaattct aaaaaatatg caagagacat agtttatgga 28500
actatatatc ttggtggaaa acctgatcag ccagcagtca ttaaaactac ctttaaccaa 28560
gaaactggat gtgaatactc tatcacattt aactttagtt ggtccaaaac ctatgaaaat 28620
gttgaatttg aaaccacctc ttttaccttc tcctatattg cccaagaatg aaagaccaat 28680
aaacgtgttt ttcatttgaa attttcatgt atctttattg atttttacac cagcacgagt 28740
agacagtctc ccaccaccag cccattttac agtgtacacg gttctctcag cacgggtagc 28800
cttaaatagg gaaatattct cattagtgcg ggaattggac ttggggtcta taatccacac 28860
agtttcctgg cgagccaaac gggggtcggt gattgaaata aagccgtcct ctgaaaagtc 28920
atccaagcgg gcctcacagt ccaaggtcac agtctggtgg aacgagaaga acgcacagat 28980
tcatactcgg aaaacaggat gggtctgtgc ctctccatca gcgccctcag cagtctctgc 29040
cgccggggct cggtgcggct gctgcaaatg ggatcgggat cacaagtctc tctgactatg 29100
atcccaacag ccttcagcat cagtctcctg gtgcgacggg cacagcaccg catcctgatc 29160
tctgccatgt tctcacagta agtgcagcac ataatcacca tgttattcag cagcccataa 29220
ttcagggcgc tccagccaaa gctcatgttg ggaatgatgg aacccacgtg accatcgtac 29280
cagatgcgac agtatatcag atgcctgccc ctcatgaaca cactgcccat gtacatgatc 29340
tctttgggca tgtttctgtt tacaatctgg cggtaccagg ggaagcgctg gttgaacatg 29400
cacccgtaaa tgactctcct gaaccacacg gccagcaggg tgcctcccgc ccgacactgc 29460

```
agggagccag gggatgaaca gtggcaatgc aggatccagc gctcgtaccc gctcaccatt 29520
tgagctctta ccaagtccag ggtagcgggg cacaggcaca ctgacataca tctttttaaa 29580
atttttattt cctctgtggt gaggatcata tcccagggga ctggaaactc ttggagcagg 29640
gtaaagccag cagcacatgg taatccacgg acagaactta cattatgata atctgcatga 29700
tcacaatcgg gcaacagggg atgttgttca gtcagtgaag ccctggtttc ctcatcagat 29760
cgtggtaaac gggccctgcg atatggatga tggcggagcg agctggattg aatctcggtt 29820
tgcattgtag tggattctct tgcgtacctt gtcgtacttc tgccagcaga aatgggccct 29880
tgaacagcat ataccccctcc tacggccgtc ctttcgctgc tgccgctcag tcatccaact 29940
aaagtacatc cattctcgaa gattctggag aagttcctct gcatctgata aaataaaaaa 30000
cccgtccatg cgaattcccc tcatcacatc agccaggact ctgtaggcca tccccatcca 30060
gttaatgctg ccttgtctat cattcagagg gggcggtggc aggactggaa gaaccatttt 30120
tattccaaac ggtctcgaag gacgataaag tgcaagtcac gcaggtgaca gcgttcccct 30180
ccgctgtgct ggtggaaaca gacagccagg tcaaaaccca ctctattttc aaggtgctcg 30240
accgtggctt cgagcagtgg ctctacgcgc acatccagca taagaatcac attaaaggct 30300
ggccctccat cgatttcatc aatcatcagg ttacattcct gcaccatccc caggtaattc 30360
tcatttttcc agccttggat tatctctaca aattgttggt gtaagtccac tccgcacatg 30420
tggaaaagct cccacagtgc cccctccact ttcataatca ggcagacctt cataatagaa 30480
acagatcctg ctgctccacc acctgcagcg tgttcaaaac aacaagattc aataaggttc 30540
tgccctccgc cctgagctcg cgcctcaatg tcagctgcaa aaagtcactt aagtcctggg 30600
ccactacagc tgacaattca gagccagggc taagcgtggg actggcaagc gtaagggaaa 30660
actttaatgc tccaaagcta gcacccaaaa actgcatgct ggaataagct ctctttgtgt 30720
ctccggtgat gccttccaaa atgtgagtga taaagcgtgg tagtttttct ttaatcattt 30780
gcgtaataga aaagtcctct aaataagtca ctaggacccc agggaccaca atgtggtagc 30840
ttacaccgcg tcgctgaagc atggttagta gagatgagag tctgaaaaac agaaagcatg 30900
cactaaacta aggtggctat tttcactgaa ggaaaaatca ctctctccag cagcagggta 30960
cccactgggt ggcccttgcg gacatacaaa aatcggtccg tgtgattaaa aagcagcaca 31020
gtaagttcct gtcttcttcc ggcaaaaatc acatcagact gggttagtat gtccctggca 31080
tggtagtcat tcaaggccat aaatctgccc tgatatccag taggaaccag cacactcact 31140
tttaggtgaa gcaataccac cccatgcgga ggaatgtgga aagattcagg gcaaaaaaat 31200
tatatctatt gctagcccct tcctggacgg gagcaatccc tccaggacta tctataaaag 31260
catacagaga ttcagccata gcttagcccg cttaccagta gacagaaagc acagcagtac 31320
aagcgccaac agcagcaact gactacccac tgacccagct ccctatttaa aggcacctta 31380
cactgacgta atgaccaaag gtctaaaaac cccgccaaaa aaaacacaca cgccctgggt 31440
gtttttcaca aaaacacttc cgcgttctca cttcctcgta tcgattttgt gactcaactt 31500
ccgggttccc acgttacgtc acttctgccc ttacatgtaa cttggccgta tggcgccatc 31560
ttgcccacgt ccaaaatggc tttcatgacc ggccacgcct ccgcgccggc cgttagccgt 31620
gcgtcgtgac gttatttgca tcaccgcttc tcgtccaatc agcgttggct ccgccccaaa 31680
accgttaaaa ttcaaaagct catttgcata ttaacttttg tttactttgt ggggtatatt 31740
attagatagt taattaagga tgcatgttta aactcgacag cgacacactt gcatcggatg 31800
cagcccggtt aacgtgccgg cacggcctgg gtaaccaggt attttgtcca cataaccgtg 31860
```

cgcaaaatgt tgtggataag caggacacag cagcaatcca cagcaggcat acaaccgcac 31920
accgaggtta ctccgttcta caggttacga cgacatgtca atacttgccc ttgacaggca 31980
ttgatggaat cgtagtctca cgctgatagt ctgatcgaca atacaagtgg gaccgtggtc 32040
ccagaccgat aatcagaccg acaacacgag tgggatcgtg gtcccagact aataatcaga 32100
ccgacgatac gagtgggacc gtggtcccag actaataatc agaccgacga tacgagtggg 32160
accgtggttc cagactaata atcagaccga cgatacgagt gggaccgtgg tcccagacta 32220
ataatcagac cgacgatacg agtgggacca tggtcccaga ctaataatca gaccgacgat 32280
acgagtggga ccgtggtccc agtctgatta tcagaccgac gatacgagtg ggaccgtggt 32340
cccagactaa taatcagacc gacgatacga gtgggaccgt ggtcccagac taataatcag 32400
accgacgata cgagtgggac cgtggtccca gtctgattat cagaccgacg atacaagtgg 32460
aacagtgggc ccagagagaa tattcaggcc agttatgctt tctggcctgt aacaaaggac 32520
attaagtaaa gacagataaa cgtagactaa aacgtggtcg catcagggtg ctggcttttc 32580
aagttcctta agaatggcct caattttctc tatacactca gttggaacac gagacctgtc 32640
caggttaagc accattttat cgcccttata caatactgtc gctccaggag caaactgatg 32700
tcgtgagctt aaactagttc ttgatgcaga tgacgtttta agcacagaag ttaaaagagt 32760
gataacttct tcagcttcaa atatcacccc agctttttc tgctcatgaa ggttagatgc 32820
ctgctgctta agtaattcct ctttatctgt aaaggctttt tgaagtgcat cacctgaccg 32880
ggcagatagt tcaccggggt gagaaaaaag agcaacaact gatttaggca atttggcggt 32940
gttgatacag cgggtaataa tcttacgtga aatattttcc gcatcagcca gcgcagaaat 33000
atttccagca aattcattct gcaatcggct tgcataacgc tgaccacgtt cataagcact 33060
tgttgggcga taatcgttac ccaatctgga taatgcagcc atctgctcat catccagctc 33120
gccaaccaga acacgataat cactttcggt aagtgcagca gctttacgac ggcgactccc 33180
atcggcaatt tctatgacac cagatactct tcgaccgaac gccggtgtct gttgaccagt 33240
cagtagaaaa gaagggatga gatcatccag tgcgtcctca gtaagcagct cctggtcacg 33300
ttcattacct gaccataccc gagaggtctt ctcaacacta tcaccccgga gcacttcaag 33360
agtaaacttc acatcccgac cacatacagg caaagtaatg gcattaccgc gagccattac 33420
tcctacgcgc gcaattaacg aatccaccat cggggcagct ggtgtcgata acgaagtatc 33480
ttcaaccggt tgagtattga gcgtatgttt tggaataaca ggcgcacgct tcattatcta 33540
atctcccagc gtggtttaat cagacgatcg aaaatttcat tgcagacagg ttcccaaata 33600
gaaagagcat ttctccaggc accagttgaa gagcgttgat caatggcctg ttcaaaaaca 33660
gttctcatcc ggatctgacc tttaccaact tcatccgttt cacgtacaac attttttaga 33720
accatgcttc cccaggcatc ccgaatttgc tcctccatcc acggggactg agagccatta 33780
ctattgctgt atttggtaag caaaatacgt acatcaggct cgaacccttt aagatcaacg 33840
ttcttgagca gatcacgaag catatcgaaa aactgcagtg cggaggtgta gtcaaacaac 33900
tcagcaggcg tgggaacaat cagcacatca gcagcacata cgacattaat cgtgccgata 33960
cccaggttag gcgcgctgtc aataactatg acatcatagt catgagcaac agtttcaatg 34020
gccagtcgga gcatcaggtg tggatcggtg ggcagtttac cttcatcaaa tttgcccatt 34080
aactcagttt caatacggtg cagagccaga caggaaggaa taatgtcaag ccccggccag 34140
caagtgggct ttattgcata agtgacatcg tccttttccc caagatagaa aggcaggaga 34200
gtgtcttctg catgaatatg aagatctggt acccatccgt gatacattga ggctgttccc 34260
tgggggtcgt taccttccac gagcaaaaca cgtagcccct tcagagccag atcctgagca 34320
agatgaacag aaactgaggt tttgtaaacg ccacctttat gggcagcaac cccgatcacc 34380
ggtggaaata cgtcttcagc acgtcgcaat cgcgtaccaa acacatcacg catatgatta 34440
atttgttcaa ttgtataacc aacacgttgc tcaacccgtc ctcgaatttc catatccggg 34500
tgcggtagtc gccctgcttt ctcggcatct ctgatagcct gagaagaaac cccaactaaa 34560
tccgctgctt cacctattct ccagcgccgg gttattttcc tcgcttccgg gctgtcatca 34620
ttaaactgtg caatggcgat agccttcgtc atttcatgac cagcgtttat gcactggtta 34680
agtgtttcca tgagtttcat tctgaacatc ctttaatcat tgctttgcgt tttttttatta 34740
aatcttgcaa tttactgcaa agcaacaaca aaatcgcaaa gtcatcaaaa aaccgcaaag 34800
ttgtttaaaa taagagcaac actacaaaag gagataagaa gagcacatac ctcagtcact 34860
tattatcact agcgctcgcc gcagccgtgt aaccgagcat agcgagcgaa ctggcgagga 34920
agcaaagaag aactgttctg tcagatagct cttacgctca gcgcaagaag aaatatccac 34980
cgtgggaaaa actccaggta gaggtacaca cgcggatagc caattcagag taataaactg 35040
tgataatcaa ccctcatcaa tgatgacgaa ctaacccccg atatcaggtc acatgacgaa 35100
gggaaagaga aggaaatcaa ctgtgacaaa ctgccctcaa atttggcttc cttaaaaatt 35160
acagttcaaa aagtatgaga aaatccatgc aggctgaagg aaacagcaaa actgtgacaa 35220
attaccctca gtaggtcaga acaaatgtga cgaaccaccc tcaaatctgt gacagataac 35280
cctcagacta tcctgtcgtc atggaagtga tatcgcggaa ggaaaatacg atatgagtcg 35340
tctggcggcc tttctttttc tcaatgtatg agaggcgcat tggagttctg ctgttgatct 35400
cattaacaca gacctgcagg aagcggcggc ggaagtcagg catacgctgg taactttgag 35460
gcagctggta acgctctatg atccagtcga ttttcagaga gacgatgcct gagccatccg 35520
gcttacgata ctgacacagg gattcgtata aacgcatggc atacggattg gtgatttctt 35580
ttgtttcact aagccgaaac tgcgtaaacc ggttctgtaa cccgataaag aagggaatga 35640
gatatgggtt gatatgtaca ctgtaaagcc ctctggatgg actgtgcgca cgtttgataa 35700
accaaggaaa agattcatag ccttttttcat cgccggcatc ctcttcaggg cgataaaaaa 35760
ccacttcctt ccccgcgaaa ctcttcaatg cctgccgtat atccttactg gcttccgcag 35820
aggtcaatcc gaatatttca gcatatttag caacatggat ctcgcagata ccgtcatgtt 35880
cctgtagggt gccatcagat tttctgatct ggtcaacgaa cagatacagc atacgttttt 35940
gatcccggga gagactatat gccgcctcag tgaggtcgtt tgactggacg attcgcgggc 36000
tatttttacg tttcttgtga ttgataaccg ctgtttccgc catgacagat ccatgtgaag 36060
tgtgacaagt ttttagattg tcacactaaa taaaaaagag tcaataagca gggataactt 36120
tgtgaaaaaa cagcttcttc tgagggcaat ttgtcacagg gttaagggca atttgtcaca 36180
gacaggactg tcatttgagg gtgatttgtc acactgaaag ggcaatttgt cacaacacct 36240
tctctagaac cagcatggat aaaggcctac aaggcgctct aaaaaagaag atctaaaaac 36300
tataaaaaaa ataattataa aaatatcccc gtggataagt ggataacccc aagggaagtt 36360
ttttcaggca tcgtgtgtaa gcagaatata taagtgctgt tccctggtgc ttcctcgctc 36420
actcgagggc ttcgccgtcg ctcgactgcg gcgagcctac tggctgtaaa aggacagacc 36480
acatcatggt tctgtgttca ttaggttgtt ctgtccattg ctgacataat ccgctccact 36540
tcaacgtaac accgcacgaa gatttctatt gttcctgaag gcatattcaa atcgttttcg 36600
ttaccgcttg caggcatcat gacagaacac tacttcctat aaacgctaca caggctcctg 36660
agattaataa tgcggatctc tacgataatg ggagattttc ccgactgttt cgttcgcttc 36720
tcagtggata acagccagct tctctgttta acagacaaaa acagcatatc cactcagttc 36780
cacatttcca tataaaggcc aaggcattta ttctcaggat aattgtttca gcatcgcaac 36840
cgcatcagac tccggcatcg caaactgcac ccggtgccgg gcagccacat ccagcgcaaa 36900
aaccttcgtg tagacttccg ttgaactgat ggacttatgt cccatcaggc tttgcagaac 36960
tttcagcggt ataccggcat acagcatgtg catcgcatag gaatggcgga acgtatgtgg 37020
tgtgaccgga acagagaacg tcacaccgtc agcagcagcg gcggcaaccg cctccccaat 37080
ccaggtcctg accgttctgt ccgtcacttc ccagatccgc gctttctctg tccttcctgt 37140
gcgacggtta cgccgctcca tgagcttatc gcgaataaat acctgtgacg gaagatcact 37200
tcgcagaata aataaatcct ggtgtccctg ttgataccgg gaagccctgg gccaactttt 37260
ggcgaaaatg agacgttgat cggcacgtaa gaggttccaa ctttcaccat aatgaaataa 37320
gatcactacc gggcgtattt tttgagttat cgagattttc aggagctaag gaagctaaaa 37380
tggagaaaaa aatcactgga tataccaccg ttgatatatc ccaatggcat cgtaaagaac 37440
attttgaggc atttcagtca gttgctcaat gtacctataa ccagaccgtt cagctggata 37500
ttacggcctt tttaaagacc gtaaagaaaa ataagcacaa gttttatccg gcctttattc 37560
acattcttgc ccgcctgatg aatgctcatc cggaattccg tatggcaatg aaagacggtg 37620
agctggtgat atgggatagt gttcaccctt gttacaccgt tttccatgag caaactgaaa 37680
cgttttcatc gctctggagt gaataccacg acgatttccg gcagtttcta cacatatatt 37740
cgcaagatgt ggcgtgttac ggtgaaaacc tggcctattt ccctaaaggg tttattgaga 37800
atatgttttt cgtctcagcc aatccctggg tgagtttcac cagttttgat ttaaacgtgg 37860
ccaatatgga caacttcttc gcccccgttt tcaccatggg caaatattat acgcaaggcg 37920
acaaggtgct gatgccgctg gcgattcagg ttcatcatgc cgtctgtgat ggcttccatg 37980
tcggcagaat gcttaatgaa ttacaacagt actgcgatga gtggcagggc ggggcgtaat 38040
ttttttaagg cagttattgg tgcccttaaa cgcctggttg ctacgcctga ataagtgata 38100
ataagcggat gaatggcaga aattcgatga taagctgtca aacatgagaa tgggtcgag 38159

<210> SEQ ID NO 4
<211> LENGTH: 37318
<212> TYPE: DNA
<213> ORGANISM: Artificial sequence
<220> FEATURE:
<223> OTHER INFORMATION: /note="Description of artificial sequence: pRAB19aGFP_5pIX"

<400> SEQUENCE: 4
gaagttccta ttccgaagtt cctattctct agaaagtata ggaacttcaa ttcccatgtc 60
agccgttaag tgttcctgtg tcactcaaaa ttgctttgag aggctctaag ggcttctcag 120
tgcgttacat ccctggcttg ttgtccacaa ccgttaaacc ttaaaagctt taaaagcctt 180
atatattctt ttttttctta taaaacttaa aaccttagag gctatttaag ttgctgattt 240
atattaattt tattgttcaa acatgagagc ttagtacgtg aaacatgaga gcttagtacg 300
ttagccatga gagcttagta cgttagccat gagggtttag ttcgttaaac atgagagctt 360
agtacgttaa acatgagagc ttagtacgtg aaacatgaga gcttagtacg tactatcaac 420
aggttgaact gctgatcttc agatcctcta cgccggacgc atcgtggccg gatccgattt 480

```
attcaacaaa gccacgttgt gtctcaaaat ctctgatgtt acattgcaca agataaaaat    540
atatcatcat gaacaataaa actgtctgct tacataaaca gtaatacaag ggtgttatg     600
agccatattc aacgggaaac gtcttgctcg aggccgcgat taaattccaa catggatgct    660
gatttatatg ggtataaatg ggctcgcgat aatgtcgggc aatcaggtgc gacaatctat    720
cgattgtatg ggaagcccga tgcgccagag ttgtttctga aacatggcaa aggtagcgtt    780
gccaatgatg ttacagatga gatggtcaga ctaaactggc tgacggaatt tatgcctctt    840
ccgaccatca agcattttat ccgtactcct gatgatgcat ggttactcac cactgcgatc    900
cccgggaaaa cagcattcca ggtattagaa gaatatcctg attcaggtga aaatattgtt    960
gatgcgctgg cagtgttcct gcgccggttg cattcgattc ctgtttgtaa ttgtcctttt   1020
aacagcgatc gcgtatttcg tctcgctcag gcgcaatcac gaatgaataa cggtttggtt   1080
gatgcgagtg attttgatga cgagcgtaat ggctggcctg ttgaacaagt ctggaaagaa   1140
atgcataagc ttttgccatt ctcaccggat tcagtcgtca ctcatggtga tttctcactt   1200
gataacctta tttttgacga ggggaaatta ataggttgta ttgatgttgg acgagtcgga   1260
atcgcagacc gataccagga tcttgccatc ctatggaact gcctcggtga gttttctcct   1320
tcattacaga aacggctttt tcaaaaatat ggtattgata atcctgatat gaataaattg   1380
cagtttcatt tgatgctcga tgagtttttc taatcagaat tggttaattg gttgtaacac   1440
tggcttaatt aactatctaa taatataccc cacaaagtaa acaaaagtta atatgcaaat   1500
gagcttttga attttaacgg ttttggggcg gagccaacgc tgattggacg agaagcggtg   1560
atgcaaataa cgtcacgacg cacggctaac ggccggcgcg gaggcgtggc ctaggccgga   1620
agcaagtcgc ggggctaatg acgtataaaa aagcggactt tagacccgga aacggccgat   1680
tttcccgcgg ccacgcccgg atatgaggta attctgggcg gatgcaagtg aaattaggtc   1740
attttggcgc caaaactgaa tgaggaagtg aaaagtgaaa aatacctgtc ccgcccaggg   1800
cggaatattt accgagggcc gagagacttt gaccgattac gtggggtttc gattgcggtg   1860
ttttttttcgc gagaaggtaa actgcccact tggcagtaca tcaagtgtat catatgccaa  1920
gtacgccccc tattgacgtc aatgacggta aatggcccgc ctggcattat gcccagtaca   1980
tgaccttatg ggactttcct acttggcagt acatctacgt attagtcatc gctattacca   2040
tggtgatgcg gttttggcag tacatcaatg ggcgtggata gcggtttgac tcacggggat   2100
ttccaagtct ccaccccatt gacgtcaatg ggagtttgtt ttggcaccaa aatcaacggg   2160
actttccaaa atgtcgtaac aactccgccc cattgacgca aatgggcggt aggcgtgtac   2220
ggtgggaggt ctatataagc agagctggtt tagtgaaccg tcagatccgc tagcgctacc   2280
ggactcagat ctcgagctca agcttcgaat tctgcagtcg acggtaccgc gggcccggga   2340
tccaccggtc gccaccatgg tgagcaaggg cgaggagctg ttcaccgggg tggtgcccat   2400
cctggtcgag ctggacggcg acgtaaacgg ccacaagttc agcgtgtccg gcgagggcga   2460
gggcgatgcc acctacggca agctgaccct gaagttcatc tgcaccaccg gcaagctgcc   2520
cgtgccctgg cccaccctcg tgaccaccct gacctacggc gtgcagtgct tcagccgcta   2580
ccccgaccac atgaagcagc acgacttctt caagtccgcc atgcccgaag gctacgtcca   2640
ggagcgcacc atcttcttca aggacgacgg caactacaag acccgcgccg aggtgaagtt   2700
cgagggcgac accctggtga accgcatcga gctgaagggc atcgacttca aggaggacgg   2760
caacatcctg gggcacaagc tggagtacaa ctacaacagc cacaacgtct atatcatggc   2820
```

-continued

```
cgacaagcag aagaacggca tcaaggtgaa cttcaagatc cgccacaaca tcgaggacgg   2880
cagcgtgcag ctcgccgacc actaccagca gaacaccccc atcggcgacg gccccgtgct   2940
gctgcccgac aaccactacc tgagcaccca gtccgccctg agcaaagacc ccaacgagaa   3000
gcgcgatcac atggtcctgc tggagttcgt gaccgccgcc gggatcactc tcggcatgga   3060
cgagctgtac aagtaaagcg gccgcgactc tagatcataa tcagccatac cacatttgta   3120
gaggttttac ttgctttaaa aaacctccca cacctccccc tgaacctgaa acataaaatg   3180
aatgcaattg ttgttgttaa cttgtttatt gcagcttata atggttacaa ataaagcaat   3240
agcatcacaa atttcacaaa taaagcattt ttttcactgc attctagttg tggtttgtcc   3300
aaactcatca atgtatctta aatcgaattc aagcatatgc tgaaatgtgt gggcgtggct   3360
taagggtggg aaagaatata taaggtgggg gtcttatgta gttttgtatc tgttttgcag   3420
cagccgccgc cgcctccgga cgcgtgaagt tcctattctc tagaaagtat aggaacttcg   3480
cgtaaattgt aagcgttaat attttgttaa aattcgcgtt aaatttttgt taaatcagct   3540
catttttaa ccaataggcc gaaatcggca aaatcccttg aagagcagac cagaccacct   3600
ggtgatggcc tgtaccggga ccgagttcag ctccagtggg gaggacacag attagaggta   3660
ggtttgagta gtgggcgtgg ctaatgtgag tataaaggcg ggtgtcttac gagggtcttt   3720
ttgcttttct gcagacatca tgaacgggac cggcggggcc ttcgaagggg ggctttttag   3780
cccttatttg acaacccgcc tgccgggatg ggccggagtt cgtcagaatg tgatgggatc   3840
tacggtggat gggcgtccag tgcttccagc aaattcctcg accatgacct acgcgaccgt   3900
ggggagctcg tcgcttgaca gcaccgccgc agccgcggca gccgcagccg ccatgacagc   3960
gacgagactg gcctcgagct atatgcccag cagcggtagc agcccctctg tgcccagttc   4020
catcatcgcc gaggagaaac tgctggccct gctggccgag ctggaagccc tgagccgcca   4080
gctggccgcc ctgacccagc aggtgtccga tctccgcgag caacagcagc agcaaaataa   4140
atgaattcaa taaacacaga ttctgattca aacagcaaag catctttatt atttattttt   4200
tcgcgcgcgg taggccctgg tccacctctc ccgatcattg agagtgcggt ggattttttc   4260
caggacccgg tagaggtggg attggatgtt gaggtacatg ggcatgagcc cgtcccgggg   4320
gtggaggtag caccactgca tggcctcgtg ctctggggtc gtgttgtaga taatccagtc   4380
atagcagggg cgctgggcgt ggtgctggat gatgtccttg aggaggagac tgatggccac   4440
ggggagcccc ttggtgtagg tgttggcaaa gcggttaagc tgggagggat gcatgcgggg   4500
ggagatgatg tgcagtttgg cctggatctt gaggttggcg atgttgccac ccagatcccg   4560
ccgggggttc atattgtgca ggaccaccag aacggtgtag cccgtgcact tggggaactt   4620
atcatgcaac ttggaaggga atgcgtggaa gaatttggag acgcccttgt gcccgcccag   4680
gttttccatg cactcatcca tgatgatggc aatgggcccg tgggctgcgg ctttggcaaa   4740
aacgtttctg ggtcagaga catcataatt atgctcctgg gtgagatcat cataagacat   4800
tttaatgaat ttggggcgaa gggtgccaga ttgggggacg atcgttccct cgggccccgg   4860
ggcgaagttc ccctcgcaga tctgcatctc ccaggctttc atctcggagg gggggatcat   4920
gtccacctgc ggggcgatga aaaaaacggt ttccggggcg gggtgatga gctgcgagga   4980
gagcaggttt cttaacagct gggacttgcc gcacccggtc gggccgtaga tgaccccgat   5040
gacgggttgc aggtggtagt tcaaggagat gcagctgccg tcgtcccgga ggagggggc   5100
cacctcgttg agcatgtctc tcacttggag gttttcccgg acgagctcgc cgaggaggcg   5160
gtccccgccc agcgagagca gctcttgcag ggaagcaaag tttttcaggg gcttgagccc   5220
```

-continued

```
gtcggccatg ggcatcttgg caagggtctg cgagaggagc tccaggcggt cccatagctc   5280
ggtgacgtgc tctacggcat ctcgatccag cagacttcct cgtttcgggg gttgggacga   5340
ctgcgactgt agggcacgag acgatgggcg tccagcgcgg ccagcgtcat gtccttccag   5400
ggtctcaggg tccgagtgag ggtggtctcc gtcacggtga aggggtgggc cccgggctgg   5460
gcgcttgcaa gggtgcgctt gagactcatc ctgctggtgc tgaaacgggc acggtcttcg   5520
ccctgcgcgt cggcgagata gcagttgacc atgagcttgt agttaagggc ctcggcggcg   5580
tggcccttgg cacggagctt gcctttggaa gagcgcccgc aggcgggaca gaggagggat   5640
tgcagggcgt agagcttggg tgcgagaaag acggactcgg gagcgaaggc gtccgctccg   5700
cagtgggcgc agacggtctc gcactcgacg agccaggtga gctcgggctg ctcggggtca   5760
aaaaccagtt ttcccccgtt ctttttgatg cgcttcttac ctcgcgtctc catgagtctg   5820
tgtccgcgtt cggtgacaaa caggctgtct gtgtccccgt agacggactt gattggcctg   5880
tcctgcaggg gcgtcccgcg gtcctcctcg tagagaaact cggaccactc tgagacaaag   5940
gcgcgcgtcc acgccaagac aaaggaggcc acgtgcgagg ggtagcggtc gttgtccacc   6000
agggggtcca ccttttccac cgtgtgcaga cacatgtccc cctcctccgc atccaagaag   6060
gtgattggct tgtaggtgta ggccacgtga ccgggggtcc ccgacggggg ggtataaaag   6120
ggggcgggtc tgtgctcgtc ctcactctct tccgcgtcgc tgtccacgag cgccagctgt   6180
tggggtaggt attccctctc gagagcgggc atgacctcgg cactcaggtt gtcagtttct   6240
agaaacgagg aggatttgat gttggcctgc cctgccgcaa tgctttttag gagactttca   6300
tccatctggt cagaaaagac tattttttta ttgtcaagct tggtggcaaa ggagccatag   6360
agggcgttgg agagaagctt ggcgatggat ctcatggtct gatttttgtc acggtcggcg   6420
cgctccttgg ccgcgatgtt gagctggaca tactcgcgcg cgacacactt ccattctggg   6480
aagacggtgg tgcgctcgtc gggcacgatc ctgacgcgcc agccgcgatt atgcagggtg   6540
accaggtcca cgctggtggc cacctcgccg cgcaggggct cgttggtcca gcagaggcgt   6600
ccgcccttgc gcgagcagaa cgggggcagc acatcaagca gatgctcgtc agggggggtcc  6660
gcatcgatgg tgaagatgcc cggacagagt tccttgtcaa aataatcgat tttgaggat    6720
gcatcatcca aggccatctg ccactcgcgg gcggccagcg ctcgctcgta ggggttgagg   6780
ggcggacccc agggcatggg atgcgtgagg gcggaggcgt acatgccgca gatgtcgtag   6840
acatagatgg gctccgagag gatgccgatg taggtgggat aacagcgccc cccgcggatg   6900
ctggcgcgca catagtcata caactcgtgc gagggggcca agaaagcggg gccgagattg   6960
gtgcgctggg gctgctcggc gcggaagacg atctggcgaa agatggcatg cgagttggag   7020
gagatggtgg gccgttggaa gatgttaaag tgggcgtggg gcaagcggac cgagtcgcgg   7080
atgaagtgcg cgtaggagtc ttgcagcttg gcaacgagct cggcggtgac aaggacgtcc   7140
atggcgcagt agtccagcgt ttcacggatg atgtcataac ccgcctcttc tttcttctcc   7200
cacagcgcgc ggttgagggc gtactcctcg tcatccttcc agtactcccg gagcgggaat   7260
cctcgatcgt ccgcacggta agagcccagc atgtagaaat ggttcacggc cttgtaggga   7320
cagcagccct tctccacggg gagggcgtaa gcttgagcgg ccttgcggag cgaggtgtgc   7380
gtcagggcga aggtatccct aaccatgact ttcaagaact ggtacttgaa atccgagtcg   7440
tcgcagccgc cgtgctccca gagctcgaaa tcggtgcgct tcttcgagag gggggttaggc  7500
agagcgaaag tgacgtcatt gaagagaatc ttgcctgccc gcggcatgaa attgcgggtg   7560
```

-continued atgcggaaag ggcccggaac ggaggctcgg ttgttgatga cctgggcggc gaggacgatc 7620
tcgtcgaagc cgttgatgtt gtgcccgacg atgtagagtt ccatgaatcg cgggcggcct 7680
ttgatgtgcg gcagcttttt gagttcctcg taggtgaggt cctcggggca ttgcaggccg 7740
tgctgctcga gcgcccactc ctggagatgt gggttggctt gcatgaatga agcccagagc 7800
tcgcgggcca tgagggtctg gagctcgtcg cgaaagaggc ggaactgctg gcccacggcc 7860
atcttttctg gggtgacgca gtagaaggtg agggggtccc gctcccagcg atcccagcgt 7920
aagcgcacgg cgagatcgcg agcgagggcg accagctcgg ggtccccgga gaatttcatg 7980
accagcatga aggggacgag ctgcttgccg aaggacccca tccaggtgta ggtttctaca 8040
tcgtaggtga caaagagccg ctccgtgcga ggatgagagc cgattgggaa gaactggatt 8100
tcctgccacc agttggtcga gtggctgttg atgtgatgaa agtagaaatc ccgccggcga 8160
accgagcact cgtgctgatg cttgtaaaag cgtccgcagt actcgcagcg ctgcacgggc 8220
tgtacctcat ccacgagata cacagcgcgt cccttgagga ggaacttcag gagtggcggc 8280
cctggctggt ggttttcatg ttcgcctgcg tgggactcac cctggggctc ctcgaggacg 8340
gagaggctga cgagcccgcg cgggagccag gtccagattt cggcgcggcg gggggcggaga 8400 gcgaaaacga gggcgcgcag ttgggagctg tccatggtgt cgcggagatc caggtccggg 8460
ggcagggttc tgaggttgac ctcgtagagg cgggtgaggg cgtgcttgag atgcagatgg 8520
tacttgatct ccacgggtga gttggtggtc gtgtccacgc attgcatgag cccgtagctg 8580
cgcggggcca cgaccgtgcc gcggtgcgct tttagaagcg gtgtcgcgga cgcgctcccg 8640
gcggcagcgg cggttccggc cccgcgggca gtggcggtag aggcacgtcg gcgtggcgct 8700
cgggcaggtc ccggtgctgc gccctgagag cgctggcgtg cgcgacgacg cggcggttga 8760
catcctggat ctgccgcctt tgcgtgaaga ccacgggccc cgtgactttg aacctgaaag 8820
acagttcaac agaatcaatc tcggcgtcat tgacggcggc ctgacgcagg atctcttgca 8880
cgtcgcccga gttgtcctgg taggcgatct cggacatgaa ctgctcgatt tcctcctcct 8940
ggagatcgcc gcggcccgcg cgctctacgg tggcggcaag gtcattcgag atgcgaccca 9000
tgagctgcga gaaggcgccc aggccgctct cgttccagac gcggctgtaa accacgtccc 9060
cgtcggcgtc gcgcgcgcgc atgaccacct gcgcgaggtt gagctccacg tgccgcgtaa 9120
agacggcgta gttgcgcagg cgctggaaga ggtagttgag ggtggtggcg atgtgctcgg 9180
tgacgaagaa gtacataatc cagcggcgca ggggcatttc gctgatgtcg ccaatggcct 9240
ccagcctttc catggcctcg tagaaatcca cggcgaagtt gaaaaactgg gcgttgcggg 9300
ccgagaccgt gagctcgtct tccaggagcc tgatgagttc ggcgatggtg gcgcgcacct 9360
cgcgctcgaa atcccagggg gcctcctcct cttcctcttc ttccatgacg acctcttctt 9420
ctatttcttc ctctgggggc ggtggtggtg gcggggcccg acgacgacgg cgacgcaccg 9480
ggagacggtc gacgaagcgc tcgatcatct ccccgcggcg gcgacgcatg gtttcggtga 9540
cggcgcgacc ccgttcgcga ggacgcagcg tgaagacgcc gccggtcatc tcccggtaat 9600
ggggtgggtc cccgttgggc agcgataggg cgctgacaat gcatcttatc aattgcggtg 9660
tagggcacgt gagcgcgtcg agatcgaccg gatcggagaa tctttcgagg aaagcgtcta 9720
gccaatcgca gtcgcaaggt aagctcaaac acgtagcagc cctgtggacg ctgttagaat 9780
tgcggttgct gatgatgtaa ttgaagtagg cgtttttgag gcggcggatg gtggcgagga 9840
ggaccaggtc cttgggtccc gcttgctgga tgcggagccg ctcggccatg ccccaggcct 9900
ggccctgaca ccggctcagg ttcttgtagt agtcatgcat gagcctctcg atgtcatcac 9960
tggcggaggc ggagtcttcc atgcgggtga ccccgacgcc cctgaacggc tgcacgagcg 10020
ccaggtcggc gacgacgcgc tcggcgagga tggcctgttg cacgcgggtg agggtgtcct 10080
ggaagtcgtc catgtcgacg aagcggtggt aggcccctgt gttgatggtg taagtgcagt 10140
tggccataag cgaccagttg acggtctgca ggccgggttg cacgacctcg gagtacctga 10200
gccgcgagaa ggcgcgcgag tcgaagacat agtcgttgca ggtgcgcacg aggtactggt 10260
atccgactag aaagtgcggc ggcggctggc ggtagagcgg ccagcgctgg gtggccggcg 10320
cgcccggggc caggtcctca agcatgagtc ggtggtagcc gtagaggtag cgggacatcc 10380
aggtgatgcc ggcggcggtg gtggaggcgc gcgggaactc gcggacgcgg ttccagatgt 10440
tgcgcagggg caggaaatag tccatggtcg gcacggtctg gccggtgaga cgcgcgcagt 10500
cattgatgct ctagaggcaa aaacgaaagc ggttgagcgg gctcttcctc cgtagcctgg 10560
cggaacgcaa acgggttagg ccgcgtgtgt accccggttc gagtcccctc gaatcaggct 10620
ggagccgcga ctaacgtggt attggcactc ccgtctcgac ccaagcccga tagccgccag 10680
gatacggcgg agagcccttt ttgtcggccg aggggagtcg ctagacttga aagcggccga 10740
aaaccctgcc gggtagtggc tcgcgcccgt agtctggaga agcatcgcca gggttgagtc 10800
gcggcagaac ccggttcaag gacggccgcg gcgagcggga cttggtcacc ccgccgattt 10860
aaagacccac agccagccga cttctccagt tacgggagcg agcccccttt tttcttttg 10920 ccagatgcat cccgtcctgc gccaaatgcg tcccaccccc ccggcgacca ccgcgaccgc 10980
ggccgtagca ggcgccggcg ctagccagcc acagccacag acagagatgg acttggaaga 11040
gggcgaaggg ctggcgagac tgggggcgcc gtccccggag cgacatcccc gcgtgcagct 11100
gcagaaggac gtgcgcccgg cgtacgtgcc tgcgcagaac ctgttcaggg accgcagcgg 11160
ggaggagccc gaggagatgc gcgactgccg gtttcgggcg ggcagggagc tgcgcgaggg 11220
cctggaccgc cagcgcgtgc tgcgcgacga ggatttcgag ccgaacgagc agacggggat 11280
cagccccgcg cgcgcgcacg tggcggcggc caacctggtg acagcctacg agcagacggt 11340
gaagcaggaa cgcaactttc aaaagagttt caacaaccac gtgcgcaccc tgatcgcgcg 11400
cgaggaggtg gccctgggcc tgatgcacct gtgggacctg gcggaggcca ttgtgcagaa 11460
cccggacagc aagcctctga cggcacaact gttcctggtg gtgcagcaca gcagggacaa 11520
cgaggcgttc agggaggcgc tgctaaacat cgccgagccc gagggccgct ggctgctgga 11580
gctgatcaac atcttgcaaa gcatcgtagt gcaggagcgc agcctgagct tggccgagaa 11640
ggtggcggcg atcaactact cggtgctaag cctgggcaag ttttacgcgc gcaagattta 11700
caagacgccg tacgtgccca tagacaagga ggtgaaaata gacagctttt acatgcgcat 11760
ggcgctcaag gtgctgacgc tgagcgacga cctgggcgtg taccgcaacg accgcatcca 11820
caaggccgtg agcacgagcc ggcggcgcga gctgagcgac cgcgagctga tgctaagcct 11880
gcgccgggcg ctggtaggtg gcgccgccgg cggcgaggag tcctacttcg acatgggggc 11940
ggacctgcat tggcagccga gccggcgcgc cttggaggcc gcctacggtc cagaggactt 12000
ggatgaggat gaggaagagg aggaggatgc acccgttgcg gggtactgac gcctccgtga 12060
tgtgttttta gatgtcccag cagcaagccc cggaccccgc cataagggcg gcgctgcaaa 12120
gccagccgtc cggtctagca tcggacgact gggaggccgc gatgcaacgc atcatggccc 12180
tgacgacccg caaccccgag tcctttagac aacagccgca ggccaacaga ctttcgacca 12240
ttctggaggc ggtggtcccc tctcggacca accccacgca cgagaaggtg ctggcgatcg 12300

-continued

```
tgaacgcgct ggcggagaac aaggctattc gtcccgacga ggctgggctg gtatacaacg  12360
ccctgctgga gcgcgtgggc cgctacaaca gcacgaacgt gcagtccaac ctggaccggc  12420
tggtgacgga cgtgcgcgag gccgtggcgc agcgcgagcg gttcaagaac gagggcctgg  12480
gctcgctggt ggcgctgaac gccttcctgg cgacgcagcc ggcgaacgtg ccgcgcgggc  12540
aggacgatta taccaacttt atcagcgcgc tgcggctgat ggtgaccgag gttccccaga  12600
gcgaggtgta ccagtcgggc ccggactact tttccagac tagcagacag ggcctgcaga  12660
cggtgaacct gagccaggct ttcaagaacc tgcgcgggct gtggggcgtg caggcgcccg  12720
tgggcgaccg gtcgacggtg agcagcttgc tgacgcccaa ctcgcggctg ctgctgctgc  12780
tgatcgcgcc cttcaccgac agcggcagcg tgaaccgcaa ctcgtacctg ggtcacctgc  12840
tgacgctgta ccgcgaggcc ataggccagg cacaggtgga cgagcagacc ttccaggaga  12900
tcactagtgt aagccgcgcg ctgggtcaga acgacaccga cagtctgagg gccaccctga  12960
acttcttgct gaccaataga cagcagaaga tcccggcgca gtatgcgctg tcggccgagg  13020
aggagcgcat cctgagatat gtgcagcaga gcgtagggct gtttctgatg caggaggggg  13080
ccacccccag cgccgcgctg gacatgaccg cgcgcaacat ggaacctagc atgtacgccg  13140
ccaaccggcc gtttatcaat aagctgatgg actacctgca ccgcgcggcg tccatgaact  13200
cggactactt taccaatgcc attttgaacc cgcactggct cccgccgccg ggtttctaca  13260
cgggcgagta cgacatgcct gaccccaacg acgggttttt gtgggacgac gtggacagcg  13320
cggtgttctc accgaccttg caaaagcgcc aggaggcggt gcgcacgccc gcgagcgagg  13380
gcgcggtggg tcggagcccc tttcctagct tagggagttt gcatagcttg ccgggctcgg  13440
tgaacagcgg cagggtgagc cggccgcgct tgctgggcga ggacgagtac ctaaacgact  13500
cgctgctgca gccgccgcgg gtcaagaacg ccatggccaa taacgggata gagagtctgg  13560
tggacaaact gaaccgctgg aagacctacg ctcaggacca tagggagcct gcgcccgcgc  13620
cgcggcgaca gcgccacgac cggcagcggg gcctggtgtg ggacgacgag gactcggccg  13680
acgatagcag cgtgttggac ttgggcggga gcggtggggt caacccgttc gcgcatctgc  13740
agcccaaact ggggcgacgg atgttttgaa tgcaaaataa aactcaccaa ggccatagcg  13800
tgcgttctct tccttgttag agatgaggcg tgcggtggtg tcttcctctc ctcctccctc  13860
gtacgagagc gtgatggcgc aggcgaccct ggaggttccg tttgtgcctc cgcggtatat  13920
ggctcctacg gagggcagaa acagcattcg ttactcagag ctggctccgc tgtacgacac  13980
cactcgcgtg tacttggtgg acaacaagtc ggcggacatc gcttccctga actaccaaaa  14040
cgaccacagc aactttctga ccacggtggt gcaaaacaac gatttcaccc ccgccgaggc  14100
tagcacgcag acgataaatt ttgacgagcg gtcgcggtgg ggcggtgatc tgaagaccat  14160
tctgcacacc aacatgccca atgtgaacga gtacatgttt accagcaagt ttaaggcgcg  14220
ggtgatggtg gctaggaaac acccacaggg ggtagaagca acagatttaa gcaaggatat  14280
cttagagtac cagtggtttg agtttaccct gcccgagggc aacttttccg agaccatgac  14340
catagacctg atgaacaacg ccatcttgga aaactacttg caagtggggc ggcaaaatgg  14400
cgtgctggag agcgatatcg gagtcaagtt tgacagcagg aatttcaagc tgggctggga  14460
ccccgtgacc aagctggtga tgccaggggt ctacacctat gaggccttcc acccggacgt  14520
ggtgctgctg cctggctgcg gggtggactt caccgagagc cgcctaagca accttctggg  14580
cattcgcaag aagcaacctt tccaagaggg cttcagaatc atgtatgagg atctcgaagg  14640
gggcaacatt cccgcacttc tgaatgtgac caagtacctg gaaagcaaga agaagctaga  14700
```

-continued

```
ggagaatgcc gctaaggcta atggtcctgc aagaggagac agtagtgtct caagagaggt  14760
ggaaaaggca gctgaaaaag agcttgtcat tgagcccatc aagcaagatg atagcaagag  14820
aagttacaac ctcattgagg gtacccatga caccctgtac cgaagctggt acctgtccta  14880
tacctacggg gaccccgaga agggggtgca gtcgtggacg ctgctcacca ccccggacgg  14940
tcactgcggc gcggagcaag tctactggtc gctgccggac ctcatgcaag accccgtcac  15000
cttccgctct acccagcaag tcagcaacta ccccgtggtc ggcgccgagc tcatgccttt  15060
ccgcgccaag agcttttaca acgacctcgc cgtctactcc cagctcatcc gcagctacac  15120
ctccctcacc cacgtcttca accgcttccc cgacaaccag atcctctgcc gcccgcccgc  15180
gcccaccatc accaccgtca gtgaaaacgt gcctgctctc acagatcacg ggacgctacc  15240
gctgcgcagc agtatccgcg gagtccagcg agtgaccgtc actgacgccc gtcgccgcac  15300
ctgtccctac gtctacaagg ccctgggcat agtcgcgccg cgcgtgcttt ccagtcgcac  15360
cttctaaaaa atgtctattc tcatctcgcc cagcaataac accggctggg gtcttactag  15420
gcccagcacc atgtacggag gagccaagaa acgctcccag cagcaccccg tccgcgtccg  15480
cggccacttt cgcgctccct ggggcgcata caagcgcggg cggacttcca ccgccgccgc  15540
cgtgcgcacc accgtcgacg acgtcatcga ctcggtggtc gccgatgcgc gcaactatac  15600
ccccgccccc tccaccgtgg acgcggtcat tgacagcgtg gtggccgacg cgcgcgacta  15660
tgccagacgc aagagccggc ggcgacggat cgccaggcgc caccggagca cgcccgccat  15720
gcgcgccgcc cgggctctgc tgcgccgcgc cagacgcacg ggccgccggg ccatgatgcg  15780
agccgcgcgc cgcgctgcca ctgcacccac ccccgcaggc aggactcgca gacgagcggc  15840
cgctgccgcc gccgcggcca tctctagcat gaccagaccc aggcgcggaa acgtgtactg  15900
ggtgcgcgac tccgtcacgg gcgtgcgcgt gcccgtgcgc actcgtcctc ctcgtccctg  15960
atctaatgct tgtgtcctcc cccgcaagcg acgatgtcaa agcgcaaaat caaggaggag  16020
atgctccagg tcgtcgcccc ggagatttac ggacccccgg accagaaacc ccgcaaaatc  16080
aagcgggtta aaaaaaagga tgaggtggac gagggggcag tagagtttgt gcgcgagttc  16140
gctccgcggc ggcgcgtaaa ttggaagggg cgcagggtgc agcgtgtgtt gcggcccggc  16200
acggcggtgg tgttcacgcc cggcgagcgg tcctcggtca ggagcaagcg tagctatgac  16260
gaggtgtacg gcgacgacga catcctggac caggcggcgg agcgggcggg cgagttcgcc  16320
tacgggaagc ggtcgcgcga agaggagctg atctcgctgc cgctggacga aagcaacccc  16380
acgccgagcc tgaagcccgt gaccctgcag caggtgctgc cccaggcggt gctgctgccg  16440
agccgcgggg ttaagcgcga gggcgagagc atgtacccga ccatgcagat catggtgccc  16500
aagcgccggc gcgtggagga cgtgctggac accgtgaaaa tggatgtgga gcccgaggtc  16560
aaggtgcgcc ccatcaagca ggtggcgccg ggcctgggcg tgcaaaccgt ggacattcag  16620
atccccaccg acatggatgt cgacaaaaaa ccctcgacca gcatcgaggt gcaaaccgac  16680
ccctggctcc cagcctccac cgctaccgcc gccacggcca ccgagcctcc caggaggcga  16740
agatggggcc ctgccaaccg gctgatgccc aactacgtgt tgcatccttc catcatcccg  16800
acgccgggct accgcggcac ccggtactac gccagccgca ggcgcccagc cagtaaacgc  16860
cgccgccgca ccgccacccg ccgccgtctg gcccccgccc gcgtgcgccg cgtgaccacg  16920
cgccggggcc gctcgctcgt tctgcccacc gtgcgctacc accccagcat cctttaatcc  16980
gtgtgctgtg atactgttgc agagagatgg ctctcacttg ccgcctgcgc atccccgtcc  17040
```

cgaattaccg aggaagatcc cgccgcagga gaggcatggc aggcagtggc ctgaaccgcc 17100
gccggcggcg ggccatgcgc aggcgcctga gtggcggctt tctgcccgcg ctcatcccca 17160
taatcgccgc ggccatcggc acgatcccgg gcatagcttc cgttgcgctg caggcgtcgc 17220
agcgccgttg atgtgcgaat aaagcctctt tagactctga cacacctggt cctgtatatt 17280
tttagaatgg aagacatcaa ttttgcgtcc ctggctccgc ggcacggcac gcggccgttc 17340
atgggcacct ggaacgagat cggcaccagc cagctgaacg gggcgcctt caattggagc 17400 agtgtctgga gcgggcttaa aaatttcggc tcgacgctcc ggacctatgg gaacaaggcc 17460
tggaatagta gcactgggca gttgttaagg gaaaagctca aagaccagaa cttccagcaa 17520
aaggtggtgg acgggctggc ctcgggcatt aacggggtgg tggacatcgc gaacccaggc 17580
cgtgcagcgc gagataaaca accgcctgga cccgcggccg cccacggtgg tggagatgga 17640
agatgcaact cctccgccgc ccaagggcga gaagcgaccg cggcccgacg cggaggagac 17700
gatcctgcag gtggacgagc cgccctcgta cgaggaggcc gtaaaggccg gcatgcccac 17760
cacgcgcatc atcgcgccac tggccacggg tgtaatgaaa cccgccaccc ttgacctgcc 17820
tccaccaccc acgcccgctc caccgaaggc agctccggta gtgcagcccc ctccggtggc 17880
gaccgccgtg cgccgcgtcc ccgcccgccg ccaggcccaa aactggcaaa gcacgctgca 17940
cagtattgtg ggcctgggag tgaaaagtct gaagcgccgc cgatgctatt gaaagagagg 18000
aaggaagaca ctaaagggag agcttaactt gtatgtgcct taccgccaga gaacgcgcga 18060
agatggccac cccctcgatg atgccgcagt gggcgtacat gcacatcgcc gggcaggacg 18120
cctcggagta cctgagcccg ggtctggtgc agtttgcccg cgccaccgac acgtacttca 18180
gcctgggcaa caagtttagg aaccccacgg tggccccaac ccacgatgtg accacggacc 18240
ggtcccagcg tctgacgctg cgcttcgtgc ccgtggatcg cgaggacacc acgtactcgt 18300
acaaggcgcg cttcactctg gccgtgggcg acaaccgggt gctagacatg gccagcactt 18360
actttgacat ccgcggcgtt ctggaccgcg gccccagctt caaaccctac tcgggcacgg 18420
cttacaacag cctggccccc aagggcgccc ccaattccag tcagtgggat gctcaagaaa 18480
aaaatggaca aggaggaaat gacatggtta ccaaaactca cacatttggc gtggctgcta 18540
tgggaggaac aaatattaca aaccagggtt tgttaattgg aactgaagaa acagccgata 18600
atcctccaaa ggaaatcttt gcagacaaat tattccagcc agaacctcaa gtaggagagg 18660
aaaactggca agacagcaat gcattctatg gaggcagggc tcttaagaag gaaactaaaa 18720
tgaaaccatg ctatggatct tatgctagac caacaaacac aagtggcgga caggctaagc 18780
ttaaaactgg tgacaatatc gatcctacca aggatttcga catagatctt gctttcttcg 18840
atactcctgg cggaaatcct ccagcaggtg gtagtggaac ggaagaatac aaagcagata 18900
ttgttatgta cactgaaaat gtcaaccttg aaacacctga cactcatgtg gtgtacaaac 18960
cagccaaaga ggatgaaagt tctcaggcca acttggttca gcagtccatg cccaacagac 19020
ccaactacat tggcttcaga gacaattttg tggggctcat gtattacaac agcactggca 19080
acatgggagt gctggctggt caggcctctc agttgaatgc tgtggtggac ttgcaagaca 19140
gaaacacaga gctgtcttac cagctcttgc tagattctct gggtgacaga accagatact 19200
ttagcatgtg gaactctgcg gtggacagct atgatccaga tgtcagaatc attgaaaatc 19260
acggtgtgga agatgagctt ccaaactatt gctttccatt ggatggctct ggtaccaatg 19320
ctgcctacca aggtgtaaag gttcaagatg gtgaagacgg ggataaagaa actgaatggg 19380
aaaaagatac caaagtcgca gatcgtaacc aactgtgcaa gggtaacatc ttcgccatgg 19440
agatcaacct ccaggccaac ctgtggaaga gttttctgta ctcgaacgtg gccctgtacc 19500
tgcccgactc ctacaagtac acgccggcca acatcacgct gcccgccaac accaacacct 19560
acgagtacat gaacggccgc gtggtagccc cctcgctggt ggacgcatac gtcaacatcg 19620
gtgcgcgctg gtcgctggac cccatggaca acgtcaaccc cttcaaccac caccgcaacg 19680
cgggcctgcg ctaccgctcc atgcttctcg gcaacggccg ctacgtgccc ttccacatcc 19740
aagtgcccca aaagttcttt gccattaaga acctgctcct gctccccggc tcctacacct 19800
acgagtggaa cttccgcaag gatgtcaaca tgatcctgca gagttccctc ggaaacgacc 19860
tgcgcgtcga cggcgcctcc gtgcgcttcg acagcgtcaa cctctacgct accttcttcc 19920
ccatggcgca caacaccgcc tccaccctgg aagccatgct gcgcaacgac accaacgacc 19980
agtcctttaa cgactacctc tcggccgcca acatgctcta ccccataccg gccaaggcca 20040
ccaacgtgcc catctccatc cctcgcgca actgggctgc cttccgcggc tggagtttca 20100
cccggctcaa gaccaaggaa actccttccc ttggctcggg tttcgacccc tactttgtct 20160
actcgggctc catcccctac ctcgacggga ccttctacct caaccacacc ttcaaaaagg 20220
tgtccattat gttcgactcc tcggtcagct ggcccggcaa cgaccggctg ctcacgccga 20280
atgagttcga gatcaagcgc agcgtcgacg gggagggcta caacgtggcc caatgcaaca 20340
taaccaagga ctggttcctc gtccagatgc tctcccacta caacatcggc taccagggct 20400
tccacgtgcc cgagggctac aaggaccgca tgtactcctt tttccgcaac ttccagccca 20460
tgagcaggca ggtggtggat gagatcaact acaaggacta caaggccgtc accctgccct 20520
tccagcacaa caactctggc ttcaccggct acctcgcacc caccatgcgt caggggcagc 20580
cttaccccgc caacttccct tacccgctca tcggctccac cgcagtcccc tccgtcaccc 20640
agaaaaagtt cctctgcgac agggtcatgt ggcgcatccc cttctccagc aacttcatgt 20700
ccatgggtgc cctcaccgac ctgggtcaga acatgctcta tgccaactcg gcccacgcgc 20760
tcgacatgac cttcgaggtg gaccccatgg atgagcccac cctcctctat cttctcttcg 20820
aagttttcga cgtggtcaga gtgcaccagc cgcaccgcgg cgtcatcgag gccgtctacc 20880
tgcgcacacc cttctccgcc ggcaacgcca ccacctaagc atgagcggtt ccagcgaacg 20940
agaactcgcg gccatcgtgc gcgacctggg ctgcgggccc tactttttgg gcacccacga 21000
caagcgcttc ccgggcttcc tagccggcga caagctggcc tgcgccatcg tcaacacggc 21060
cggccgcgag accggaggcg tgcactggct cgccttcggc tggaacccgc gctcgcgcac 21120
ctgctacatg ttcgacccct ttgggttctc ggaccgccgg ctcaagcaga tttacagctt 21180
cgagtacgag gccatgctgc gccgaagcgc cctggcctcc tcgcccgacc gctgtctcag 21240
cctcgaacag tccacccaga ccgtgcaggg gcccgactcc gccgcctgcg gactttttttg 21300
ttgcatgttc ttgcatgcgt tcgtgcactg gcccgaccga cccatggacg gaaaccccac 21360
catgaacttg ctgacggggg tgcccaacgg catgctacaa tcgccacagg tgctgcccac 21420
cctccggcgc aaccaggagg agctctaccg cttcctcgcg cgccactccc cttacttccg 21480
atcccaccgc gccgccatcg aacacgccac cgcttttgac aaaatgaaac aactgcgtgt 21540
atctcaataa acagcacttt ttattttaca tgcactggag tatatgcaag ttatttaaaa 21600
gtcgaagggg ttctcgcgct cgtcgttgtg cgccgcgctg gggagggcca cgttgcggta 21660
ctggtacttg gaaagccact tgaactcggg gatcaccagt ttgggcactg gggtctcggg 21720
gaaggtctcg ctccacatgc gccggctcat ctgcagggcg cccagcatgt cagggccgga 21780

```
gatcttgaaa tcacagttgg ggccggtgct ctgcgcgcgc gagttgcggt acacggggtt  21840
gcagcactgg aacaccatca gactggggta cttcacactg gcaagcacgc tcttgtcgct  21900
aatctgatcc ttgtccaggt cctcggcgtt gctcaggccg aacggggtca tcttgcacag  21960
ctggcggccc aggaagggca cgctctgagg cttgtggtta cactcgcagt gcacgggcat  22020
cagcatcatc cccgcgccgc gctgcatatt cgggtagagg gccttgacga aggccgcgat  22080
ctgcttgaaa gcttgctggg ccttggcccc ctcgctgaag aacagaccgc agctcttccc  22140
gctgaactgg ttattcccgc acccggcatc atgcacgcag cagcgcgcgt catggctggt  22200
cagttgcacc acgctccgtc cccagcggtt ctgggtcacc ttagccttgc tgggctgctc  22260
cttcagcgcg cgctgtccgt tctcgctggt cacatccatc tccaccacgt ggtccttgtg  22320
aatcatcacc gttccatgca gacacttgag ctgaccttcc acctcggtgc agccgtgatc  22380
ccacaggacg cagccggtgc actcccaatt cttgtgcgcg atcccgctgt ggctgaaaat  22440
gtaaccttgc aacaggcgac ccataatggt gctaaatgat ttctgggtgg tgaatgtcag  22500
ttgcatcccg cgggcctcct cgttcatcca ggtctggcac atcttctgga agatctcggt  22560
ctgctccggc atgagcttgt aagcatcgcg caagccgctg tcgacgcggt agcgttccat  22620
cagcacgttc atggtatcca tgcccttctc ccatgacgag accagaggca gactcagggg  22680
gttgcgcacg ttcaggacac caggggtcgc gggctcgacg atgcgttttc cgtccttgcc  22740
ttccttcaac agaaccggag gctggctgaa tcccactccc acgatcacgg cgtcttcctg  22800
gggcatctct tcgtcggggt ctaccttggt cacatgcttg gtctttctgg cttgcttctt  22860
ttttggaggg ctgtccacgg ggaccacgtc ctcctcggaa gacccggagc ccacccgctg  22920
atactttcgg cgcttggtgg gcagaggagg tggcggcggc gaggggctcc tctcctgctc  22980
cggcggatag cgcgccgacc cgtggccccg gggcggagtg gcctctcgct ccatgaaccg  23040
gcgcacgtcc tgactgccgc cggccattgt ttcctagggg aagatggagg agcagccgcg  23100
taagcaggag caggaggagg acttaaccac ccacgagcaa cccaaaatcg agcaggacct  23160
gggcttcgaa gagccggctc gtctaaaacc cccacaggat gaacaggagc acgagcaaga  23220
cgcaggccag gaggagaccg acgctgggct cgagcatggc tacctgggag gagaggagga  23280
tgtgctgcta aaacacctgc agcgccagtc cctcatcctc cgggacgccc tggccgaccg  23340
gagcgaaacc cccctcagcg tcgaggagct gtgtcgggcc tacgagctca acctcttctc  23400
gccgcgcgtg ccccccaaac gccagcccaa cggcacctgc gagcccaacc cgcgtctcaa  23460
cttctatccc gtctttgcgg tccccgaggc ccttgccacc tatcacatct ttttcaagaa  23520
ccaaaagatc cccatctcct gtcgcgccaa tcgcactcgc gccgacgcgc tcctcgctct  23580
ggggcccggc gcgcgcatac ctgatatcgc ttccctggaa gaggtgccca agatcttcga  23640
agggctcggt cgggacgaga cgcgcgcggc aaacgctctg aaagaaacag cagaggaaga  23700
gggttacact agcgccctgg tagagttgga aggcgacaac gccaggctgg ccgtgcttaa  23760
gcgcagcgtc gagctcaccc atttcgccta ccccgccgtc aacctcccgc ccaaggtcat  23820
gcgtcgcatc atggatcagc tcatcatgcc ccacatcgag gcccttgatg aaagtcagga  23880
acagcgcccc gagaacgccc agcccgtggt cagcgacgag atgctcgcgc gctggctcgg  23940
gacccgcgac ccccaggccc tggagcagcg gcgcaagctc atgctggccg tggtcctggt  24000
cacccttgag ctcgaatgca tgcgccgctt ttttaccgac cccgagaccc tgcgcaaggt  24060
cgaggagacc ctgcactaca ctttcagaca cggtttcgtc aggcaggcct gcaagatctc  24120
caacgtggag ctgaccaacc tggtctcctg cctggggatc ctacacgaga accgcttggg  24180
```

```
acagaccgtg ctccactcta ccctgaaggg cgaggcgcgg cgggactaca tccgcgactg  24240
cgtctttctc tttctctgcc acacatggca agcggccatg ggcgtgtggc agcagtgtct  24300
cgaggacgag aacctgaagg agctggacaa gcttcttgct agaaacctta aaaagctgtg  24360
gacgggcttc gacgagcgca ccgtcgcctc ggacctggcc gagatcgtct tccccgagcg  24420
cctgaggcag acgctgaaag gagggctgcc cgacttcatg agccagagca tgttgcaaaa  24480
ctaccgcact ttcattctcg agcgatctgg gatgctgccc gccacctgca acgccttccc  24540
ctccgacttt gtcccgctga gctaccgcga gtgtcccccg ccgctgtgga gccactgcta  24600
cctcttgcag ctggccaact acattgccca ccactcggat gtgatcgagg acgtgagcgg  24660
cgaggggctg ctcgagtgcc actgtcgctg caacctatgc tccccgcacc gctccctggt  24720
ctgcaacccc cagctactga gcgagaccca ggtcatcggt acctttgagc tgcaaggtcc  24780
gcaggagtcc accgctccgc tgaaactcac gccggggttg tggacttccg cgtacctgcg  24840
caaatttgta cccgaggact actacgccca tgagataaag ttcttcgagg accaatcgcg  24900
tccgcagcac gcggatctca cggcctgcgt catcacccag ggcgcgatcc tcgcccaatt  24960
gcacgccatc caaaaatccc gccaagagtt tcttctgaaa aagggtagag ggtctacct  25020
ggacccccag acgggcgagg tgctcaaccc gggtctcccc cagcatgccg aggaagaagc  25080
aggagccgct agtggaggag atggaagaag aatgggacag ccaggcagag gaggacgaat  25140
gggaggagga gacagaggag gaagacttgg aagaggtgga agaggagcag gcaacagagc  25200
agcccgtcgc cgcaccatcc gcgccggcag cccctccggt cacggataca acctccgcag  25260
ctccggccaa gcctcctcgt agatgggatc gagtgaaggg tgacggtaag cacgagcgac  25320
agggctaccg atcatggagg gcccacaaag ccgcgatcat cgcctgcttg caagactgcg  25380
gggggaacat cgctttcgcc cgccgctacc tgctcttcca ccgcggggtg aacatccccc  25440
gcaacgtgtt gcattactac cgtcaccttc acagctaaga aaaagcaagt caaaggagtc  25500
gccggaggag gaggcctgag gatcgcggcg aacgagccct tgaccaccag ggagctgagg  25560
aaccggatct tccccactct ttatgccatt tttcagcaaa gtcgaggtca gcagcaagag  25620
ctcaaagtaa aaaaccggtc tctgcgctcg ctcacccgca gttgcttgta ccacaaaaac  25680
gaagatcagc tgcagcgcac tctcgaagac gccgaggctc tgttccacaa gtactgcgcg  25740
ctgactctta aagactaagg cgcgcccacc cggaaaaaag gcgggaatta cctcatcgcc  25800
accatgagca aggagattcc caccccttac atgtggagct atcagcccca gatgggcctg  25860
gccgcgggcg cctcccagga ctactccacc cgcatgaact ggcttagtgc cggcccctcg  25920
atgatctcac gggtcaacgg ggtccgtaac catcgaaacc agatattgtt gcagcaggcg  25980
gcggtcacct ccacgcccag ggcaaagctc aacccgcgta attggccctc caccctggtg  26040
tatcaggaaa tccccgggcc gactaccgta ctacttccgc gtgacgcact ggccgaagtc  26100
cgcatgacta actcaggtgt ccagctggcc ggcggcgctt cccggtgccc gctccgccca  26160
caatcgggta taaaaaccct ggtgatccga ggcagaggca cacagctcaa cgacgagttg  26220
gtgagctctt acaatcgtct gcgaccggac ggagtgttcc aactagccgg agccgggaga  26280
tcgtccttca ctcccaacca ggcctacctg accttgcaga gcagctcttc ggagcctcgc  26340
tcgggaggca tcggaaccca ccagttcgtg gaggagtttg tgccctcggt ctacttcaac  26400
cccttctcgg gctcgccagg cctctacccg gacgagttta taccgaactt cgacgcagtg  26460
agagaagcgg tggacggcta cgactgaagc ttgttgatta aaagcccaga aaccaatcag  26520
```

-continued

```
acccttcctc atttccccat cccaatactc ataagaataa atcattggaa ttaatcattc  26580
aataaagatc acttacttga aatctgaaag tatgtctctg gtgtagttgc tcagcaacac  26640
ctcggtaccc tcctcccagc tctggtactc cagtccccgg cgggcggcga acttcctcca  26700
caccttgaaa gggatgtcaa agaggctccg ggtggaagat gacttcaacc ccgtctaccc  26760
ctatggctac gcgcggaatc agaatatccc cttcctcact ccccccttg tctcctccga  26820
tggattcaaa aacttccccc ctggggtact gtcactcaaa ctggctgatc caatcaccat  26880
taccaatggg gatgtatccc tcaaggtggg aggtggtctc actttgcaag atggaagcct  26940
aactgtaaac cctaaggctc cactgcaagt taatactgat aaaaaacttg agcttgcata  27000
tgataatcca tttgaaagta gtgctaataa acttagttta aaagtaggac atggattaaa  27060
agtattagat gaaaaaagtg ctgcggggtt aaaagattta attggcaaac ttgtggtttt  27120
aacaggaaaa ggaataggca ctgaaaattt agaaaataca gatggtagca gcagaggaat  27180
tggtataaat gtaagagcaa gagaagggtt gacatttgac aatgatggat acttggtagc  27240
atggaaccca aagtatgaca cgcgcacact ttggacaaca ccagacacat ctccaaactg  27300
cacaattgct caagataagg actctaaact cactttggta cttacaaagt gtggaagtca  27360
aatattagct aatgtgtctt tgattgtggt cgcaggaaag taccacatca taaataataa  27420
gacaaatcca aaaataaaaa gttttactat taaactgcta tttaataaga acggagtgct  27480
tttagacaac tcaaatcttg gaaaagctta ttggaacttt agaagtggaa attccaatgt  27540
ttcgacagct tatgaaaaag caattggttt tatgcctaat ttggtagcgt atccaaaacc  27600
cagtaattct aaaaaatatg caagagacat agtttatgga actatatatc ttggtggaaa  27660
acctgatcag ccagcagtca ttaaaactac ctttaaccaa gaaactggat gtgaatactc  27720
tatcacattt aactttagtt ggtccaaaac ctatgaaaat gttgaatttg aaaccacctc  27780
ttttaccttc tcctatattg cccaagaatg aaagaccaat aaacgtgttt ttcatttgaa  27840
attttcatgt atctttattg atttttacac cagcacgagt agacagtctc ccaccaccag  27900
cccattttac agtgtacacg gttctctcag cacgggtagc cttaaatagg gaaatattct  27960
cattagtgcg ggaattggac ttggggtcta taatccacac agtttcctgg cgagccaaac  28020
gggggtcggt gattgaaata aagccgtcct ctgaaaagtc atccaagcgg gcctcacagt  28080
ccaaggtcac agtctggtgg aacgagaaga acgcacagat tcatactcgg aaaacaggat  28140
gggtctgtgc ctctccatca gcgccctcag cagtctctgc cgccggggct cggtgcggct  28200
gctgcaaatg ggatcgggat cacaagtctc tctgactatg atcccaacag ccttcagcat  28260
cagtctcctg gtgcgacggg cacagcaccg catcctgatc tctgccatgt tctcacagta  28320
agtgcagcac ataatcacca tgttattcag cagcccataa ttcagggcgc tccagccaaa  28380
gctcatgttg ggaatgatgg aacccacgtg accatcgtac cagatgcgac agtatatcag  28440
atgcctgccc ctcatgaaca cactgcccat gtacatgatc tctttgggca tgtttctgtt  28500
tacaatctgg cggtaccagg ggaagcgctg gttgaacatg cacccgtaaa tgactctcct  28560
gaaccacacg gccagcaggg tgcctcccgc ccgacactgc agggagccag gggatgaaca  28620
gtggcaatgc aggatccagc gctcgtaccc gctcaccatt tgagctctta ccaagtccag  28680
ggtagcgggg cacaggcaca ctgacataca tctttttaaa atttttattt cctctgtggt  28740
gaggatcata tcccagggga ctggaaactc ttggagcagg gtaaagccag cagcacatgg  28800
taatccacgg acagaactta cattatgata atctgcatga tcacaatcgg gcaacagggg  28860
atgttgttca gtcagtgaag ccctggtttc ctcatcagat cgtggtaaac gggccctgcg  28920
```

```
atatggatga tggcggagcg agctggattg aatctcggtt tgcattgtag tggattctct  28980
tgcgtacctt gtcgtacttc tgccagcaga aatgggccct tgaacagcat atacccctcc  29040
tacggccgtc ctttcgctgc tgccgctcag tcatccaact aaagtacatc cattctcgaa  29100
gattctggag aagttcctct gcatctgata aaataaaaaa cccgtccatg cgaattcccc  29160
tcatcacatc agccaggact ctgtaggcca tccccatcca gttaatgctg ccttgtctat  29220
cattcagagg gggcggtggc aggactggaa gaaccatttt tattccaaac ggtctcgaag  29280
gacgataaag tgcaagtcac gcaggtgaca gcgttcccct ccgctgtgct ggtggaaaca  29340
gacagccagg tcaaaaccca ctctattttc aaggtgctcg accgtggctt cgagcagtgg  29400
ctctacgcgc acatccagca taagaatcac attaaaggct ggccctccat cgatttcatc  29460
aatcatcagg ttacattcct gcaccatccc caggtaattc tcatttttcc agccttggat  29520
tatctctaca aattgttggt gtaagtccac tccgcacatg tggaaaagct cccacagtgc  29580
cccctccact ttcataatca ggcagacctt cataatagaa acagatcctg ctgctccacc  29640
acctgcagcg tgttcaaaac aacaagattc aataaggttc tgccctccgc cctgagctcg  29700
cgcctcaatg tcagctgcaa aaagtcactt aagtcctggg ccactacagc tgacaattca  29760
gagccagggc taagcgtggg actggcaagc gtaagggaaa actttaatgc tccaaagcta  29820
gcacccaaaa actgcatgct ggaataagct ctctttgtgt ctccggtgat gccttccaaa  29880
atgtgagtga taaagcgtgg tagtttttct ttaatcattt gcgtaataga aaagtcctct  29940
aaataagtca ctaggacccc agggaccaca atgtggtagc ttacaccgcg tcgctgaagc  30000
atggttagta gagatgagag tctgaaaaac agaaagcatg cactaaacta aggtggctat  30060
tttcactgaa ggaaaaatca ctctctccag cagcagggta cccactgggt ggcccttgcg  30120
gacatacaaa aatcggtccg tgtgattaaa aagcagcaca gtaagttcct gtcttcttcc  30180
ggcaaaaatc acatcagact gggttagtat gtccctggca tggtagtcat tcaaggccat  30240
aaatctgccc tgatatccag taggaaccag cacactcact tttaggtgaa gcaataccac  30300
cccatgcgga ggaatgtgga aagattcagg gcaaaaaaat tatatctatt gctagcccct  30360
tcctggacgg gagcaatccc tccaggacta tctataaaag catacagaga ttcagccata  30420
gcttagcccg cttaccagta gacagaaagc acagcagtac aagcgccaac agcagcaact  30480
gactacccac tgacccagct ccctatttaa aggcacctta cactgacgta atgaccaaag  30540
gtctaaaaac cccgccaaaa aaaacacaca cgccctgggt gtttttcaca aaaacacttc  30600
cgcgttctca cttcctcgta tcgattttgt gactcaactt ccgggttccc acgttacgtc  30660
acttctgccc ttacatgtaa cttggccgta tggcgccatc ttgcccacgt ccaaaatggc  30720
tttcatgacc ggccacgcct ccgcgccggc cgttagccgt gcgtcgtgac gttatttgca  30780
tcaccgcttc tcgtccaatc agcgttggct ccgccccaaa accgttaaaa ttcaaaagct  30840
catttgcata ttaacttttg tttactttgt ggggtatatt attagatagt taattaagga  30900
tgcatgttta aactcgacag cgacacactt gcatcggatg cagcccggtt aacgtgccgg  30960
cacggcctgg gtaaccaggt attttgtcca cataaccgtg cgcaaaatgt tgtggataag  31020
caggacacag cagcaatcca cagcaggcat acaaccgcac accgaggtta ctccgttcta  31080
caggttacga cgacatgtca atacttgccc ttgacaggca ttgatggaat cgtagtctca  31140
cgctgatagt ctgatcgaca atacaagtgg gaccgtggtc ccagaccgat aatcagaccg  31200
acaacacgag tgggatcgtg gtcccagact aataatcaga ccgacgatac gagtgggacc  31260
```

gtggtcccag actaataatc agaccgacga tacgagtggg accgtggttc cagactaata 31320
atcagaccga cgatacgagt gggaccgtgg tcccagacta ataatcagac cgacgatacg 31380
agtgggacca tggtcccaga ctaataatca gaccgacgat acgagtggga ccgtggtccc 31440
agtctgatta tcagaccgac gatacgagtg ggaccgtggt cccagactaa taatcagacc 31500
gacgatacga gtgggaccgt ggtcccagac taataatcag accgacgata cgagtgggac 31560
cgtggtccca gtctgattat cagaccgacg atacaagtgg aacagtgggc ccagagagaa 31620
tattcaggcc agttatgctt tctggcctgt aacaaaggac attaagtaaa gacagataaa 31680
cgtagactaa aacgtggtcg catcagggtg ctggcttttc aagttcctta agaatggcct 31740
caattttctc tatacactca gttggaacac gagacctgtc caggttaagc accattttat 31800
cgcccttata caatactgtc gctccaggag caaactgatg tcgtgagctt aaactagttc 31860
ttgatgcaga tgacgtttta agcacagaag ttaaaagagt gataacttct tcagcttcaa 31920
atatcacccc agcttttttc tgctcatgaa ggttagatgc ctgctgctta agtaattcct 31980
ctttatctgt aaaggctttt tgaagtgcat cacctgaccg ggcagatagt tcaccggggt 32040
gagaaaaaag agcaacaact gatttaggca atttggcggt gttgatacag cgggtaataa 32100
tcttacgtga aatattttcc gcatcagcca gcgcagaaat atttccagca aattcattct 32160
gcaatcggct tgcataacgc tgaccacgtt cataagcact tgttgggcga taatcgttac 32220
ccaatctgga taatgcagcc atctgctcat catccagctc gccaaccaga acacgataat 32280
cactttcggt aagtgcagca gctttacgac ggcgactccc atcggcaatt tctatgacac 32340
cagatactct tcgaccgaac gccggtgtct gttgaccagt cagtagaaaa gaagggatga 32400
gatcatccag tgcgtcctca gtaagcagct cctggtcacg ttcattacct gaccataccc 32460
gagaggtctt ctcaacacta tcaccccgga gcacttcaag agtaaacttc acatcccgac 32520
cacatacagg caaagtaatg gcattaccgc gagccattac tcctacgcgc gcaattaacg 32580
aatccaccat cggggcagct ggtgtcgata acgaagtatc ttcaaccggt tgagtattga 32640
gcgtatgttt tggaataaca ggcgcacgct tcattatcta atctcccagc gtggtttaat 32700
cagacgatcg aaaatttcat tgcagacagg ttcccaaata gaaagagcat ttctccaggc 32760
accagttgaa gagcgttgat caatggcctg ttcaaaaaca gttctcatcc ggatctgacc 32820
tttaccaact tcatccgttt cacgtacaac attttttaga accatgcttc cccaggcatc 32880
ccgaatttgc tcctccatcc acggggactg agagccatta ctattgctgt atttggtaag 32940
caaaatacgt acatcaggct cgaacccttt aagatcaacg ttcttgagca gatcacgaag 33000
catatcgaaa aactgcagtg cggaggtgta gtcaaacaac tcagcaggcg tgggaacaat 33060
cagcacatca gcagcacata cgacattaat cgtgccgata cccaggttag gcgcgctgtc 33120
aataactatg acatcatagt catgagcaac agtttcaatg gccagtcgga gcatcaggtg 33180
tggatcggtg ggcagtttac cttcatcaaa tttgcccatt aactcagttt caatacggtg 33240
cagagccaga caggaaggaa taatgtcaag ccccggccag caagtgggct ttattgcata 33300
agtgacatcg tccttttccc caagatagaa aggcaggaga gtgtcttctg catgaatatg 33360
aagatctggt acccatccgt gatacattga ggctgttccc tgggggtcgt taccttccac 33420
gagcaaaaca cgtagcccct tcagagccag atcctgagca agatgaacag aaactgaggt 33480
tttgtaaacg ccacctttat gggcagcaac cccgatcacc ggtggaaata cgtcttcagc 33540
acgtcgcaat cgcgtaccaa acacatcacg catatgatta atttgttcaa ttgtataacc 33600
aacacgttgc tcaacccgtc ctcgaatttc catatccggg tgcggtagtc gccctgcttt 33660

```
ctcggcatct ctgatagcct gagaagaaac cccaactaaa tccgctgctt cacctattct  33720
ccagcgccgg gttattttcc tcgcttccgg gctgtcatca ttaaactgtg caatggcgat  33780
agccttcgtc atttcatgac cagcgtttat gcactggtta agtgtttcca tgagtttcat  33840
tctgaacatc ctttaatcat tgctttgcgt ttttttatta aatcttgcaa tttactgcaa  33900
agcaacaaca aaatcgcaaa gtcatcaaaa aaccgcaaag ttgtttaaaa taagagcaac  33960
actacaaaag gagataagaa gagcacatac ctcagtcact tattatcact agcgctcgcc  34020
gcagccgtgt aaccgagcat agcgagcgaa ctggcgagga agcaaagaag aactgttctg  34080
tcagatagct cttacgctca gcgcaagaag aaatatccac cgtgggaaaa actccaggta  34140
gaggtacaca cgcggatagc caattcagag taataaactg tgataatcaa ccctcatcaa  34200
tgatgacgaa ctaacccccg atatcaggtc acatgacgaa gggaaagaga aggaaatcaa  34260
ctgtgacaaa ctgccctcaa atttggcttc cttaaaaatt acagttcaaa aagtatgaga  34320
aaatccatgc aggctgaagg aaacagcaaa actgtgacaa attaccctca gtaggtcaga  34380
acaaatgtga cgaaccaccc tcaaatctgt gacagataac cctcagacta tcctgtcgtc  34440
atggaagtga tatcgcggaa ggaaaatacg atatgagtcg tctggcggcc tttctttttc  34500
tcaatgtatg agaggcgcat tggagttctg ctgttgatct cattaacaca gacctgcagg  34560
aagcggcggc ggaagtcagg catacgctgg taactttgag gcagctggta acgctctatg  34620
atccagtcga ttttcagaga gacgatgcct gagccatccg gcttacgata ctgacacagg  34680
gattcgtata aacgcatggc atacggattg gtgatttctt ttgtttcact aagccgaaac  34740
tgcgtaaacc ggttctgtaa cccgataaag aagggaatga gatatgggtt gatatgtaca  34800
ctgtaaagcc ctctggatgg actgtgcgca cgtttgataa accaaggaaa agattcatag  34860
ccttttttcat cgccggcatc ctcttcaggg cgataaaaaa ccacttcctt ccccgcgaaa  34920
ctcttcaatg cctgccgtat atccttactg gcttccgcag aggtcaatcc gaatatttca  34980
gcatatttag caacatggat ctcgcagata ccgtcatgtt cctgtagggt gccatcagat  35040
tttctgatct ggtcaacgaa cagatacagc atacgttttt gatcccggga gagactatat  35100
gccgcctcag tgaggtcgtt tgactggacg attcgcgggc tatttttacg tttcttgtga  35160
ttgataaccg ctgtttccgc catgacagat ccatgtgaag tgtgacaagt ttttagattg  35220
tcacactaaa taaaaaagag tcaataagca gggataactt tgtgaaaaaa cagcttcttc  35280
tgagggcaat ttgtcacagg gttaagggca atttgtcaca gacaggactg tcatttgagg  35340
gtgatttgtc acactgaaag ggcaatttgt cacaacacct tctctagaac cagcatggat  35400
aaaggcctac aaggcgctct aaaaaagaag atctaaaaac tataaaaaaa ataattataa  35460
aaatatcccc gtggataagt ggataacccc aagggaagtt ttttcaggca tcgtgtgtaa  35520
gcagaatata taagtgctgt tccctggtgc ttcctcgctc actcgagggc ttcgccgtcg  35580
ctcgactgcg gcgagcctac tggctgtaaa aggacagacc acatcatggt tctgtgttca  35640
ttaggttgtt ctgtccattg ctgacataat ccgctccact tcaacgtaac accgcacgaa  35700
gatttctatt gttcctgaag gcatattcaa atcgttttcg ttaccgcttg caggcatcat  35760
gacagaacac tacttcctat aaacgctaca caggctcctg agattaataa tgcggatctc  35820
tacgataatg ggagattttc ccgactgttt cgttcgcttc tcagtggata acagccagct  35880
tctctgttta acagacaaaa acagcatatc cactcagttc cacatttcca tataaaggcc  35940
aaggcattta ttctcaggat aattgtttca gcatcgcaac cgcatcagac tccggcatcg  36000
```

caaactgcac ccggtgccgg gcagccacat ccagcgcaaa aaccttcgtg tagacttccg 36060
ttgaactgat ggacttatgt cccatcaggc tttgcagaac tttcagcggt ataccggcat 36120
acagcatgtg catcgcatag gaatggcgga acgtatgtgg tgtgaccgga acagagaacg 36180
tcacaccgtc agcagcagcg gcggcaaccg cctccccaat ccaggtcctg accgttctgt 36240
ccgtcacttc ccagatccgc gctttctctg tccttcctgt gcgacggtta cgccgctcca 36300
tgagcttatc gcgaataaat acctgtgacg gaagatcact tcgcagaata aataaatcct 36360
ggtgtccctg ttgataccgg gaagccctgg gccaactttt ggcgaaaatg agacgttgat 36420
cggcacgtaa gaggttccaa ctttcaccat aatgaaataa gatcactacc gggcgtattt 36480
tttgagttat cgagattttc aggagctaag gaagctaaaa tggagaaaaa aatcactgga 36540
tataccaccg ttgatatatc ccaatggcat cgtaaagaac attttgaggc atttcagtca 36600
gttgctcaat gtacctataa ccagaccgtt cagctggata ttacggcctt tttaaagacc 36660
gtaaagaaaa ataagcacaa gttttatccg gcctttattc acattcttgc ccgcctgatg 36720
aatgctcatc cggaattccg tatggcaatg aaagacggtg agctggtgat atgggatagt 36780
gttcaccctt gttacaccgt tttccatgag caaactgaaa cgttttcatc gctctggagt 36840
gaataccacg acgatttccg gcagtttcta cacatatatt cgcaagatgt ggcgtgttac 36900
ggtgaaaacc tggcctattt ccctaaaggg tttattgaga atatgttttt cgtctcagcc 36960
aatccctggg tgagtttcac cagttttgat ttaaacgtgg ccaatatgga caacttcttc 37020
gcccccgttt tcaccatggg caaatattat acgcaaggcg acaaggtgct gatgccgctg 37080
gcgattcagg ttcatcatgc cgtctgtgat ggcttccatg tcggcagaat gcttaatgaa 37140
ttacaacagt actgcgatga gtggcagggc ggggcgtaat ttttttaagg cagttattgg 37200
tgcccttaaa cgcctggttg ctacgcctga ataagtgata ataagcggat gaatggcaga 37260
aattcgatga taagctgtca aacatgagaa tgggtcgaga acatgagaat gggtcgag 37318

<210> SEQ ID NO 5
<211> LENGTH: 3431
<212> TYPE: DNA
<213> ORGANISM: Artificial sequence
<220> FEATURE:
<223> OTHER INFORMATION: /note="Description of artificial sequence: pDonorSir19aGFP_5pIX"

<400> SEQUENCE: 5
ctatctaata atatacccca caaagtaaac aaaagttaat atgcaaatga gcttttgaat 60
tttaacggtt ttggggcgga gccaacgctg attggacgag aagcggtgat gcaaataacg 120
tcacgacgca cggctaacgg ccggcgcgga ggcgtggcct aggccggaag caagtcgcgg 180
ggctaatgac gtataaaaaa gcggacttta gacccggaaa cggccgattt tcccgcggcc 240
acgcccggat atgaggtaat tctgggcgga tgcaagtgaa attaggtcat tttggcgcca 300
aaactgaatg aggaagtgaa aagtgaaaaa tacctgtccc gcccagggcg gaatatttac 360
cgagggccga gagactttga ccgattacgt ggggtttcga ttgcggtgtt tttttcgcga 420
gaaggtaaac tgcccacttg gcagtacatc aagtgtatca tatgccaagt acgcccccta 480
ttgacgtcaa tgacggtaaa tggcccgcct ggcattatgc ccagtacatg accttatggg 540
actttcctac ttggcagtac atctacgtat tagtcatcgc tattaccatg gtgatgcggt 600
tttggcagta catcaatggg cgtggatagc ggtttgactc acggggattt ccaagtctcc 660
accccattga cgtcaatggg agtttgtttt ggcaccaaaa tcaacgggac tttccaaaat 720

-continued

```
gtcgtaacaa ctccgcccca ttgacgcaaa tgggcggtag gcgtgtacgg tgggaggtct    780
atataagcag agctggttta gtgaaccgtc agatccgcta gcgctaccgg actcagatct    840
cgagctcaag cttcgaattc tgcagtcgac ggtaccgcgg gcccgggatc caccggtcgc    900
caccatggtg agcaagggcg aggagctgtt caccggggtg gtgcccatcc tggtcgagct    960
ggacggcgac gtaaacggcc acaagttcag cgtgtccggc gagggcgagg gcgatgccac   1020
ctacggcaag ctgaccctga agttcatctg caccaccggc aagctgcccg tgccctggcc   1080
caccctcgtg accaccctga cctacggcgt gcagtgcttc agccgctacc ccgaccacat   1140
gaagcagcac gacttcttca agtccgccat gcccgaaggc tacgtccagg agcgcaccat   1200
cttcttcaag gacgacggca actacaagac ccgcgccgag gtgaagttcg agggcgacac   1260
cctggtgaac cgcatcgagc tgaagggcat cgacttcaag gaggacggca acatcctggg   1320
gcacaagctg gagtacaact acaacagcca caacgtctat atcatggccg acaagcagaa   1380
gaacggcatc aaggtgaact tcaagatccg ccacaacatc gaggacggca gcgtgcagct   1440
cgccgaccac taccagcaga acacccccat cggcgacggc cccgtgctgc tgcccgacaa   1500
ccactacctg agcacccagt ccgccctgag caaagacccc aacgagaagc gcgatcacat   1560
ggtcctgctg gagttcgtga ccgccgccgg gatcactctc ggcatggacg agctgtacaa   1620
gtaaagcggc cgcgactcta gatcataatc agccatacca catttgtaga ggttttactt   1680
gctttaaaaa acctcccaca cctccccctg aacctgaaac ataaaatgaa tgcaattgtt   1740
gttgttaact tgtttattgc agcttataat ggttacaaat aaagcaatag catcacaaat   1800
ttcacaaata aagcattttt ttcactgcat tctagttgtg gtttgtccaa actcatcaat   1860
gtatcttaaa tcgaattcaa gcatatgctg aaatgtgtgg gcgtggctta agggtgggaa   1920
agaatatata aggtgggggt cttatgtagt tttgtatctg ttttgcagca gccgccgccg   1980
cctccggacg cgtgaagttc ctattctcta gaaagtatag gaacttcaat tcccatgtca   2040
gccgttaagt gttcctgtgt cactcaaaat tgctttgaga ggctctaagg gcttctcagt   2100
gcgttacatc cctggcttgt tgtccacaac cgttaaacct taaaagcttt aaaagcctta   2160
tatattcttt tttttcttat aaaacttaaa accttagagg ctatttaagt tgctgattta   2220
tattaatttt attgttcaaa catgagagct tagtacgtga aacatgagag cttagtacgt   2280
tagccatgag agcttagtac gttagccatg agggtttagt tcgttaaaca tgagagctta   2340
gtacgttaaa catgagagct tagtacgtga aacatgagag cttagtacgt actatcaaca   2400
ggttgaactg ctgatcttca gatcctctac gccggacgca tcgtggccgg atccgattta   2460
ttcaacaaag ccacgttgtg tctcaaaatc tctgatgtta cattgcacaa gataaaaata   2520
tatcatcatg aacaataaaa ctgtctgctt acataaacag taatacaagg ggtgttatga   2580
gccatattca acgggaaacg tcttgctcga ggccgcgatt aaattccaac atggatgctg   2640
atttatatgg gtataaatgg gctcgcgata atgtcgggca atcaggtgcg acaatctatc   2700
gattgtatgg gaagcccgat gcgccagagt tgtttctgaa acatggcaaa ggtagcgttg   2760
ccaatgatgt tacagatgag atggtcagac taaactggct gacggaattt atgcctcttc   2820
cgaccatcaa gcattttatc cgtactcctg atgatgcatg gttactcacc actgcgatcc   2880
ccgggaaaac agcattccag gtattagaag aatatcctga ttcaggtgaa aatattgttg   2940
atgcgctggc agtgttcctg cgccggttgc attcgattcc tgtttgtaat tgtcctttta   3000
acagcgatcg cgtatttcgt ctcgctcagg cgcaatcacg aatgaataac ggtttggttg   3060
atgcgagtga ttttgatgac gagcgtaatg gctggcctgt tgaacaagtc tggaaagaaa   3120
```

```
tgcataagct tttgccattc tcaccggatt cagtcgtcac tcatggtgat ttctcacttg   3180

ataaccttat ttttgacgag gggaaattaa taggttgtat tgatgttgga cgagtcggaa   3240

tcgcagaccg ataccaggat cttgccatcc tatggaactg cctcggtgag ttttctcctt   3300

cattacagaa acggcttttt caaaaatatg gtattgataa tcctgatatg aataaattgc   3360

agtttcattt gatgctcgat gagtttttct aatcagaatt ggttaattgg ttgtaacact   3420

ggcttaatta a                                                        3431
```

<210> SEQ ID NO 6
<211> LENGTH: 33868
<212> TYPE: DNA
<213> ORGANISM: Artificial sequence
<220> FEATURE:
<223> OTHER INFORMATION: /note="Description of artificial sequence: pBACSir19A"

<400> SEQUENCE: 6

```
gaagttccta ttccgaagtt cctattctct agaaagtata ggaacttcgc gtaaattgta     60

agcgttaata ttttgttaaa attcgcgtta aatttttgtt aaatcagctc attttttaac    120

caataggccg aaatcggcaa aatcccttga agagcagacc agaccacctg gtgatggcct    180

gtaccgggac cgagttcagc tccagtgggg aggacacaga ttagaggtag gtttgagtag    240

tgggcgtggc taatgtgagt ataaaggcgg gtgtcttacg agggtctttt tgcttttctg    300

cagacatcat gaacgggacc ggcggggcct tcgaaggggg gctttttagc ccttatttga    360

caacccgcct gccgggatgg gccggagttc gtcagaatgt gatgggatct acggtggatg    420

ggcgtccagt gcttccagca aattcctcga ccatgaccta cgcgaccgtg ggagctcgt     480

cgcttgacag caccgccgca gccgcggcag ccgcagccgc catgacagcg acgagactgg    540

cctcgagcta tatgcccagc agcggtagca gcccctctgt gcccagttcc atcatcgccg    600

aggagaaact gctggccctg ctggccgagc tggaagccct gagccgccag ctggccgccc    660

tgacccagca ggtgtccgat ctccgcgagc aacagcagca gcaaaataaa tgaattcaat    720

aaacacagat tctgattcaa acagcaaagc atctttatta tttatttttt cgcgcgcggt    780

aggccctggt ccacctctcc cgatcattga gagtgcggtg gatttttttcc aggacccggt   840

agaggtggga ttggatgttg aggtacatgg gcatgagccc gtcccggggg tggaggtagc    900

accactgcat ggcctcgtgc tctggggtcg tgttgtagat aatccagtca tagcaggggc    960

gctgggcgtg gtgctggatg atgtccttga ggaggagact gatggccacg ggagcccct    1020

tggtgtaggt gttggcaaag cggttaagct gggagggatg catgcggggg gagatgatgt   1080

gcagtttggc ctggatcttg aggttggcga tgttgccacc cagatcccgc cgggggttca   1140

tattgtgcag gaccaccaga acggtgtagc ccgtgcactt ggggaactta tcatgcaact   1200

tggaagggaa tgcgtggaag aatttggaga cgcccttgtg cccgcccagg ttttccatgc   1260

actcatccat gatgatggca atgggcccgt gggctgcggc tttggcaaaa acgtttctgg   1320

ggtcagagac atcataatta tgctcctggg tgagatcatc ataagacatt ttaatgaatt   1380

tggggcgaag ggtgccagat tgggggacga tcgttccctc gggccccggg gcgaagttcc   1440

cctcgcagat ctgcatctcc caggctttca tctcggaggg ggggatcatg tccacctgcg   1500

gggcgatgaa aaaaacggtt tccggggcgg gggtgatgag ctgcgaggag agcaggtttc   1560

ttaacagctg ggacttgccg cacccggtcg ggccgtagat gaccccgatg acgggttgca   1620

ggtggtagtt caaggagatg cagctgccgt cgtcccggag gagggggggcc acctcgttga  1680
```

gcatgtctct cacttggagg ttttcccgga cgagctcgcc gaggaggcgg tccccgccca 1740
gcgagagcag ctcttgcagg gaagcaaagt ttttcagggg cttgagcccg tcggccatgg 1800
gcatcttggc aagggtctgc gagaggagct ccaggcggtc ccatagctcg gtgacgtgct 1860
ctacggcatc tcgatccagc agacttcctc gtttcggggg ttgggacgac tgcgactgta 1920
gggcacgaga cgatgggcgt ccagcgcggc cagcgtcatg tccttccagg gtctcagggt 1980
ccgagtgagg gtggtctccg tcacggtgaa ggggtgggcc ccgggctggg cgcttgcaag 2040
ggtgcgcttg agactcatcc tgctggtgct gaaacgggca cggtcttcgc cctgcgcgtc 2100
ggcgagatag cagttgacca tgagcttgta gttaagggcc tcggcggcgt ggcccttggc 2160
acggagcttg cctttggaag agcgcccgca ggcgggacag aggagggatt gcagggcgta 2220
gagcttgggt gcgagaaaga cggactcggg agcgaaggcg tccgctccgc agtgggcgca 2280
gacggtctcg cactcgacga gccaggtgag ctcgggctgc tcggggtcaa aaaccagttt 2340
tcccccgttc tttttgatgc gcttcttacc tcgcgtctcc atgagtctgt gtccgcgttc 2400
ggtgacaaac aggctgtctg tgtccccgta gacggacttg attggcctgt cctgcagggg 2460
cgtcccgcgg tcctcctcgt agagaaactc ggaccactct gagacaaagg cgcgcgtcca 2520
cgccaagaca aaggaggcca cgtgcgaggg gtagcggtcg ttgtccacca gggggtccac 2580
cttttccacc gtgtgcagac acatgtcccc ctcctccgca tccaagaagg tgattggctt 2640
gtaggtgtag gccacgtgac cgggggtccc cgacgggggg gtataaaagg gggcgggtct 2700
gtgctcgtcc tcactctctt ccgcgtcgct gtccacgagc gccagctgtt ggggtaggta 2760
ttccctctcg agagcgggca tgacctcggc actcaggttg tcagtttcta gaaacgagga 2820
ggatttgatg ttggcctgcc ctgccgcaat gctttttagg agactttcat ccatctggtc 2880
agaaaagact atttttttat tgtcaagctt ggtggcaaag gagccataga gggcgttgga 2940
gagaagcttg gcgatggatc tcatggtctg atttttgtca cggtcggcgc gctccttggc 3000
cgcgatgttg agctggacat actcgcgcgc gacacacttc cattctggga agacggtggt 3060
gcgctcgtcg ggcacgatcc tgacgcgcca gccgcgatta tgcagggtga ccaggtccac 3120
gctggtggcc acctcgccgc gcaggggctc gttggtccag cagaggcgtc cgcccttgcg 3180
cgagcagaac gggggcagca catcaagcag atgctcgtca ggggggtccg catcgatggt 3240
gaagatgccc ggacagagtt ccttgtcaaa ataatcgatt tttgaggatg catcatccaa 3300
ggccatctgc cactcgcggg cggccagcgc tcgctcgtag ggttgaggg gcggacccca 3360
gggcatggga tgcgtgaggg cggaggcgta catgccgcag atgtcgtaga catagatggg 3420
ctccgagagg atgccgatgt aggtgggata acagcgcccc ccgcggatgc tggcgcgcac 3480
atagtcatac aactcgtgcg agggggccaa gaaagcgggg ccgagattgg tgcgctgggg 3540
ctgctcggcg cggaagacga tctggcgaaa gatggcatgc gagttggagg agatggtggg 3600
ccgttggaag atgttaaagt gggcgtgggg caagcggacc gagtcgcgga tgaagtgcgc 3660
gtaggagtct tgcagcttgg caacgagctc ggcggtgaca aggacgtcca tggcgcagta 3720
gtccagcgtt tcacggatga tgtcataacc cgcctcttct ttcttctccc acagcgcgcg 3780
gttgagggcg tactcctcgt catccttcca gtactcccgg agcgggaatc ctcgatcgtc 3840
cgcacggtaa gagcccagca tgtagaaatg gttcacggcc ttgtagggac agcagccctt 3900
ctccacgggg agggcgtaag cttgagcggc cttgcggagc gaggtgtgcg tcagggcgaa 3960
ggtatcccta accatgactt tcaagaactg gtacttgaaa tccgagtcgt cgcagccgcc 4020

-continued gtgctcccag agctcgaaat cggtgcgctt cttcgagagg gggttaggca gagcgaaagt 4080
gacgtcattg aagagaatct tgcctgcccg cggcatgaaa ttgcgggtga tgcggaaagg 4140
gcccggaacg gaggctcggt tgttgatgac ctgggcggcg aggacgatct cgtcgaagcc 4200
gttgatgttg tgcccgacga tgtagagttc catgaatcgc gggcggcctt tgatgtgcgg 4260 cagcttttttg agttcctcgt aggtgaggtc ctcggggcat tgcaggccgt gctgctcgag 4320
cgcccactcc tggagatgtg ggttggcttg catgaatgaa gcccagagct cgcgggccat 4380
gagggtctgg agctcgtcgc gaaagaggcg gaactgctgg cccacggcca tcttttctgg 4440
ggtgacgcag tagaaggtga gggggtcccg ctcccagcga tcccagcgta agcgcacggc 4500
gagatcgcga gcgagggcga ccagctcggg gtccccggag aatttcatga ccagcatgaa 4560
ggggacgagc tgcttgccga aggaccccat ccaggtgtag gtttctacat cgtaggtgac 4620
aaagagccgc tccgtgcgag gatgagagcc gattgggaag aactggattt cctgccacca 4680
gttggtcgag tggctgttga tgtgatgaaa gtagaaatcc cgccggcgaa ccgagcactc 4740
gtgctgatgc ttgtaaaagc gtccgcagta ctcgcagcgc tgcacgggct gtacctcatc 4800
cacgagatac acagcgcgtc ccttgaggag gaacttcagg agtggcggcc ctggctggtg 4860
gttttcatgt tcgcctgcgt gggactcacc ctggggctcc tcgaggacgg agaggctgac 4920
gagcccgcgc gggagccagg tccagatttc ggcgcggcgg gggcggagag cgaaaacgag 4980
ggcgcgcagt tgggagctgt ccatggtgtc gcggagatcc aggtccgggg gcagggttct 5040
gaggttgacc tcgtagaggc gggtgagggc gtgcttgaga tgcagatggt acttgatctc 5100
cacgggtgag ttggtggtcg tgtccacgca ttgcatgagc ccgtagctgc gcggggccac 5160
gaccgtgccg cggtgcgctt ttagaagcgg tgtcgcggac gcgctcccgg cggcagcggc 5220
ggttccggcc ccgcgggcag tggcggtaga ggcacgtcgg cgtggcgctc gggcaggtcc 5280
cggtgctgcg ccctgagagc gctggcgtgc gcgacgacgc ggcggttgac atcctggatc 5340
tgccgccttt gcgtgaagac cacgggcccc gtgactttga acctgaaaga cagttcaaca 5400
gaatcaatct cggcgtcatt gacggcggcc tgacgcagga tctcttgcac gtcgcccgag 5460
ttgtcctggt aggcgatctc ggacatgaac tgctcgattt cctcctcctg gagatcgccg 5520
cggcccgcgc gctctacggt ggcggcaagg tcattcgaga tgcgacccat gagctgcgag 5580
aaggcgccca ggccgctctc gttccagacg cggctgtaaa ccacgtcccc gtcggcgtcg 5640
cgcgcgcgca tgaccacctg cgcgaggttg agctccacgt gccgcgtaaa gacggcgtag 5700
ttgcgcaggc gctggaagag gtagttgagg gtggtggcga tgtgctcggt gacgaagaag 5760
tacataatcc agcggcgcag gggcatttcg ctgatgtcgc caatggcctc cagcctttcc 5820
atggcctcgt agaaatccac ggcgaagttg aaaaactggg cgttgcgggc cgagaccgtg 5880
agctcgtctt ccaggagcct gatgagttcg gcgatggtgg cgcgcacctc gcgctcgaaa 5940
tcccaggggg cctcctcctc ttcctcttct tccatgacga cctcttcttc tatttcttcc 6000
tctgggggcg gtggtggtgg cggggcccga cgacgacggc gacgcaccgg gagacggtcg 6060
acgaagcgct cgatcatctc cccgcggcgg cgacgcatgg tttcggtgac ggcgcgaccc 6120
cgttcgcgag gacgcagcgt gaagacgccg ccggtcatct cccggtaatg gggtgggtcc 6180
ccgttgggca gcgatagggc gctgacaatg catcttatca attgcggtgt agggcacgtg 6240
agcgcgtcga gatcgaccgg atcggagaat ctttcgagga aagcgtctag ccaatcgcag 6300
tcgcaaggta agctcaaaca cgtagcagcc ctgtggacgc tgttagaatt gcggttgctg 6360
atgatgtaat tgaagtaggc gtttttgagg cggcggatgg tggcgaggag gaccaggtcc 6420
ttgggtcccg cttgctggat gcggagccgc tcggccatgc cccaggcctg gccctgacac 6480
cggctcaggt tcttgtagta gtcatgcatg agcctctcga tgtcatcact ggcggaggcg 6540
gagtcttcca tgcgggtgac cccgacgccc ctgaacggct gcacgagcgc caggtcggcg 6600
acgacgcgct cggcgaggat ggcctgttgc acgcgggtga gggtgtcctg gaagtcgtcc 6660
atgtcgacga agcggtggta ggcccctgtg ttgatggtgt aagtgcagtt ggccataagc 6720
gaccagttga cggtctgcag gccgggttgc acgacctcgg agtacctgag ccgcgagaag 6780
gcgcgcgagt cgaagacata gtcgttgcag gtgcgcacga ggtactggta tccgactaga 6840
aagtgcggcg gcggctggcg gtagagcggc cagcgctggg tggccggcgc gcccggggcc 6900
aggtcctcaa gcatgagtcg gtggtagccg tagaggtagc gggacatcca ggtgatgccg 6960
gcggcggtgg tggaggcgcg cgggaactcg cggacgcggt tccagatgtt gcgcaggggc 7020
aggaaatagt ccatggtcgg cacggtctgg ccggtgagac gcgcgcagtc attgatgctc 7080
tagaggcaaa aacgaaagcg gttgagcggg ctcttcctcc gtagcctggc ggaacgcaaa 7140
cgggttaggc cgcgtgtgta ccccggttcg agtcccctcg aatcaggctg gagccgcgac 7200
taacgtggta ttggcactcc cgtctcgacc caagcccgat agccgccagg atacggcgga 7260
gagccctttt tgtcggccga ggggagtcgc tagacttgaa agcggccgaa aaccctgccg 7320
ggtagtggct cgcgcccgta gtctggagaa gcatcgccag ggttgagtcg cggcagaacc 7380
cggttcaagg acggccgcgg cgagcgggac ttggtcaccc cgccgattta aagacccaca 7440
gccagccgac ttctccagtt acgggagcga gccccctttt ttctttttgc cagatgcatc 7500
ccgtcctgcg ccaaatgcgt cccacccccc cggcgaccac cgcgaccgcg gccgtagcag 7560
gcgccggcgc tagccagcca cagccacaga cagagatgga cttggaagag ggcgaagggc 7620
tggcgagact gggggcgccg tccccggagc gacatccccg cgtgcagctg cagaaggacg 7680
tgcgcccggc gtacgtgcct gcgcagaacc tgttcaggga ccgcagcggg gaggagcccg 7740
aggagatgcg cgactgccgg tttcgggcgg gcagggagct gcgcgagggc ctggaccgcc 7800
agcgcgtgct gcgcgacgag gatttcgagc cgaacgagca gacggggatc agccccgcgc 7860
gcgcgcacgt ggcggcggcc aacctggtga cagcctacga gcagacggtg aagcaggaac 7920
gcaactttca aaagagtttc aacaaccacg tgcgcaccct gatcgcgcgc gaggaggtgg 7980
ccctgggcct gatgcacctg tgggacctgg cggaggccat tgtgcagaac ccggacagca 8040
agcctctgac ggcacaactg ttcctggtgg tgcagcacag cagggacaac gaggcgttca 8100
gggaggcgct gctaaacatc gccgagcccg agggccgctg gctgctggag ctgatcaaca 8160
tcttgcaaag catcgtagtg caggagcgca gcctgagctt ggccgagaag gtggcggcga 8220
tcaactactc ggtgctaagc ctgggcaagt tttacgcgcg caagatttac aagacgccgt 8280
acgtgcccat agacaaggag gtgaaaatag acagctttta catgcgcatg gcgctcaagg 8340
tgctgacgct gagcgacgac ctgggcgtgt accgcaacga ccgcatccac aaggccgtga 8400
gcacgagccg gcggcgcgag ctgagcgacc gcgagctgat gctaagcctg cgccgggcgc 8460
tggtaggtgg cgccgccggc ggcgaggagt cctacttcga catgggggcg gacctgcatt 8520
ggcagccgag ccggcgcgcc ttggaggccg cctacggtcc agaggacttg gatgaggatg 8580
aggaagagga ggaggatgca cccgttgcgg ggtactgacg cctccgtgat gtgtttttag 8640
atgtcccagc agcaagcccc ggaccccgcc ataagggcgg cgctgcaaag ccagccgtcc 8700
ggtctagcat cggacgactg ggaggccgcg atgcaacgca tcatggccct gacgacccgc 8760

-continued

```
aaccccgagt cctttagaca acagccgcag gccaacagac tttcgaccat tctggaggcg   8820
gtggtcccct ctcggaccaa ccccacgcac gagaaggtgc tggcgatcgt gaacgcgctg   8880
gcggagaaca aggctattcg tcccgacgag gctgggctgg tatacaacgc cctgctggag   8940
cgcgtgggcc gctacaacag cacgaacgtg cagtccaacc tggaccggct ggtgacggac   9000
gtgcgcgagg ccgtggcgca gcgcgagcgg ttcaagaacg agggcctggg ctcgctggtg   9060
gcgctgaacg ccttcctggc gacgcagccg gcgaacgtgc cgcgcgggca ggacgattat   9120
accaacttta tcagcgcgct gcggctgatg gtgaccgagg ttccccagag cgaggtgtac   9180
cagtcgggcc cggactactt tttccagact agcagacagg gcctgcagac ggtgaacctg   9240
agccaggctt tcaagaacct gcgcgggctg tggggcgtgc aggcgcccgt gggcgaccgg   9300
tcgacggtga gcagcttgct gacgcccaac tcgcggctgc tgctgctgct gatcgcgccc   9360
ttcaccgaca gcggcagcgt gaaccgcaac tcgtacctgg gtcacctgct gacgctgtac   9420
cgcgaggcca taggccaggc acaggtggac gagcagacct tccaggagat cactagtgta   9480
agccgcgcgc tgggtcagaa cgacaccgac agtctgaggg ccaccctgaa cttcttgctg   9540
accaatagac agcagaagat cccggcgcag tatgcgctgt cggccgagga ggagcgcatc   9600
ctgagatatg tgcagcagag cgtagggctg tttctgatgc aggagggggc cacccccagc   9660
gccgcgctgg acatgaccgc gcgcaacatg gaacctagca tgtacgccgc caaccggccg   9720
tttatcaata agctgatgga ctacctgcac cgcgcggcgt ccatgaactc ggactacttt   9780
accaatgcca ttttgaaccc gcactggctc ccgccgccgg ggttctacac gggcgagtac   9840
gacatgcctg accccaacga cgggtttttg tgggacgacg tggacagcgc ggtgttctca   9900
ccgaccttgc aaaagcgcca ggaggcggtg cgcacgcccg cgagcgaggg cgcggtgggt   9960
cggagcccct ttcctagctt agggagtttg catagcttgc cgggctcggt gaacagcggc  10020
agggtgagcc ggccgcgctt gctgggcgag gacgagtacc taaacgactc gctgctgcag  10080
ccgccgcggg tcaagaacgc catggccaat aacgggatag agagtctggt ggacaaactg  10140
aaccgctgga agacctacgc tcaggaccat agggagcctg cgcccgcgcc gcggcgacag  10200
cgccacgacc ggcagcgggg cctggtgtgg gacgacgagg actcggccga cgatagcagc  10260
gtgttggact tgggcgggag cggtggggtc aacccgttcg cgcatctgca gcccaaactg  10320
gggcgacgga tgttttgaat gcaaaataaa actcaccaag gccatagcgt gcgttctctt  10380
ccttgttaga gatgaggcgt gcggtggtgt cttcctctcc tcctccctcg tacgagagcg  10440
tgatggcgca ggcgaccctg gaggttccgt ttgtgcctcc gcggtatatg gctcctacgg  10500
agggcagaaa cagcattcgt tactcagagc tggctccgct gtacgacacc actcgcgtgt  10560
acttggtgga caacaagtcg gcggacatcg cttccctgaa ctaccaaaac gaccacagca  10620
actttctgac cacggtggtg caaaacaacg atttcacccc cgccgaggct agcacgcaga  10680
cgataaattt tgacgagcgg tcgcggtggg gcggtgatct gaagaccatt ctgcacacca  10740
acatgcccaa tgtgaacgag tacatgttta ccagcaagtt taaggcgcgg gtgatggtgg  10800
ctaggaaaca cccacagggg gtagaagcaa cagatttaag caaggatatc ttagagtacc  10860
agtggtttga gtttaccctg cccgagggca acttttccga gaccatgacc atagacctga  10920
tgaacaacgc catcttggaa aactacttgc aagtggggcg gcaaaatggc gtgctggaga  10980
gcgatatcgg agtcaagttt gacagcagga atttcaagct gggctgggac cccgtgacca  11040
agctggtgat gccaggggtc tacacctatg aggccttcca cccggacgtg gtgctgctgc  11100
ctggctgcgg ggtggacttc accgagagcc gcctaagcaa ccttctgggc attcgcaaga  11160
```

agcaaccttt ccaagagggc ttcagaatca tgtatgagga tctcgaaggg ggcaacattc 11220
ccgcacttct gaatgtgacc aagtacctgg aaagcaagaa gaagctagag gagaatgccg 11280
ctaaggctaa tggtcctgca agaggagaca gtagtgtctc aagagaggtg gaaaaggcag 11340
ctgaaaaaga gcttgtcatt gagcccatca agcaagatga tagcaagaga agttacaacc 11400
tcattgaggg tacccatgac accctgtacc gaagctggta cctgtcctat acctacgggg 11460
accccgagaa gggggtgcag tcgtggacgc tgctcaccac cccggacggt cactgcggcg 11520
cggagcaagt ctactggtcg ctgccggacc tcatgcaaga ccccgtcacc ttccgctcta 11580
cccagcaagt cagcaactac cccgtggtcg gcgccgagct catgcctttc cgcgccaaga 11640
gcttttacaa cgacctcgcc gtctactccc agctcatccg cagctacacc tccctcaccc 11700
acgtcttcaa ccgcttcccc gacaaccaga tcctctgccg cccgcccgcg cccaccatca 11760
ccaccgtcag tgaaaacgtg cctgctctca cagatcacgg gacgctaccg ctgcgcagca 11820
gtatccgcgg agtccagcga gtgaccgtca ctgacgcccg tcgccgcacc tgtccctacg 11880
tctacaaggc cctgggcata gtcgcgccgc gcgtgctttc cagtcgcacc ttctaaaaaa 11940
tgtctattct catctcgccc agcaataaca ccggctgggg tcttactagg cccagcacca 12000
tgtacggagg agccaagaaa cgctcccagc agcaccccgt ccgcgtccgc ggccactttc 12060
gcgctccctg gggcgcatac aagcgcgggc ggacttccac cgccgccgcc gtgcgcacca 12120
ccgtcgacga cgtcatcgac tcggtggtcg ccgatgcgcg caactatacc cccgccccct 12180
ccaccgtgga cgcggtcatt gacagcgtgg tggccgacgc gcgcgactat gccagacgca 12240
agagccggcg gcgacggatc gccaggcgcc accggagcac gcccgccatg cgcgccgccc 12300
gggctctgct gcgccgcgcc agacgcacgg gccgccgggc catgatgcga gccgcgcgcc 12360
gcgctgccac tgcacccacc cccgcaggca ggactcgcag acgagcggcc gctgccgccg 12420
ccgcggccat ctctagcatg accagaccca ggcgcggaaa cgtgtactgg gtgcgcgact 12480
ccgtcacggg cgtgcgcgtg cccgtgcgca ctcgtcctcc tcgtccctga tctaatgctt 12540
gtgtcctccc ccgcaagcga cgatgtcaaa gcgcaaaatc aaggaggaga tgctccaggt 12600
cgtcgccccg gagatttacg gacccccgga ccagaaaccc cgcaaaatca agcgggttaa 12660
aaaaaaggat gaggtggacg agggggcagt agagtttgtg cgcgagttcg ctccgcggcg 12720
gcgcgtaaat tggaaggggc gcagggtgca gcgtgtgttg cggcccggca cggcggtggt 12780
gttcacgccc ggcgagcggt cctcggtcag gagcaagcgt agctatgacg aggtgtacgg 12840
cgacgacgac atcctggacc aggcggcgga gcgggcgggc gagttcgcct acgggaagcg 12900
gtcgcgcgaa gaggagctga tctcgctgcc gctggacgaa agcaacccca cgccgagcct 12960
gaagcccgtg accctgcagc aggtgctgcc ccaggcggtg ctgctgccga gccgcggggt 13020
taagcgcgag ggcgagagca tgtacccgac catgcagatc atggtgccca agcgccggcg 13080
cgtggaggac gtgctggaca ccgtgaaaat ggatgtggag cccgaggtca aggtgcgccc 13140
catcaagcag gtggcgccgg gcctgggcgt gcaaaccgtg gacattcaga tccccaccga 13200
catggatgtc gacaaaaaac cctcgaccag catcgaggtg caaaccgacc cctggctccc 13260
agcctccacc gctaccgccg ccacggccac cgagcctccc aggaggcgaa gatggggccc 13320
tgccaaccgg ctgatgccca actacgtgtt gcatccttcc atcatcccga cgccgggcta 13380
ccgcggcacc cggtactacg ccagccgcag gcgcccagcc agtaaacgcc gccgccgcac 13440
cgccacccgc cgccgtctgg cccccgcccg cgtgcgccgc gtgaccacgc gccggggccg 13500
ctcgctcgtt ctgcccaccg tgcgctacca ccccagcatc ctttaatccg tgtgctgtga 13560
tactgttgca gagagatggc tctcacttgc cgcctgcgca tccccgtccc gaattaccga 13620
ggaagatccc gccgcaggag aggcatggca ggcagtggcc tgaaccgccg ccggcggcgg 13680
gccatgcgca ggcgcctgag tggcggcttt ctgcccgcgc tcatccccat aatcgccgcg 13740
gccatcggca cgatcccggg catagcttcc gttgcgctgc aggcgtcgca gcgccgttga 13800
tgtgcgaata aagcctcttt agactctgac acacctggtc ctgtatattt ttagaatgga 13860
agacatcaat tttgcgtccc tggctccgcg gcacggcacg cggccgttca tgggcacctg 13920
gaacgagatc ggcaccagcc agctgaacgg gggcgccttc aattggagca gtgtctggag 13980
cgggcttaaa aatttcggct cgacgctccg gacctatggg aacaaggcct ggaatagtag 14040
cactgggcag ttgttaaggg aaaagctcaa agaccagaac ttccagcaaa aggtggtgga 14100
cgggctggcc tcgggcatta acggggtggt ggacatcgcg aacccaggcc gtgcagcgcg 14160
agataaacaa ccgcctggac ccgcggccgc ccacggtggt ggagatggaa gatgcaactc 14220
ctccgccgcc caagggcgag aagcgaccgc ggcccgacgc ggaggagacg atcctgcagg 14280
tggacgagcc gccctcgtac gaggaggccg taaaggccgg catgcccacc acgcgcatca 14340
tcgcgccact ggccacgggt gtaatgaaac ccgccaccct tgacctgcct ccaccaccca 14400
cgcccgctcc accgaaggca gctccggtag tgcagccccc tccggtggcg accgccgtgc 14460
gccgcgtccc cgcccgccgc caggcccaaa actggcaaag cacgctgcac agtattgtgg 14520
gcctgggagt gaaaagtctg aagcgccgcc gatgctattg aaagagagga aggaagacac 14580
taaagggaga gcttaacttg tatgtgcctt accgccagag aacgcgcgaa gatggccacc 14640
ccctcgatga tgccgcagtg ggcgtacatg cacatcgccg ggcaggacgc ctcggagtac 14700
ctgagcccgg gtctggtgca gtttgcccgc gccaccgaca cgtacttcag cctgggcaac 14760
aagtttagga accccacggt ggccccaacc cacgatgtga ccacggaccg gtcccagcgt 14820
ctgacgctgc gcttcgtgcc cgtggatcgc gaggacacca cgtactcgta caaggcgcgc 14880
ttcactctgg ccgtgggcga caaccgggtg ctagacatgg ccagcactta ctttgacatc 14940
cgcggcgttc tggaccgcgg ccccagcttc aaaccctact cgggcacggc ttacaacagc 15000
ctggccccca agggcgcccc caattccagt cagtgggatg ctcaagaaaa aaatggacaa 15060
ggaggaaatg acatggttac caaaactcac acatttggcg tggctgctat gggaggaaca 15120
aatattacaa accagggttt gttaattgga actgaagaaa cagccgataa tcctccaaag 15180
gaaatctttg cagacaaatt attccagcca gaacctcaag taggagagga aaactggcaa 15240
gacagcaatg cattctatgg aggcagggct cttaagaagg aaactaaaat gaaaccatgc 15300
tatggatctt atgctagacc aacaaacaca agtggcggac aggctaagct taaaactggt 15360
gacaatatcg atcctaccaa ggatttcgac atagatcttg ctttcttcga tactcctggc 15420
ggaaatcctc cagcaggtgg tagtggaacg gaagaataca aagcagatat tgttatgtac 15480
actgaaaatg tcaaccttga aacacctgac actcatgtgg tgtacaaacc agccaaagag 15540
gatgaaagtt ctcaggccaa cttggttcag cagtccatgc ccaacagacc caactacatt 15600
ggcttcagag acaattttgt ggggctcatg tattacaaca gcactggcaa catgggagtg 15660
ctggctggtc aggcctctca gttgaatgct gtggtggact tgcaagacag aaacacagag 15720
ctgtcttacc agctcttgct agattctctg ggtgacagaa ccagatactt tagcatgtgg 15780
aactctgcgg tggacagcta tgatccagat gtcagaatca ttgaaaatca cggtgtggaa 15840
gatgagcttc caaactattg ctttccattg gatggctctg gtaccaatgc tgcctaccaa 15900

```
ggtgtaaagg ttcaagatgg tgaagacggg gataaagaaa ctgaatggga aaaagatacc  15960
aaagtcgcag atcgtaacca actgtgcaag ggtaacatct tcgccatgga gatcaacctc  16020
caggccaacc tgtggaagag ttttctgtac tcgaacgtgg ccctgtacct gcccgactcc  16080
tacaagtaca cgccggccaa catcacgctg cccgccaaca ccaacaccta cgagtacatg  16140
aacggccgcg tggtagcccc ctcgctggtg gacgcatacg tcaacatcgg tgcgcgctgg  16200
tcgctggacc ccatggacaa cgtcaacccc ttcaaccacc accgcaacgc gggcctgcgc  16260
taccgctcca tgcttctcgg caacggccgc tacgtgccct tccacatcca agtgccccaa  16320
aagttctttg ccattaagaa cctgctcctg ctccccggct cctacaccta cgagtggaac  16380
ttccgcaagg atgtcaacat gatcctgcag agttccctcg gaaacgacct gcgcgtcgac  16440
ggcgcctccg tgcgcttcga cagcgtcaac ctctacgcta ccttcttccc catggcgcac  16500
aacaccgcct ccaccctgga agccatgctg cgcaacgaca ccaacgacca gtcctttaac  16560
gactacctct cggccgccaa catgctctac cccataccgg ccaaggccac caacgtgccc  16620
atctccatcc cctcgcgcaa ctgggctgcc ttccgcggct ggagtttcac ccggctcaag  16680
accaaggaaa ctccttccct tggctcgggt ttcgacccct actttgtcta ctcgggctcc  16740
atcccctacc tcgacgggac cttctacctc aaccacacct tcaaaaaggt gtccattatg  16800
ttcgactcct cggtcagctg gcccggcaac gaccggctgc tcacgccgaa tgagttcgag  16860
atcaagcgca gcgtcgacgg ggagggctac aacgtggccc aatgcaacat aaccaaggac  16920
tggttcctcg tccagatgct ctcccactac aacatcggct accagggctt ccacgtgccc  16980
gagggctaca aggaccgcat gtactccttt ttccgcaact tccagcccat gagcaggcag  17040
gtggtggatg agatcaacta caaggactac aaggccgtca ccctgccctt ccagcacaac  17100
aactctggct tcaccggcta cctcgcaccc accatgcgtc aggggcagcc ttaccccgcc  17160
aacttccctt acccgctcat cggctccacc gcagtcccct ccgtcaccca gaaaaagttc  17220
ctctgcgaca gggtcatgtg gcgcatcccc ttctccagca acttcatgtc catgggtgcc  17280
ctcaccgacc tgggtcagaa catgctctat gccaactcgg cccacgcgct cgacatgacc  17340
ttcgaggtgg accccatgga tgagcccacc ctcctctatc ttctcttcga agttttcgac  17400
gtggtcagag tgcaccagcc gcaccgcggc gtcatcgagg ccgtctacct gcgcacaccc  17460
ttctccgccg gcaacgccac cacctaagca tgagcggttc cagcgaacga gaactcgcgg  17520
ccatcgtgcg cgacctgggc tgcgggccct actttttggg cacccacgac aagcgcttcc  17580
cgggcttcct agccggcgac aagctggcct gcgccatcgt caacacggcc ggccgcgaga  17640
ccggaggcgt gcactggctc gccttcggct ggaacccgcg ctcgcgcacc tgctacatgt  17700
tcgacccctt tgggttctcg gaccgccggc tcaagcagat ttacagcttc gagtacgagg  17760
ccatgctgcg ccgaagcgcc ctggcctcct cgcccgaccg ctgtctcagc ctcgaacagt  17820
ccacccagac cgtgcagggg cccgactccg ccgcctgcgg actttttgt tgcatgttct  17880
tgcatgcgtt cgtgcactgg cccgaccgac ccatggacgg aaaccccacc atgaacttgc  17940
tgacgggggt gcccaacggc atgctacaat cgccacaggt gctgcccacc ctccggcgca  18000
accaggagga gctctaccgc ttcctcgcgc gccactcccc ttacttccga tcccaccgcg  18060
ccgccatcga acacgccacc gcttttgaca aaatgaaaca actgcgtgta tctcaataaa  18120
cagcactttt tattttacat gcactggagt atatgcaagt tatttaaaag tcgaaggggt  18180
tctcgcgctc gtcgttgtgc gccgcgctgg ggagggccac gttgcggtac tggtacttgg  18240
```

-continued

```
aaagccactt gaactcgggg atcaccagtt tgggcactgg ggtctcgggg aaggtctcgc  18300
tccacatgcg ccggctcatc tgcagggcgc ccagcatgtc agggccggag atcttgaaat  18360
cacagttggg gccggtgctc tgcgcgcgcg agttgcggta cacggggttg cagcactgga  18420
acaccatcag actggggtac ttcacactgg caagcacgct cttgtcgcta atctgatcct  18480
tgtccaggtc ctcggcgttg ctcaggccga acggggtcat cttgcacagc tggcggccca  18540
ggaagggcac gctctgaggc ttgtggttac actcgcagtg cacgggcatc agcatcatcc  18600
ccgcgccgcg ctgcatattc gggtagaggg ccttgacgaa ggccgcgatc tgcttgaaag  18660
cttgctgggc cttggccccc tcgctgaaga acagaccgca gctcttcccg ctgaactggt  18720
tattcccgca cccggcatca tgcacgcagc agcgcgcgtc atggctggtc agttgcacca  18780
cgctccgtcc ccagcggttc tgggtcacct tagccttgct gggctgctcc ttcagcgcgc  18840
gctgtccgtt ctcgctggtc acatccatct ccaccacgtg gtccttgtga atcatcaccg  18900
ttccatgcag acacttgagc tgaccttcca cctcggtgca gccgtgatcc cacaggacgc  18960
agccggtgca ctcccaattc ttgtgcgcga tcccgctgtg gctgaaaatg taaccttgca  19020
acaggcgacc cataatggtg ctaaatgatt tctgggtggt gaatgtcagt tgcatcccgc  19080
gggcctcctc gttcatccag gtctggcaca tcttctggaa gatctcggtc tgctccggca  19140
tgagcttgta agcatcgcgc aagccgctgt cgacgcggta gcgttccatc agcacgttca  19200
tggtatccat gcccttctcc catgacgaga ccagaggcag actcaggggg ttgcgcacgt  19260
tcaggacacc aggggtcgcg ggctcgacga tgcgttttcc gtccttgcct tccttcaaca  19320
gaaccggagg ctggctgaat cccactccca cgatcacggc gtcttcctgg ggcatctctt  19380
cgtcggggtc taccttggtc acatgcttgg tctttctggc ttgcttcttt tttggagggc  19440
tgtccacggg gaccacgtcc tcctcggaag acccggagcc cacccgctga tactttcggc  19500
gcttggtggg cagaggaggt ggcggcggcg aggggctcct ctcctgctcc ggcggatagc  19560
gcgccgaccc gtggccccgg ggcggagtgg cctctcgctc catgaaccgg cgcacgtcct  19620
gactgccgcc ggccattgtt tcctagggga agatggagga gcagccgcgt aagcaggagc  19680
aggaggagga cttaaccacc cacgagcaac ccaaaatcga gcaggacctg ggcttcgaag  19740
agccggctcg tctaaaaccc ccacaggatg aacaggagca cgagcaagac gcaggccagg  19800
aggagaccga cgctgggctc gagcatggct acctgggagg agaggaggat gtgctgctaa  19860
aacacctgca gcgccagtcc ctcatcctcc gggacgccct ggccgaccgg agcgaaaccc  19920
ccctcagcgt cgaggagctg tgtcgggcct acgagctcaa cctcttctcg ccgcgcgtgc  19980
cccccaaacg ccagcccaac ggcacctgcg agcccaaccc gcgtctcaac ttctatcccg  20040
tctttgcggt ccccgaggcc cttgccacct atcacatctt tttcaagaac caaaagatcc  20100
ccatctcctg tcgcgccaat cgcactcgcg ccgacgcgct cctcgctctg gggcccggcg  20160
cgcgcatacc tgatatcgct tccctggaag aggtgcccaa gatcttcgaa gggctcggtc  20220
gggacgagac gcgcgcggca aacgctctga aagaaacagc agaggaagag ggttacacta  20280
gcgccctggt agagttggaa ggcgacaacg ccaggctggc cgtgcttaag cgcagcgtcg  20340
agctcaccca tttcgcctac cccgccgtca acctcccgcc caaggtcatg cgtcgcatca  20400
tggatcagct catcatgccc cacatcgagg cccttgatga aagtcaggaa cagcgccccg  20460
agaacgccca gcccgtggtc agcgacgaga tgctcgcgcg ctggctcggg acccgcgacc  20520
cccaggccct ggagcagcgg cgcaagctca tgctggccgt ggtcctggtc acccttgagc  20580
tcgaatgcat gcgccgcttt tttaccgacc ccgagaccct gcgcaaggtc gaggagaccc  20640
```

```
tgcactacac tttcagacac ggtttcgtca ggcaggcctg caagatctcc aacgtggagc  20700
tgaccaacct ggtctcctgc ctggggatcc tacacgagaa ccgcttggga cagaccgtgc  20760
tccactctac cctgaagggc gaggcgcggc gggactacat ccgcgactgc gtctttctct  20820
ttctctgcca cacatggcaa gcggccatgg gcgtgtggca gcagtgtctc gaggacgaga  20880
acctgaagga gctggacaag cttcttgcta gaaaccttaa aaagctgtgg acgggcttcg  20940
acgagcgcac cgtcgcctcg gacctggccg agatcgtctt ccccgagcgc ctgaggcaga  21000
cgctgaaagg agggctgccc gacttcatga gccagagcat gttgcaaaac taccgcactt  21060
tcattctcga gcgatctggg atgctgcccg ccacctgcaa cgccttcccc tccgactttg  21120
tcccgctgag ctaccgcgag tgtcccccgc cgctgtggag ccactgctac ctcttgcagc  21180
tggccaacta cattgcccac cactcggatg tgatcgagga cgtgagcggc gaggggctgc  21240
tcgagtgcca ctgtcgctgc aacctatgct ccccgcaccg ctccctggtc tgcaaccccc  21300
agctactgag cgagacccag gtcatcggta cctttgagct gcaaggtccg caggagtcca  21360
ccgctccgct gaaactcacg ccggggttgt ggacttccgc gtacctgcgc aaatttgtac  21420
ccgaggacta ctacgcccat gagataaagt tcttcgagga ccaatcgcgt ccgcagcacg  21480
cggatctcac ggcctgcgtc atcacccagg gcgcgatcct cgcccaattg cacgccatcc  21540
aaaaatcccg ccaagagttt cttctgaaaa agggtagagg ggtctacctg gacccccaga  21600
cgggcgaggt gctcaacccg ggtctccccc agcatgccga ggaagaagca ggagccgcta  21660
gtggaggaga tggaagaaga atgggacagc caggcagagg aggacgaatg ggaggaggag  21720
acagaggagg aagacttgga agaggtggaa gaggagcagg caacagagca gcccgtcgcc  21780
gcaccatccg cgccggcagc cccctccggtc acggatacaa cctccgcagc tccggccaag  21840
cctcctcgta gatgggatcg agtgaagggt gacggtaagc acgagcgaca gggctaccga  21900
tcatggaggg cccacaaagc cgcgatcatc gcctgcttgc aagactgcgg ggggaacatc  21960
gctttcgccc gccgctacct gctcttccac cgcggggtga acatcccccg caacgtgttg  22020
cattactacc gtcaccttca cagctaagaa aaagcaagtc aaaggagtcg ccggaggagg  22080
aggcctgagg atcgcggcga acgagccctt gaccaccagg gagctgagga accggatctt  22140
ccccactctt tatgccattt ttcagcaaag tcgaggtcag cagcaagagc tcaaagtaaa  22200
aaaccggtct ctgcgctcgc tcacccgcag ttgcttgtac cacaaaaacg aagatcagct  22260
gcagcgcact ctcgaagacg ccgaggctct gttccacaag tactgcgcgc tgactcttaa  22320
agactaaggc gcgcccaccc ggaaaaaagg cgggaattac ctcatcgcca ccatgagcaa  22380
ggagattccc accccttaca tgtggagcta tcagccccag atgggcctgg ccgcgggcgc  22440
ctcccaggac tactccaccc gcatgaactg gcttagtgcc ggcccctcga tgatctcacg  22500
ggtcaacggg gtccgtaacc atcgaaacca gatattgttg cagcaggcgg cggtcacctc  22560
cacgcccagg gcaaagctca acccgcgtaa ttggccctcc accctggtgt atcaggaaat  22620
ccccgggccg actaccgtac tacttccgcg tgacgcactg gccgaagtcc gcatgactaa  22680
ctcaggtgtc cagctggccg gcggcgcttc ccggtgcccg ctccgcccac aatcgggtat  22740
aaaaaccctg gtgatccgag gcagaggcac acagctcaac gacgagttgg tgagctctta  22800
caatcgtctg cgaccggacg gagtgttcca actagccgga gccgggagat cgtccttcac  22860
tcccaaccag gcctacctga ccttgcagag cagctcttcg gagcctcgct cgggaggcat  22920
cggaacccac cagttcgtgg aggagtttgt gccctcggtc tacttcaacc ccttctcggg  22980
```

```
ctcgccaggc ctctacccgg acgagtttat accgaacttc gacgcagtga gagaagcggt  23040
ggacggctac gactgaagct tgttgattaa aagcccagaa accaatcaga cccttcctca  23100
tttccccatc ccaatactca taagaataaa tcattggaat taatcattca ataaagatca  23160
cttacttgaa atctgaaagt atgtctctgg tgtagttgct cagcaacacc tcggtaccct  23220
cctcccagct ctggtactcc agtccccggc gggcggcgaa cttcctccac accttgaaag  23280
ggatgtcaaa gaggctccgg gtggaagatg acttcaaccc cgtctacccc tatggctacg  23340
cgcggaatca gaatatcccc ttcctcactc ccccctttgt ctcctccgat ggattcaaaa  23400
acttcccccc tggggtactg tcactcaaac tggctgatcc aatcaccatt accaatgggg  23460
atgtatccct caaggtggga ggtggtctca ctttgcaaga tggaagccta actgtaaacc  23520
ctaaggctcc actgcaagtt aatactgata aaaaacttga gcttgcatat gataatccat  23580
ttgaaagtag tgctaataaa cttagtttaa aagtaggaca tggattaaaa gtattagatg  23640
aaaaaagtgc tgcggggtta aaagatttaa ttggcaaact tgtggtttta acaggaaaag  23700
gaataggcac tgaaaattta gaaaatacag atggtagcag cagaggaatt ggtataaatg  23760
taagagcaag agaagggttg acatttgaca atgatggata cttggtagca tggaacccaa  23820
agtatgacac gcgcacactt tggacaacac cagacacatc tccaaactgc acaattgctc  23880
aagataagga ctctaaactc actttggtac ttacaaagtg tggaagtcaa atattagcta  23940
atgtgtcttt gattgtggtc gcaggaaagt accacatcat aaataataag acaaatccaa  24000
aaataaaaag ttttactatt aaactgctat ttaataagaa cggagtgctt ttagacaact  24060
caaatcttgg aaaagcttat tggaacttta gaagtggaaa ttccaatgtt tcgacagctt  24120
atgaaaaagc aattggtttt atgcctaatt tggtagcgta tccaaaaccc agtaattcta  24180
aaaaatatgc aagagacata gtttatggaa ctatatatct tggtggaaaa cctgatcagc  24240
cagcagtcat taaaactacc tttaaccaag aaactggatg tgaatactct atcacattta  24300
actttagttg gtccaaaacc tatgaaaatg ttgaatttga aaccacctct tttaccttct  24360
cctatattgc ccaagaatga aagaccaata aacgtgtttt tcatttgaaa ttttcatgta  24420
tctttattga tttttacacc agcacgagta gacagtctcc caccaccagc ccattttaca  24480
gtgtacacgg ttctctcagc acgggtagcc ttaaataggg aaatattctc attagtgcgg  24540
gaattggact tggggtctat aatccacaca gtttcctggc gagccaaacg gggtcggtg  24600
attgaaataa agccgtcctc tgaaaagtca tccaagcggg cctcacagtc caaggtcaca  24660
gtctggtgga acgagaagaa cgcacagatt catactcgga aaacaggatg ggtctgtgcc  24720
tctccatcag cgccctcagc agtctctgcc gccggggctc ggtgcggctg ctgcaaatgg  24780
gatcgggatc acaagtctct ctgactatga tcccaacagc cttcagcatc agtctcctgg  24840
tgcgacgggc acagcaccgc atcctgatct ctgccatgtt ctcacagtaa gtgcagcaca  24900
taatcaccat gttattcagc agcccataat tcagggcgct ccagccaaag ctcatgttgg  24960
gaatgatgga acccacgtga ccatcgtacc agatgcgaca gtatatcaga tgcctgcccc  25020
tcatgaacac actgcccatg tacatgatct ctttgggcat gtttctgttt acaatctggc  25080
ggtaccaggg gaagcgctgg ttgaacatgc acccgtaaat gactctcctg aaccacacgg  25140
ccagcagggt gcctcccgcc cgacactgca gggagccagg ggatgaacag tggcaatgca  25200
ggatccagcg ctcgtacccg ctcaccattt gagctcttac caagtccagg gtagcggggc  25260
acaggcacac tgacatacat ctttttaaaa tttttatttc ctctgtggtg aggatcatat  25320
cccaggggac tggaaactct tggagcaggg taaagccagc agcacatggt aatccacgga  25380
```

```
cagaacttac attatgataa tctgcatgat cacaatcggg caacagggga tgttgttcag  25440
tcagtgaagc cctggtttcc tcatcagatc gtggtaaacg ggccctgcga tatggatgat  25500
ggcggagcga gctggattga atctcggttt gcattgtagt ggattctctt gcgtaccttg  25560
tcgtacttct gccagcagaa atgggccctt gaacagcata tacccctcct acggccgtcc  25620
tttcgctgct gccgctcagt catccaacta aagtacatcc attctcgaag attctggaga  25680
agttcctctg catctgataa aataaaaaac ccgtccatgc gaattcccct catcacatca  25740
gccaggactc tgtaggccat ccccatccag ttaatgctgc cttgtctatc attcagaggg  25800
ggcggtggca ggactggaag aaccattttt attccaaacg gtctcgaagg acgataaagt  25860
gcaagtcacg caggtgacag cgttcccctc cgctgtgctg gtggaaacag acagccaggt  25920
caaaacccac tctattttca aggtgctcga ccgtggcttc gagcagtggc tctacgcgca  25980
catccagcat aagaatcaca ttaaaggctg gccctccatc gatttcatca atcatcaggt  26040
tacattcctg caccatcccc aggtaattct catttttcca gccttggatt atctctacaa  26100
attgttggtg taagtccact ccgcacatgt ggaaaagctc ccacagtgcc ccctccactt  26160
tcataatcag gcagaccttc ataatagaaa cagatcctgc tgctccacca cctgcagcgt  26220
gttcaaaaca acaagattca ataaggttct gccctccgcc ctgagctcgc gcctcaatgt  26280
cagctgcaaa aagtcactta agtcctgggc cactacagct gacaattcag agccagggct  26340
aagcgtggga ctggcaagcg taagggaaaa ctttaatgct ccaaagctag cacccaaaaa  26400
ctgcatgctg gaataagctc tctttgtgtc tccggtgatg ccttccaaaa tgtgagtgat  26460
aaagcgtggt agtttttctt taatcatttg cgtaatagaa aagtcctcta aataagtcac  26520
taggacccca gggaccacaa tgtggtagct tacaccgcgt cgctgaagca tggttagtag  26580
agatgagagt ctgaaaaaca gaaagcatgc actaaactaa ggtggctatt ttcactgaag  26640
gaaaaatcac tctctccagc agcagggtac ccactgggtg gcccttgcgg acatacaaaa  26700
atcggtccgt gtgattaaaa agcagcacag taagttcctg tcttcttccg gcaaaaatca  26760
catcagactg ggttagtatg tccctggcat ggtagtcatt caaggccata aatctgccct  26820
gatatccagt aggaaccagc acactcactt ttaggtgaag caataccacc ccatgcggag  26880
gaatgtggaa agattcaggg caaaaaaatt atatctattg ctagcccctt cctggacggg  26940
agcaatccct ccaggactat ctataaaagc atacagagat tcagccatag cttagcccgc  27000
ttaccagtag acagaaagca cagcagtaca agcgccaaca gcagcaactg actacccact  27060
gacccagctc cctatttaaa ggcaccttac actgacgtaa tgaccaaagg tctaaaaacc  27120
ccgccaaaaa aaacacacac gccctgggtg tttttcacaa aaacacttcc gcgttctcac  27180
ttcctcgtat cgattttgtg actcaacttc cgggttccca cgttacgtca cttctgccct  27240
tacatgtaac ttggccgtat ggcgccatct tgcccacgtc caaaatggct ttcatgaccg  27300
gccacgcctc cgcgccggcc gttagccgtg cgtcgtgacg ttatttgcat caccgcttct  27360
cgtccaatca gcgttggctc cgccccaaaa ccgttaaaat tcaaaagctc atttgcatat  27420
taacttttgt ttactttgtg ggtatatta ttagatagtt aattaaggat gcatgtttaa  27480
actcgacagc gacacacttg catcggatgc agcccggtta acgtgccggc acggcctggg  27540
taaccaggta ttttgtccac ataaccgtgc gcaaaatgtt gtggataagc aggacacagc  27600
agcaatccac agcaggcata caaccgcaca ccgaggttac tccgttctac aggttacgac  27660
gacatgtcaa tacttgccct tgacaggcat tgatggaatc gtagtctcac gctgatagtc  27720
```

```
tgatcgacaa tacaagtggg accgtggtcc cagaccgata atcagaccga caacacgagt  27780
gggatcgtgg tcccagacta ataatcagac cgacgatacg agtgggaccg tggtcccaga  27840
ctaataatca gaccgacgat acgagtggga ccgtggttcc agactaataa tcagaccgac  27900
gatacgagtg ggaccgtggt cccagactaa taatcagacc gacgatacga gtgggaccat  27960
ggtcccagac taataatcag accgacgata cgagtgggac cgtggtccca gtctgattat  28020
cagaccgacg atacgagtgg gaccgtggtc ccagactaat aatcagaccg acgatacgag  28080
tgggaccgtg gtcccagact aataatcaga ccgacgatac gagtgggacc gtggtcccag  28140
tctgattatc agaccgacga tacaagtgga acagtgggcc cagagagaat attcaggcca  28200
gttatgcttt ctggcctgta acaaaggaca ttaagtaaag acagataaac gtagactaaa  28260
acgtggtcgc atcagggtgc tggcttttca agttccttaa gaatggcctc aattttctct  28320
atacactcag ttggaacacg agacctgtcc aggttaagca ccattttatc gcccttatac  28380
aatactgtcg ctccaggagc aaactgatgt cgtgagctta aactagttct tgatgcagat  28440
gacgttttaa gcacagaagt taaaagagtg ataacttctt cagcttcaaa tatcacccca  28500
gctttttttct gctcatgaag gttagatgcc tgctgcttaa gtaattcctc tttatctgta  28560
aaggcttttt gaagtgcatc acctgaccgg gcagatagtt caccggggtg agaaaaaaga  28620
gcaacaactg atttaggcaa tttggcggtg ttgatacagc gggtaataat cttacgtgaa  28680
atattttccg catcagccag cgcagaaata tttccagcaa attcattctg caatcggctt  28740
gcataacgct gaccacgttc ataagcactt gttgggcgat aatcgttacc caatctggat  28800
aatgcagcca tctgctcatc atccagctcg ccaaccagaa cacgataatc actttcggta  28860
agtgcagcag ctttacgacg gcgactccca tcggcaattt ctatgacacc agatactctt  28920
cgaccgaacg ccggtgtctg ttgaccagtc agtagaaaag aagggatgag atcatccagt  28980
gcgtcctcag taagcagctc ctggtcacgt tcattacctg accataccg agaggtcttc  29040
tcaacactat caccccggag cacttcaaga gtaaacttca catcccgacc acatacaggc  29100
aaagtaatgg cattaccgcg agccattact cctacgcgcg caattaacga atccaccatc  29160
ggggcagctg gtgtcgataa cgaagtatct tcaaccggtt gagtattgag cgtatgtttt  29220
ggaataacag gcgcacgctt cattatctaa tctcccagcg tggtttaatc agacgatcga  29280
aaatttcatt gcagacaggt tcccaaatag aaagagcatt tctccaggca ccagttgaag  29340
agcgttgatc aatggcctgt tcaaaaacag ttctcatccg gatctgacct ttaccaactt  29400
catccgtttc acgtacaaca ttttttagaa ccatgcttcc ccaggcatcc cgaatttgct  29460
cctccatcca cggggactga gagccattac tattgctgta tttggtaagc aaaatacgta  29520
catcaggctc gaaccettta agatcaacgt tcttgagcag atcacgaagc atatcgaaaa  29580
actgcagtgc ggaggtgtag tcaaacaact cagcaggcgt gggaacaatc agcacatcag  29640
cagcacatac gacattaatc gtgccgatac ccaggttagg cgcgctgtca ataactatga  29700
catcatagtc atgagcaaca gtttcaatgg ccagtcggag catcaggtgt ggatcggtgg  29760
gcagtttacc ttcatcaaat ttgcccatta actcagtttc aatacggtgc agagccagac  29820
aggaaggaat aatgtcaagc cccggccagc aagtgggctt tattgcataa gtgacatcgt  29880
ccttttcccc aagatagaaa ggcaggagag tgtcttctgc atgaatatga agatctggta  29940
cccatccgtg atacattgag gctgttccct gggggtcgtt accttccacg agcaaaacac  30000
gtagcccctt cagagccaga tcctgagcaa gatgaacaga aactgaggtt ttgtaaacgc  30060
cacctttatg ggcagcaacc ccgatcaccg gtggaaatac gtcttcagca cgtcgcaatc  30120
```

gcgtaccaaa cacatcacgc atatgattaa tttgttcaat tgtataacca acacgttgct 30180
caacccgtcc tcgaatttcc atatccgggt gcggtagtcg ccctgctttc tcggcatctc 30240
tgatagcctg agaagaaacc ccaactaaat ccgctgcttc acctattctc cagcgccggg 30300
ttattttcct cgcttccggg ctgtcatcat taaactgtgc aatggcgata gccttcgtca 30360
tttcatgacc agcgtttatg cactggttaa gtgtttccat gagtttcatt ctgaacatcc 30420
tttaatcatt gctttgcgtt tttttattaa atcttgcaat ttactgcaaa gcaacaacaa 30480
aatcgcaaag tcatcaaaaa accgcaaagt tgtttaaaat aagagcaaca ctacaaaagg 30540
agataagaag agcacatacc tcagtcactt attatcacta gcgctcgccg cagccgtgta 30600
accgagcata gcgagcgaac tggcgaggaa gcaaagaaga actgttctgt cagatagctc 30660
ttacgctcag cgcaagaaga aatatccacc gtgggaaaaa ctccaggtag aggtacacac 30720
gcggatagcc aattcagagt aataaactgt gataatcaac cctcatcaat gatgacgaac 30780
taacccccga tatcaggtca catgacgaag ggaaagagaa ggaaatcaac tgtgacaaac 30840
tgccctcaaa tttggcttcc ttaaaaatta cagttcaaaa agtatgagaa aatccatgca 30900
ggctgaagga aacagcaaaa ctgtgacaaa ttaccctcag taggtcagaa caaatgtgac 30960
gaaccaccct caaatctgtg acagataacc ctcagactat cctgtcgtca tggaagtgat 31020
atcgcggaag gaaaatacga tatgagtcgt ctggcggcct ttcttttttct caatgtatga 31080 gaggcgcatt ggagttctgc tgttgatctc attaacacag acctgcagga agcggcggcg 31140
gaagtcaggc atacgctggt aactttgagg cagctggtaa cgctctatga tccagtcgat 31200
tttcagagag acgatgcctg agccatccgg cttacgatac tgacacaggg attcgtataa 31260
acgcatggca tacggattgg tgatttcttt tgtttcacta agccgaaact gcgtaaaccg 31320
gttctgtaac ccgataaaga agggaatgag atatgggttg atatgtacac tgtaaagccc 31380
tctggatgga ctgtgcgcac gtttgataaa ccaaggaaaa gattcatagc ctttttcatc 31440
gccggcatcc tcttcagggc gataaaaaac cacttccttc cccgcgaaac tcttcaatgc 31500
ctgccgtata tccttactgg cttccgcaga ggtcaatccg aatatttcag catatttagc 31560
aacatggatc tcgcagatac cgtcatgttc ctgtagggtg ccatcagatt ttctgatctg 31620
gtcaacgaac agatacagca tacgtttttg atcccgggag agactatatg ccgcctcagt 31680
gaggtcgttt gactggacga ttcgcgggct atttttacgt ttcttgtgat tgataaccgc 31740
tgtttccgcc atgacagatc catgtgaagt gtgacaagtt tttagattgt cacactaaat 31800
aaaaaagagt caataagcag ggataacttt gtgaaaaaac agcttcttct gagggcaatt 31860
tgtcacaggg ttaagggcaa tttgtcacag acaggactgt catttgaggg tgatttgtca 31920
cactgaaagg gcaatttgtc acaacacctt ctctagaacc agcatggata aaggcctaca 31980
aggcgctcta aaaaagaaga tctaaaaact ataaaaaaaa taattataaa aatatccccg 32040
tggataagtg gataacccca agggaagttt tttcaggcat cgtgtgtaag cagaatatat 32100
aagtgctgtt ccctggtgct tcctcgctca ctcgagggct tcgccgtcgc tcgactgcgg 32160
cgagcctact ggctgtaaaa ggacagacca catcatggtt ctgtgttcat taggttgttc 32220
tgtccattgc tgacataatc cgctccactt caacgtaaca ccgcacgaag atttctattg 32280
ttcctgaagg catattcaaa tcgttttcgt taccgcttgc aggcatcatg acagaacact 32340
acttcctata aacgctacac aggctcctga gattaataat gcggatctct acgataatgg 32400
gagattttcc cgactgtttc gttcgcttct cagtggataa cagccagctt ctctgtttaa 32460

```
cagacaaaaa cagcatatcc actcagttcc acatttccat ataaaggcca aggcatttat  32520

tctcaggata attgtttcag catcgcaacc gcatcagact ccggcatcgc aaactgcacc  32580

cggtgccggg cagccacatc cagcgcaaaa accttcgtgt agacttccgt tgaactgatg  32640

gacttatgtc ccatcaggct ttgcagaact ttcagcggta taccggcata cagcatgtgc  32700

atcgcatagg aatggcggaa cgtatgtggt gtgaccggaa cagagaacgt cacaccgtca  32760

gcagcagcgg cggcaaccgc ctccccaatc caggtcctga ccgttctgtc cgtcacttcc  32820

cagatccgcg ctttctctgt ccttcctgtg cgacggttac gccgctccat gagcttatcg  32880

cgaataaata cctgtgacgg aagatcactt cgcagaataa ataaatcctg gtgtccctgt  32940

tgataccggg aagccctggg ccaacttttg gcgaaaatga gacgttgatc ggcacgtaag  33000

aggttccaac tttcaccata atgaaataag atcactaccg ggcgtatttt ttgagttatc  33060

gagattttca ggagctaagg aagctaaaat ggagaaaaaa atcactggat ataccaccgt  33120

tgatatatcc caatggcatc gtaaagaaca ttttgaggca tttcagtcag ttgctcaatg  33180

tacctataac cagaccgttc agctggatat tacggccttt ttaaagaccg taaagaaaaa  33240

taagcacaag ttttatccgg cctttattca cattcttgcc cgcctgatga atgctcatcc  33300

ggaattccgt atggcaatga aagacggtga gctggtgata tgggatagtg ttcacccttg  33360

ttacaccgtt ttccatgagc aaactgaaac gttttcatcg ctctggagtg aataccacga  33420

cgatttccgg cagtttctac acatatattc gcaagatgtg gcgtgttacg gtgaaaacct  33480

ggcctatttc cctaaagggt ttattgagaa tatgtttttc gtctcagcca atccctgggt  33540

gagtttcacc agttttgatt taaacgtggc caatatggac aacttcttcg cccccgtttt  33600

caccatgggc aaatattata cgcaaggcga caaggtgctg atgccgctgg cgattcaggt  33660

tcatcatgcc gtctgtgatg gcttccatgt cggcagaatg cttaatgaat tacaacagta  33720

ctgcgatgag tggcagggcg gggcgtaatt tttttaaggc agttattggt gcccttaaac  33780

gcctggttgc tacgcctgaa taagtgataa taagcggatg aatggcagaa attcgatgat  33840

aagctgtcaa acatgagaat gggtcgag                                    33868
```

<210> SEQ ID NO 7
<211> LENGTH: 37218
<212> TYPE: DNA
<213> ORGANISM: Artificial sequence
<220> FEATURE:
<223> OTHER INFORMATION: /note=“Description of artificial sequence: pRAB19aGFP”

<400> SEQUENCE: 7

```
gaagttccta ttccgaagtt cctattctct agaaagtata ggaacttcga agttcctatt     60

ctctagaaag tataggaact tcaattccca tgtcagccgt taagtgttcc tgtgtcactc    120

aaaattgctt tgagaggctc taagggcttc tcagtgcgtt acatccctgg cttgttgtcc    180

acaaccgtta aaccttaaaa gctttaaaag ccttatatat tctttttttt cttataaaac    240

ttaaaacctt agaggctatt taagttgctg atttatatta attttattgt tcaaacatga    300

gagcttagta cgtgaaacat gagagcttag tacgttagcc atgagagctt agtacgttag    360

ccatgagggt ttagttcgtt aaacatgaga gcttagtacg ttaaacatga gagcttagta    420

cgtgaaacat gagagcttag tacgtactat caacaggttg aactgctgat cttcagatcc    480

tctacgccgg acgcatcgtg gccggatccg atttattcaa caaagccacg ttgtgtctca    540

aaatctctga tgttacattg cacaagataa aaatatatca tcatgaacaa taaaactgtc    600
```

-continued

```
tgcttacata aacagtaata caaggggtgt tatgagccat attcaacggg aaacgtcttg    660
ctcgaggccg cgattaaatt ccaacatgga tgctgattta tatgggtata aatgggctcg    720
cgataatgtc gggcaatcag gtgcgacaat ctatcgattg tatgggaagc ccgatgcgcc    780
agagttgttt ctgaaacatg gcaaaggtag cgttgccaat gatgttacag atgagatggt    840
cagactaaac tggctgacgg aatttatgcc tcttccgacc atcaagcatt ttatccgtac    900
tcctgatgat gcatggttac tcaccactgc gatccccggg aaaacagcat tccaggtatt    960
agaagaatat cctgattcag gtgaaaatat tgttgatgcg ctggcagtgt tcctgcgccg   1020
gttgcattcg attcctgttt gtaattgtcc ttttaacagc gatcgcgtat ttcgtctcgc   1080
tcaggcgcaa tcacgaatga ataacggttt ggttgatgcg agtgattttg atgacgagcg   1140
taatggctgg cctgttgaac aagtctggaa agaaatgcat aagcttttgc cattctcacc   1200
ggattcagtc gtcactcatg gtgatttctc acttgataac cttatttttg acgaggggaa   1260
attaataggt tgtattgatg ttggacgagt cggaatcgca gaccgatacc aggatcttgc   1320
catcctatgg aactgcctcg gtgagttttc tccttcatta cagaaacggc tttttcaaaa   1380
atatggtatt gataatcctg atatgaataa attgcagttt catttgatgc tcgatgagtt   1440
tttctaatca gaattggtta attggttgta acactggctt aattaactat ctaataatat   1500
accccacaaa gtaaacaaaa gttaatatgc aaatgagctt ttgaatttta acggttttgg   1560
ggcggagcca acgctgattg gacgagaagc ggtgatgcaa ataacgtcac gacgcacggc   1620
taacggccgg cgcggaggcg tggcctaggc cggaagcaag tcgcggggct aatgacgtat   1680
aaaaaagcgg actttagacc cggaaacggc cgattttccc gcggccacgc ccggatatga   1740
ggtaattctg ggcggatgca agtgaaatta ggtcattttg gcgccaaaac tgaatgagga   1800
agtgaaaagt gaaaaatacc tgtcccgccc agggcggaat atttaccgag ggccgagaga   1860
ctttgaccga ttacgtgggg tttcgattgc ggtgtttttt tcgcgagaag gtaaactgcc   1920
cacttggcag tacatcaagt gtatcatatg ccaagtacgc cccctattga cgtcaatgac   1980
ggtaaatggc ccgcctggca ttatgcccag tacatgacct tatgggactt tcctacttgg   2040
cagtacatct acgtattagt catcgctatt accatggtga tgcggttttg gcagtacatc   2100
aatgggcgtg gatagcggtt tgactcacgg ggatttccaa gtctccaccc cattgacgtc   2160
aatgggagtt tgttttggca ccaaaatcaa cgggactttc caaaatgtcg taacaactcc   2220
gccccattga cgcaaatggg cggtaggcgt gtacggtggg aggtctatat aagcagagct   2280
ggtttagtga accgtcagat ccgctagcgc taccggactc agatctcgag ctcaagcttc   2340
gaattctgca gtcgacggta ccgcgggccc gggatccacc ggtcgccacc atggtgagca   2400
agggcgagga gctgttcacc ggggtggtgc ccatcctggt cgagctggac ggcgacgtaa   2460
acggccacaa gttcagcgtg tccggcgagg gcgagggcga tgccacctac ggcaagctga   2520
ccctgaagtt catctgcacc accggcaagc tgcccgtgcc ctggcccacc ctcgtgacca   2580
ccctgaccta cggcgtgcag tgcttcagcc gctaccccga ccacatgaag cagcacgact   2640
tcttcaagtc cgccatgccc gaaggctacg tccaggagcg caccatcttc ttcaaggacg   2700
acggcaacta caagacccgc gccgaggtga agttcgaggg cgacaccctg gtgaaccgca   2760
tcgagctgaa gggcatcgac ttcaaggagg acggcaacat cctggggcac aagctggagt   2820
acaactacaa cagccacaac gtctatatca tggccgacaa gcagaagaac ggcatcaagg   2880
tgaacttcaa gatccgccac aacatcgagg acggcagcgt gcagctcgcc gaccactacc   2940
agcagaacac ccccatcggc gacggccccg tgctgctgcc cgacaaccac tacctgagca   3000
```

-continued

```
cccagtccgc cctgagcaaa gaccccaacg agaagcgcga tcacatggtc ctgctggagt   3060
tcgtgaccgc cgccgggatc actctcggca tggacgagct gtacaagtaa agcggccgcg   3120
actctagatc ataatcagcc ataccacatt tgtagaggtt ttacttgctt taaaaaacct   3180
cccacacctc cccctgaacc tgaaacataa aatgaatgca attgttgttg ttaacttgtt   3240
tattgcagct tataatggtt acaaataaag caatagcatc acaaatttca caaataaagc   3300
atttttttca ctgcattcta gttgtggttt gtccaaactc atcaatgtat cttaaatcga   3360
attcaagctt gtcgactcga agatctgagc tcacgcgtgc gtaaattgta agcgttaata   3420
ttttgttaaa attcgcgtta aatttttgtt aaatcagctc attttttaac caataggccg   3480
aaatcggcaa aatcccttga agagcagacc agaccacctg gtgatggcct gtaccgggac   3540
cgagttcagc tccagtgggg aggacacaga ttagaggtag gtttgagtag tgggcgtggc   3600
taatgtgagt ataaaggcgg gtgtcttacg agggtctttt tgcttttctg cagacatcat   3660
gaacgggacc ggcggggcct tcgaaggggg gctttttagc ccttatttga caacccgcct   3720
gccgggatgg gccggagttc gtcagaatgt gatgggatct acggtggatg ggcgtccagt   3780
gcttccagca aattcctcga ccatgaccta cgcgaccgtg gggagctcgt cgcttgacag   3840
caccgccgca gccgcggcag ccgcagccgc catgacagcg acgagactgg cctcgagcta   3900
tatgcccagc agcggtagca gcccctctgt gcccagttcc atcatcgccg aggagaaact   3960
gctggccctg ctggccgagc tggaagccct gagccgccag ctggccgccc tgacccagca   4020
ggtgtccgat ctccgcgagc aacagcagca gcaaaataaa tgaattcaat aaacacagat   4080
tctgattcaa acagcaaagc atctttatta tttatttttt cgcgcgcggt aggccctggt   4140
ccacctctcc cgatcattga gagtgcggtg gatttttttcc aggacccggt agaggtggga   4200
ttggatgttg aggtacatgg gcatgagccc gtcccggggg tggaggtagc accactgcat   4260
ggcctcgtgc tctggggtcg tgttgtagat aatccagtca tagcaggggc gctgggcgtg   4320
gtgctggatg atgtccttga ggaggagact gatggccacg gggagcccct tggtgtaggt   4380
gttggcaaag cggttaagct gggagggatg catgcggggg gagatgatgt gcagtttggc   4440
ctggatcttg aggttggcga tgttgccacc cagatcccgc cgggggttca tattgtgcag   4500
gaccaccaga acggtgtagc ccgtgcactt ggggaactta tcatgcaact tggaagggaa   4560
tgcgtggaag aatttggaga cgcccttgtg cccgcccagg ttttccatgc actcatccat   4620
gatgatggca atgggcccgt gggctgcggc tttggcaaaa acgtttctgg ggtcagagac   4680
atcataatta tgctcctggg tgagatcatc ataagacatt ttaatgaatt tggggcgaag   4740
ggtgccagat tgggggacga tcgttccctc gggccccggg gcgaagttcc cctcgcagat   4800
ctgcatctcc caggctttca tctcggaggg ggggatcatg tccacctgcg gggcgatgaa   4860
aaaaacggtt tccggggcgg gggtgatgag ctgcgaggag agcaggtttc ttaacagctg   4920
ggacttgccg cacccggtcg ggccgtagat gaccccgatg acgggttgca ggtggtagtt   4980
caaggagatg cagctgccgt cgtcccggag gagggggggcc acctcgttga gcatgtctct   5040
cacttggagg ttttcccgga cgagctcgcc gaggaggcgg tccccgccca gcgagagcag   5100
ctcttgcagg gaagcaaagt ttttcagggg cttgagcccg tcggccatgg gcatcttggc   5160
aagggtctgc gagaggagct ccaggcggtc ccatagctcg gtgacgtgct ctacggcatc   5220
tcgatccagc agacttcctc gtttcggggg ttgggacgac tgcgactgta gggcacgaga   5280
cgatgggcgt ccagcgcggc cagcgtcatg tccttccagg gtctcagggt ccgagtgagg   5340
```

-continued gtggtctccg tcacggtgaa ggggtgggcc ccgggctggg cgcttgcaag ggtgcgcttg 5400
agactcatcc tgctggtgct gaaacgggca cggtcttcgc cctgcgcgtc ggcgagatag 5460
cagttgacca tgagcttgta gttaagggcc tcggcggcgt ggcccttggc acggagcttg 5520
cctttggaag agcgcccgca ggcgggacag aggagggatt gcagggcgta gagcttgggt 5580
gcgagaaaga cggactcggg agcgaaggcg tccgctccgc agtgggcgca gacggtctcg 5640
cactcgacga gccaggtgag ctcgggctgc tcggggtcaa aaaccagttt tcccccgttc 5700
tttttgatgc gcttcttacc tcgcgtctcc atgagtctgt gtccgcgttc ggtgacaaac 5760
aggctgtctg tgtccccgta gacggacttg attggcctgt cctgcagggg cgtcccgcgg 5820
tcctcctcgt agagaaactc ggaccactct gagacaaagg cgcgcgtcca cgccaagaca 5880
aaggaggcca cgtgcgaggg gtagcggtcg ttgtccacca gggggtccac cttttccacc 5940
gtgtgcagac acatgtcccc ctcctccgca tccaagaagg tgattggctt gtaggtgtag 6000
gccacgtgac cgggggtccc cgacgggggg gtataaaagg gggcgggtct gtgctcgtcc 6060
tcactctctt ccgcgtcgct gtccacgagc gccagctgtt ggggtaggta ttccctctcg 6120
agagcgggca tgacctcggc actcaggttg tcagtttcta gaaacgagga ggatttgatg 6180
ttggcctgcc ctgccgcaat gctttttagg agactttcat ccatctggtc agaaaagact 6240
atttttttat tgtcaagctt ggtggcaaag gagccataga gggcgttgga gagaagcttg 6300
gcgatggatc tcatggtctg atttttgtca cggtcggcgc gctccttggc cgcgatgttg 6360
agctggacat actcgcgcgc gacacacttc cattctggga agacggtggt gcgctcgtcg 6420
ggcacgatcc tgacgcgcca gccgcgatta tgcagggtga ccaggtccac gctggtggcc 6480
acctcgccgc gcaggggctc gttggtccag cagaggcgtc cgcccttgcg cgagcagaac 6540
gggggcagca catcaagcag atgctcgtca ggggggtccg catcgatggt gaagatgccc 6600
ggacagagtt ccttgtcaaa ataatcgatt tttgaggatg catcatccaa ggccatctgc 6660
cactcgcggg cggccagcgc tcgctcgtag ggttgaggg gcggacccca gggcatggga 6720
tgcgtgaggg cggaggcgta catgccgcag atgtcgtaga catagatggg ctccgagagg 6780
atgccgatgt aggtgggata acagcgcccc ccgcggatgc tggcgcgcac atagtcatac 6840
aactcgtgcg agggggccaa gaaagcgggg ccgagattgg tgcgctgggg ctgctcggcg 6900
cggaagacga tctggcgaaa gatggcatgc gagttggagg agatggtggg ccgttggaag 6960
atgttaaagt gggcgtgggg caagcggacc gagtcgcgga tgaagtgcgc gtaggagtct 7020
tgcagcttgg caacgagctc ggcggtgaca aggacgtcca tggcgcagta gtccagcgtt 7080
tcacggatga tgtcataacc cgcctcttct ttcttctccc acagcgcgcg gttgagggcg 7140
tactcctcgt catccttcca gtactcccgg agcgggaatc ctcgatcgtc cgcacggtaa 7200
gagcccagca tgtagaaatg gttcacggcc ttgtagggac agcagccctt ctccacgggg 7260
agggcgtaag cttgagcggc cttgcggagc gaggtgtgcg tcagggcgaa ggtatcccta 7320
accatgactt tcaagaactg gtacttgaaa tccgagtcgt cgcagccgcc gtgctcccag 7380
agctcgaaat cggtgcgctt cttcgagagg gggttaggca gagcgaaagt gacgtcattg 7440
aagagaatct tgcctgcccg cggcatgaaa ttgcgggtga tgcggaaagg gcccggaacg 7500
gaggctcggt tgttgatgac ctgggcggcg aggacgatct cgtcgaagcc gttgatgttg 7560
tgcccgacga tgtagagttc catgaatcgc gggcggcctt tgatgtgcgg cagctttttg 7620
agttcctcgt aggtgaggtc ctcggggcat tgcaggccgt gctgctcgag cgcccactcc 7680
tggagatgtg ggttggcttg catgaatgaa gcccagagct cgcgggccat gagggtctgg 7740

-continued agctcgtcgc gaaagaggcg gaactgctgg cccacggcca tcttttctgg ggtgacgcag 7800
tagaaggtga gggggtcccg ctcccagcga tcccagcgta agcgcacggc gagatcgcga 7860
gcgagggcga ccagctcggg gtccccggag aatttcatga ccagcatgaa ggggacgagc 7920
tgcttgccga aggaccccat ccaggtgtag gtttctacat cgtaggtgac aaagagccgc 7980
tccgtgcgag gatgagagcc gattgggaag aactggattt cctgccacca gttggtcgag 8040
tggctgttga tgtgatgaaa gtagaaatcc cgccggcgaa ccgagcactc gtgctgatgc 8100
ttgtaaaagc gtccgcagta ctcgcagcgc tgcacgggct gtacctcatc cacgagatac 8160
acagcgcgtc ccttgaggag gaacttcagg agtggcggcc ctggctggtg gttttcatgt 8220
tcgcctgcgt gggactcacc ctggggctcc tcgaggacgg agaggctgac gagcccgcgc 8280
gggagccagg tccagatttc ggcgcggcgg gggcggagag cgaaaacgag ggcgcgcagt 8340
tgggagctgt ccatggtgtc gcggagatcc aggtccgggg gcagggttct gaggttgacc 8400
tcgtagaggc gggtgagggc gtgcttgaga tgcagatggt acttgatctc cacgggtgag 8460
ttggtggtcg tgtccacgca ttgcatgagc ccgtagctgc gcggggccac gaccgtgccg 8520
cggtgcgctt ttagaagcgg tgtcgcggac gcgctcccgg cggcagcggc ggttccggcc 8580
ccgcgggcag tggcggtaga ggcacgtcgg cgtggcgctc gggcaggtcc cggtgctgcg 8640
ccctgagagc gctggcgtgc gcgacgacgc ggcggttgac atcctggatc tgccgccttt 8700
gcgtgaagac cacgggcccc gtgactttga acctgaaaga cagttcaaca gaatcaatct 8760
cggcgtcatt gacggcggcc tgacgcagga tctcttgcac gtcgcccgag ttgtcctggt 8820
aggcgatctc ggacatgaac tgctcgattt cctcctcctg gagatcgccg cggcccgcgc 8880
gctctacggt ggcggcaagg tcattcgaga tgcgacccat gagctgcgag aaggcgccca 8940
ggccgctctc gttccagacg cggctgtaaa ccacgtcccc gtcggcgtcg cgcgcgcgca 9000
tgaccacctg cgcgaggttg agctccacgt gccgcgtaaa gacggcgtag ttgcgcaggc 9060
gctggaagag gtagttgagg gtggtggcga tgtgctcggt gacgaagaag tacataatcc 9120
agcggcgcag gggcatttcg ctgatgtcgc caatggcctc cagcctttcc atggcctcgt 9180
agaaatccac ggcgaagttg aaaaactggg cgttgcgggc cgagaccgtg agctcgtctt 9240
ccaggagcct gatgagttcg gcgatggtgg cgcgcacctc gcgctcgaaa tcccaggggg 9300
cctcctcctc ttcctcttct tccatgacga cctcttcttc tatttcttcc tctgggggcg 9360
gtggtggtgg cggggcccga cgacgacggc gacgcaccgg gagacggtcg acgaagcgct 9420
cgatcatctc cccgcggcgg cgacgcatgg tttcggtgac ggcgcgaccc cgttcgcgag 9480
gacgcagcgt gaagacgccg ccggtcatct cccggtaatg ggtgggtcc ccgttgggca 9540 gcgatagggc gctgacaatg catcttatca attgcggtgt agggcacgtg agcgcgtcga 9600
gatcgaccgg atcggagaat ctttcgagga aagcgtctag ccaatcgcag tcgcaaggta 9660
agctcaaaca cgtagcagcc ctgtggacgc tgttagaatt gcggttgctg atgatgtaat 9720
tgaagtaggc gtttttgagg cggcggatgg tggcgaggag gaccaggtcc ttgggtcccg 9780
cttgctggat gcggagccgc tcggccatgc cccaggcctg gccctgacac cggctcaggt 9840
tcttgtagta gtcatgcatg agcctctcga tgtcatcact ggcggaggcg gagtcttcca 9900
tgcgggtgac cccgacgccc ctgaacggct gcacgagcgc caggtcggcg acgacgcgct 9960
cggcgaggat ggcctgttgc acgcgggtga gggtgtcctg gaagtcgtcc atgtcgacga 10020
agcggtggta ggcccctgtg ttgatggtgt aagtgcagtt ggccataagc gaccagttga 10080
cggtctgcag gccgggttgc acgacctcgg agtacctgag ccgcgagaag gcgcgcgagt 10140
cgaagacata gtcgttgcag gtgcgcacga ggtactggta tccgactaga aagtgcggcg 10200
gcggctggcg gtagagcggc cagcgctggg tggccggcgc gcccggggcc aggtcctcaa 10260
gcatgagtcg gtggtagccg tagaggtagc gggacatcca ggtgatgccg gcggcggtgg 10320
tggaggcgcg cgggaactcg cggacgcggt tccagatgtt gcgcaggggc aggaaatagt 10380
ccatggtcgg cacggtctgg ccggtgagac gcgcgcagtc attgatgctc tagaggcaaa 10440
aacgaaagcg gttgagcggg ctcttcctcc gtagcctggc ggaacgcaaa cgggttaggc 10500
cgcgtgtgta ccccggttcg agtcccctcg aatcaggctg gagccgcgac taacgtggta 10560
ttggcactcc cgtctcgacc caagcccgat agccgccagg atacggcgga gagccctttt 10620
tgtcggccga ggggagtcgc tagacttgaa agcggccgaa aaccctgccg ggtagtggct 10680
cgcgcccgta gtctggagaa gcatcgccag ggttgagtcg cggcagaacc cggttcaagg 10740
acggccgcgg cgagcgggac ttggtcaccc cgccgattta aagacccaca gccagccgac 10800
ttctccagtt acgggagcga gcccccttttt ttcttttgc cagatgcatc ccgtcctgcg 10860
ccaaatgcgt cccacccccc cggcgaccac cgcgaccgcg gccgtagcag gcgccggcgc 10920
tagccagcca cagccacaga cagagatgga cttggaagag ggcgaagggc tggcgagact 10980
gggggcgccg tccccggagc gacatccccg cgtgcagctg cagaaggacg tgcgcccggc 11040
gtacgtgcct gcgcagaacc tgttcaggga ccgcagcggg gaggagcccg aggagatgcg 11100
cgactgccgg tttcgggcgg gcagggagct gcgcgagggc ctggaccgcc agcgcgtgct 11160
gcgcgacgag gatttcgagc cgaacgagca gacggggatc agccccgcgc gcgcgcacgt 11220
ggcggcggcc aacctggtga cagcctacga gcagacggtg aagcaggaac gcaactttca 11280
aaagagtttc aacaaccacg tgcgcaccct gatcgcgcgc gaggaggtgg ccctgggcct 11340
gatgcacctg tgggacctgg cggaggccat tgtgcagaac ccggacagca agcctctgac 11400
ggcacaactg ttcctggtgg tgcagcacag cagggacaac gaggcgttca gggaggcgct 11460
gctaaacatc gccgagcccg agggccgctg gctgctggag ctgatcaaca tcttgcaaag 11520
catcgtagtg caggagcgca gcctgagctt ggccgagaag gtggcggcga tcaactactc 11580
ggtgctaagc ctgggcaagt tttacgcgcg caagatttac aagacgccgt acgtgcccat 11640
agacaaggag gtgaaaatag acagctttta catgcgcatg gcgctcaagg tgctgacgct 11700
gagcgacgac ctgggcgtgt accgcaacga ccgcatccac aaggccgtga gcacgagccg 11760
gcggcgcgag ctgagcgacc gcgagctgat gctaagcctg cgccgggcgc tggtaggtgg 11820
cgccgccggc ggcgaggagt cctacttcga catgggggcg gacctgcatt ggcagccgag 11880
ccggcgcgcc ttggaggccg cctacggtcc agaggacttg gatgaggatg aggaagagga 11940
ggaggatgca cccgttgcgg ggtactgacg cctccgtgat gtgtttttag atgtcccagc 12000
agcaagcccc ggaccccgcc ataagggcgg cgctgcaaag ccagccgtcc ggtctagcat 12060
cggacgactg ggaggccgcg atgcaacgca tcatggccct gacgacccgc aaccccgagt 12120
cctttagaca acagccgcag gccaacagac tttcgaccat tctggaggcg gtggtcccct 12180
ctcggaccaa ccccacgcac gagaaggtgc tggcgatcgt gaacgcgctg gcggagaaca 12240
aggctattcg tcccgacgag gctgggctgg tatacaacgc cctgctggag cgcgtgggcc 12300
gctacaacag cacgaacgtg cagtccaacc tggaccggct ggtgacggac gtgcgcgagg 12360
ccgtggcgca gcgcgagcgg ttcaagaacg agggcctggg ctcgctggtg gcgctgaacg 12420
ccttcctggc gacgcagccg gcgaacgtgc cgcgcgggca ggacgattat accaacttta 12480

```
tcagcgcgct gcggctgatg gtgaccgagg ttccccagag cgaggtgtac cagtcgggcc  12540
cggactactt tttccagact agcagacagg gcctgcagac ggtgaacctg agccaggctt  12600
tcaagaacct gcgcgggctg tggggcgtgc aggcgcccgt gggcgaccgg tcgacggtga  12660
gcagcttgct gacgcccaac tcgcggctgc tgctgctgct gatcgcgccc ttcaccgaca  12720
gcggcagcgt gaaccgcaac tcgtacctgg gtcacctgct gacgctgtac cgcgaggcca  12780
taggccaggc acaggtggac gagcagacct tccaggagat cactagtgta agccgcgcgc  12840
tgggtcagaa cgacaccgac agtctgaggg ccaccctgaa cttcttgctg accaatagac  12900
agcagaagat cccggcgcag tatgcgctgt cggccgagga ggagcgcatc ctgagatatg  12960
tgcagcagag cgtagggctg tttctgatgc aggagggggc cacccccagc gccgcgctgg  13020
acatgaccgc gcgcaacatg gaacctagca tgtacgccgc caaccggccg tttatcaata  13080
agctgatgga ctacctgcac cgcgcggcgt ccatgaactc ggactacttt accaatgcca  13140
ttttgaaccc gcactggctc ccgccgccgg ggttctacac gggcgagtac gacatgcctg  13200
accccaacga cgggtttttg tgggacgacg tggacagcgc ggtgttctca ccgaccttgc  13260
aaaagcgcca ggaggcggtg cgcacgcccg cgagcgaggg cgcggtgggt cggagcccct  13320
ttcctagctt agggagtttg catagcttgc cgggctcggt gaacagcggc agggtgagcc  13380
ggccgcgctt gctgggcgag gacgagtacc taaacgactc gctgctgcag ccgccgcggg  13440
tcaagaacgc catggccaat aacgggatag agagtctggt ggacaaactg aaccgctgga  13500
agacctacgc tcaggaccat agggagcctg cgcccgcgcc gcggcgacag cgccacgacc  13560
ggcagcgggg cctggtgtgg gacgacgagg actcggccga cgatagcagc gtgttggact  13620
tgggcgggag cggtggggtc aacccgttcg cgcatctgca gcccaaactg gggcgacgga  13680
tgttttgaat gcaaaataaa actcaccaag gccatagcgt gcgttctctt ccttgttaga  13740
gatgaggcgt gcggtggtgt cttcctctcc tcctccctcg tacgagagcg tgatggcgca  13800
ggcgaccctg gaggttccgt ttgtgcctcc gcggtatatg gctcctacgg agggcagaaa  13860
cagcattcgt tactcagagc tggctccgct gtacgacacc actcgcgtgt acttggtgga  13920
caacaagtcg gcggacatcg cttccctgaa ctaccaaaac gaccacagca actttctgac  13980
cacggtggtg caaaacaacg atttcacccc cgccgaggct agcacgcaga cgataaattt  14040
tgacgagcgg tcgcggtggg gcggtgatct gaagaccatt ctgcacacca acatgcccaa  14100
tgtgaacgag tacatgttta ccagcaagtt taaggcgcgg gtgatggtgg ctaggaaaca  14160
cccacagggg gtagaagcaa cagatttaag caaggatatc ttagagtacc agtggtttga  14220
gtttaccctg cccgagggca acttttccga gaccatgacc atagacctga tgaacaacgc  14280
catcttggaa aactacttgc aagtggggcg gcaaaatggc gtgctggaga gcgatatcgg  14340
agtcaagttt gacagcagga atttcaagct gggctgggac cccgtgacca agctggtgat  14400
gccaggggtc tacacctatg aggccttcca cccggacgtg gtgctgctgc ctggctgcgg  14460
ggtggacttc accgagagcc gcctaagcaa ccttctgggc attcgcaaga agcaaccttt  14520
ccaagagggc ttcagaatca tgtatgagga tctcgaaggg ggcaacattc ccgcacttct  14580
gaatgtgacc aagtacctgg aaagcaagaa gaagctagag gagaatgccg ctaaggctaa  14640
tggtcctgca agaggagaca gtagtgtctc aagagaggtg gaaaaggcag ctgaaaaaga  14700
gcttgtcatt gagcccatca agcaagatga tagcaagaga agttacaacc tcattgaggg  14760
tacccatgac accctgtacc gaagctggta cctgtcctat acctacgggg accccgagaa  14820
```

-continued gggggtgcag tcgtggacgc tgctcaccac cccggacggt cactgcggcg cggagcaagt 14880
ctactggtcg ctgccggacc tcatgcaaga ccccgtcacc ttccgctcta cccagcaagt 14940
cagcaactac cccgtggtcg gcgccgagct catgcctttc cgcgccaaga gcttttacaa 15000
cgacctcgcc gtctactccc agctcatccg cagctacacc tccctcaccc acgtcttcaa 15060
ccgcttcccc gacaaccaga tcctctgccg cccgcccgcg cccaccatca ccaccgtcag 15120
tgaaaacgtg cctgctctca cagatcacgg gacgctaccg ctgcgcagca gtatccgcgg 15180
agtccagcga gtgaccgtca ctgacgcccg tcgccgcacc tgtccctacg tctacaaggc 15240
cctgggcata gtcgcgccgc gcgtgctttc cagtcgcacc ttctaaaaaa tgtctattct 15300
catctcgccc agcaataaca ccggctgggg tcttactagg cccagcacca tgtacggagg 15360
agccaagaaa cgctcccagc agcaccccgt ccgcgtccgc ggccactttc gcgctccctg 15420
gggcgcatac aagcgcgggc ggacttccac cgccgccgcc gtgcgcacca ccgtcgacga 15480
cgtcatcgac tcggtggtcg ccgatgcgcg caactatacc cccgccccct ccaccgtgga 15540
cgcggtcatt gacagcgtgg tggccgacgc gcgcgactat gccagacgca agagccggcg 15600
gcgacggatc gccaggcgcc accggagcac gcccgccatg cgcgccgccc gggctctgct 15660
gcgccgcgcc agacgcacgg gccgccgggc catgatgcga gccgcgcgcc gcgctgccac 15720
tgcacccacc cccgcaggca ggactcgcag acgagcggcc gctgccgccg ccgcggccat 15780
ctctagcatg accagaccca ggcgcggaaa cgtgtactgg gtgcgcgact ccgtcacggg 15840
cgtgcgcgtg cccgtgcgca ctcgtcctcc tcgtccctga tctaatgctt gtgtcctccc 15900
ccgcaagcga cgatgtcaaa gcgcaaaatc aaggaggaga tgctccaggt cgtcgccccg 15960
gagatttacg gaccccccga ccagaaaccc cgcaaaatca agcgggttaa aaaaaaggat 16020
gaggtggacg agggggcagt agagtttgtg cgcgagttcg ctccgcggcg gcgcgtaaat 16080
tggaaggggc gcagggtgca gcgtgtgttg cggcccggca cggcggtggt gttcacgccc 16140
ggcgagcggt cctcggtcag gagcaagcgt agctatgacg aggtgtacgg cgacgacgac 16200
atcctggacc aggcggcgga gcgggcgggc gagttcgcct acgggaagcg gtcgcgcgaa 16260
gaggagctga tctcgctgcc gctggacgaa agcaacccca cgccgagcct gaagcccgtg 16320
accctgcagc aggtgctgcc ccaggcggtg ctgctgccga gccgcggggt taagcgcgag 16380
ggcgagagca tgtacccgac catgcagatc atggtgccca agcgccggcg cgtggaggac 16440
gtgctggaca ccgtgaaaat ggatgtggag ccccgaggtca aggtgcgccc catcaagcag 16500
gtggcgccgg gcctgggcgt gcaaaccgtg gacattcaga tccccaccga catggatgtc 16560
gacaaaaaac cctcgaccag catcgaggtg caaaccgacc cctggctccc agcctccacc 16620
gctaccgccg ccacggccac cgagcctccc aggaggcgaa gatggggccc tgccaaccgg 16680
ctgatgccca actacgtgtt gcatccttcc atcatcccga cgccgggcta ccgcggcacc 16740
cggtactacg ccagccgcag gcgcccagcc agtaaacgcc gccgccgcac cgccacccgc 16800
cgccgtctgg cccccgcccg cgtgcgccgc gtgaccacgc gccggggccg ctcgctcgtt 16860
ctgcccaccg tgcgctacca ccccagcatc ctttaatccg tgtgctgtga tactgttgca 16920
gagagatggc tctcacttgc cgcctgcgca tccccgtccc gaattaccga ggaagatccc 16980
gccgcaggag aggcatggca ggcagtggcc tgaaccgccg ccggcggcgg gccatgcgca 17040
ggcgcctgag tggcggcttt ctgcccgcgc tcatccccat aatcgccgcg gccatcggca 17100
cgatcccggg catagcttcc gttgcgctgc aggcgtcgca gcgccgttga tgtgcgaata 17160
aagcctcttt agactctgac acacctggtc ctgtatattt ttagaatgga agacatcaat 17220

-continued

```
tttgcgtccc tggctccgcg gcacggcacg cggccgttca tgggcacctg gaacgagatc  17280
ggcaccagcc agctgaacgg gggcgccttc aattggagca gtgtctggag cgggcttaaa  17340
aatttcggct cgacgctccg gacctatggg aacaaggcct ggaatagtag cactgggcag  17400
ttgttaaggg aaaagctcaa agaccagaac ttccagcaaa aggtggtgga cgggctggcc  17460
tcgggcatta acggggtggt ggacatcgcg aacccaggcc gtgcagcgcg agataaacaa  17520
ccgcctggac ccgcggccgc ccacggtggt ggagatggaa gatgcaactc ctccgccgcc  17580
caagggcgag aagcgaccgc ggcccgacgc ggaggagacg atcctgcagg tggacgagcc  17640
gccctcgtac gaggaggccg taaaggccgg catgcccacc acgcgcatca tcgcgccact  17700
ggccacgggt gtaatgaaac ccgccaccct tgacctgcct ccaccaccca cgcccgctcc  17760
accgaaggca gctccggtag tgcagccccc tccggtggcg accgccgtgc gccgcgtccc  17820
cgcccgccgc caggcccaaa actggcaaag cacgctgcac agtattgtgg gcctgggagt  17880
gaaaagtctg aagcgccgcc gatgctattg aaagagagga aggaagacac taaagggaga  17940
gcttaacttg tatgtgcctt accgccagag aacgcgcgaa gatggccacc ccctcgatga  18000
tgccgcagtg ggcgtacatg cacatcgccg ggcaggacgc ctcggagtac ctgagcccgg  18060
gtctggtgca gtttgcccgc gccaccgaca cgtacttcag cctgggcaac aagtttagga  18120
accccacggt ggccccaacc cacgatgtga ccacggaccg gtcccagcgt ctgacgctgc  18180
gcttcgtgcc cgtggatcgc gaggacacca cgtactcgta caaggcgcgc ttcactctgg  18240
ccgtgggcga caaccgggtg ctagacatgg ccagcactta ctttgacatc cgcggcgttc  18300
tggaccgcgg ccccagcttc aaaccctact cgggcacggc ttacaacagc ctggccccca  18360
agggcgcccc caattccagt cagtgggatg ctcaagaaaa aaatggacaa ggaggaaatg  18420
acatggttac caaaactcac acatttggcg tggctgctat gggaggaaca aatattacaa  18480
accagggttt gttaattgga actgaagaaa cagccgataa tcctccaaag gaaatctttg  18540
cagacaaatt attccagcca gaacctcaag taggagagga aaactggcaa gacagcaatg  18600
cattctatgg aggcagggct cttaagaagg aaactaaaat gaaaccatgc tatggatctt  18660
atgctagacc aacaaacaca agtggcggac aggctaagct taaaactggt gacaatatcg  18720
atcctaccaa ggatttcgac atagatcttg ctttcttcga tactcctggc ggaaatcctc  18780
cagcaggtgg tagtggaacg gaagaataca aagcagatat tgttatgtac actgaaaatg  18840
tcaaccttga aacacctgac actcatgtgg tgtacaaacc agccaaagag gatgaaagtt  18900
ctcaggccaa cttggttcag cagtccatgc ccaacagacc caactacatt ggcttcagag  18960
acaattttgt ggggctcatg tattacaaca gcactggcaa catgggagtg ctggctggtc  19020
aggcctctca gttgaatgct gtggtggact tgcaagacag aaacacagag ctgtcttacc  19080
agctcttgct agattctctg ggtgacagaa ccagatactt tagcatgtgg aactctgcgg  19140
tggacagcta tgatccagat gtcagaatca ttgaaaatca cggtgtggaa gatgagcttc  19200
caaactattg ctttccattg gatggctctg gtaccaatgc tgcctaccaa ggtgtaaagg  19260
ttcaagatgg tgaagacggg gataaagaaa ctgaatggga aaaagatacc aaagtcgcag  19320
atcgtaacca actgtgcaag ggtaacatct tcgccatgga gatcaacctc caggccaacc  19380
tgtggaagag ttttctgtac tcgaacgtgg ccctgtacct gcccgactcc tacaagtaca  19440
cgccggccaa catcacgctg cccgccaaca ccaacaccta cgagtacatg aacggccgcg  19500
tggtagcccc ctcgctggtg gacgcatacg tcaacatcgg tgcgcgctgg tcgctggacc  19560
```

ccatggacaa cgtcaacccc ttcaaccacc accgcaacgc gggcctgcgc taccgctcca 19620
tgcttctcgg caacggccgc tacgtgccct tccacatcca agtgccccaa aagttctttg 19680
ccattaagaa cctgctcctg ctccccggct cctacaccta cgagtggaac ttccgcaagg 19740
atgtcaacat gatcctgcag agttccctcg gaaacgacct gcgcgtcgac ggcgcctccg 19800
tgcgcttcga cagcgtcaac ctctacgcta ccttcttccc catggcgcac aacaccgcct 19860
ccaccctgga agccatgctg cgcaacgaca ccaacgacca gtcctttaac gactacctct 19920
cggccgccaa catgctctac cccataccgg ccaaggccac caacgtgccc atctccatcc 19980
cctcgcgcaa ctgggctgcc ttccgcggct ggagtttcac ccggctcaag accaaggaaa 20040
ctccttccct tggctcgggt ttcgacccct actttgtcta ctcgggctcc atcccctacc 20100
tcgacgggac cttctacctc aaccacacct tcaaaaaggt gtccattatg ttcgactcct 20160
cggtcagctg gcccggcaac gaccggctgc tcacgccgaa tgagttcgag atcaagcgca 20220
gcgtcgacgg ggagggctac aacgtggccc aatgcaacat aaccaaggac tggttcctcg 20280
tccagatgct ctcccactac aacatcggct accagggctt ccacgtgccc gagggctaca 20340
aggaccgcat gtactccttt ttccgcaact tccagcccat gagcaggcag gtggtggatg 20400
agatcaacta caaggactac aaggccgtca ccctgccctt ccagcacaac aactctggct 20460
tcaccggcta cctcgcaccc accatgcgtc aggggcagcc ttaccccgcc aacttccctt 20520
acccgctcat cggctccacc gcagtcccct ccgtcaccca gaaaaagttc ctctgcgaca 20580
gggtcatgtg gcgcatcccc ttctccagca acttcatgtc catgggtgcc ctcaccgacc 20640
tgggtcagaa catgctctat gccaactcgg cccacgcgct cgacatgacc ttcgaggtgg 20700
accccatgga tgagcccacc ctcctctatc ttctcttcga agttttcgac gtggtcagag 20760
tgcaccagcc gcaccgcggc gtcatcgagg ccgtctacct gcgcacaccc ttctccgccg 20820
gcaacgccac cacctaagca tgagcggttc cagcgaacga gaactcgcgg ccatcgtgcg 20880
cgacctgggc tgcgggccct actttttggg cacccacgac aagcgcttcc cgggcttcct 20940
agccggcgac aagctggcct gcgccatcgt caacacggcc ggccgcgaga ccggaggcgt 21000
gcactggctc gccttcggct ggaacccgcg ctcgcgcacc tgctacatgt tcgacccctt 21060
tgggttctcg gaccgccggc tcaagcagat ttacagcttc gagtacgagg ccatgctgcg 21120
ccgaagcgcc ctggcctcct cgcccgaccg ctgtctcagc ctcgaacagt ccacccagac 21180
cgtgcagggg cccgactccg ccgcctgcgg actttttttgt tgcatgttct tgcatgcgtt 21240
cgtgcactgg cccgaccgac ccatggacgg aaaccccacc atgaacttgc tgacgggggt 21300
gcccaacggc atgctacaat cgccacaggt gctgcccacc ctccggcgca accaggagga 21360
gctctaccgc ttcctcgcgc gccactcccc ttacttccga tcccaccgcg ccgccatcga 21420
acacgccacc gcttttgaca aaatgaaaca actgcgtgta tctcaataaa cagcactttt 21480
tattttacat gcactggagt atatgcaagt tatttaaaag tcgaaggggt tctcgcgctc 21540
gtcgttgtgc gccgcgctgg ggagggccac gttgcggtac tggtacttgg aaagccactt 21600
gaactcgggg atcaccagtt tgggcactgg ggtctcgggg aaggtctcgc tccacatgcg 21660
ccggctcatc tgcagggcgc ccagcatgtc agggccggag atcttgaaat cacagttggg 21720
gccggtgctc tgcgcgcgcg agttgcggta cacggggttg cagcactgga acaccatcag 21780
actggggtac ttcacactgg caagcacgct cttgtcgcta atctgatcct tgtccaggtc 21840
ctcggcgttg ctcaggccga acggggtcat cttgcacagc tggcggccca ggaagggcac 21900
gctctgaggc ttgtggttac actcgcagtg cacgggcatc agcatcatcc ccgcgccgcg 21960
ctgcatattc gggtagaggg ccttgacgaa ggccgcgatc tgcttgaaag cttgctgggc 22020
cttggccccc tcgctgaaga acagaccgca gctcttcccg ctgaactggt tattcccgca 22080
cccggcatca tgcacgcagc agcgcgcgtc atggctggtc agttgcacca cgctccgtcc 22140
ccagcggttc tgggtcacct tagccttgct gggctgctcc ttcagcgcgc gctgtccgtt 22200
ctcgctggtc acatccatct ccaccacgtg gtccttgtga atcatcaccg ttccatgcag 22260
acacttgagc tgaccttcca cctcggtgca gccgtgatcc cacaggacgc agccggtgca 22320
ctcccaattc ttgtgcgcga tcccgctgtg gctgaaaatg taaccttgca acaggcgacc 22380
cataatggtg ctaaatgatt tctgggtggt gaatgtcagt tgcatcccgc gggcctcctc 22440
gttcatccag gtctggcaca tcttctggaa gatctcggtc tgctccggca tgagcttgta 22500
agcatcgcgc aagccgctgt cgacgcggta gcgttccatc agcacgttca tggtatccat 22560
gcccttctcc catgacgaga ccagaggcag actcaggggg ttgcgcacgt tcaggacacc 22620
aggggtcgcg ggctcgacga tgcgttttcc gtccttgcct tccttcaaca gaaccggagg 22680
ctggctgaat cccactccca cgatcacggc gtcttcctgg ggcatctctt cgtcggggtc 22740
taccttggtc acatgcttgg tctttctggc ttgcttcttt tttggagggc tgtccacggg 22800
gaccacgtcc tcctcggaag acccggagcc cacccgctga tactttcggc gcttggtggg 22860
cagaggaggt ggcggcggcg aggggctcct ctcctgctcc ggcggatagc gcgccgaccc 22920
gtggccccgg ggcggagtgg cctctcgctc catgaaccgg cgcacgtcct gactgccgcc 22980
ggccattgtt tcctagggga agatggagga gcagccgcgt aagcaggagc aggaggagga 23040
cttaaccacc cacgagcaac ccaaaatcga gcaggacctg ggcttcgaag agccggctcg 23100
tctaaaaccc ccacaggatg aacaggagca cgagcaagac gcaggccagg aggagaccga 23160
cgctgggctc gagcatggct acctgggagg agaggaggat gtgctgctaa aacacctgca 23220
gcgccagtcc ctcatcctcc gggacgccct ggccgaccgg agcgaaaccc ccctcagcgt 23280
cgaggagctg tgtcgggcct acgagctcaa cctcttctcg ccgcgcgtgc cccccaaacg 23340
ccagcccaac ggcacctgcg agcccaaccc gcgtctcaac ttctatcccg tctttgcggt 23400
ccccgaggcc cttgccacct atcacatctt tttcaagaac caaaagatcc ccatctcctg 23460
tcgcgccaat cgcactcgcg ccgacgcgct cctcgctctg ggcccggcg cgcgcatacc 23520
tgatatcgct tccctggaag aggtgcccaa gatcttcgaa gggctcggtc gggacgagac 23580
gcgcgcggca aacgctctga aagaaacagc agaggaagag ggttacacta gcgccctggt 23640
agagttggaa ggcgacaacg ccaggctggc cgtgcttaag cgcagcgtcg agctcaccca 23700
tttcgcctac cccgccgtca acctcccgcc caaggtcatg cgtcgcatca tggatcagct 23760
catcatgccc cacatcgagg cccttgatga aagtcaggaa cagcgccccg agaacgccca 23820
gcccgtggtc agcgacgaga tgctcgcgcg ctggctcggg acccgcgacc cccaggccct 23880
ggagcagcgg cgcaagctca tgctggccgt ggtcctggtc acccttgagc tcgaatgcat 23940
gcgccgcttt tttaccgacc ccgagaccct gcgcaaggtc gaggagaccc tgcactacac 24000
tttcagacac ggtttcgtca ggcaggcctg caagatctcc aacgtggagc tgaccaacct 24060
ggtctcctgc ctggggatcc tacacgagaa ccgcttggga cagaccgtgc tccactctac 24120
cctgaagggc gaggcgcggc gggactacat ccgcgactgc gtctttctct ttctctgcca 24180
cacatggcaa gcggccatgg gcgtgtggca gcagtgtctc gaggacgaga acctgaagga 24240
gctggacaag cttcttgcta gaaaccttaa aaagctgtgg acgggcttcg acgagcgcac 24300
cgtcgcctcg gacctggccg agatcgtctt ccccgagcgc ctgaggcaga cgctgaaagg 24360
agggctgccc gacttcatga gccagagcat gttgcaaaac taccgcactt tcattctcga 24420
gcgatctggg atgctgcccg ccacctgcaa cgccttcccc tccgactttg tcccgctgag 24480
ctaccgcgag tgtcccccgc cgctgtggag ccactgctac ctcttgcagc tggccaacta 24540
cattgcccac cactcggatg tgatcgagga cgtgagcggc gaggggctgc tcgagtgcca 24600
ctgtcgctgc aacctatgct ccccgcaccg ctccctggtc tgcaaccccc agctactgag 24660
cgagacccag gtcatcggta cctttgagct gcaaggtccg caggagtcca ccgctccgct 24720
gaaactcacg ccggggttgt ggacttccgc gtacctgcgc aaatttgtac ccgaggacta 24780
ctacgcccat gagataaagt tcttcgagga ccaatcgcgt ccgcagcacg cggatctcac 24840
ggcctgcgtc atcacccagg gcgcgatcct cgcccaattg cacgccatcc aaaaatcccg 24900
ccaagagttt cttctgaaaa agggtagagg ggtctacctg gacccccaga cgggcgaggt 24960
gctcaacccg ggtctccccc agcatgccga ggaagaagca ggagccgcta gtggaggaga 25020
tggaagaaga atgggacagc caggcagagg aggacgaatg ggaggaggag acagaggagg 25080
aagacttgga agaggtggaa gaggagcagg caacagagca gcccgtcgcc gcaccatccg 25140
cgccggcagc ccctccggtc acggatacaa cctccgcagc tccggccaag cctcctcgta 25200
gatgggatcg agtgaagggt gacggtaagc acgagcgaca gggctaccga tcatggaggg 25260
cccacaaagc cgcgatcatc gcctgcttgc aagactgcgg ggggaacatc gctttcgccc 25320
gccgctacct gctcttccac cgcggggtga acatcccccg caacgtgttg cattactacc 25380
gtcaccttca cagctaagaa aaagcaagtc aaaggagtcg ccggaggagg aggcctgagg 25440
atcgcggcga acgagccctt gaccaccagg gagctgagga accggatctt ccccactctt 25500
tatgccattt ttcagcaaag tcgaggtcag cagcaagagc tcaaagtaaa aaaccggtct 25560
ctgcgctcgc tcacccgcag ttgcttgtac cacaaaaacg aagatcagct gcagcgcact 25620
ctcgaagacg ccgaggctct gttccacaag tactgcgcgc tgactcttaa agactaaggc 25680
gcgcccaccc ggaaaaaagg cgggaattac ctcatcgcca ccatgagcaa ggagattccc 25740 acccccttaca tgtggagcta tcagccccag atgggcctgg ccgcgggcgc ctcccaggac 25800
tactccaccc gcatgaactg gcttagtgcc ggcccctcga tgatctcacg ggtcaacggg 25860
gtccgtaacc atcgaaacca gatattgttg cagcaggcgg cggtcacctc cacgcccagg 25920
gcaaagctca acccgcgtaa ttggccctcc accctggtgt atcaggaaat ccccgggccg 25980
actaccgtac tacttccgcg tgacgcactg gccgaagtcc gcatgactaa ctcaggtgtc 26040
cagctggccg gcggcgcttc ccggtgcccg ctccgcccac aatcgggtat aaaaaccctg 26100
gtgatccgag gcagaggcac acagctcaac gacgagttgg tgagctctta caatcgtctg 26160
cgaccggacg gagtgttcca actagccgga gccgggagat cgtccttcac tcccaaccag 26220
gcctacctga ccttgcagag cagctcttcg gagcctcgct cgggaggcat cggaacccac 26280
cagttcgtgg aggagtttgt gccctcggtc tacttcaacc ccttctcggg ctcgccaggc 26340
ctctacccgg acgagtttat accgaacttc gacgcagtga gagaagcggt ggacggctac 26400
gactgaagct tgttgattaa aagcccagaa accaatcaga cccttcctca tttccccatc 26460
ccaatactca taagaataaa tcattggaat taatcattca ataaagatca cttacttgaa 26520
atctgaaagt atgtctctgg tgtagttgct cagcaacacc tcggtaccct cctcccagct 26580
ctggtactcc agtccccggc gggcggcgaa cttcctccac accttgaaag ggatgtcaaa 26640
gaggctccgg gtggaagatg acttcaaccc cgtctacccc tatggctacg cgcggaatca 26700

-continued gaatatcccc ttcctcactc cccccttttgt ctcctccgat ggattcaaaa acttcccccc 26760
tggggtactg tcactcaaac tggctgatcc aatcaccatt accaatgggg atgtatccct 26820
caaggtggga ggtggtctca ctttgcaaga tggaagccta actgtaaacc ctaaggctcc 26880
actgcaagtt aatactgata aaaaacttga gcttgcatat gataatccat ttgaaagtag 26940
tgctaataaa cttagtttaa aagtaggaca tggattaaaa gtattagatg aaaaaagtgc 27000
tgcggggtta aaagatttaa ttggcaaact tgtggtttta acaggaaaag gaataggcac 27060
tgaaaattta gaaaatacag atggtagcag cagaggaatt ggtataaatg taagagcaag 27120
agaagggttg acatttgaca atgatggata cttggtagca tggaacccaa agtatgacac 27180
gcgcacactt tggacaacac cagacacatc tccaaactgc acaattgctc aagataagga 27240
ctctaaactc actttggtac ttacaaagtg tggaagtcaa atattagcta atgtgtcttt 27300
gattgtggtc gcaggaaagt accacatcat aaataataag acaaatccaa aaataaaaag 27360
ttttactatt aaactgctat ttaataagaa cggagtgctt ttagacaact caaatcttgg 27420
aaaagcttat tggaacttta gaagtggaaa ttccaatgtt tcgacagctt atgaaaaagc 27480
aattggtttt atgcctaatt tggtagcgta tccaaaaccc agtaattcta aaaaatatgc 27540
aagagacata gtttatggaa ctatatatct tggtggaaaa cctgatcagc cagcagtcat 27600
taaaactacc tttaaccaag aaactggatg tgaatactct atcacattta actttagttg 27660
gtccaaaacc tatgaaaatg ttgaatttga aaccacctct tttaccttct cctatattgc 27720
ccaagaatga aagaccaata aacgtgtttt tcatttgaaa ttttcatgta tctttattga 27780
tttttacacc agcacgagta gacagtctcc caccaccagc ccattttaca gtgtacacgg 27840
ttctctcagc acgggtagcc ttaaataggg aaatattctc attagtgcgg gaattggact 27900
tggggtctat aatccacaca gtttcctggc gagccaaacg ggggtcggtg attgaaataa 27960
agccgtcctc tgaaaagtca tccaagcggg cctcacagtc caaggtcaca gtctggtgga 28020
acgagaagaa cgcacagatt catactcgga aaacaggatg ggtctgtgcc tctccatcag 28080
cgccctcagc agtctctgcc gccggggctc ggtgcggctg ctgcaaatgg gatcgggatc 28140
acaagtctct ctgactatga tcccaacagc cttcagcatc agtctcctgg tgcgacgggc 28200
acagcaccgc atcctgatct ctgccatgtt ctcacagtaa gtgcagcaca taatcaccat 28260
gttattcagc agcccataat tcagggcgct ccagccaaag ctcatgttgg gaatgatgga 28320
acccacgtga ccatcgtacc agatgcgaca gtatatcaga tgcctgcccc tcatgaacac 28380
actgcccatg tacatgatct ctttgggcat gtttctgttt acaatctggc ggtaccaggg 28440
gaagcgctgg ttgaacatgc acccgtaaat gactctcctg aaccacacgg ccagcagggt 28500
gcctcccgcc cgacactgca gggagccagg ggatgaacag tggcaatgca ggatccagcg 28560
ctcgtacccg ctcaccattt gagctcttac caagtccagg gtagcggggc acaggcacac 28620
tgacatacat ctttttaaaa tttttatttc ctctgtggtg aggatcatat cccaggggac 28680
tggaaactct tggagcaggg taaagccagc agcacatggt aatccacgga cagaacttac 28740
attatgataa tctgcatgat cacaatcggg caacagggga tgttgttcag tcagtgaagc 28800
cctggtttcc tcatcagatc gtggtaaacg ggccctgcga tatggatgat ggcggagcga 28860
gctggattga atctcggttt gcattgtagt ggattctctt gcgtaccttg tcgtacttct 28920
gccagcagaa atgggccctt gaacagcata tacccctcct acggccgtcc tttcgctgct 28980
gccgctcagt catccaacta aagtacatcc attctcgaag attctggaga agttcctctg 29040

```
catctgataa aataaaaaac ccgtccatgc gaattcccct catcacatca gccaggactc  29100
tgtaggccat ccccatccag ttaatgctgc cttgtctatc attcagaggg ggcggtggca  29160
ggactggaag aaccattttt attccaaacg gtctcgaagg acgataaagt gcaagtcacg  29220
caggtgacag cgttcccctc cgctgtgctg gtggaaacag acagccaggt caaaacccac  29280
tctattttca aggtgctcga ccgtggcttc gagcagtggc tctacgcgca catccagcat  29340
aagaatcaca ttaaaggctg gccctccatc gatttcatca atcatcaggt tacattcctg  29400
caccatcccc aggtaattct catttttcca gccttggatt atctctacaa attgttggtg  29460
taagtccact ccgcacatgt ggaaaagctc ccacagtgcc ccctccactt tcataatcag  29520
gcagaccttc ataatagaaa cagatcctgc tgctccacca cctgcagcgt gttcaaaaca  29580
acaagattca ataaggttct gccctccgcc ctgagctcgc gcctcaatgt cagctgcaaa  29640
aagtcactta agtcctgggc cactacagct gacaattcag agccagggct aagcgtggga  29700
ctggcaagcg taagggaaaa ctttaatgct ccaaagctag cacccaaaaa ctgcatgctg  29760
gaataagctc tctttgtgtc tccggtgatg ccttccaaaa tgtgagtgat aaagcgtggt  29820
agtttttctt taatcatttg cgtaatagaa aagtcctcta aataagtcac taggacccca  29880
gggaccacaa tgtggtagct tacaccgcgt cgctgaagca tggttagtag agatgagagt  29940
ctgaaaaaca gaaagcatgc actaaactaa ggtggctatt ttcactgaag gaaaaatcac  30000
tctctccagc agcagggtac ccactgggtg gcccttgcgg acatacaaaa atcggtccgt  30060
gtgattaaaa agcagcacag taagttcctg tcttcttccg gcaaaaatca catcagactg  30120
ggttagtatg tccctggcat ggtagtcatt caaggccata aatctgccct gatatccagt  30180
aggaaccagc acactcactt ttaggtgaag caataccacc ccatgcggag gaatgtggaa  30240
agattcaggg caaaaaaatt atatctattg ctagcccctt cctggacggg agcaatccct  30300
ccaggactat ctataaaagc atacagagat tcagccatag cttagcccgc ttaccagtag  30360
acagaaagca cagcagtaca agcgccaaca gcagcaactg actacccact gacccagctc  30420
cctatttaaa ggcaccttac actgacgtaa tgaccaaagg tctaaaaacc ccgccaaaaa  30480
aaacacacac gccctgggtg tttttcacaa aaacacttcc gcgttctcac ttcctcgtat  30540
cgattttgtg actcaacttc cgggttccca cgttacgtca cttctgccct tacatgtaac  30600
ttggccgtat ggcgccatct tgcccacgtc caaaatggct ttcatgaccg gccacgcctc  30660
cgcgccggcc gttagccgtg cgtcgtgacg ttatttgcat caccgcttct cgtccaatca  30720
gcgttggctc cgccccaaaa ccgttaaaat tcaaaagctc atttgcatat taacttttgt  30780
ttactttgtg ggtatatta ttagatagtt aattaaggat gcatgtttaa actcgacagc  30840
gacacacttg catcggatgc agcccggtta acgtgccggc acggcctggg taaccaggta  30900
ttttgtccac ataaccgtgc gcaaaatgtt gtggataagc aggacacagc agcaatccac  30960
agcaggcata caaccgcaca ccgaggttac tccgttctac aggttacgac gacatgtcaa  31020
tacttgccct tgacaggcat tgatggaatc gtagtctcac gctgatagtc tgatcgacaa  31080
tacaagtggg accgtggtcc cagaccgata atcagaccga caacacgagt gggatcgtgg  31140
tcccagacta ataatcagac cgacgatacg agtgggaccg tggtcccaga ctaataatca  31200
gaccgacgat acgagtggga ccgtggttcc agactaataa tcagaccgac gatacgagtg  31260
ggaccgtggt cccagactaa taatcagacc gacgatacga gtgggaccat ggtcccagac  31320
taataatcag accgacgata cgagtgggac cgtggtccca gtctgattat cagaccgacg  31380
atacgagtgg gaccgtggtc ccagactaat aatcagaccg acgatacgag tgggaccgtg  31440
```

```
gtcccagact aataatcaga ccgacgatac gagtgggacc gtggtcccag tctgattatc  31500
agaccgacga tacaagtgga acagtgggcc cagagagaat attcaggcca gttatgcttt  31560
ctggcctgta acaaaggaca ttaagtaaag acagataaac gtagactaaa acgtggtcgc  31620
atcagggtgc tggcttttca agttccttaa gaatggcctc aattttctct atacactcag  31680
ttggaacacg agacctgtcc aggttaagca ccattttatc gcccttatac aatactgtcg  31740
ctccaggagc aaactgatgt cgtgagctta aactagttct tgatgcagat gacgttttaa  31800
gcacagaagt taaaagagtg ataacttctt cagcttcaaa tatcacccca gctttttttct  31860
gctcatgaag gttagatgcc tgctgcttaa gtaattcctc tttatctgta aaggcttttt  31920
gaagtgcatc acctgaccgg gcagatagtt caccggggtg agaaaaaaga gcaacaactg  31980
atttaggcaa tttggcggtg ttgatacagc gggtaataat cttacgtgaa atattttccg  32040
catcagccag cgcagaaata tttccagcaa attcattctg caatcggctt gcataacgct  32100
gaccacgttc ataagcactt gttgggcgat aatcgttacc caatctggat aatgcagcca  32160
tctgctcatc atccagctcg ccaaccagaa cacgataatc actttcggta agtgcagcag  32220
ctttacgacg gcgactccca tcggcaattt ctatgacacc agatactctt cgaccgaacg  32280
ccggtgtctg ttgaccagtc agtagaaaag aagggatgag atcatccagt gcgtcctcag  32340
taagcagctc ctggtcacgt tcattacctg accatacccg agaggtcttc tcaacactat  32400
caccccggag cacttcaaga gtaaacttca catcccgacc acatacaggc aaagtaatgg  32460
cattaccgcg agccattact cctacgcgcg caattaacga atccaccatc ggggcagctg  32520
gtgtcgataa cgaagtatct tcaaccggtt gagtattgag cgtatgtttt ggaataacag  32580
gcgcacgctt cattatctaa tctcccagcg tggtttaatc agacgatcga aaatttcatt  32640
gcagacaggt tcccaaatag aaagagcatt tctccaggca ccagttgaag agcgttgatc  32700
aatggcctgt tcaaaaacag ttctcatccg gatctgacct ttaccaactt catccgtttc  32760
acgtacaaca ttttttagaa ccatgcttcc ccaggcatcc cgaatttgct cctccatcca  32820
cggggactga gagccattac tattgctgta tttggtaagc aaaatacgta catcaggctc  32880
gaaccctta agatcaacgt tcttgagcag atcacgaagc atatcgaaaa actgcagtgc  32940
ggaggtgtag tcaaacaact cagcaggcgt gggaacaatc agcacatcag cagcacatac  33000
gacattaatc gtgccgatac ccaggttagg cgcgctgtca ataactatga catcatagtc  33060
atgagcaaca gtttcaatgg ccagtcggag catcaggtgt ggatcggtgg gcagtttacc  33120
ttcatcaaat ttgcccatta actcagtttc aatacggtgc agagccagac aggaaggaat  33180
aatgtcaagc cccggccagc aagtgggctt tattgcataa gtgacatcgt ccttttcccc  33240
aagatagaaa ggcaggagag tgtcttctgc atgaatatga agatctggta cccatccgtg  33300
atacattgag gctgttccct gggggtcgtt accttccacg agcaaaacac gtagcccctt  33360
cagagccaga tcctgagcaa gatgaacaga aactgaggtt ttgtaaacgc cacctttatg  33420
ggcagcaacc ccgatcaccg gtggaaatac gtcttcagca cgtcgcaatc gcgtaccaaa  33480
cacatcacgc atatgattaa tttgttcaat tgtataacca acacgttgct caacccgtcc  33540
tcgaatttcc atatccgggt gcggtagtcg ccctgctttc tcggcatctc tgatagcctg  33600
agaagaaacc ccaactaaat ccgctgcttc acctattctc cagcgccggg ttattttcct  33660
cgcttccggg ctgtcatcat taaactgtgc aatggcgata gccttcgtca tttcatgacc  33720
agcgtttatg cactggttaa gtgtttccat gagtttcatt ctgaacatcc tttaatcatt  33780
```

gctttgcgtt tttttattaa atcttgcaat ttactgcaaa gcaacaacaa aatcgcaaag 33840
tcatcaaaaa accgcaaagt tgtttaaaat aagagcaaca ctacaaaagg agataagaag 33900
agcacatacc tcagtcactt attatcacta gcgctcgccg cagccgtgta accgagcata 33960
gcgagcgaac tggcgaggaa gcaaagaaga actgttctgt cagatagctc ttacgctcag 34020
cgcaagaaga aatatccacc gtgggaaaaa ctccaggtag aggtacacac gcggatagcc 34080
aattcagagt aataaactgt gataatcaac cctcatcaat gatgacgaac taacccccga 34140
tatcaggtca catgacgaag ggaaagagaa ggaaatcaac tgtgacaaac tgccctcaaa 34200
tttggcttcc ttaaaaatta cagttcaaaa agtatgagaa aatccatgca ggctgaagga 34260
aacagcaaaa ctgtgacaaa ttaccctcag taggtcagaa caaatgtgac gaaccaccct 34320
caaatctgtg acagataacc ctcagactat cctgtcgtca tggaagtgat atcgcggaag 34380
gaaaatacga tatgagtcgt ctggcggcct ttctttttct caatgtatga gaggcgcatt 34440
ggagttctgc tgttgatctc attaacacag acctgcagga agcggcggcg gaagtcaggc 34500
atacgctggt aactttgagg cagctggtaa cgctctatga tccagtcgat tttcagagag 34560
acgatgcctg agccatccgg cttacgatac tgacacaggg attcgtataa acgcatggca 34620
tacggattgg tgatttcttt tgtttcacta agccgaaact gcgtaaaccg gttctgtaac 34680
ccgataaaga agggaatgag atatgggttg atatgtacac tgtaaagccc tctggatgga 34740
ctgtgcgcac gtttgataaa ccaaggaaaa gattcatagc ctttttcatc gccggcatcc 34800
tcttcagggc gataaaaaac cacttccttc cccgcgaaac tcttcaatgc ctgccgtata 34860
tccttactgg cttccgcaga ggtcaatccg aatatttcag catatttagc aacatggatc 34920
tcgcagatac cgtcatgttc ctgtagggtg ccatcagatt ttctgatctg gtcaacgaac 34980
agatacagca tacgtttttg atcccgggag agactatatg ccgcctcagt gaggtcgttt 35040
gactggacga ttcgcgggct atttttacgt ttcttgtgat tgataaccgc tgtttccgcc 35100
atgacagatc catgtgaagt gtgacaagtt tttagattgt cacactaaat aaaaaagagt 35160
caataagcag ggataacttt gtgaaaaaac agcttcttct gagggcaatt tgtcacaggg 35220
ttaagggcaa tttgtcacag acaggactgt catttgaggg tgatttgtca cactgaaagg 35280
gcaatttgtc acaacacctt ctctagaacc agcatggata aaggcctaca aggcgctcta 35340
aaaaagaaga tctaaaaact ataaaaaaaa taattataaa aatatccccg tggataagtg 35400
gataacccca agggaagttt tttcaggcat cgtgtgtaag cagaatatat aagtgctgtt 35460
ccctggtgct tcctcgctca ctcgagggct tcgccgtcgc tcgactgcgg cgagcctact 35520
ggctgtaaaa ggacagacca catcatggtt ctgtgttcat taggttgttc tgtccattgc 35580
tgacataatc cgctccactt caacgtaaca ccgcacgaag atttctattg ttcctgaagg 35640
catattcaaa tcgttttcgt taccgcttgc aggcatcatg acagaacact acttcctata 35700
aacgctacac aggctcctga gattaataat gcggatctct acgataatgg gagattttcc 35760
cgactgtttc gttcgcttct cagtggataa cagccagctt ctctgtttaa cagacaaaaa 35820
cagcatatcc actcagttcc acatttccat ataaaggcca aggcatttat tctcaggata 35880
attgtttcag catcgcaacc gcatcagact ccggcatcgc aaactgcacc cggtgccggg 35940
cagccacatc cagcgcaaaa accttcgtgt agacttccgt tgaactgatg gacttatgtc 36000
ccatcaggct ttgcagaact ttcagcggta taccggcata cagcatgtgc atcgcatagg 36060
aatggcggaa cgtatgtggt gtgaccggaa cagagaacgt cacaccgtca gcagcagcgg 36120
cggcaaccgc ctccccaatc caggtcctga ccgttctgtc cgtcacttcc cagatccgcg 36180
ctttctctgt ccttcctgtg cgacggttac gccgctccat gagcttatcg cgaataaata 36240
cctgtgacgg aagatcactt cgcagaataa ataaatcctg gtgtccctgt tgataccggg 36300
aagccctggg ccaacttttg gcgaaaatga gacgttgatc ggcacgtaag aggttccaac 36360
tttcaccata atgaaataag atcactaccg ggcgtatttt ttgagttatc gagattttca 36420
ggagctaagg aagctaaaat ggagaaaaaa atcactggat ataccaccgt tgatatatcc 36480
caatggcatc gtaaagaaca ttttgaggca tttcagtcag ttgctcaatg tacctataac 36540
cagaccgttc agctggatat tacggccttt ttaaagaccg taaagaaaaa taagcacaag 36600
ttttatccgg cctttattca cattcttgcc cgcctgatga atgctcatcc ggaattccgt 36660
atggcaatga aagacggtga gctggtgata tgggatagtg ttcacccttg ttacaccgtt 36720
ttccatgagc aaactgaaac gttttcatcg ctctggagtg aataccacga cgatttccgg 36780
cagtttctac acatatattc gcaagatgtg gcgtgttacg gtgaaaacct ggcctatttc 36840
cctaaagggt ttattgagaa tatgtttttc gtctcagcca atccctgggt gagtttcacc 36900
agttttgatt taaacgtggc caatatggac aacttcttcg cccccgtttt caccatgggc 36960
aaatattata cgcaaggcga caaggtgctg atgccgctgg cgattcaggt tcatcatgcc 37020
gtctgtgatg gcttccatgt cggcagaatg cttaatgaat tacaacagta ctgcgatgag 37080
tggcagggcg gggcgtaatt tttttaaggc agttattggt gcccttaaac gcctggttgc 37140
tacgcctgaa taagtgataa taagcggatg aatggcagaa attcgatgat aagctgtcaa 37200
acatgagaat gggtcgag 37218

<210> SEQ ID NO 8
<211> LENGTH: 38240
<212> TYPE: DNA
<213> ORGANISM: Artificial sequence
<220> FEATURE:
<223> OTHER INFORMATION: /note="Description of artificial sequence: pRAB19aGFP_5pIX+SV40"

<400> SEQUENCE: 8
gaagttccta ttccgaagtt cctattctct agaaagtata ggaacttcaa ttcccatgtc 60
agccgttaag tgttcctgtg tcactcaaaa ttgctttgag aggctctaag ggcttctcag 120
tgcgttacat ccctggcttg ttgtccacaa ccgttaaacc ttaaaagctt taaaagcctt 180
atatattctt ttttttctta taaaacttaa aaccttagag gctatttaag ttgctgattt 240
atattaattt tattgttcaa acatgagagc ttagtacgtg aaacatgaga gcttagtacg 300
ttagccatga gagcttagta cgttagccat gagggtttag ttcgttaaac atgagagctt 360
agtacgttaa acatgagagc ttagtacgtg aaacatgaga gcttagtacg tactatcaac 420
aggttgaact gctgatcttc agatcctcta cgccggacgc atcgtggccg gatccgattt 480
attcaacaaa gccacgttgt gtctcaaaat ctctgatgtt acattgcaca agataaaaat 540
atatcatcat gaacaataaa actgtctgct tacataaaca gtaatacaag gggtgttatg 600
agccatattc aacgggaaac gtcttgctcg aggccgcgat taaattccaa catggatgct 660
gatttatatg ggtataaatg ggctcgcgat aatgtcgggc aatcaggtgc gacaatctat 720
cgattgtatg ggaagcccga tgcgccagag ttgtttctga aacatggcaa aggtagcgtt 780
gccaatgatg ttacagatga gatggtcaga ctaaactggc tgacggaatt tatgcctctt 840
ccgaccatca agcattttat ccgtactcct gatgatgcat ggttactcac cactgcgatc 900
cccgggaaaa cagcattcca ggtattagaa gaatatcctg attcaggtga aaatattgtt 960

-continued

```
gatgcgctgg cagtgttcct gcgccggttg cattcgattc ctgtttgtaa ttgtcctttt   1020
aacagcgatc gcgtatttcg tctcgctcag gcgcaatcac gaatgaataa cggtttggtt   1080
gatgcgagtg attttgatga cgagcgtaat ggctggcctg ttgaacaagt ctggaaagaa   1140
atgcataagc ttttgccatt ctcaccggat tcagtcgtca ctcatggtga tttctcactt   1200
gataacctta tttttgacga ggggaaatta ataggttgta ttgatgttgg acgagtcgga   1260
atcgcagacc gataccagga tcttgccatc ctatggaact gcctcggtga gttttctcct   1320
tcattacaga aacggctttt tcaaaaatat ggtattgata atcctgatat gaataaattg   1380
cagtttcatt tgatgctcga tgagtttttc taatcagaat tggttaattg gttgtaacac   1440
tggcttaatt aactatctaa taatataccc cacaaagtaa acaaaagtta atatgcaaat   1500
gagcttttga attttaacgg ttttggggcg gagccaacgc tgattggacg agaagcggtg   1560
atgcaaataa cgtcacgacg cacggctaac ggccggcgcg gaggcgtggc ctaggccgga   1620
agcaagtcgc ggggctaatg acgtataaaa aagcggactt tagacccgga aacggccgat   1680
tttcccgcgg ccacgcccgg atatgaggta attctgggcg gatgcaagtg aaattaggtc   1740
attttggcgc caaaactgaa tgaggaagtg aaaagtgaaa aatacctgtc ccgcccaggg   1800
cggaatattt accgagggcc gagagacttt gaccgattac gtggggtttc gattgcggtg   1860
tttttttcgc gagaaggtaa actgcccact tggcagtaca tcaagtgtat catatgccaa   1920
gtacgccccc tattgacgtc aatgacggta aatggcccgc ctggcattat gcccagtaca   1980
tgaccttatg ggactttcct acttggcagt acatctacgt attagtcatc gctattacca   2040
tggtgatgcg gttttggcag tacatcaatg ggcgtggata gcggtttgac tcacggggat   2100
ttccaagtct ccaccccatt gacgtcaatg ggagtttgtt ttggcaccaa aatcaacggg   2160
actttccaaa atgtcgtaac aactccgccc cattgacgca aatgggcggt aggcgtgtac   2220
ggtgggaggt ctatataagc agagctggtt tagtgaaccg tcagatccgc tagcgctacc   2280
ggactcagat ctcgagctca agcttcgaat tctgcagtcg acggtaccgc gggcccggga   2340
tccaccggtc gccaccatgg tgagcaaggg cgaggagctg ttcaccgggg tggtgcccat   2400
cctggtcgag ctggacggcg acgtaaacgg ccacaagttc agcgtgtccg gcgagggcga   2460
gggcgatgcc acctacggca agctgaccct gaagttcatc tgcaccaccg gcaagctgcc   2520
cgtgccctgg cccaccctcg tgaccaccct gacctacggc gtgcagtgct tcagccgcta   2580
ccccgaccac atgaagcagc acgacttctt caagtccgcc atgcccgaag gctacgtcca   2640
ggagcgcacc atcttcttca aggacgacgg caactacaag acccgcgccg aggtgaagtt   2700
cgagggcgac accctggtga accgcatcga gctgaagggc atcgacttca aggaggacgg   2760
caacatcctg gggcacaagc tggagtacaa ctacaacagc cacaacgtct atatcatggc   2820
cgacaagcag aagaacggca tcaaggtgaa cttcaagatc cgccacaaca tcgaggacgg   2880
cagcgtgcag ctcgccgacc actaccagca gaacaccccc atcggcgacg gccccgtgct   2940
gctgcccgac aaccactacc tgagcaccca gtccgccctg agcaaagacc ccaacgagaa   3000
gcgcgatcac atggtcctgc tggagttcgt gaccgccgcc gggatcactc tcggcatgga   3060
cgagctgtac aagtaaagcg gccgcgactc tagatcataa tcagccatac cacatttgta   3120
gaggttttac ttgctttaaa aaacctccca cacctccccc tgaacctgaa acataaaatg   3180
aatgcaattg ttgttgttaa cttgtttatt gcagcttata atggttacaa ataaagcaat   3240
agcatcacaa atttcacaaa taaagcattt ttttcactgc attctagttg tggtttgtcc   3300
```

-continued aaactcatca atgtatctta aatcgaattc aagcatatgc tgaaatgtgt gggcgtggct 3360
taagggtggg aaagaatata taaggtgggg gtcttatgta gttttgtatc tgttttgcag 3420
cagccgccgc cgcctccgga cgcgtgaagt tcctattctc tagaaagtat aggaacttcg 3480
cgtaaattgt aagcgttaat attttgttaa aattcgcgtt aaatttttgt taaatcagct 3540 catttttttaa ccaataggcc gaaatcggca aaatccctta taaatcaaaa gaatagaccg 3600
agatagggtt gagtgttgtt ccagtttgga acaagagtcc actattaaag aacgtggact 3660
ccaacgtcaa agggcgaaaa accgtctatc agggcgatgg cccactacgt gaaccatcac 3720
cctaatcaag ttttttgggg tcgaggtgcc gtaaagcact aaatcggaac cctaaaggga 3780
gcccccgatt tagagcttga cggggaaagc cggcgaacgt ggcgagaaag gaagggaaga 3840
aagcgaaagg agcgggcgct agggcgctgg caagtgtagc ggtcacgctg cgcgtaacca 3900
ccacacccgc cgcgcttaat gcgccgctac agggcgcgtc aggtggcact tttcggggaa 3960
atgtgcgcgg aacccctatt tgtttatttt tctaaataca ttcaaatatg tatccgctca 4020
tgagacaata accctgataa atgcttcaat aatattgaaa aaggaagagt cctgaggcgg 4080
aaagaaccag ctgtggaatg tgtgtcagtt agggtgtgga aagtccccag gctccccagc 4140
aggcagaagt atgcaaagca tgcatctcaa ttagtcagca accaggtgtg gaaagtcccc 4200
aggctcccca gcaggcagaa gtatgcaaag catgcatctc aattagtcag caaccatagt 4260
cccgccccta actccgccca tcccgcccct aactccgccc agttccgccc attctccgcc 4320
ccatggctga ctaatttttt ttatttatgc agaggccgag gccgcctcgg cctctgagct 4380
attccagaag tagtgaggag gcttttttgg aggggggtggg gtaccaggta agtgtaccca 4440
attcgcccta tagtgagtcg tattacaatt cactggccgt cgttttacaa cgtcgtgact 4500
gggaaaaccc tggcgttacc caacgtgaga ccagaccacc tggtgatggc ctgtaccggg 4560
accgagttca gctccagtgg ggaggacaca gattagaggt aggtttgagt agtgggcgtg 4620
gctaatgtga gtataaaggc gggtgtctta cgagggtctt tttgcttttc tgcagacatc 4680
atgaacggga ccggcggggc cttcgaaggg gggcttttta gcccttattt gacaacccgc 4740
ctgccgggat gggccggagt tcgtcagaat gtgatgggat ctacggtgga tgggcgtcca 4800
gtgcttccag caaattcctc gaccatgacc tacgcgaccg tggggagctc gtcgcttgac 4860
agcaccgccg cagccgcggc agccgcagcc gccatgacag cgacgagact ggcctcgagc 4920
tatatgccca gcagcggtag cagcccctct gtgcccagtt ccatcatcgc cgaggagaaa 4980
ctgctggccc tgctggccga gctggaagcc ctgagccgcc agctggccgc cctgacccag 5040
caggtgtccg atctccgcga gcaacagcag cagcaaaata aatgaattca ataaacacag 5100
attctgattc aaacagcaaa gcatctttat tatttatttt ttcgcgcgcg gtaggccctg 5160
gtccacctct cccgatcatt gagagtgcgg tggatttttt ccaggacccg gtagaggtgg 5220
gattggatgt tgaggtacat gggcatgagc ccgtcccggg ggtggaggta gcaccactgc 5280
atggcctcgt gctctggggt cgtgttgtag ataatccagt catagcaggg gcgctgggcg 5340
tggtgctgga tgatgtcctt gaggaggaga ctgatggcca cggggagccc cttggtgtag 5400
gtgttggcaa agcggttaag ctgggaggga tgcatgcggg gggagatgat gtgcagtttg 5460
gcctggatct tgaggttggc gatgttgcca cccagatccc gccgggggtt catattgtgc 5520
aggaccacca gaacggtgta gcccgtgcac ttggggaact tatcatgcaa cttggaaggg 5580
aatgcgtgga agaatttgga gacgcccttg tgcccgccca ggttttccat gcactcatcc 5640
atgatgatgg caatgggccc gtgggctgcg gctttggcaa aaacgtttct ggggtcagag 5700

```
acatcataat tatgctcctg ggtgagatca tcataagaca ttttaatgaa tttggggcga   5760
agggtgccag attgggggac gatcgttccc tcgggccccg gggcgaagtt cccctcgcag   5820
atctgcatct cccaggcttt catctcggag ggggggatca tgtccacctg cggggcgatg   5880
aaaaaaacgg tttccggggc gggggtgatg agctgcgagg agagcaggtt tcttaacagc   5940
tgggacttgc cgcacccggt cgggccgtag atgaccccga tgacgggttg caggtggtag   6000
ttcaaggaga tgcagctgcc gtcgtcccgg aggagggggg ccacctcgtt gagcatgtct   6060
ctcacttgga ggttttcccg gacgagctcg ccgaggaggc ggtccccgcc cagcgagagc   6120
agctcttgca gggaagcaaa gtttttcagg ggcttgagcc cgtcggccat gggcatcttg   6180
gcaagggtct gcgagaggag ctccaggcgg tcccatagct cggtgacgtg ctctacggca   6240
tctcgatcca gcagacttcc tcgtttcggg ggttgggacg actgcgactg tagggcacga   6300
gacgatgggc gtccagcgcg gccagcgtca tgtccttcca gggtctcagg gtccgagtga   6360
gggtggtctc cgtcacggtg aaggggtggg ccccgggctg ggcgcttgca agggtgcgct   6420
tgagactcat cctgctggtg ctgaaacggg cacggtcttc gccctgcgcg tcggcgagat   6480
agcagttgac catgagcttg tagttaaggg cctcggcggc gtggcccttg gcacggagct   6540
tgcctttgga agagcgcccg caggcgggac agaggaggga ttgcagggcg tagagcttgg   6600
gtgcgagaaa gacggactcg ggagcgaagg cgtccgctcc gcagtgggcg cagacggtct   6660
cgcactcgac gagccaggtg agctcgggct gctcggggtc aaaaaccagt ttcccccgt    6720
tctttttgat gcgcttctta cctcgcgtct ccatgagtct gtgtccgcgt tcggtgacaa   6780
acaggctgtc tgtgtccccg tagacggact tgattggcct gtcctgcagg ggcgtcccgc   6840
ggtcctcctc gtagagaaac tcggaccact ctgagacaaa ggcgcgcgtc cacgccaaga   6900
caaaggaggc cacgtgcgag ggtagcggt cgttgtccac caggggtcc acctttcca      6960
ccgtgtgcag acacatgtcc ccctcctccg catccaagaa ggtgattggc ttgtaggtgt   7020
aggccacgtg accgggggtc cccgacgggg gggtataaaa gggggcgggt ctgtgctcgt   7080
cctcactctc ttccgcgtcg ctgtccacga gcgccagctg ttggggtagg tattccctct   7140
cgagagcggg catgacctcg gcactcaggt tgtcagtttc tagaaacgag gaggatttga   7200
tgttggcctg ccctgccgca atgcttttta ggagactttc atccatctgg tcagaaaaga   7260
ctattttttt attgtcaagc ttggtggcaa aggagccata gagggcgttg gagagaagct   7320
tggcgatgga tctcatggtc tgatttttgt cacggtcggc gcgctccttg gccgcgatgt   7380
tgagctggac atactcgcgc gcgacacact tccattctgg gaagacggtg gtgcgctcgt   7440
cgggcacgat cctgacgcgc cagccgcgat tatgcagggt gaccaggtcc acgctggtgg   7500
ccacctcgcc gcgcaggggc tcgttggtcc agcagaggcg tccgcccttg cgcgagcaga   7560
acgggggcag cacatcaagc agatgctcgt cagggggtc cgcatcgatg gtgaagatgc    7620
ccggacagag ttccttgtca aaataatcga tttttgagga tgcatcatcc aaggccatct   7680
gccactcgcg ggcggccagc gctcgctcgt aggggttgag ggcggaccc cagggcatgg    7740
gatgcgtgag ggcggaggcg tacatgccgc agatgtcgta gacatagatg ggctccgaga   7800
ggatgccgat gtaggtggga taacagcgcc ccccgcggat gctggcgcgc acatagtcat   7860
acaactcgtg cgagggggcc aagaaagcgg ggccgagatt ggtgcgctgg ggctgctcgg   7920
cgcggaagac gatctggcga aagatggcat gcgagttgga ggagatggtg ggccgttgga   7980
agatgttaaa gtgggcgtgg ggcaagcgga ccgagtcgcg gatgaagtgc gcgtaggagt   8040
```

-continued

```
cttgcagctt ggcaacgagc tcggcggtga caaggacgtc catggcgcag tagtccagcg   8100
tttcacggat gatgtcataa cccgcctctt ctttcttctc ccacagcgcg cggttgaggg   8160
cgtactcctc gtcatccttc cagtactccc ggagcgggaa tcctcgatcg tccgcacggt   8220
aagagcccag catgtagaaa tggttcacgg ccttgtaggg acagcagccc ttctccacgg   8280
ggagggcgta agcttgagcg gccttgcgga gcgaggtgtg cgtcagggcg aaggtatccc   8340
taaccatgac tttcaagaac tggtacttga aatccgagtc gtcgcagccg ccgtgctccc   8400
agagctcgaa atcggtgcgc ttcttcgaga gggggttagg cagagcgaaa gtgacgtcat   8460
tgaagagaat cttgcctgcc cgcggcatga aattgcgggt gatgcggaaa gggcccggaa   8520
cggaggctcg gttgttgatg acctgggcgg cgaggacgat ctcgtcgaag ccgttgatgt   8580
tgtgcccgac gatgtagagt tccatgaatc gcgggcggcc tttgatgtgc ggcagctttt   8640
tgagttcctc gtaggtgagg tcctcggggc attgcaggcc gtgctgctcg agcgcccact   8700
cctggagatg tgggttggct tgcatgaatg aagcccagag ctcgcgggcc atgagggtct   8760
ggagctcgtc gcgaaagagg cggaactgct ggcccacggc catcttttct ggggtgacgc   8820
agtagaaggt gagggggtcc cgctcccagc gatcccagcg taagcgcacg gcgagatcgc   8880
gagcgagggc gaccagctcg ggtccccggg agaatttcat gaccagcatg aaggggacga   8940
gctgcttgcc gaaggacccc atccaggtgt aggtttctac atcgtaggtg acaaagagcc   9000
gctccgtgcg aggatgagag ccgattggga agaactggat ttcctgccac cagttggtcg   9060
agtggctgtt gatgtgatga aagtagaaat cccgccggcg aaccgagcac tcgtgctgat   9120
gcttgtaaaa gcgtccgcag tactcgcagc gctgcacggg ctgtacctca tccacgagat   9180
acacagcgcg tcccttgagg aggaacttca ggagtggcgg ccctggctgg tggttttcat   9240
gttcgcctgc gtgggactca ccctggggct cctcgaggac ggagaggctg acgagcccgc   9300
gcgggagcca ggtccagatt tcggcgcggc gggggcggag agcgaaaacg agggcgcgca   9360
gttgggagct gtccatggtg tcgcggagat ccaggtccgg gggcagggtt ctgaggttga   9420
cctcgtagag gcgggtgagg gcgtgcttga gatgcagatg gtacttgatc tccacgggtg   9480
agttggtggt cgtgtccacg cattgcatga gcccgtagct gcgcggggcc acgaccgtgc   9540
cgcggtgcgc ttttagaagc ggtgtcgcgg acgcgctccc ggcggcagcg gcggttccgg   9600
ccccgcgggc agtggcggta gaggcacgtc ggcgtggcgc tcgggcaggt cccggtgctg   9660
cgccctgaga gcgctggcgt gcgcgacgac gcggcggttg acatcctgga tctgccgcct   9720
ttgcgtgaag accacgggcc ccgtgacttt gaacctgaaa gacagttcaa cagaatcaat   9780
ctcggcgtca ttgacggcgg cctgacgcag gatctcttgc acgtcgcccg agttgtcctg   9840
gtaggcgatc tcggacatga actgctcgat ttcctcctcc tggagatcgc cgcggcccgc   9900
gcgctctacg gtggcggcaa ggtcattcga gatgcgaccc atgagctgcg agaaggcgcc   9960
caggccgctc tcgttccaga cgcggctgta aaccacgtcc ccgtcggcgt cgcgcgcgcg  10020
catgaccacc tgcgcgaggt tgagctccac gtgccgcgta aagacggcgt agttgcgcag  10080
gcgctggaag aggtagttga gggtggtggc gatgtgctcg gtgacgaaga agtacataat  10140
ccagcggcgc aggggcattt cgctgatgtc gccaatggcc tccagccttt ccatggcctc  10200
gtagaaatcc acggcgaagt tgaaaaactg ggcgttgcgg gccgagaccg tgagctcgtc  10260
ttccaggagc ctgatgagtt cggcgatggt ggcgcgcacc tcgcgctcga aatcccaggg  10320
ggcctcctcc tcttcctctt cttccatgac gacctcttct tctatttctt cctctggggg  10380
cggtggtggt ggcggggccc gacgacgacg gcgacgcacc gggagacggt cgacgaagcg  10440
```

-continued

```
ctcgatcatc tccccgcggc ggcgacgcat ggtttcggtg acggcgcgac cccgttcgcg  10500
aggacgcagc gtgaagacgc cgccggtcat ctcccggtaa tggggtgggt ccccgttggg  10560
cagcgatagg gcgctgacaa tgcatcttat caattgcggt gtagggcacg tgagcgcgtc  10620
gagatcgacc ggatcggaga atctttcgag gaaagcgtct agccaatcgc agtcgcaagg  10680
taagctcaaa cacgtagcag ccctgtggac gctgttagaa ttgcggttgc tgatgatgta  10740
attgaagtag gcgtttttga ggcggcggat ggtggcgagg aggaccaggt ccttgggtcc  10800
cgcttgctgg atgcggagcc gctcggccat gccccaggcc tggccctgac accggctcag  10860
gttcttgtag tagtcatgca tgagcctctc gatgtcatca ctggcggagg cggagtcttc  10920
catgcgggtg accccgacgc ccctgaacgg ctgcacgagc gccaggtcgg cgacgacgcg  10980
ctcggcgagg atggcctgtt gcacgcgggt gagggtgtcc tggaagtcgt ccatgtcgac  11040
gaagcggtgg taggcccctg tgttgatggt gtaagtgcag ttggccataa gcgaccagtt  11100
gacggtctgc aggccgggtt gcacgacctc ggagtacctg agccgcgaga aggcgcgcga  11160
gtcgaagaca tagtcgttgc aggtgcgcac gaggtactgg tatccgacta gaaagtgcgg  11220
cggcggctgg cggtagagcg gccagcgctg ggtggccggc gcgcccgggg ccaggtcctc  11280
aagcatgagt cggtggtagc cgtagaggta gcgggacatc caggtgatgc cggcggcggt  11340
ggtggaggcg cgcgggaact cgcggacgcg gttccagatg ttgcgcaggg gcaggaaata  11400
gtccatggtc ggcacggtct ggccggtgag acgcgcgcag tcattgatgc tctagaggca  11460
aaaacgaaag cggttgagcg ggctcttcct ccgtagcctg gcggaacgca aacgggttag  11520
gccgcgtgtg taccccggtt cgagtcccct cgaatcaggc tggagccgcg actaacgtgg  11580
tattggcact cccgtctcga cccaagcccg atagccgcca ggatacggcg gagagccctt  11640
tttgtcggcc gaggggagtc gctagacttg aaagcggccg aaaaccctgc cgggtagtgg  11700
ctcgcgcccg tagtctggag aagcatcgcc agggttgagt cgcggcagaa cccggttcaa  11760
ggacggccgc ggcgagcggg acttggtcac cccgccgatt taaagaccca cagccagccg  11820
acttctccag ttacgggagc gagccccctt ttttcttttt gccagatgca tcccgtcctg  11880
cgccaaatgc gtcccacccc cccggcgacc accgcgaccg cggccgtagc aggcgccggc  11940
gctagccagc cacagccaca gacagagatg gacttggaag agggcgaagg gctggcgaga  12000
ctgggggcgc cgtccccgga gcgacatccc cgcgtgcagc tgcagaagga cgtgcgcccg  12060
gcgtacgtgc ctgcgcagaa cctgttcagg gaccgcagcg gggaggagcc cgaggagatg  12120
cgcgactgcc ggtttcgggc gggcagggag ctgcgcgagg gcctggaccg ccagcgcgtg  12180
ctgcgcgacg aggatttcga gccgaacgag cagacgggga tcagccccgc gcgcgcgcac  12240
gtggcggcgg ccaacctggt gacagcctac gagcagacgg tgaagcagga acgcaacttt  12300
caaaagagtt tcaacaacca cgtgcgcacc ctgatcgcgc gcgaggaggt ggccctgggc  12360
ctgatgcacc tgtgggacct ggcggaggcc attgtgcaga acccggacag caagcctctg  12420
acggcacaac tgttcctggt ggtgcagcac agcagggaca acgaggcgtt cagggaggcg  12480
ctgctaaaca tcgccgagcc cgagggccgc tggctgctgg agctgatcaa catcttgcaa  12540
agcatcgtag tgcaggagcg cagcctgagc ttggccgaga aggtggcggc gatcaactac  12600
tcggtgctaa gcctgggcaa gttttacgcg cgcaagattt acaagacgcc gtacgtgccc  12660
atagacaagg aggtgaaaat agacagcttt tacatgcgca tggcgctcaa ggtgctgacg  12720
ctgagcgacg acctgggcgt gtaccgcaac gaccgcatcc acaaggccgt gagcacgagc  12780
```

-continued

```
cggcggcgcg agctgagcga ccgcgagctg atgctaagcc tgcgccgggc gctggtaggt  12840
ggcgccgccg gcggcgagga gtcctacttc gacatggggg cggacctgca ttggcagccg  12900
agccggcgcg ccttggaggc cgcctacggt ccagaggact tggatgagga tgaggaagag  12960
gaggaggatg cacccgttgc ggggtactga cgcctccgtg atgtgttttt agatgtccca  13020
gcagcaagcc ccggaccccg ccataagggc ggcgctgcaa agccagccgt ccggtctagc  13080
atcggacgac tgggaggccg cgatgcaacg catcatggcc ctgacgaccc gcaaccccga  13140
gtcctttaga caacagccgc aggccaacag actttcgacc attctggagg cggtggtccc  13200
ctctcggacc aaccccacgc acgagaaggt gctggcgatc gtgaacgcgc tggcggagaa  13260
caaggctatt cgtcccgacg aggctgggct ggtatacaac gccctgctgg agcgcgtggg  13320
ccgctacaac agcacgaacg tgcagtccaa cctggaccgg ctggtgacgg acgtgcgcga  13380
ggccgtggcg cagcgcgagc ggttcaagaa cgagggcctg ggctcgctgg tggcgctgaa  13440
cgccttcctg gcgacgcagc cggcgaacgt gccgcgcggg caggacgatt ataccaactt  13500
tatcagcgcg ctgcggctga tggtgaccga ggttccccag agcgaggtgt accagtcggg  13560
cccggactac tttttccaga ctagcagaca gggcctgcag acggtgaacc tgagccaggc  13620
tttcaagaac ctgcgcgggc tgtggggcgt gcaggcgccc gtgggcgacc ggtcgacggt  13680
gagcagcttg ctgacgccca actcgcggct gctgctgctg ctgatcgcgc ccttcaccga  13740
cagcggcagc gtgaaccgca actcgtacct gggtcacctg ctgacgctgt accgcgaggc  13800
cataggccag gcacaggtgg acgagcagac cttccaggag atcactagtg taagccgcgc  13860
gctgggtcag aacgacaccg acagtctgag ggccaccctg aacttcttgc tgaccaatag  13920
acagcagaag atcccggcgc agtatgcgct gtcggccgag gaggagcgca tcctgagata  13980
tgtgcagcag agcgtagggc tgtttctgat gcaggagggg gccacccccca gcgccgcgct  14040
ggacatgacc gcgcgcaaca tggaacctag catgtacgcc gccaaccggc cgtttatcaa  14100
taagctgatg gactacctgc accgcgcggc gtccatgaac tcggactact ttaccaatgc  14160
cattttgaac ccgcactggc tcccgccgcc ggggttctac acgggcgagt acgacatgcc  14220
tgaccccaac gacgggtttt tgtgggacga cgtggacagc gcggtgttct caccgacctt  14280
gcaaaagcgc caggaggcgg tgcgcacgcc cgcgagcgag ggcgcggtgg gtcggagccc  14340
ctttcctagc ttagggagtt tgcatagctt gccgggctcg gtgaacagcg gcagggtgag  14400
ccggccgcgc ttgctgggcg aggacgagta cctaaacgac tcgctgctgc agccgccgcg  14460
ggtcaagaac gccatggcca ataacgggat agagagtctg gtggacaaac tgaaccgctg  14520
gaagacctac gctcaggacc atagggagcc tgcgcccgcg ccgcggcgac agcgccacga  14580
ccggcagcgg ggcctggtgt gggacgacga ggactcggcc gacgatagca gcgtgttgga  14640
cttgggcggg agcggtgggg tcaacccgtt cgcgcatctg cagcccaaac tggggcgacg  14700
gatgttttga atgcaaaata aaactcacca aggccatagc gtgcgttctc ttccttgtta  14760
gagatgaggc gtgcggtggt gtcttcctct cctcctccct cgtacgagag cgtgatggcg  14820
caggcgaccc tggaggttcc gtttgtgcct ccgcggtata tggctcctac ggagggcaga  14880
aacagcattc gttactcaga gctggctccg ctgtacgaca ccactcgcgt gtacttggtg  14940
gacaacaagt cggcggacat cgcttccctg aactaccaaa acgaccacag caactttctg  15000
accacggtgg tgcaaaacaa cgatttcacc cccgccgagg ctagcacgca gacgataaat  15060
tttgacgagc ggtcgcggtg gggcggtgat ctgaagacca ttctgcacac caacatgccc  15120
aatgtgaacg agtacatgtt taccagcaag tttaaggcgc gggtgatggt ggctaggaaa  15180
```

```
cacccacagg gggtagaagc aacagattta agcaaggata tcttagagta ccagtggttt  15240
gagtttaccc tgcccgaggg caacttttcc gagaccatga ccatagacct gatgaacaac  15300
gccatcttgg aaaactactt gcaagtgggg cggcaaaatg gcgtgctgga gagcgatatc  15360
ggagtcaagt ttgacagcag gaatttcaag ctgggctggg accccgtgac caagctggtg  15420
atgccagggg tctacaccta tgaggccttc cacccggacg tggtgctgct gcctggctgc  15480
ggggtggact tcaccgagag ccgcctaagc aaccttctgg gcattcgcaa gaagcaacct  15540
ttccaagagg gcttcagaat catgtatgag gatctcgaag gggggcaacat tcccgcactt  15600
ctgaatgtga ccaagtacct ggaaagcaag aagaagctag aggagaatgc cgctaaggct  15660
aatggtcctg caagaggaga cagtagtgtc tcaagagagg tggaaaaggc agctgaaaaa  15720
gagcttgtca ttgagcccat caagcaagat gatagcaaga gaagttacaa cctcattgag  15780
ggtacccatg acaccctgta ccgaagctgg tacctgtcct atacctacgg ggaccccgag  15840
aagggggtgc agtcgtggac gctgctcacc accccggacg gtcactgcgg cgcggagcaa  15900
gtctactggt cgctgccgga cctcatgcaa gaccccgtca ccttccgctc tacccagcaa  15960
gtcagcaact accccgtggt cggcgccgag ctcatgcctt tccgcgccaa gagcttttac  16020
aacgacctcg ccgtctactc ccagctcatc cgcagctaca cctccctcac ccacgtcttc  16080
aaccgcttcc ccgacaacca gatcctctgc cgcccgcccg cgcccaccat caccaccgtc  16140
agtgaaaacg tgcctgctct cacagatcac gggacgctac cgctgcgcag cagtatccgc  16200
ggagtccagc gagtgaccgt cactgacgcc cgtcgccgca cctgtcccta cgtctacaag  16260
gccctgggca tagtcgcgcc gcgcgtgctt tccagtcgca ccttctaaaa aatgtctatt  16320
ctcatctcgc ccagcaataa caccggctgg ggtcttacta ggcccagcac catgtacgga  16380
ggagccaaga aacgctccca gcagcacccc gtccgcgtcc gcggccactt tcgcgctccc  16440
tggggcgcat acaagcgcgg gcggacttcc accgccgccg ccgtgcgcac caccgtcgac  16500
gacgtcatcg actcggtggt cgccgatgcg cgcaactata cccccgcccc ctccaccgtg  16560
gacgcggtca ttgacagcgt ggtggccgac gcgcgcgact atgccagacg caagagccgg  16620
cggcgacgga tcgccaggcg ccaccggagc acgcccgcca tgcgcgccgc ccgggctctg  16680
ctgcgccgcg ccagacgcac gggccgccgg gccatgatgc gagccgcgcg ccgcgctgcc  16740
actgcaccca cccccgcagg caggactcgc agacgagcgg ccgctgccgc cgccgcggcc  16800
atctctagca tgaccagacc caggcgcgga aacgtgtact gggtgcgcga ctccgtcacg  16860
ggcgtgcgcg tgcccgtgcg cactcgtcct cctcgtccct gatctaatgc ttgtgtcctc  16920
ccccgcaagc gacgatgtca aagcgcaaaa tcaaggagga gatgctccag gtcgtcgccc  16980
cggagattta cggacccccg gaccagaaac cccgcaaaat caagcgggtt aaaaaaaagg  17040
atgaggtgga cgagggggca gtagagtttg tgcgcgagtt cgctccgcgg cggcgcgtaa  17100
attggaaggg gcgcagggtg cagcgtgtgt tgcggcccgg cacggcggtg gtgttcacgc  17160
ccggcgagcg gtcctcggtc aggagcaagc gtagctatga cgaggtgtac ggcgacgacg  17220
acatcctgga ccaggcggcg gagcgggcgg gcgagttcgc ctacgggaag cggtcgcgcg  17280
aagaggagct gatctcgctg ccgctggacg aaagcaaccc cacgccgagc ctgaagcccg  17340
tgaccctgca gcaggtgctg ccccaggcgg tgctgctgcc gagccgcggg gttaagcgcg  17400
agggcgagag catgtacccg accatgcaga tcatggtgcc caagcgccgg cgcgtggagg  17460
acgtgctgga caccgtgaaa atggatgtgg agcccgaggt caaggtgcgc cccatcaagc  17520
```

aggtggcgcc gggcctgggc gtgcaaaccg tggacattca gatccccacc gacatggatg 17580
tcgacaaaaa accctcgacc agcatcgagg tgcaaaccga cccctggctc ccagcctcca 17640
ccgctaccgc cgccacggcc accgagcctc ccaggaggcg aagatggggc cctgccaacc 17700
ggctgatgcc caactacgtg ttgcatcctt ccatcatccc gacgccgggc taccgcggca 17760
cccggtacta cgccagccgc aggcgcccag ccagtaaacg ccgccgccgc accgccaccc 17820
gccgccgtct ggcccccgcc cgcgtgcgcc gcgtgaccac gcgccggggc cgctcgctcg 17880
ttctgcccac cgtgcgctac caccccagca tcctttaatc cgtgtgctgt gatactgttg 17940
cagagagatg gctctcactt gccgcctgcg catccccgtc ccgaattacc gaggaagatc 18000
ccgccgcagg agaggcatgg caggcagtgg cctgaaccgc cgccggcggc gggccatgcg 18060
caggcgcctg agtggcggct ttctgcccgc gctcatcccc ataatcgccg cggccatcgg 18120
cacgatcccg ggcatagctt ccgttgcgct gcaggcgtcg cagcgccgtt gatgtgcgaa 18180
taaagcctct ttagactctg acacacctgg tcctgtatat ttttagaatg gaagacatca 18240
attttgcgtc cctggctccg cggcacggca cgcggccgtt catgggcacc tggaacgaga 18300
tcggcaccag ccagctgaac gggggcgcct tcaattggag cagtgtctgg agcgggctta 18360
aaaatttcgg ctcgacgctc cggacctatg ggaacaaggc ctggaatagt agcactgggc 18420
agttgttaag ggaaaagctc aaagaccaga acttccagca aaaggtggtg gacgggctgg 18480
cctcgggcat taacggggtg gtggacatcg cgaacccagg ccgtgcagcg cgagataaac 18540
aaccgcctgg acccgcggcc gcccacggtg gtggagatgg aagatgcaac tcctccgccg 18600
cccaagggcg agaagcgacc gcggcccgac gcggaggaga cgatcctgca ggtggacgag 18660
ccgccctcgt acgaggaggc cgtaaaggcc ggcatgccca ccacgcgcat catcgcgcca 18720
ctggccacgg gtgtaatgaa acccgccacc cttgacctgc ctccaccacc cacgcccgct 18780
ccaccgaagg cagctccggt agtgcagccc cctccggtgg cgaccgccgt gcgccgcgtc 18840
cccgcccgcc gccaggccca aaactggcaa agcacgctgc acagtattgt gggcctggga 18900
gtgaaaagtc tgaagcgccg ccgatgctat tgaaagagag gaaggaagac actaaaggga 18960
gagcttaact tgtatgtgcc ttaccgccag agaacgcgcg aagatggcca ccccctcgat 19020
gatgccgcag tgggcgtaca tgcacatcgc cgggcaggac gcctcggagt acctgagccc 19080
gggtctggtg cagtttgccc gcgccaccga cacgtacttc agcctgggca acaagtttag 19140
gaaccccacg gtggccccaa cccacgatgt gaccacggac cggtcccagc gtctgacgct 19200
gcgcttcgtg cccgtggatc gcgaggacac cacgtactcg tacaaggcgc gcttcactct 19260
ggccgtgggc gacaaccggg tgctagacat ggccagcact tactttgaca tccgcggcgt 19320
tctggaccgc ggccccagct tcaaacccta ctcgggcacg gcttacaaca gcctggcccc 19380
caagggcgcc cccaattcca gtcagtggga tgctcaagaa aaaaatggac aaggaggaaa 19440
tgacatggtt accaaaactc acacatttgg cgtggctgct atgggaggaa caaatattac 19500
aaaccagggt ttgttaattg gaactgaaga aacagccgat aatcctccaa aggaaatctt 19560
tgcagacaaa ttattccagc cagaacctca agtaggagag gaaaactggc aagacagcaa 19620
tgcattctat ggaggcaggg ctcttaagaa ggaaactaaa atgaaaccat gctatggatc 19680
ttatgctaga ccaacaaaca caagtggcgg acaggctaag cttaaaactg gtgacaatat 19740
cgatcctacc aaggatttcg acatagatct tgctttcttc gatactcctg gcggaaatcc 19800
tccagcaggt ggtagtggaa cggaagaata caaagcagat attgttatgt acactgaaaa 19860
tgtcaacctt gaaacacctg acactcatgt ggtgtacaaa ccagccaaag aggatgaaag 19920

-continued ttctcaggcc aacttggttc agcagtccat gcccaacaga cccaactaca ttggcttcag 19980
agacaatttt gtggggctca tgtattacaa cagcactggc aacatgggag tgctggctgg 20040
tcaggcctct cagttgaatg ctgtggtgga cttgcaagac agaaacacag agctgtctta 20100
ccagctcttg ctagattctc tgggtgacag aaccagatac tttagcatgt ggaactctgc 20160
ggtggacagc tatgatccag atgtcagaat cattgaaaat cacggtgtgg aagatgagct 20220
tccaaactat tgctttccat tggatggctc tggtaccaat gctgcctacc aaggtgtaaa 20280
ggttcaagat ggtgaagacg gggataaaga aactgaatgg gaaaaagata ccaaagtcgc 20340
agatcgtaac caactgtgca agggtaacat cttcgccatg gagatcaacc tccaggccaa 20400
cctgtggaag agttttctgt actcgaacgt ggccctgtac ctgcccgact cctacaagta 20460
cacgccggcc aacatcacgc tgcccgccaa caccaacacc tacgagtaca tgaacggccg 20520
cgtggtagcc ccctcgctgg tggacgcata cgtcaacatc ggtgcgcgct ggtcgctgga 20580
ccccatggac aacgtcaacc ccttcaacca ccaccgcaac gcgggcctgc gctaccgctc 20640
catgcttctc ggcaacggcc gctacgtgcc cttccacatc caagtgcccc aaaagttctt 20700
tgccattaag aacctgctcc tgctccccgg ctcctacacc tacgagtgga acttccgcaa 20760
ggatgtcaac atgatcctgc agagttccct cggaaacgac ctgcgcgtcg acggcgcctc 20820
cgtgcgcttc gacagcgtca acctctacgc taccttcttc cccatggcgc acaacaccgc 20880
ctccaccctg gaagccatgc tgcgcaacga caccaacgac cagtccttta acgactacct 20940
ctcggccgcc aacatgctct accccatacc ggccaaggcc accaacgtgc ccatctccat 21000
cccctcgcgc aactgggctg ccttccgcgg ctggagtttc acccggctca agaccaagga 21060
aactccttcc cttggctcgg gtttcgaccc ctactttgtc tactcgggct ccatccccta 21120
cctcgacggg accttctacc tcaaccacac cttcaaaaag gtgtccatta tgttcgactc 21180
ctcggtcagc tggcccggca acgaccggct gctcacgccg aatgagttcg agatcaagcg 21240
cagcgtcgac ggggagggct acaacgtggc ccaatgcaac ataaccaagg actggttcct 21300
cgtccagatg ctctcccact acaacatcgg ctaccagggc ttccacgtgc ccgagggcta 21360
caaggaccgc atgtactcct tttccgcaa cttccagccc atgagcaggc aggtggtgga 21420
tgagatcaac tacaaggact acaaggccgt caccctgccc ttccagcaca acaactctgg 21480
cttcaccggc tacctcgcac ccaccatgcg tcaggggcag ccttaccccg ccaacttccc 21540
ttacccgctc atcggctcca ccgcagtccc ctccgtcacc cagaaaaagt tcctctgcga 21600
cagggtcatg tggcgcatcc ccttctccag caacttcatg tccatgggtg ccctcaccga 21660
cctgggtcag aacatgctct atgccaactc ggcccacgcg ctcgacatga ccttcgaggt 21720
ggaccccatg gatgagccca ccctcctcta tcttctcttc gaagttttcg acgtggtcag 21780
agtgcaccag ccgcaccgcg gcgtcatcga ggccgtctac ctgcgcacac ccttctccgc 21840
cggcaacgcc accacctaag catgagcggt tccagcgaac gagaactcgc ggccatcgtg 21900
cgcgacctgg gctgcgggcc ctactttttg ggcacccacg acaagcgctt cccgggcttc 21960
ctagccggcg acaagctggc ctgcgccatc gtcaacacgg ccggccgcga gaccggaggc 22020
gtgcactggc tcgccttcgg ctggaacccg cgctcgcgca cctgctacat gttcgacccc 22080
tttgggttct cggaccgccg gctcaagcag atttacagct tcgagtacga ggccatgctg 22140
cgccgaagcg ccctggcctc ctcgcccgac cgctgtctca gcctcgaaca gtccacccag 22200
accgtgcagg ggcccgactc cgccgcctgc ggactttttt gttgcatgtt cttgcatgcg 22260

-continued ttcgtgcact ggcccgaccg acccatggac ggaaacccca ccatgaactt gctgacgggg 22320
gtgcccaacg gcatgctaca atcgccacag gtgctgccca ccctccggcg caaccaggag 22380
gagctctacc gcttcctcgc gcgccactcc ccttacttcc gatcccaccg cgccgccatc 22440
gaacacgcca ccgcttttga caaaatgaaa caactgcgtg tatctcaata aacagcactt 22500
tttattttac atgcactgga gtatatgcaa gttatttaaa agtcgaaggg gttctcgcgc 22560
tcgtcgttgt gcgccgcgct ggggagggcc acgttgcggt actggtactt ggaaagccac 22620
ttgaactcgg ggatcaccag tttgggcact ggggtctcgg ggaaggtctc gctccacatg 22680
cgccggctca tctgcagggc gcccagcatg tcagggccgg agatcttgaa atcacagttg 22740
gggccggtgc tctgcgcgcg cgagttgcgg tacacggggt tgcagcactg gaacaccatc 22800
agactggggt acttcacact ggcaagcacg ctcttgtcgc taatctgatc cttgtccagg 22860
tcctcggcgt tgctcaggcc gaacggggtc atcttgcaca gctggcggcc caggaagggc 22920
acgctctgag gcttgtggtt acactcgcag tgcacgggca tcagcatcat ccccgcgccg 22980
cgctgcatat tcgggtagag ggccttgacg aaggccgcga tctgcttgaa agcttgctgg 23040
gccttggccc cctcgctgaa gaacagaccg cagctcttcc cgctgaactg gttattcccg 23100
cacccggcat catgcacgca gcagcgcgcg tcatggctgg tcagttgcac cacgctccgt 23160
ccccagcggt tctgggtcac cttagccttg ctgggctgct ccttcagcgc gcgctgtccg 23220
ttctcgctgg tcacatccat ctccaccacg tggtccttgt gaatcatcac cgttccatgc 23280
agacacttga gctgaccttc cacctcggtg cagccgtgat cccacaggac gcagccggtg 23340
cactcccaat tcttgtgcgc gatcccgctg tggctgaaaa tgtaaccttg caacaggcga 23400
cccataatgg tgctaaatga tttctgggtg gtgaatgtca gttgcatccc gcgggcctcc 23460
tcgttcatcc aggtctggca catcttctgg aagatctcgg tctgctccgg catgagcttg 23520
taagcatcgc gcaagccgct gtcgacgcgg tagcgttcca tcagcacgtt catggtatcc 23580
atgcccttct cccatgacga gaccagaggc agactcaggg ggttgcgcac gttcaggaca 23640
ccaggggtcg cgggctcgac gatgcgtttt ccgtccttgc cttccttcaa cagaaccgga 23700
ggctggctga atcccactcc cacgatcacg gcgtcttcct ggggcatctc ttcgtcgggg 23760
tctaccttgg tcacatgctt ggtctttctg gcttgcttct tttttggagg gctgtccacg 23820
gggaccacgt cctcctcgga agacccggag cccacccgct gatactttcg gcgcttggtg 23880
ggcagaggag gtggcggcgg cgaggggctc ctctcctgct ccggcggata gcgcgccgac 23940
ccgtggcccc ggggcggagt ggcctctcgc tccatgaacc ggcgcacgtc ctgactgccg 24000
ccggccattg tttcctaggg gaagatggag gagcagccgc gtaagcagga gcaggaggag 24060
gacttaacca cccacgagca acccaaaatc gagcaggacc tgggcttcga agagccggct 24120
cgtctaaaac ccccacagga tgaacaggag cacgagcaag acgcaggcca ggaggagacc 24180
gacgctgggc tcgagcatgg ctacctggga ggagaggagg atgtgctgct aaaacacctg 24240
cagcgccagt ccctcatcct ccgggacgcc ctggccgacc ggagcgaaac ccccctcagc 24300
gtcgaggagc tgtgtcgggc ctacgagctc aacctcttct cgccgcgcgt gccccccaaa 24360
cgccagccca acggcacctg cgagcccaac ccgcgtctca acttctatcc cgtctttgcg 24420
gtccccgagg cccttgccac ctatcacatc tttttcaaga accaaaagat ccccatctcc 24480
tgtcgcgcca atcgcactcg cgccgacgcg ctcctcgctc tggggcccgg cgcgcgcata 24540
cctgatatcg cttccctgga agaggtgccc aagatcttcg aagggctcgg tcgggacgag 24600
acgcgcgcgg caaacgctct gaaagaaaca gcagaggaag agggttacac tagcgccctg 24660
gtagagttgg aaggcgacaa cgccaggctg gccgtgctta agcgcagcgt cgagctcacc 24720
catttcgcct accccgccgt caacctcccg cccaaggtca tgcgtcgcat catggatcag 24780
ctcatcatgc cccacatcga ggcccttgat gaaagtcagg aacagcgccc cgagaacgcc 24840
cagcccgtgg tcagcgacga gatgctcgcg cgctggctcg ggacccgcga cccccaggcc 24900
ctggagcagc ggcgcaagct catgctggcc gtggtcctgg tcacccttga gctcgaatgc 24960
atgcgccgct tttttaccga ccccgagacc ctgcgcaagg tcgaggagac cctgcactac 25020
actttcagac acggtttcgt caggcaggcc tgcaagatct ccaacgtgga gctgaccaac 25080
ctggtctcct gcctggggat cctacacgag aaccgcttgg gacagaccgt gctccactct 25140
accctgaagg gcgaggcgcg gcgggactac atccgcgact gcgtctttct ctttctctgc 25200
cacacatggc aagcggccat gggcgtgtgg cagcagtgtc tcgaggacga gaacctgaag 25260
gagctggaca agcttcttgc tagaaacctt aaaaagctgt ggacgggctt cgacgagcgc 25320
accgtcgcct cggacctggc cgagatcgtc ttccccgagc gcctgaggca gacgctgaaa 25380
ggagggctgc ccgacttcat gagccagagc atgttgcaaa actaccgcac tttcattctc 25440
gagcgatctg ggatgctgcc cgccacctgc aacgccttcc cctccgactt tgtcccgctg 25500
agctaccgcg agtgtccccc gccgctgtgg agccactgct acctcttgca gctggccaac 25560
tacattgccc accactcgga tgtgatcgag gacgtgagcg gcgaggggct gctcgagtgc 25620
cactgtcgct gcaacctatg ctccccgcac cgctccctgg tctgcaaccc ccagctactg 25680
agcgagaccc aggtcatcgg tacctttgag ctgcaaggtc cgcaggagtc caccgctccg 25740
ctgaaactca cgccggggtt gtggacttcc gcgtacctgc gcaaatttgt acccgaggac 25800
tactacgccc atgagataaa gttcttcgag gaccaatcgc gtccgcagca cgcggatctc 25860
acggcctgcg tcatcaccca gggcgcgatc ctcgcccaat tgcacgccat ccaaaaatcc 25920
cgccaagagt ttcttctgaa aaagggtaga ggggtctacc tggaccccca gacgggcgag 25980
gtgctcaacc cgggtctccc ccagcatgcc gaggaagaag caggagccgc tagtggagga 26040
gatggaagaa gaatgggaca gccaggcaga ggaggacgaa tgggaggagg agacagagga 26100
ggaagacttg gaagaggtgg aagaggagca ggcaacagag cagcccgtcg ccgcaccatc 26160
cgcgccggca gcccctccgg tcacggatac aacctccgca gctccggcca agcctcctcg 26220
tagatgggat cgagtgaagg gtgacggtaa gcacgagcga cagggctacc gatcatggag 26280
ggcccacaaa gccgcgatca tcgcctgctt gcaagactgc gggggggaaca tcgctttcgc 26340
ccgccgctac ctgctcttcc accgcggggt gaacatcccc cgcaacgtgt tgcattacta 26400
ccgtcacctt cacagctaag aaaaagcaag tcaaaggagt cgccggagga ggaggcctga 26460
ggatcgcggc gaacgagccc ttgaccacca gggagctgag gaaccggatc ttccccactc 26520
tttatgccat tttcagcaa agtcgaggtc agcagcaaga gctcaaagta aaaaaccggt 26580
ctctgcgctc gctcacccgc agttgcttgt accacaaaaa cgaagatcag ctgcagcgca 26640
ctctcgaaga cgccgaggct ctgttccaca agtactgcgc gctgactctt aaagactaag 26700
gcgcgcccac ccggaaaaaa ggcgggaatt acctcatcgc caccatgagc aaggagattc 26760
ccaccccctta catgtggagc tatcagcccc agatgggcct ggccgcgggc gcctcccagg 26820
actactccac ccgcatgaac tggcttagtg ccggcccctc gatgatctca cgggtcaacg 26880
gggtccgtaa ccatcgaaac cagatattgt tgcagcaggc ggcggtcacc tccacgccca 26940
gggcaaagct caacccgcgt aattggccct ccaccctggt gtatcaggaa atccccgggc 27000

```
cgactaccgt actacttccg cgtgacgcac tggccgaagt ccgcatgact aactcaggtg  27060
tccagctggc cggcggcgct tcccggtgcc cgctccgccc acaatcgggt ataaaaaccc  27120
tggtgatccg aggcagaggc acacagctca acgacgagtt ggtgagctct tacaatcgtc  27180
tgcgaccgga cggagtgttc caactagccg gagccgggag atcgtccttc actcccaacc  27240
aggcctacct gaccttgcag agcagctctt cggagcctcg ctcgggaggc atcggaaccc  27300
accagttcgt ggaggagttt gtgccctcgg tctacttcaa cccccttctcg ggctcgccag  27360
gcctctaccc ggacgagttt ataccgaact tcgacgcagt gagagaagcg gtggacggct  27420
acgactgaag cttgttgatt aaaagcccag aaaccaatca gacccttcct catttcccca  27480
tcccaatact cataagaata aatcattgga attaatcatt caataaagat cacttacttg  27540
aaatctgaaa gtatgtctct ggtgtagttg ctcagcaaca cctcggtacc ctcctcccag  27600
ctctggtact ccagtccccg gcgggcggcg aacttcctcc acaccttgaa agggatgtca  27660
aagaggctcc gggtggaaga tgacttcaac cccgtctacc cctatggcta cgcgcggaat  27720
cagaatatcc ccttcctcac tccccccttt gtctcctccg atggattcaa aaacttcccc  27780
cctggggtac tgtcactcaa actggctgat ccaatcacca ttaccaatgg ggatgtatcc  27840
ctcaaggtgg gaggtggtct cactttgcaa gatggaagcc taactgtaaa ccctaaggct  27900
ccactgcaag ttaatactga taaaaaactt gagcttgcat atgataatcc atttgaaagt  27960
agtgctaata aacttagttt aaaagtagga catggattaa aagtattaga tgaaaaaagt  28020
gctgcggggt taaaagattt aattggcaaa cttgtggttt taacaggaaa aggaataggc  28080
actgaaaatt tagaaaatac agatggtagc agcagaggaa ttggtataaa tgtaagagca  28140
agagaagggt tgacatttga caatgatgga tacttggtag catggaaccc aaagtatgac  28200
acgcgcacac tttggacaac accagacaca tctccaaact gcacaattgc tcaagataag  28260
gactctaaac tcactttggt acttacaaag tgtggaagtc aaatattagc taatgtgtct  28320
ttgattgtgg tcgcaggaaa gtaccacatc ataaataata agacaaatcc aaaaataaaa  28380
agttttacta ttaaactgct atttaataag aacggagtgc ttttagacaa ctcaaatctt  28440
ggaaaagctt attggaactt tagaagtgga aattccaatg tttcgacagc ttatgaaaaa  28500
gcaattggtt ttatgcctaa tttggtagcg tatccaaaac ccagtaattc taaaaaatat  28560
gcaagagaca tagtttatgg aactatatat cttggtggaa aacctgatca gccagcagtc  28620
attaaaacta cctttaacca agaaactgga tgtgaatact ctatcacatt taactttagt  28680
tggtccaaaa cctatgaaaa tgttgaattt gaaaccacct cttttacctt ctcctatatt  28740
gcccaagaat gaaagaccaa taaacgtgtt tttcatttga aattttcatg tatctttatt  28800
gatttttaca ccagcacgag tagacagtct cccaccacca gcccatttta cagtgtacac  28860
ggttctctca gcacgggtag ccttaaatag ggaaatattc tcattagtgc gggaattgga  28920
cttggggtct ataatccaca cagtttcctg gcgagccaaa cgggggtcgg tgattgaaat  28980
aaagccgtcc tctgaaaagt catccaagcg ggcctcacag tccaaggtca cagtctggtg  29040
gaacgagaag aacgcacaga ttcatactcg gaaaacagga tgggtctgtg cctctccatc  29100
agcgccctca gcagtctctg ccgccggggc tcggtgcggc tgctgcaaat gggatcggga  29160
tcacaagtct ctctgactat gatcccaaca gccttcagca tcagtctcct ggtgcgacgg  29220
gcacagcacc gcatcctgat ctctgccatg ttctcacagt aagtgcagca cataatcacc  29280
atgttattca gcagcccata attcagggcg ctccagccaa agctcatgtt gggaatgatg  29340
gaacccacgt gaccatcgta ccagatgcga cagtatatca gatgcctgcc cctcatgaac  29400
```

acactgccca tgtacatgat ctctttgggc atgtttctgt ttacaatctg gcggtaccag 29460
gggaagcgct ggttgaacat gcacccgtaa atgactctcc tgaaccacac ggccagcagg 29520
gtgcctcccg cccgacactg cagggagcca ggggatgaac agtggcaatg caggatccag 29580
cgctcgtacc cgctcaccat ttgagctctt accaagtcca gggtagcggg gcacaggcac 29640
actgacatac atctttttaa aatttttatt tcctctgtgg tgaggatcat atcccagggg 29700
actggaaact cttggagcag ggtaaagcca gcagcacatg gtaatccacg gacagaactt 29760
acattatgat aatctgcatg atcacaatcg ggcaacaggg gatgttgttc agtcagtgaa 29820
gccctggttt cctcatcaga tcgtggtaaa cgggccctgc gatatggatg atggcggagc 29880
gagctggatt gaatctcggt ttgcattgta gtggattctc ttgcgtacct tgtcgtactt 29940
ctgccagcag aaatgggccc ttgaacagca tataccccctc ctacggccgt cctttcgctg 30000
ctgccgctca gtcatccaac taaagtacat ccattctcga agattctgga gaagttcctc 30060
tgcatctgat aaaataaaaa acccgtccat gcgaattccc ctcatcacat cagccaggac 30120
tctgtaggcc atccccatcc agttaatgct gccttgtcta tcattcagag ggggcggtgg 30180
caggactgga agaaccattt ttattccaaa cggtctcgaa ggacgataaa gtgcaagtca 30240
cgcaggtgac agcgttcccc tccgctgtgc tggtggaaac agacagccag gtcaaaaccc 30300
actctatttt caaggtgctc gaccgtggct tcgagcagtg gctctacgcg cacatccagc 30360
ataagaatca cattaaaggc tggccctcca tcgatttcat caatcatcag gttacattcc 30420
tgcaccatcc ccaggtaatt ctcatttttc cagccttgga ttatctctac aaattgttgg 30480
tgtaagtcca ctccgcacat gtggaaaagc tcccacagtg cccccctccac tttcataatc 30540 aggcagacct tcataataga aacagatcct gctgctccac cacctgcagc gtgttcaaaa 30600
caacaagatt caataaggtt ctgccctccg ccctgagctc gcgcctcaat gtcagctgca 30660
aaaagtcact taagtcctgg gccactacag ctgacaattc agagccaggg ctaagcgtgg 30720
gactggcaag cgtaagggaa aactttaatg ctccaaagct agcacccaaa aactgcatgc 30780
tggaataagc tctctttgtg tctccggtga tgccttccaa aatgtgagtg ataaagcgtg 30840
gtagtttttc tttaatcatt tgcgtaatag aaaagtcctc taaataagtc actaggaccc 30900
cagggaccac aatgtggtag cttacaccgc gtcgctgaag catggttagt agagatgaga 30960
gtctgaaaaa cagaaagcat gcactaaact aaggtggcta ttttcactga aggaaaaatc 31020
actctctcca gcagcagggt acccactggg tggcccttgc ggacatacaa aaatcggtcc 31080
gtgtgattaa aaagcagcac agtaagttcc tgtcttcttc cggcaaaaat cacatcagac 31140
tgggttagta tgtccctggc atggtagtca ttcaaggcca taaatctgcc ctgatatcca 31200
gtaggaacca gcacactcac ttttaggtga agcaatacca ccccatgcgg aggaatgtgg 31260
aaagattcag ggcaaaaaaa ttatatctat tgctagcccc ttcctggacg ggagcaatcc 31320
ctccaggact atctataaaa gcatacagag attcagccat agcttagccc gcttaccagt 31380
agacagaaag cacagcagta caagcgccaa cagcagcaac tgactaccca ctgacccagc 31440
tccctattta aaggcacctt acactgacgt aatgaccaaa ggtctaaaaa ccccgccaaa 31500
aaaaacacac acgccctggg tgtttttcac aaaaacactt ccgcgttctc acttcctcgt 31560
atcgattttg tgactcaact tccgggttcc cacgttacgt cacttctgcc cttacatgta 31620
acttggccgt atggcgccat cttgcccacg tccaaaatgg ctttcatgac cggccacgcc 31680
tccgcgccgg ccgttagccg tgcgtcgtga cgttatttgc atcaccgctt ctcgtccaat 31740

```
cagcgttggc tccgccccaa aaccgttaaa attcaaaagc tcatttgcat attaactttt  31800
gtttactttg tggggtatat tattagatag ttaattaagg atgcatgttt aaactcgaca  31860
gcgacacact tgcatcggat gcagcccggt taacgtgccg gcacggcctg ggtaaccagg  31920
tattttgtcc acataaccgt gcgcaaaatg ttgtggataa gcaggacaca gcagcaatcc  31980
acagcaggca tacaaccgca caccgaggtt actccgttct acaggttacg acgacatgtc  32040
aatacttgcc cttgacaggc attgatggaa tcgtagtctc acgctgatag tctgatcgac  32100
aatacaagtg ggaccgtggt cccagaccga taatcagacc gacaacacga gtgggatcgt  32160
ggtcccagac taataatcag accgacgata cgagtgggac cgtggtccca gactaataat  32220
cagaccgacg atacgagtgg gaccgtggtt ccagactaat aatcagaccg acgatacgag  32280
tgggaccgtg gtcccagact aataatcaga ccgacgatac gagtgggacc atggtcccag  32340
actaataatc agaccgacga tacgagtggg accgtggtcc cagtctgatt atcagaccga  32400
cgatacgagt gggaccgtgg tcccagacta ataatcagac cgacgatacg agtgggaccg  32460
tggtcccaga ctaataatca gaccgacgat acgagtggga ccgtggtccc agtctgatta  32520
tcagaccgac gatacaagtg gaacagtggg cccagagaga atattcaggc cagttatgct  32580
ttctggcctg taacaaagga cattaagtaa agacagataa acgtagacta aaacgtggtc  32640
gcatcagggt gctggctttt caagttcctt aagaatggcc tcaattttct ctatacactc  32700
agttggaaca cgagacctgt ccaggttaag caccatttta tcgcccttat acaatactgt  32760
cgctccagga gcaaactgat gtcgtgagct taaactagtt cttgatgcag atgacgtttt  32820
aagcacagaa gttaaaagag tgataacttc ttcagcttca aatatcaccc cagctttttt  32880
ctgctcatga aggttagatg cctgctgctt aagtaattcc tctttatctg taaaggcttt  32940
ttgaagtgca tcacctgacc gggcagatag ttcaccgggg tgagaaaaaa gagcaacaac  33000
tgatttaggc aatttggcgg tgttgataca gcgggtaata atcttacgtg aaatattttc  33060
cgcatcagcc agcgcagaaa tatttccagc aaattcattc tgcaatcggc ttgcataacg  33120
ctgaccacgt tcataagcac ttgttgggcg ataatcgtta cccaatctgg ataatgcagc  33180
catctgctca tcatccagct cgccaaccag aacacgataa tcactttcgg taagtgcagc  33240
agctttacga cggcgactcc catcggcaat ttctatgaca ccagatactc ttcgaccgaa  33300
cgccggtgtc tgttgaccag tcagtagaaa agaagggatg agatcatcca gtgcgtcctc  33360
agtaagcagc tcctggtcac gttcattacc tgaccatacc cgagaggtct tctcaacact  33420
atcaccccgg agcacttcaa gagtaaactt cacatcccga ccacatacag gcaaagtaat  33480
ggcattaccg cgagccatta ctcctacgcg cgcaattaac gaatccacca tcggggcagc  33540
tggtgtcgat aacgaagtat cttcaaccgg ttgagtattg agcgtatgtt ttggaataac  33600
aggcgcacgc ttcattatct aatctcccag cgtggtttaa tcagacgatc gaaaatttca  33660
ttgcagacag gttcccaaat agaaagagca tttctccagg caccagttga agagcgttga  33720
tcaatggcct gttcaaaaac agttctcatc cggatctgac ctttaccaac ttcatccgtt  33780
tcacgtacaa cattttttag aaccatgctt ccccaggcat cccgaatttg ctcctccatc  33840
cacggggact gagagccatt actattgctg tatttggtaa gcaaaatacg tacatcaggc  33900
tcgaaccctt taagatcaac gttcttgagc agatcacgaa gcatatcgaa aaactgcagt  33960
gcggaggtgt agtcaaacaa ctcagcaggc gtgggaacaa tcagcacatc agcagcacat  34020
acgacattaa tcgtgccgat acccaggtta ggcgcgctgt caataactat gacatcatag  34080
tcatgagcaa cagtttcaat ggccagtcgg agcatcaggt gtggatcggt gggcagttta  34140
```

```
ccttcatcaa atttgcccat taactcagtt tcaatacggt gcagagccag acaggaagga  34200
ataatgtcaa gccccggcca gcaagtgggc tttattgcat aagtgacatc gtccttttcc  34260
ccaagataga aaggcaggag agtgtcttct gcatgaatat gaagatctgg tacccatccg  34320
tgatacattg aggctgttcc ctgggggtcg ttaccttcca cgagcaaaac acgtagcccc  34380
ttcagagcca gatcctgagc aagatgaaca gaaactgagg ttttgtaaac gccaccttta  34440
tgggcagcaa ccccgatcac cggtggaaat acgtcttcag cacgtcgcaa tcgcgtacca  34500
aacacatcac gcatatgatt aatttgttca attgtataac caacacgttg ctcaacccgt  34560
cctcgaattt ccatatccgg gtgcggtagt cgccctgctt tctcggcatc tctgatagcc  34620
tgagaagaaa ccccaactaa atccgctgct tcacctattc tccagcgccg ggttattttc  34680
ctcgcttccg ggctgtcatc attaaactgt gcaatggcga tagccttcgt catttcatga  34740
ccagcgttta tgcactggtt aagtgtttcc atgagtttca ttctgaacat cctttaatca  34800
ttgctttgcg ttttttttatt aaatcttgca atttactgca aagcaacaac aaaatcgcaa  34860
agtcatcaaa aaaccgcaaa gttgtttaaa ataagagcaa cactacaaaa ggagataaga  34920
agagcacata cctcagtcac ttattatcac tagcgctcgc cgcagccgtg taaccgagca  34980
tagcgagcga actggcgagg aagcaaagaa gaactgttct gtcagatagc tcttacgctc  35040
agcgcaagaa gaaatatcca ccgtgggaaa aactccaggt agaggtacac acgcggatag  35100
ccaattcaga gtaataaact gtgataatca accctcatca atgatgacga actaaccccc  35160
gatatcaggt cacatgacga agggaaagag aaggaaatca actgtgacaa actgccctca  35220
aatttggctt ccttaaaaat tacagttcaa aaagtatgag aaaatccatg caggctgaag  35280
gaaacagcaa aactgtgaca aattaccctc agtaggtcag aacaaatgtg acgaaccacc  35340
ctcaaatctg tgacagataa ccctcagact atcctgtcgt catggaagtg atatcgcgga  35400
aggaaaatac gatatgagtc gtctggcggc ctttcttttt ctcaatgtat gagaggcgca  35460
ttggagttct gctgttgatc tcattaacac agacctgcag gaagcggcgg cggaagtcag  35520
gcatacgctg gtaactttga ggcagctggt aacgctctat gatccagtcg attttcagag  35580
agacgatgcc tgagccatcc ggcttacgat actgacacag ggattcgtat aaacgcatgg  35640
catacggatt ggtgatttct tttgtttcac taagccgaaa ctgcgtaaac cggttctgta  35700
acccgataaa gaagggaatg agatatgggt tgatatgtac actgtaaagc cctctggatg  35760
gactgtgcgc acgtttgata aaccaaggaa aagattcata gcctttttca tcgccggcat  35820
cctcttcagg gcgataaaaa accacttcct tccccgcgaa actcttcaat gcctgccgta  35880
tatccttact ggcttccgca gaggtcaatc cgaatatttc agcatattta gcaacatgga  35940
tctcgcagat accgtcatgt tcctgtaggg tgccatcaga ttttctgatc tggtcaacga  36000
acagatacag catacgtttt tgatcccggg agagactata tgccgcctca gtgaggtcgt  36060
ttgactggac gattcgcggg ctatttttac gtttcttgtg attgataacc gctgtttccg  36120
ccatgacaga tccatgtgaa gtgtgacaag tttttagatt gtcacactaa ataaaaaaga  36180
gtcaataagc agggataact ttgtgaaaaa acagcttctt ctgagggcaa tttgtcacag  36240
ggttaagggc aatttgtcac agacaggact gtcatttgag ggtgatttgt cacactgaaa  36300
gggcaatttg tcacaacacc ttctctagaa ccagcatgga taaaggccta caaggcgctc  36360
taaaaaagaa gatctaaaaa ctataaaaaa aataattata aaaatatccc cgtggataag  36420
tggataaccc caagggaagt tttttcaggc atcgtgtgta agcagaatat ataagtgctg  36480
```

-continued

```
ttccctggtg cttcctcgct cactcgaggg cttcgccgtc gctcgactgc ggcgagccta  36540
ctggctgtaa aaggacagac cacatcatgg ttctgtgttc attaggttgt tctgtccatt  36600
gctgacataa tccgctccac ttcaacgtaa caccgcacga agatttctat tgttcctgaa  36660
ggcatattca aatcgttttc gttaccgctt gcaggcatca tgacagaaca ctacttccta  36720
taaacgctac acaggctcct gagattaata atgcggatct ctacgataat gggagatttt  36780
cccgactgtt tcgttcgctt ctcagtggat aacagccagc ttctctgttt aacagacaaa  36840
aacagcatat ccactcagtt ccacatttcc atataaaggc caaggcattt attctcagga  36900
taattgtttc agcatcgcaa ccgcatcaga ctccggcatc gcaaactgca cccggtgccg  36960
ggcagccaca tccagcgcaa aaaccttcgt gtagacttcc gttgaactga tggacttatg  37020
tcccatcagg ctttgcagaa ctttcagcgg tataccggca tacagcatgt gcatcgcata  37080
ggaatggcgg aacgtatgtg gtgtgaccgg aacagagaac gtcacaccgt cagcagcagc  37140
ggcggcaacc gcctccccaa tccaggtcct gaccgttctg tccgtcactt cccagatccg  37200
cgctttctct gtccttcctg tgcgacggtt acgccgctcc atgagcttat cgcgaataaa  37260
tacctgtgac ggaagatcac ttcgcagaat aaataaatcc tggtgtccct gttgataccg  37320
ggaagccctg ggccaacttt tggcgaaaat gagacgttga tcggcacgta agaggttcca  37380
actttcacca taatgaaata agatcactac cgggcgtatt ttttgagtta tcgagatttt  37440
caggagctaa ggaagctaaa atggagaaaa aaatcactgg atataccacc gttgatatat  37500
cccaatggca tcgtaaagaa cattttgagg catttcagtc agttgctcaa tgtacctata  37560
accagaccgt tcagctggat attacggcct ttttaaagac cgtaaagaaa aataagcaca  37620
agttttatcc ggcctttatt cacattcttg cccgcctgat gaatgctcat ccggaattcc  37680
gtatggcaat gaaagacggt gagctggtga tatgggatag tgttcaccct tgttacaccg  37740
ttttccatga gcaaactgaa acgttttcat cgctctggag tgaataccac gacgatttcc  37800
ggcagtttct acacatatat tcgcaagatg tggcgtgtta cggtgaaaac ctggcctatt  37860
tccctaaagg gtttattgag aatatgtttt tcgtctcagc caatccctgg gtgagtttca  37920
ccagttttga tttaaacgtg gccaatatgg acaacttctt cgcccccgtt ttcaccatgg  37980
gcaaatatta tacgcaaggc gacaaggtgc tgatgccgct ggcgattcag gttcatcatg  38040
ccgtctgtga tggcttccat gtcggcagaa tgcttaatga attacaacag tactgcgatg  38100
agtggcaggg cggggcgtaa tttttttaag gcagttattg gtgcccttaa acgcctggtt  38160
gctacgcctg aataagtgat aataagcgga tgaatggcag aaattcgatg ataagctgtc  38220
aaacatgaga atgggtcgag                                              38240
```